United States Patent
Mehmet et al.

(10) Patent No.: US 9,493,513 B2
(45) Date of Patent: Nov. 15, 2016

(54) POLYPEPTIDES AND THEIR USE

(71) Applicant: UNIVERSITY OF WASHINGTON THROUGH ITS CENTER FOR COMMERCIALIZATION, Seattle, WA (US)

(72) Inventors: Sarikaya Mehmet, Seattle, WA (US); Yuhei Hayamizu, Seattle, WA (US); Christopher R. So, Palo Alto, CA (US); Candan Tamerler-Behar, Seattle, WA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 48 days.

(21) Appl. No.: 14/349,634

(22) PCT Filed: Oct. 24, 2012

(86) PCT No.: PCT/US2012/061541
§ 371 (c)(1),
(2) Date: Apr. 3, 2014

(87) PCT Pub. No.: WO2013/063008
PCT Pub. Date: May 2, 2013

(65) Prior Publication Data
US 2014/0249052 A1    Sep. 4, 2014

Related U.S. Application Data

(60) Provisional application No. 61/550,721, filed on Oct. 24, 2011.

(51) Int. Cl.
| A61K 38/00 | (2006.01) |
| C07K 14/00 | (2006.01) |
| C07K 7/08 | (2006.01) |
| C07K 17/14 | (2006.01) |

(52) U.S. Cl.
CPC ............... *C07K 14/001* (2013.01); *C07K 7/08* (2013.01); *C07K 17/14* (2013.01)

(58) Field of Classification Search
None
See application file for complete search history.

(56) References Cited

U.S. PATENT DOCUMENTS 7,538,194 B2 * 5/2009 Jacobson ............... C07K 16/40
435/18
2005/0277160 A1   12/2005 Shiba et al.

FOREIGN PATENT DOCUMENTS

WO    WO 2009/088949    *  7/2009

OTHER PUBLICATIONS

Kim, et al., "Preferential Binding of Peptides to Graphene Edges and Planes," Journal of the American Chemical Society, vol. 133, No. 37, pp. 14480-14483, 2011.
Kowalewski, et al., "In Situ Atomic Force Microscopy Study of Alzheimer's β-Amyloid Peptide on Different Substrates: New Insights into Mechanism of β-Sheet Formation," Proceedings of the National Academy of Sciences USA, vol. 96, No. 7, pp. 3688-3693, 1999.
Krook, et al., "Novel peptides binding to the Fc-portion of immunoglobulins obtained from a combinatorial phage display peptide library," Journal of Immunological Methods, vol. 221, No. 1-2, pp. 151-157, 1998.
Kuila, et al., "Chemical functionalization of graphene and its applications," Progress in Materials Science, vol. 57, No. 7, pp. 1061-1105, 2012.
Kyte, et al., "A Simple Method for Displaying the Hydropathic Character of a Protein," Journal of Molecular Biology, vol. 157, No. 1, pp. 105-132, 1982.
Langer, et al., "Advances in Biomaterials, Drug Delivery, and Bionanotechnology," AIChE Journal, vol. 49, No. 12, pp. 2990-3006, 2003.
Langmuir, "The Constitution and Fundamental Properties of Solids and Liquids. Part I. Solids," Journal of the American Chemical Society, vol. 38, No. 11, pp. 2221-2295, 1916.
Le, et al., "DNA-Templated Self-Assembly of Metallic Nanocomponent Arrays on a Surface," Nano Letters, vol. 4, No. 12, pp. 2343-2347, 2004.
Lee, et al., "Adhesion of MC3T3-E1 cells to RGD peptides of different flanking residues: Detachment strength and correlation with long-term cellular function," Journal of Biomedical Materials Research Part A, vol. 81A, No. 1, pp. 150-160, 2007.
Lee, et al., "Measurement of the elastic properties and intrinsic strength of monolayer graphene," Science, vol. 321, No. 5887, pp. 385-388, 2008.
Lee, et al., "Modification of electronic properties of graphene with self-assembled monolayers," Nano Letters, vol. 10, No. 7, pp. 2427-2432, 2010.
Lee, et al., "Ordering of Quantum Dots Using Genetically Engineered Viruses," Science, vol. 296, No. 5569, pp. 892-895, 2002.
Leong, et al., "Cooperative Near-Field Surface Plasmon Enhanced Quantum Dot Nanoarrays," Advanced Functional Materials, vol. 20, No. 16, pp. 2675-2682, 2010.
Levesque, et al., "Probing charge transfer at surfaces using graphene transistors," Nano Letters, vol. 11, No. 1, pp. 132-137, 2011.
Lévy, et al., "Rational and combinatorial design of peptide capping Ligands for gold nanoparticles," Journal of the American Chemical Society, vol. 126, No. 32, pp. 10076-10084, 2004).
Li, et al,. "Processable aqueous dispersions of graphene nanosheets," Nature Nanotechnology, vol. 3, No. 2, pp. 101-105, 2008.
Li, et al "DNA-templated self-assembly of protein and nanoparticle linear arrays," Journal of the American Chemical Society, vol. 126, No. 2, pp. 418-419, 2004.

(Continued)

*Primary Examiner* — Lianko Garyu
*Assistant Examiner* — Sergio Coffa
(74) *Attorney, Agent, or Firm* — McDonnell Boehnen Hulbert & Berghoff LLP

(57) ABSTRACT

The present invention provides polypeptides that bind to inorganic solid surfaces, structures comprising such polypeptides, and methods of making such structures.

23 Claims, 34 Drawing Sheets

(56) References Cited

OTHER PUBLICATIONS

Lin, et al., "Glucose Biosensors Based on Carbon Nanotube Nanoelectrode Ensembles," Nano Letters, vol. 4, No. 2, pp. 191-195, online publication date: Dec. 2003, 2004.

Lin, et al., "Self-assembly of virus particles on flat surfaces via controlled evaporation," Langmuir, vol. 27, No. 4, pp. 1398-1402, 2011.

Lin, et al., "Self-directed self-assembly of nanoparticle/copolymer mixtures," Nature, vol. 434, No. 7029, pp. 55-59, 2005.

Liu, et al., "A one-step homogeneous immunoassay for cancer biomarker detection using gold nanoparticle probes coupled with dynamic light scattering," Journal of the American Chemical Society, vol. 130, No. 9, pp. 2780-2782, 2008.

Liu, et al., "Carbon nanomaterials field-effect-transistor-based biosensors," NPG Asia Materials, vol. 4, No. e23, 10 pages, 2012.

Liu et al., "Disposable electrochemical immunosensor diagnosis device based on nanoparticle probe and immunochromatographic strip," Analytical Chemistry, vol. 79, No. 20, pp. 7644-7653, 2007.

Liu et al., "Porogen-induced surface modification of nano-fibrous poly(L-lactic acid) scaffolds for tissue engineering," Biomaterials, vol. 27, No. 21, pp. 3980-3987, 2006.

Lopes, "Hierarchical self-assembly of metal nanostructures on diblock copolymer scaffolds," Nature, vol. 414, No. 6865, pp. 735-738, 2001.

Lowenstam, et al., "On Biomineralization," Oxford University Press, pp. 182-202, 1989.

Lu, et al., "Expression of Thioredoxin Random Peptide Libraries on the *Escherichia-coli* Cell-Surface as Functional Fusions to Flagelin—a System Designed for Exploring Protein-Protein Interactions," Nature Biotechnology, vol. 13, No. 4, pp. 366-372, 1995.

Lu, et al., "Nanometal-decorated exfoliated graphite nanoplatelet based glucose biosensors with high sensitivity and fast response," ACS Nano, vol. 2, No. 9, pp. 1825-1832, 2008.

Ludwig, "Biomarkers in cancer staging, prognosis and treatment selection," Nature Reviews Cancer, vol. 5, No. 11, pp. 845-856, 2005.

Lui, et al., "Ultraflat graphene," Nature, vol. 462, No. 7271, pp. 339-341, 2009.

Mak, et al., "Atomically thin MoS2: a new direct-gap semiconductor," Physical Review Letters, vol. 105, No. 13, pp. 136805+, 2010.

Mani, et al., "Ultrasensitive Immunosensor for Cancer Biomarker Proteins Using Gold Nanoparticle Film Electrodes and Multienzyme-Particle Amplification," ACS Nano, vol. 3, No. 3, pp. 585-594, 2009.

Mann, "Molecular Recognition in Biomineralization," Nature, vol. 332, pp. 119-124, 1988.

Mao, et al., "Specific protein detection using thermally reduced graphene oxide sheet decorated with gold nanoparticle-antibody conjugates," Advanced Materials, vol. 22, No. 32, pp. 3521-3526, 2010.

Mao, et al., "Viral assembly of oriented quantum dot nanowires," Proceedings of the National Academy of Sciences USA, vol. 100, No. 12, pp. 6946-6951, 2003.

Matmor , et al., "Peptide directed growth of gold films," Journal of Materials Chemistry, vol. 21, No. 4, pp. 968-974, 2011.

McMillan, et al., "Ordered nanoparticle arrays formed on engineered chaperonin protein templates," Nature Materials, vol. 1, No. 4, pp. 247-252, 2002.

Menzies, et al., "The Impact of Contact Angle on the Biocompatibility of Biomaterials," Optometry and Vision Science, vol. 87, No. 6, pp. 387-399, 2010.

Meyers, et al., "The development of peptide-based interfacial biomaterials for generating biological functionality on the surface of bioinert materials," Biomaterials, vol. 30, No. 3, pp. 277-286, 2009.

Moser, et al., "Current-induced cleaning of graphene," Applied Physics Letters, vol. 91, No. 163513+, 4 pages, 2007.

Mrksich, et al., "Using self-assembled monolayers to understand the interactions of man-made surfaces with proteins and cells," Annual Review of Biophysics and Biomolecular Structure, vol. 25, pp. 55-78, 1996.

Munday, "Toxicity of thiols and disulphides: Involvement of free-radical species," Free Radical Biology and Medicine, vol. 7, No. 6, pp. 659-673, 1989.

Murugesan, et al., "Immobilization of heparin: Approaches and applications," Current Topics in Medicinal Chemistry, vol. 8, No. 2, pp. 80-100, 2008.

Naik, et al., "Biomimetic synthesis and patterning of silver nanoparticles," Nature Materials, vol. 1, No. 3, pp. 169-172, 2002.

Naik, et al., "Silica-Precipitating Peptides Isolated from a Combinatorial Phage Display Peptide Library," Journal of Nanoscience and Nanotechnology, vol. 2, No. 1, pp. 95-100, 2002.

Nam, et al., "Peptide-mediated reduction of silver ions on engineered biological scaffolds," ACS Nano, vol. 2, No. 7, pp. 1480-1486, 2008.

Natale, et al., "Lung cancer identification by the analysis of breath by means of an array of non-selective gas sensors," Biosensors & Bioelectronics, vol. 18, No. 10, pp. 1209-1218, 2003.

Nath, et al., "Label-free biosensing by surface plasmon resonance of nanoparticles on glass: Optimization of nanoparticle size," Analytical Chemistry, vol. 76, No. 18, pp. 5370-5378, 2004.

Nel, et al., "Understanding Biophysicochemical Interactions at the Nano-Bio Interface," Nature Materials, vol. 8, No. 7, pp. 543-557, 2009.

Newaz, et al., "Probing charge scattering mechanisms in suspended graphene by varying its dielectric environment," Nature Communications, vol. 3, No. 734, 6 pages, 2012.

Xie et al., "Ranking the Affinity of Aromatic Residues for Carbon Nanotubes by Using Designed Surfactant Peptides," Journal of Peptide Science, vol. 14, No. 2, pp. 139-151, 2008.

Yalow, et al., "Immunoassay of endogenous plasma insulin in man," Journal of Clinical Investigation, vol. 39, No. 7, pp. 1157-1175, 1960.

Yan, et al., "Electric field effect tuning of electron-phonon coupling in graphene," Physical Review Letters, vol. 98, No. 16, pp. 166802+, 2007.

Yang, et al., "Carbon nanomaterials in biosensors: should you use nanotubes or graphene?," Angewandte Chemie International Edition, vol. 49, No. 12, pp. 2114-2138, 2010.

Yang, et al., "Ionic-complementary peptide-modified highly ordered pyrolytic graphite electrode for biosensor application," Biotechnology Progress, vol. 24, No. 4, pp. 964-971, 2008.

Yu, et al., "Carbon nanotube amplification strategies for highly sensitive immunodetection of cancer biomarkers," Journal of the American Chemical Society, vol. 128, No. 34, pp. 11199-11205, 2006.

Yu, et al., "Surface Gradient Material: From Superhydrophobicity to Superhydrophilicity," Langmuir, vol. 22, No. 10, pp. 4483-4486, 2006.

Yuca, et al., "In Vitro Labeling of Hydroxyapatite Minerals by an Engineered Protein," Biotechnology and Bioengineering, vol. 108, No. 5, pp. 1021-1030, 2011.

Zhang et al., "Ultra-sensitive suspended graphene nanocomposite cancer sensors with strong suppression of electrical noise," Biosensors & Bioelectronics, vol. 31, No. 1, pp. 105-109, 2012.

Zhang, et al., "Direct observation of a widely tunable bandgap in bilayer graphene," Nature, vol. 459, No. 7248, pp. 820-823, 2009.

Zhang, et al., "Epitaxial Growth of Peptide Nanofilaments on Inorganic Surfaces: Effects of Interfacial Hydrophobicity/Hydrophilicity," Angewandte Chemie International Edition, vol. 45, No. 22, pp. 3611-3613, 2006.

Zhang, et al., "Experimental observation of the quantum Hall effect and Berry's phase in graphene," Nature, vol. 438, No. 7065, pp. 201-204, 2005.

Zhang, et al., "Layer-by-layer assembled carbon nanotubes for selective determination of dopamine in the presence of ascorbic acid," Biosensors & Bioelectronics, vol. 20, No. 7, pp. 1270-1276, 2005.

Zhao, et al., "Binary-Component Self-Assembled Monolayer Comprising Tetrathiafulvalene and n-Tetradecane Molecules with Peri-

(56) References Cited

OTHER PUBLICATIONS odic Ordered Phase Separation Structures on a Highly Oriented Pyrolytic Graphite Surface," Journal of Physical Chemistry C, 114(3):1646-1650, 2010.
Zhu, et al., "Global Analysis of Protein Activities Using Proteome Chips," Science, vol. 293, No. 5537, pp. 2101-2105, 2001.
ISR/WO mailed Jan. 28, 2013 for PCT/US2012/061541 filed Oct. 24, 2012.
Mohanty, et al., "Graphene-based single-bacterium resolution bioevidence and DNA transistor:interfacing graphene derivatives with nanoscale and microscale biocomponents," Nano Letters, 8(12): 4469-4476, 2008.
Niyogi, et al., "Solution properties of graphite and graphene," Journal of the American Chemical Society, vol. 128, No. 24, pp. 7720-7721, 2006.
Nogales, et al., "Structure of the $\alpha\beta$ tubulin dimer by electron crystallography," Nature, vol. 391, No. 6663, pp. 199-203, 1998.
Novoselov, et al., "Electric field effect in atomically thin carbon films," Science, vol. 306, No. 5696, pp. 666-669, 2004.
Novoselov, et al., "Two-dimensional atomic crystals," Proceedings of the National Academy of Sciences USA, vol. 102, No. 30, pp. 10451-10453, 2005.
Nuraje, et al., "Biological bottom-up assembly of antibody nanotubes on patterned antigen arrays," Journal of the American Chemical Society, vol. 126, No. 26, pp. 8088-8089, 2004.
Offenhäusser, et al., Nanobioelectronics: for electronics, biology, and medicine, Springer-Verlag: New York, pp. 103-180, 2009.
Oghedo, "Raman Studies in Graphene," National Nanotechnology Infrastructure Network, pp. 102-103, retrieved online from: http://www.nnin.org/sites/default/files/files/2010nninreura/2010NNINireuOghedoN.pdf, 2010.
Ohno, et al., "Chemical and biological sensing applications based on graphene field-effect transistors," Biosensors and Bioelectronics, vol. 26, No. 4, pp. 1727-1730, 2010.
Ohno, et al., "Electrolyte-Gated Graphene Field-Effect Transistors for Detecting pH Protein Adsorption," Nano Letters, vol. 9, No. 9, pp. 3318-3322, 2009.
Ohno, et al., "Label-Free Biosensors Based on Aptamer-Modified Graphene Field-Effect Transistors," Journal of the American Chemical Society, vol. 132, No. 51, pp. 18012-18013, 2010.
Ona, et al., "Carcinoembryonic antigen (CEA) in the diagnosis of pancreatic cancer," Cancer, vol. 31, No. 2, pp. 324-327, 1973.
Oren, et al., "A novel knowledge-based approach to design inorganic-binding peptides," Bioinformatics, vol. 23, No. 21, pp. 2816-2822, 2007.
Page, et al., "Electrical detection of biomolecular adsorption on sprayed graphene sheets," Biosensors & Bioelectronics, vol. 33, No. 1, pp. 304-308, 2012.
Pantarotto, et al., "Synthesis, Structural Characterization, and Immunological Properties of Carbon Nanotubes Functionalized with Peptides," Journal of the American Chemical Society, vol. 125, No. 20, pp. 6160-6164, 2003.
Pattani, et al., "Microcontact printing of quantum dot bioconjugate arrays for localized capture and detection of biomolecules," Biomedical Microdevices, vol. 10, No. 3, pp. 367-374, 2008.
Pauling, "Molecular Architecture and Biological Reactions," Chemical and Engineering News, vol. 24, No. 10, pp. 1375-1377, 1946.
Peelle, et al., "Design criteria for engineering inorganic material-specific peptides," Langmuir, vol. 21, No. 15, pp. 6929-6933, 2005.
Pierschbacher, et al., "Cell Attachment Activity of Fibronectin Can Be Duplicated by Small Synthectic Fragments of the Molecule," Nature, vol. 309, No. 5963, pp. 30-33, 1984.
Pollard, et al., "Supramolecular assemblies formed on an epitaxial graphene superstructure," Angewandte Chemie International Edition, vol. 49, No. 10, pp. 1794-1799, 2010.
Porter, et al., "Spontaneously organized molecular assemblies .4. Structural characterization of normal-alkyl thiol monolayers on gold by optical ellipsometry, infrared-spectroscopy, and electrochemistry," Journal of the American Chemical Society, vol. 109, No. 12, pp. 3559-3568, 1987.
Qin, et al., "Soft lithography for micro- and nanoscale patterning," Nature Protocols, vol. 5, No. 3, pp. 491-502, 2010.
Radisavljevic, et al., "Single-layer MoS2 transistors," Nature Nanotechnology, vol. 6, No. 3, pp. 147-150, 2011.
Rajesh, et al,. "A theoretical study on the interaction of aromatic amino acids with graphene and single walled carbon nanotube," Journal of Chemical Physics, vol. 130, No. 12, pp. 124911+, 7 pages, 2009.
Ratinac, "Graphene and Related Materials in Electrochemical Sensing," Electroanalysis, vol. 23, No. 4, pp. 803-826, 2011.
Regot, et al., "Distributed biological computation with multicellular engineered networks," Nature, vol. 469, No. 7329, pp. 207-211, 2011.
Rezania, et al., "Bioactivation of metal oxide surfaces. 1. Surface characterization and cell response," Langmuir, vol. 15, No. 20, pp. 6931-6939, 1999.
Salim, et al., "Non-fouling microfluidic chip produced by radio frequency tetraglyme plasma deposition," Lab on a Chip, vol. 7, No. 4, pp. 523-525, 2007.
Sano, et al., "A Hexapeptide Motif That Electrostatically Binds to the Surface of Titanium," Journal of the American Chemical Society, vol. 125, No. 47, pp. 14234-14235, 2003.
Sano, et al., "Utilization of the Pleiotropy of a Peptidic Aptamer to Fabricate Heterogeneous Nanodot-Containing Multilayer Nanostructures," Journal of the American Chemical Society, vol. 128, No. 5, pp. 1717-1722, 2006.
Sarikaya et al., "Molecular Biomimetics: Nanotechnology through Biology," Nature Materials, vol. 2, No. 9, pp. 577-585, 2003.
Sarikaya, "Biomimetics: Materials fabrication through biology," Proceedings of the National Academy of Sciences USA, vol. 96, No. 25, pp. 14183-14185, 1999.
Schedin, et al., "Detection of individual gas molecules adsorbed on graphene," Nature Materials, vol. 6, No. 9, pp. 652-655, 2007.
Scheibel, et al., "Conducting nanowires built by controlled self-assembly of amyloid fibers and selective metal deposition," Proceedings of the National Academy of Sciences USA, vol. 100, No. 8, pp. 4527-4532, 2003.
Schierholz, et al. "Implant infections: a haven for opportunistic bacteria," Journal of Hospital Infection, vol. 49, No. 2, pp. 87-93, 2001.
Schreiber, "Structure and growth of self-assembling monolayers," Progress in Surface Science, vol. 65, pp. 151-256, 2000.
Schwartz, "Mechanisms and Kinetics of Self-Assembled Monolayer Formation," Annual Review of Physical Chemistry, vol. 52, No. pp. 107-137, 2001.
Sedlak, et al., "An Engineered DNA-Binding Protein Self-assembles Metallic Nanostructures," ChemBioChem., vol. 11, No. 15, pp. 2108-2112, 2010.
Seker, et al., "Adsorption behavior of linear and cyclic genetically engineered platinum binding peptides," Langmuir, vol. 23, No. 15, pp. 7895-7900, 2007.
Seo, et al., "A Three-Dimensional Nanostructured Array of Protein Nanoparticles," Advanced Functional Materials, No. 20, vol. 23, pp. 4055-4061, 2010.
Shang et al. "Catalyst-Free Efficient Growth, Orientation and Biosensing Properties of Multilayer Graphene Nanoflake Films with Sharp Edge Planes," Advanced Functional Materials, vol. 18, No. 21, pp. 3506-3514, 2008.
Sharma, et al., "DNA-templated self-assembly of two-dimensional and periodical gold nanoparticle arrays," Angewandte Chemie International Edition, vol. 45, No. 5, pp. 730-735, 2006.
Shiba, "Exploitation of peptide motif sequences and their use in nanobiotechnology," Current Opinion in Biotechnology, vol. 21, No. 4, pp. 412-425, 2010.
Shih, et al., "Understanding surfactant/graphene interactions using a graphene field effect transistor: relating molecular structure to hysteresis and carrier mobility," Langmuir, vol. 28, No. 22, pp. 8579-8586, 2012.
Siegel, et al., "Cancer statistics, 2013," CA: A Cancer Journal for Clinicians, vol. 63, No. 1, pp. 11-30, 2013.

(56) References Cited

OTHER PUBLICATIONS

Siegel, et al., "Computational Design of an Enzyme Catalyst for a Stereoselective Bimolecular Diels-Alder Reaction," Science, vol. 329, No. 5989, pp. 309-313, 2010.
Sleytr, et al., "Crystalline surface-layers on bacteria," Annu. Rev. Microbiol., vol. 37, pp. 311-339, 1983.
Slocik, et al. "Biologically programmed synthesis of bimetallic nanostructures," Advanced Materials, vol. 18, No. 15, pp. 1988-1992, 2006.
Slocik, et al. "Viral templates for gold nanoparticle synthesis," Journal of Materials Chemistry, vol. 15, No. 7, pp. 749-753, 2005.
Slocik, et al., "Synthesis of gold nanoparticles using multifunctional peptides," Small, vol. 1, pp. 11, pp. 1048-1052, 2005.
Smith, "Filamentous fusion phage: novel expression vectors that display cloned antigens on the virion surface," Science, vol. 228, No. 4705, pp. 1315-1317, 1985.
Smith, "Phage display," Chemical Reviews, vol. 97, No. 2, pp. 391-410, 1997.
Smith, et al., "Cancer Screening in the United States, 2009: A Review of Current American Cancer Society Guidelines and Issues in Cancer Screening," CA: A Cancer Journal for Clinicians, vol. 59, No. 1, pp. 27-41, 2009.
Sneer, et al., "Parallel β-Sheet Assemblies at Interfaces," ChemPhysChem, vol. 5, No. 5, pp. 747-750, 2004.
So et al., "Adsorption, Diffusion, and Self-Assembly of an Engineered Gold-Binding Peptide on Au(111) Investigated by Atomic Force Microscopy," Angewandte Chemie International Edition, vol. 48, No. 28, pp. 5174-5177, 2009.
So et al., "Molecular Recognition and Supramolecular Self-Assembly of a Genetically Engineered Gold Binding Peptide on Au(111)," ACS Nano, vol. 3, No. 6, pp. 1525-1531, 2009.
So, et al., "Controlling Self-Assembly of Engineered Peptides on Graphite by Rational Mutation," ACS Nano, vol. 6, No. 2, pp. 1648-1656, 2012.
Sohn, et al., "Resected adenocarcinoma of the pancreas—616 patients: Results, outcomes, and prognostic indicators," Journal of Gastrointestinal Surgery, vol. 4, No. 6, pp. 567-579, 2000.
Someya, et al., "Alcohol vapor sensors based on single-walled carbon nanotube field effect transistors," Nano Letters, vol. 3, No. 7, pp. 877-881, 2003.
Soper, et al., "Point-of-care biosensor systems for cancer diagnostics/prognostics," Biosensors and Bioelectronics, vol. 21, No. 10, pp. 1932-1942, 2006.
Sotiropoulou, et al., "Biotemplated Nanostructured Materials," Chemistry of Materials, vol. 20, No. 3, pp. 821-834, 2008.
Sowerby, et al., "Primordial Coding of Amino Acids by Adsorbed Purine Bases," Origins of Life and Evolution of the Biosphere, vol. 32, No. 1, pp. 35-46, 2002.
Splendiani, et al., "Emerging photoluminescence in monolayer MoS2," Nano Letters, vol. 10, No. 4, pp. 1271-1275, 2010.
Srivastava, et al., "Nanoparticle assembly for 1D and 2D ordered structures," Soft Matter, vol. 5, No. 6, pp. 1146-1156, 2009.
Stathis, et al. "Advanced pancreatic carcinoma: current treatment and future challenges," Nature Reviews Clinical Oncology, vol. 7, No. 3, pp. 163-172, 2010.
Steinberg, "The Clinical Utility of the CA 19-9 Tumor-Associated Antigen," American Journal of Gastroenterology, vol. 85, No. 4, pp. 350-355, 1990.
Stine, et al., "Real-Time DNA Detection Using Reduced Graphene Oxide Field Effect Transistors," Advanced Materials, vol. 22, No. 46, pp. 5297-5300, 2010.
Stroganova et al. (Sep. 2003) "Glass-Based Bomaterials: Present and Future (A Review)," Glass and Ceramics, 60 (9-10):315-319.
Sudibya, et al., "Interfacing Glycosylated Carbon-Nanotube-Network Devices with Living Cells to Detect Dynamic Secretion of Biomolecules," Angewandte Chemie International Edition, vol. 48, No. 15, pp. 2723-2726, 2009.

Tamerler, et al., "Adsorption kinetics of an engineered gold binding peptide by surface plasmon resonance spectroscopy and a quartz crystal microbalance," Langmuir, vol. 22, No. 18, pp. 7712-7718, 2006.
Tamerler, et al., "Molecular Biomimetics: GEPI-Based Biological Routes to Technology," Biopolymers, vol. 94, No. 1, pp. 78-94, 2010.
Tamerler, et al., "Molecular biomimetics: nanotechnology and bionanotechnology using genetically engineered peptides," Philosophical Transactions of the Royal Society A-Mathematical Physical and Engineering Sciences, vol. 367, No. 1894, pp. 1705-1726, 2009.
Tang, "Inflammatory Responses to Biomaterials," American Journal of Clinical Pathology, vol. 103, No. 4, pp. 466-471, 1995.
Tang, et al., "One-Dimensional Assemblies of Nanoparticles: Preparation, Properties, and Promise," Advanced Materials, vol. 17, No. 8, pp. 951-962, 2005.
Tao, et al., "Self-assembly and odd-even effects of cis-unsaturated carboxylic acids on highly oriented pyrolytic graphite," Journal of Physical Chemistry B, vol. 110, No. 9, pp. 4199-4206, 2006.
Templin, "Protein Microarray Technology," Trends in Biotechnology, vol. 20, No. 4, pp. 160-166, 2002.
Thai, et al., "Identification and characterization of Cu2O- and ZnO-binding polypeptides by *Escherichia coli* cell surface display: Toward an understanding of metal oxide binding," Biotechnology and Bioengineering, vol. 87, No. 2, pp. 129-137, 2004.
Thompson, et al. "Prevalence of prostate cancer among men with a prostate-specific antigen level < or =4.0 ng per milliliter," New England Journal of Medicine, vol. 350, No. 22, pp. 2239-2246, 2004.
Thygesen, et al., "Peptides on nanoparticles: Linkers for chemoselective, biocompatible immobilization," Peptide Science, Special Issue: Program and Abstracts for the 20th American Peptide Symposium, vol. 88, No. 4, pp. 616, 2007.
Tomasio, "Atomistic modeling of the interaction between peptides and carbon nanotubes," Molecular Physics, vol. 105, No. 221, 2007.
Tomasio, et al, "Modeling the Binding Affinity of Peptides for Graphitic Surfaces. Influences of Aromatic Content and Interfacial Shape," J. Phys. Chem. C, vol. 113, No. 20, pp. 8778-8785, 2009.
Toniolo, et al., "A Bioactive Fullerene Peptide," Journal of Medicinal Chemistry, vol. 37, No. 26, pp. 4558-4562, 1994.
Turkevich, "A study of the nucleation and growth processes in the synthesis of colloidal gold," Discussions of the Faraday Society, vol. 11, pp. 55-75, 1951.
Ulman, "Formation and Structure of Self-Assembled Monolayers," Chemical Reviews, vol. 96, No. 4, pp. 1533-1554, 1996.
Vaisocherova, et al. "Ultralow fouling and functionalizable surface chemistry based on a zwitterionic polymer enabling sensitive and specific protein detection in undiluted blood plasma," Analytical Chemistry, vol. 80, No. 20, pp. 7894-7901, 2008.
Walton, et al., "Platinum Pacemaker Electrodes—Origins and Effects of the Electrode-Tissue Interface Impedance," Pacing and Clinical Electrophysiology, vol. 10, vol. 1, Pt. 1, pp. 87-99, 1987.
Wang, et al., "Atomic layer deposition of metal oxides on pristine and functionalized graphene," Journal of the American Chemical Society, vol. 130, No. 26, pp. 8152-8153, 2008.
Wang, et al., "Mirror-like photoconductive layer-by-layer thin films of Te nanowires: The fusion of semiconductor, metal, and insulator properties," Advanced Materials, vol. 18, No. 4, pp. 518-522, 2006.
Wang, et al., "Peptides with Selective Affinity for Carbon Nanotubes," Nature Materials, vol. 2, 3, pp. 196-200, 2003.
Wang, et al., "Room-temperature molecular-resolution characterization of self-assembled organic monolayers on epitaxial graphene," Nature Chemistry, vol. 1, No. 3, pp. 206-211, 2009.
Wang, et al., "The peptide route to multifunctional gold nanoparticles," Bioconjugate Chemistry, vol. 16, No. 3, pp. 497-500, 2005.
Wei, et al., "Nanopatterning Peptides as Bifunctional Inks for Templated Assembly," Small, vol. 5, No. 6, pp. 689-693, 2009.
Weisenhorn, et al., "Streptavidin binding observed with an atomic force microscope," Ultramicroscopy, vol. 42-44(Pt 2), pp. 1125-1132, 1992.

(56) References Cited

OTHER PUBLICATIONS

Weissbuch, et al., "Molecular recognition at crystal interfaces," Science, vol. 253, No. 5020, pp. 637-645, 1991.
Whaley et al., "Selection of Peptides with Semiconductor Binding Specificity for Directed Nanocrystal Assembly," Nature, vol. 405, No. 6787, pp. 665-668, 2000.
Whitehouse, et al., "Adsorption and Self-Assembly of Peptides on Mica Substrates," Angewandte Chemie International Edition, vol. 44, No. 13, pp. 1965-1968, 2005.
Whitesides, et al., "Molecular self-assembly and nanochemistry—a chemical strategy for the synthesis of nanostructures," Science, vol. 254, No. 5036, pp. 1312-1319, 1991.
Williams, "On the mechanisms of biocompatibility," Biomaterials, vol. 29, No. 20, pp. 2941-2953, 2008.
Willner, et al., "Integrated nanoparticle-biomolecule systems for biosensing and bioelectronics," Biosensors & Bioelectronics, vol. 22, No. 9-10, pp. 1841-1852, 2007.
Wu, et al., "Simultaneous determination of dopamine and serotonin on a glassy carbon electrode coated with a film of carbon nanotubes," Analytical Biochemistry, vol. 318, No. 1, 100-106, 2003.
Xia, et al., "Soft lithography," Annual Review of Materials Science, vol. 28, pp. 153-184, 1998.
Dickerson, et al., "Protein- and Peptide-Directed Syntheses of Inorganic Materials," Chemical Reviews, vol. 108, No. 11, pp. 4935-4978, 2008.
Donatan, et al., "Physical elution in phage display selection of inorganic-binding peptides," Materials Science and Engineering C, vol. 29, No. 1, pp. 14-19, 2009.
Dong, et al., "Doping single-layer graphene with aromatic molecules," Small, vol. 5, No. 12, pp. 1422-1426, 2009.
Dong, et al., "Electrical detection of DNA hybridization with single-base specificity using transistors based on CVD-grown graphene sheets," Advanced Materials, vol. 22, No. 14, pp. 1649-1653, 2010.
Du, et al., "Sensitive Immunosensor for Cancer Biomarker Based on Dual Signal Amplification Strategy of Graphene Sheets and Multienzyme Functionalized Carbon Nanospheres," Analytical Chemistry, vol. 82, No. 7, pp. 2989-2995, 2010.
Engel, "Biological Applications of Scanning Probe Microscopes," Annual Review of Biophysics and Biophysical Chemistry, vol. 20, No. 79-108, 1991.
Farmer, et al., "Behavior of a chemically doped graphene junction," Applied Physics Letters, vol. 94, pp. 213106+, 4 pages, 2009.
Faucheux, et al., "Self-assembled monolayers with different terminating groups as model substrates for cell adhesion studies," Biomaterials, vol. 25, No. 14, pp. 2721-2730, 2004.
Gaskin, et al., "Identification of inorganic crystal-specific sequences using phage display combinatorial library of short peptides: A feasibility study," Biotechnology Letters, vol. 22, No. 15, pp. 1211-1216, 2000.
Gawalt, et al., "Self-Assembly and Bonding of Alkanephosphonic Acids on the Native Oxide Surface of Titanium," Langmuir, vol. 17, No. 19, pp. 5736-5738, 2001.
Ghosh, et al., "Non-covalent functionalization, solubilization of graphene and single-walled carbon nanotubes with aromatic donor and acceptor molecules," Chemical Physics Letters, vol. 488, No. 4-6, pp. 198-201, 2010.
Girit, et al., "Soldering to a single atomic layer," Applied Physics Letters, vol. 91, No. 193512+, 4 pages, 2007.
Gold, et al. "Demonstration of tumor-specific antigens in human colonic carcinomata by immunological tolerance and absorption techniques," Journal of Experimental Medicine, vol. 121, pp. 439-462, 1965.
Griffith, "Tissue engineering—Current challenges and expanding opportunities," Science, vol. 295, No. 5557, pp. 1009-1014, 2002.
Grigoryan, et al., "Computational Design of Virus-Like Protein Assemblies on Carbon Nanotube Surfaces," Science, vol. 332, No. 6033, pp. 1071-1076, 2011.
Gross, "High Resolution Metal Replication of Freeze-Dried Specimens," in Cryotechniques in Biological Electron Microscopy, 1st edition, pp. 205-215, 1987.
Grzelczak, et al., "Directed self-assembly of nanoparticles," ACS Nano, vol. 4, No. 7, pp. 3591-3605, 2010.
Gu, et al., "DNA nanowire fabrication," Nanotechnology, vol. 17, No. 1, pp. R14-R25, 2006.
Gungormus, et al., "Regulation of in vitro calcium phosphate mineralization by combinatorially selected hydroxyapatite-binding peptides," Biomacromolecules, vol. 9, No. 3, pp. 966-973, 2008.
Guo, et al., "Label free DNA detection using large area graphene based field effect transistor biosensors," Journal of Nanoscience and Nanotechnology, vol. 11, No. 6, pp. 5258-5263, 2011.
Gyorvary, et al., "Self-Assembly and Recrystallization of Bacterial S-Layer Proteins at Silicon Supports Imaged in Real Time by Atomic Force Microscopy," Journal of Microscopy, vol. 212, Pt 3, pp. 300-306, 2003.
Hamley, "Nanostructure fabrication using block copolymers," Nanotechnology, vol. 14, No. 10, pp. R39-R54, 2003.
Hammarström "The carcinoembryonic antigen (CEA) family: structures, suggested functions and expression in normal and malignant tissues," Seminars in Cancer Biology, vol. 9, No. 2, pp. 67-81, 1999.
Hammond, "Form and function in multilayer assembly: New applications at the nanoscale," Advanced Materials, vol. 16, No. 15, pp. 1271-1293, 2004.
Han, et al., "Energy Band Gap Engineering of Graphene Nanoribbons," Physical Review Letters, vol. 98, No. 20, pp. 206805+, 4 pages, 2007.
Han, et al., "Peptide/Graphene Hybrid Assembly into Core/Shell Nanowires," Advanced Materials, vol. 22, No. 18, pp. 2060-2064, 2010.
Harder, et al., "Molecular conformation in oligo(ethylene glycol)-terminated self-assembled monolayers on gold and silver surfaces determines their ability to resist protein adsorption," Journal of Physical Chemistry B, vol. 102, No. 2, pp. 426-436, 1998.
Harper, et al. "Observation of Metastable Abeta Amyloid Protofibrils by Atomic Force Microscopy," Chemistry and Biology, vol. 4, No. 2, pp. 119-125, 1997.
Haynes, et al., "Nanosphere lithography: A versatile nanofabrication tool for studies of size-dependent nanoparticle optics," Journal of Physical Chemistry B, vol. 105, No. 24, pp. 5599-5611, 2001.
Hench, "Bioceramics," Journal of the American Ceramic Society, vol. 81, No. 7, pp. 1705-1728, 1998.
Herreros-Villanueva, et al., "Molecular markers in pancreatic cancer diagnosis," Clinica Chimica Acta, vol. 418, pp. 22-29, 2013.
Hnilova, et al., "Effect of Molecular Conformations on the Adsorption Behavior of Gold-Binding Peptides," Langmuir, vol. 24, No. 21, pp. 12440-12445, pp. 2008.
Hnilova, et al., "Peptide-directed co-assembly of nanoprobes on multimaterial patterned solid surfaces," Soft Matter, vol. 8, No. 16, 4327-4334, 2012.
Hnilova, et al., "Single-Step Fabrication of Patterned Gold Film Array by an Engineered Multi-Functional Peptide," Journal of Colloid and Interface Science, vol. 365, No. 1, pp. 97-102, 2012.
Hollingsworth, et al. "Mucins in cancer: Protection and control of the cell surface," Nature Reviews Cancer, vol. 4, No. 1, pp. 45-60, 2004.
Holmberg, et al., "The biotin-streptavidin interaction can be reversibly broken using water at elevated temperatures," Electrophoresis, vol. 26, No. 3, pp. 501-510, 2005.
Hu, et al., "Graphene-Based Antibacterial Paper," ACS Nano, vol. 4, No. 7, pp. 4317-4323, 2010.
Huang, et al., "Programmable assembly of nanoarchitectures using genetically engineered viruses," Nano Letters, vol. 5, No. 7, pp. 1429-1434, 2005.
Hubbell, et al. "Biomaterials in Tissue Engineering," Nature Biotechnology, vol. 13, No. 6, pp. 565-576, 1995.
Jensen, et al., "Deposition, Diffusion, and Aggregation of Atoms on Surfaces: A Model for Nanostructure Growth," Physical Review B, vol. 50, No. 20, pp. 15316-15329, 1994.
Joachim et al., "Electronics Using Hybrid-Molecular and Mono-Molecular Devices," Nature, vol. 408, No. 6812, pp. 541-548, 2000.

(56) References Cited

OTHER PUBLICATIONS

Kacar, et al. "Quartz Binding Peptides as Molecular Linkers towards Fabricating Multifunctional Micropatterned Substrates," Advanced Materials, vol. 21, No. 3, pp. 295-299, 2009.
Kacar, et al., "Directed Self-Immobilization of Alkaline Phosphatase on Micro-Patterned Substrates Via Genetically Fused Metal-Binding Peptide," Biotechnol. Bioeng., vol. 103, No. 4, pp. 696-705, 2009.
Kase, et al., "Affinity selection of peptide phage libraries against single-wall carbon nanohorns identifies a peptide aptamer with conformational variability," Langmuir, vol. 20, No. 20, pp. 8939-8941, 2004.
Katz, et al., "Integrated nanoparticle-biomolecule hybrid systems: synthesis, properties, and applications," Angewandte Chemie International Edition, vol. 43, No. 45, pp. 6042-6108, 2004.
Khatayevich, et al., "Biofunctionalization of materials for implants using engineered peptides," Acta Biomaterialia, vol. 6, No. 12, pp. 4634-4641, 2010.
Khatayevich, "Bio-Inorganic Interface Engineering via Solid-Binding Peptides toward Nano-sensing Applications," Ph. D. Dissertation, University of Washington, 114 pages, 2013.
Khatayevich, et al., "Controlling the Surface Chemistry of Graphite by Engineered Self-Assembled Peptides," Langmuir, vol. 28, No. 23, pp. 8589-8593, 2012.
Khatayevich, et al., "Selective detection of target proteins by peptide-enabled graphene biosensor," Small, vol. 10, No. 8, pp. 1505-1513, 2014.
Kim, et al., "Epitaxial self-assembly of block copolymers on lithographically defined nanopatterned substrates," Nature, vol. 424, No. 6947, pp. 411-414, 2003.
Acosta, et al., "Linker-based bio-compatible microemulsions," Environmental Science & Technology, vol. 39, No. 5, pp. 1275-1282, 2005.
Addadi, "Interactions Between Acidic Proteins and Crystals: Stereochemical Requirements in Biomineralization," Proceedings of the National Academy of Sciences USA, vol. 82, No. 12, pp. 4110-4114, 1985.
Adler-Abramovich et al., "Self-assembled arrays of peptide nanotubes by vapour deposition," Nature Nanotechnology, vol. 4, No. 12, pp. 849-854, 2009.
Alam, et al., "Electrolyte-gated transistors based on conducting polymer nanowire junction arrays," Journal of Physical Chemistry B, vol. 109, No. 26, pp. 12777-12784, 2005.
Allen, et al., "Carbon nanotube field-effect-transistor-based biosensors," Advanced Materials, vol. 19, No. 11, pp. 1439-1451, 2007.
Alwarappan, et al., "Probing the Electrochemical Properties of Graphene Nanosheets for Biosensing Applications," Journal of Physical Chemistry C, vol. 113, No. 20, pp. 8853-8857, 2009.
Anker, et al., "Biosensing with plasmonic nanosensors," Nature Materials, vol. 7, No. 6, pp. 442-453, 2008.
Anselme, "Osteoblast adhesion on biomaterials," Biomaterials, vol. 21, No. 7, 667-681, 2000.
Bai, et al., "Fabrication of Au nanowires of uniform length and diameter using a monodisperse and rigid biomolecular template: collagen-like triple helix," Angewandte Chemie International Edition, vol. 46, No. 18, pp. 3319-3322, 2007.
Balandin et al. "Superior thermal conductivity of single-layer graphene," Nano Letters, vol. 8, No. 3, pp. 902-907, 2008.
Balk, et al., "Biology of prostate-specific antigen," Journal of Clinical Oncology, vol. 21, No. 2, pp. 383-391, 2003.
Baneyx, "Recombinant Protein Folding and Misfolding in *Escherichia coli*," Nature Biotechnology, vol. 22, No. 11, pp. 1399-1408, 2004.
Bartelt, et al., "Scaling analysis of diffusion-mediated island growth in surface-adsorption processes," Phys. Rev. B, vol. 46, No. 19, pp. 12675-12687, 1992.
Barth, et al., "Engineering Atomic and Molecular Nanostructures at Surfaces," Nature, vol. 437, No. 7059, pp. 671-679, 2005.
Barth, et al., "Stereochemical effects in supramolecular self-assembly at surfaces: 1-D versus 2-D enantiomorphic ordering for PVBA and PEBA on Ag(111)," Journal of the American Chemical Society, vol. 124, No. 27, pp. 7991-8000, 2002.
Besteman, et al., "Enzyme-coated carbon nanotubes as single-molecule biosensors," Nano Letters, vol. 3, No. 6, pp. 727-730, 2003.
Bolotin et al., "Ultrahigh electron mobility in suspended graphene," Solid State Communications, vol. 146, No. 9-10, pp. 351-355, 2008.
Bradley, "Ultrastructure of Bacteriophages and Bacteriocins," Bacteriological Reviews, vol. 31, No. 4, pp. 230-314, 1967.
Brodbeck, et al., "Influence of biomaterial surface chemistry on the apoptosis of adherent cells," Journal of Biomedical Materials Research, vol. 55, No. 4, pp. 661-668, 2001.
Brown "Metal-Recognition by Repeating Polypeptides," Nature Biotechnology, vol. 15, No. 3, pp. 269-272, 1997.
Brown et al., "A genetic analysis of crystal growth," Journal of Molecular Biology, vol. 299, No. 3, pp. 725-735, 2000.
Brown et al., "Template-Directed Assembly of a De Novo Designed Protein," Journal of the American Chemical Society, vol. 124, No. 24, pp. 6846-6848, 2002.
Brown, "Engineered iron oxide adhesion mutants of the *Escherichia coli* phage-lambda receptor," Proceedings of the National Academy of Sciences USA, vol. 89, No. 18, pp. 8651-8655, 1992.
Brown, et al., "A genetic analysis of carbon-nanotube-binding proteins," Small, vol. 4, No. 4, pp. 416-420, 2008.
Bui, et al., "Programmable periodicity of quantum dot arrays with DNA origami nanotubes," Nano Letters, vol. 10, No. 9, pp. 3367-3372, 2010.
Bumm, et al., "Are single molecular wires conducting?" Science, vol. 271, No. 5256, pp. 1705-1707, 1996.
Bünger, et al., "Serum biomarkers for improved diagnostic of pancreatic cancer: a current overview," Journal of Cancer Research and Clinical Oncology, vol. 137, No. 3, pp. 375-389, 2011.
Cassie, et al., "Wettability of Porous Surfaces," Transactions of the Faraday Society, vol. 40, pp. 546-551, 1944.
Castro Neto, et al., "The electronic properties of graphene," Reviews of Modern Physics, vol. 81, pp. 109-162, 2009.
Cha, et al., "Enzymatic Activity on a Chip: The Critical Role of Protein Orientation," Proteomics, vol. 5, No. 2, pp. 416-419, 2005.
Cha et al., "Silicatein Filaments and Subunits from a Marine Sponge Direct the Polymerization of Silica and Silicones in Vitro," Proceedings of the National Academy of Sciences, vol. 96, No. 2, pp. 361-365, 1999.
Chang, et al., "Single-walled carbon nanotube field-effect transistors with graphene oxide passivation for fast, sensitive, and selective protein detection," Biosensors and Bioelectronics, vol. 42, pp. 186-192, 2013.
Chen, et al., "Charged-impurity scattering in graphene," Nature Physics, vol. 4, No. 377-381, 2008.
Chen, et al., "Dielectric screening enhanced performance in graphene FET," Nano Letters, vol. 9, No. 7, pp. 2571-2574, 2009.
Chen, et al., "Geometric Control of Cell Life and Death," Science, vol. 276, No. 5317, pp. 1425-1428, 1997.
Chen, et al. "Interfacial bioelectrochemistry: Fabrication, properties and applications of functional nanostructured biointerfaces," Journal of Physical Chemistry C, vol. 111, No. 6, pp. 2351-2367, 2007.
Chen, et al., "Ionic screening of charged-impurity scattering in graphene," Nano Letters, vol. 9, No. 4, pp. 1621-1625, 2009.
Chen, et al., "Peptide-Based Methods for the Preparation of Nanostructured Inorganic Materials," Angewandte Chemie International Edition, vol. 49, No. 11, pp. 1924-1942, 2010.
Cheng, et al., "High-quality graphene p-n junctions via resist-free fabrication and solution-based noncovalent functionalization," ACS Nano, vol. 5, No. 3, pp. 2051-2059, 2011.
Choi, et al., "Noncovalent functionalization of graphene with end-functional polymers," Journal of Materials Chemistry, vol. 20, No. 10, pp. 1907-1912, 2010.
Chou, et al., "Development of an immunosensor for human ferritin, a nonspecific tumor marker, based on surface plasmon resonance," Biosensors & Bioelectronics, vol. No. 19, No. 9, pp. 999-1005, 2004.
Chua, et al., "Surface functionalization of titanium with hyaluronic acid/chitosan polyelectrolyte multilayers and RGD for promoting

(56) References Cited

OTHER PUBLICATIONS osteoblast functions and inhibiting bacterial adhesion," Biomaterials, vol. 29, No. 10, pp. 1412-1421, 2008.

Chung, et al., "Biomedical applications of graphene and graphene oxide," Accounts of Chemical Research, vol. 46, No. 10, pp. 2211-2224, 2013.

Chung et al., "Growth of human endothelial cells on photochemically grafted Gly-Arg-Gly-Asp (GRGD) chitosans," Biomaterials, vol. 23, No. 24, 4803-4809, 2002.

Cui, et al., " Chemical functionalization of graphene enabled by phage displayed peptides," Nano Letters, vol. 10, No. 11, pp. 4559-4565, 2010.

Curreli, et al., "Real-Time, Label-Free Detection of Biological Entities Using Nanowire-Based FETs," IEEE Transactions on Nanotechnology, vol. 7, No. 6, pp. 651-667, 2008.

Dai, "Carbon Nanotubes: Synthesis, Integration, and Properties," Accounts of Chemical Research, vol. 35, No. 12, pp. 1035-1044, 2002.

Dalsin, et al., "Mussel adhesive protein mimetic polymers for the preparation of nonfouling surfaces," Journal of the American Chemical Society, vol. 125, No. 14, pp. 4253-4258, 2003.

Dalsin, et al., "Protein resistance of titanium oxide surfaces modified by biologically inspired mPEG-DOPA," Langmuir, vol. 21, pp. 640-646, 2005.

Das, et al., "Monitoring dopants by Raman scattering in an electrochemically top-gated graphene transistor," Nature Nanotechnology, vol. 3, No. 4, pp. 210-215, 2008.

\* cited by examiner

SEQUENCE LISTING

<160> NUMBER OF SEQ ID NOS: 36

<210> SEQ ID NO 1
<211> LENGTH: 101
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is a molecular tag or is absent
<220> FEATURE:
<221> NAME/KEY: MISC_FEATURE
<222> LOCATION: (2)..(89)
<223> OTHER INFORMATION: X is any amino acid or is absent
<220> FEATURE:
<221> NAME/KEY: MISC_FEATURE
<222> LOCATION: (90)..(90)
<223> OTHER INFORMATION: X is I, T, A, V, or L
<220> FEATURE:
<221> NAME/KEY: MISC_FEATURE
<222> LOCATION: (91)..(91)
<223> OTHER INFORMATION: X is M, Q, A, V, L, or I
<220> FEATURE:
<221> NAME/KEY: MISC_FEATURE
<222> LOCATION: (92)..(92)
<223> OTHER INFORMATION: X is V, S, T, I, L, or A
<220> FEATURE:
<221> NAME/KEY: MISC_FEATURE
<222> LOCATION: (94)..(94)
<223> OTHER INFORMATION: X is E, K, D, N, T, S, or A
<220> FEATURE:
<221> NAME/KEY: MISC_FEATURE
<222> LOCATION: (95)..(95)
<223> OTHER INFORMATION: X is S or P
<220> FEATURE:
<221> NAME/KEY: MISC_FEATURE
<222> LOCATION: (96)..(96)
<223> OTHER INFORMATION: X is S or P
<220> FEATURE:
<221> NAME/KEY: MISC_FEATURE
<222> LOCATION: (97)..(97)
<223> OTHER INFORMATION: X is D, R, N, or A
<220> FEATURE:
<221> NAME/KEY: MISC_FEATURE
<222> LOCATION: (98)..(98)
<223> OTHER INFORMATION: X is W, F, F-phenyl, Amino-F, A or Y
<220> FEATURE:
<221> NAME/KEY: MISC_FEATURE
<222> LOCATION: (99)..(100)
<223> OTHER INFORMATION: X is S, D or R
<220> FEATURE:
<221> NAME/KEY: MISC_FEATURE
<222> LOCATION: (101)..(101)
<223> OTHER INFORMATION: X is W, F, A, or Y

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Thr Xaa Xaa Xaa
                85                  90                  95

Xaa Xaa Xaa Xaa Xaa
            100

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Ile Met Val Thr Ala Ser Ser Ala Tyr Asp Asp Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Ile Met Val Thr Ala Ser Ser Ala Tyr Arg Arg Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Glu Pro Ile His Arg Ser Thr Leu Thr Ala Leu Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(12)
<223> OTHER INFORMATION: The amino acids have D-chirality

<400> SEQUENCE: 5

Ile Met Val Thr Glu Ser Ser Asp Tyr Ser Ser Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic

```
<400> SEQUENCE: 6

Ile Met Val Thr Glu Ser Ser Asp Ala Ser Ser Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Ile Met Val Thr Glu Ser Ser Asp Trp Ser Ser Trp
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Ile Met Val Thr Lys Ser Ser Arg Phe Ser Ser Phe
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Thr Gln Ser Thr Lys Ser Ser Arg Tyr Ser Ser Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Ile Met Val Thr Glu Ser Ser Arg Tyr Ser Ser Tyr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Ile Met Val Thr Ala Ser Ser Ala Tyr Arg Asp Tyr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 12

Ile Met Val Thr Ala Ser Ser Asp Tyr Ser Ser Tyr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic

<400> SEQUENCE: 13

His Ile Met Val Thr Glu Ser Ser Asp Tyr Ser Ser Tyr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic

<400> SEQUENCE: 14

Trp Ile Met Val Thr Glu Ser Ser Asp Tyr Ser Ser Tyr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Val Val Ile Met Val Thr Glu Ser Ser Asp Tyr Ser Ser Tyr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic

<400> SEQUENCE: 16

Ser Ser Ile Met Val Thr Glu Ser Ser Asp Tyr Ser Ser Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic

<400> SEQUENCE: 17

Leu Ile Ala Thr Glu Ser Ser Asp Tyr Ser Ser Tyr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18
```

```
Ala Gln Thr Thr Glu Ser Ser Asp Tyr Ser Ser Tyr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

Ile Met Val Thr Ala Ser Ser Ala Tyr Ser Ser Tyr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Bio-

<400> SEQUENCE: 20

Ile Met Val Thr Glu Ser Ser Asp Tyr Ser Ser Tyr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic

<400> SEQUENCE: 21

Ile Met Val Thr Glu Pro Pro Asp Tyr Ser Ser Tyr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic

<400> SEQUENCE: 22

Cys Ile Met Val Thr Glu Ser Ser Asp Tyr Ser Ser Tyr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: DOPA-

<400> SEQUENCE: 23

Ile Met Val Thr Glu Ser Ser Asp Tyr Ser Ser Tyr
1               5                   10

<210> SEQ ID NO 24
```

<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Non-Natural F

<400> SEQUENCE: 24

Ile Met Val Thr Glu Ser Ser Asp Phe Ser Ser Tyr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: F-Phenyl

<400> SEQUENCE: 25

Ile Met Val Thr Glu Ser Ser Asp Phe Ser Ser Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(12)
<223> OTHER INFORMATION: The amino acids have an L-chirality

<400> SEQUENCE: 26

Ile Met Val Thr Glu Ser Ser Asp Tyr Ser Ser Tyr
1               5                   10

<210> SEQ ID NO 27
<211> LENGTH: 26
<212> TYPE: PRT
<213> ORGANISM: Artificial Sequence
<220> FEATURE:
<223> OTHER INFORMATION: Synthetic

<400> SEQUENCE: 27

Glu Pro Ile His Arg Ser Thr Leu Thr Ala Leu Leu Ser Ser Ile Met
1               5                   10                  15

Val Thr Glu Ser Ser Asp Tyr Ser Ser Tyr
            20                  25

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Ile Met Val Thr Asn Ser Ser Asn Trp Ser Ser Trp
1               5                   10

```
<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Ile Met Val Thr Glu Ser Ser Asp Phe Ser Ser Phe
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic

<400> SEQUENCE: 30

Thr Gln Ser Thr Glu Ser Ser Asp Tyr Ser Ser Tyr
1               5                   10

<210> SEQ ID NO 31
<211> LENGTH: 4
<212> TYPE: PRT
<213> ORGANISM: Artificial Sequence
<220> FEATURE:
<223> OTHER INFORMATION: Synthetic

<400> SEQUENCE: 31

Tyr Ser Ser Tyr
1

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
ccctctagtt agcgtaacg                                              19

<210> SEQ ID NO 33
<211> LENGTH: 13
<212> TYPE: PRT
<213> ORGANISM: Artificial Sequence
<220> FEATURE:
<223> OTHER INFORMATION: Synthetic

<400> SEQUENCE: 33

Ile Met Val Glu Thr Glu Ser Ser Asp Tyr Ser Ser Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic

<400> SEQUENCE: 34

Thr His Pro Leu Pro Ile His Ala Asn Glu Leu Thr
1               5                   10

<210> SEQ ID NO 35
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 35

Ile Met Val Thr Asp Ser Ser Ala Tyr Ser Ser Tyr
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: X is any amino acid, wherein at least two of
      the amino acids are hydrophobic and non-aromatic.
<220> FEATURE:
<221> NAME/KEY: MISC_FEATURE
<222> LOCATION: (1)..(2)
<223> OTHER INFORMATION: X is optionally absent
<220> FEATURE:
<221> NAME/KEY: MISC_FEATURE
<222> LOCATION: (6)..(10)
<223> OTHER INFORMATION: X is any amino acid, wherein at least three of
      the amino acids are hydrophilic.
<220> FEATURE:
<221> NAME/KEY: MISC_FEATURE
<222> LOCATION: (11)..(15)
<223> OTHER INFORMATION: X is any amino acid, wherein at least two of
      the amino acids in D3 have an aromatic ring.

<400> SEQUENCE: 36

Xaa Xaa Xaa Xaa Xaa Xaa Xaa Xaa Xaa Xaa Xaa Xaa Xaa Xaa
1               5                   10
```

POLYPEPTIDES AND THEIR USE

CROSS REFERENCE

This application claims priority to U.S. Provisional Patent Application Ser. No. 61/550,721 filed Oct. 24, 2011, incorporated by reference herein it its entirety.

STATEMENT OF U.S. GOVERNMENT INTEREST

This work was funded by grant number DMR-0520567 and DMR-0706655, awarded by the National Science Foundation. The U.S. government has certain rights in the invention.

BACKGROUND

Over the last several decades, self-assembly has become a viable approach to create nanostructures by allowing control over feature size and organization at the molecular and mesoscopic length scales[1,2]. In organisms, proteins often display exquisite self-assembly[3-5] through molecular recognition[6], determined by their rich chemistry and wide range of conformations. Proteins also control solid interfaces in hard tissues, e.g., bones, spicules, shells, and teeth[7-9], where they initiate nucleation or regulate specific mineral growth to form intricate solid structures[10-12]. It is, therefore, desirable to use proteins as molecular building blocks to control practical bio-solid interfaces. Earlier studies have used proteins to form organized nanostructures on solid surfaces, e.g., assembly of bacterial surface-layer proteins[13], amyloids[14,15], and de novo designed peptides on practical solids[16,17]. As in all protein self-assembly[24], molecular recognition of solids must be governed by specific, non-covalent, interactions inherent in their sequence[21, 22,25]. Correlation between primary amino acid sequences and their molecular interactions that lead to self-assembly on solid surfaces has not been established due to the complexities of protein/solid systems. Therefore, there have been no universal method to create proteins/peptides which can self-assemble into long-range ordered nanostructures or confluent ordered film on various materials. Furthermore, the interaction of ordered proteins or peptides with nanomaterials has been unrevealed and uncontrolled. Still further, there have been no peptides found to form long-range ordered structures on graphene, the single atomic layer of graphite, or other atomic single layer materials.

SUMMARY OF THE INVENTION

In a first aspect, the present invention provides polypeptides of the general formula:

(SEQ ID NO: 1)
Z1-Z2-R1-R2-R3-T-R5-R6-R7-R8-R9-R10-R11-R12 , wherein
 Z1 is absent or is a molecular tag;
 Z2 is absent or is any sequence of 1-88 amino acids;
 R1 is selected from the group consisting of I, T, A, V, and L;
 R2 is selected from the group consisting of M, Q, A, V, L, and I;
 R3 is selected from the group consisting of V, S, T, I, L, and A;
 R5 is selected from the group consisting of E, K, D, N, T, S and A;
 R6 is selected from the group consisting of S and P;
 R7 is selected from the group consisting of S and P;
 R8 is selected from the group consisting of D, R, N, and A;
 R9 is selected from the group consisting of W, F, F-phenyl, Amino-F, A, and Y;
 R10 is selected from the group consisting of S, D, and R;
 R11 is selected from the group consisting of S, D, and R; and
 R12 is selected from the group consisting of W, F, A, and Y.

In a second aspect, the present invention provides polypeptides comprising an amino acid sequence according to the general formula:

(SEQ ID NO: 36)
D1-D2-D3, wherein D1 is a domain of about 3-5 amino acids, wherein at least two of the amino acids are hydrophobic and non-aromatic;
 wherein D2 is a domain of about 5 amino acids, wherein at least three of the amino acids are hydrophilic;
 wherein D3 is a domain of about 4 amino acids, wherein at least two of the amino acids in D3 have an aromatic ring;
 wherein the polypeptide is capable of binding to an inorganic solid surface, such as graphite, graphene, $MoS_2$, $MoSe_2$, $WSe_2$, $WS_2$, or BN.

In a further aspect, the present invention provides compositions comprising two or more different polypeptides of the invention.

In another aspect, the present invention provides isolated nucleic acids encoding the polypeptide of embodiment of the invention. In a further aspect, the present invention provides recombinant expression vectors comprising the isolated nucleic acid of the invention operatively linked to a promoter. In a still further aspect, the invention provides recombinant host cells comprising the recombinant expression vector of any embodiment of the invention.

In a further aspect, the present invention provides structures, comprising:
 (a) an inorganic solid surface; and
 (b) a polypeptide array bound to the solid surface, wherein the polypeptide array comprises the polypeptide or composition of any embodiment or combination of embodiment of the invention. In various embodiments, the inorganic solid surface is selected from the group consisting of graphite, graphene, $MoS_2$, $MoSe_2$, $WSe_2$, $WS_2$, or BN, or combinations thereof.

The present invention further provides methods for making a structure, comprising contacting an inorganic solid surface with the polypeptide or composition of any of embodiment or combination of embodiments of the invention, under conditions suitable to promote self-assembly of the polypeptides into a patterned array on the surface.

In another aspect, the present invention provides methods for designing polypeptides that bind to inorganic solid surfaces, comprising:
 (a) providing a polypeptide according to the general formula D1-D2-D3 (SEQ ID NO: 36),
  (i) wherein D1 is a domain of about 3 amino acids, wherein at least two of the amino acids are hydrophobic and non-aromatic;

(ii) wherein D2 is a domain of about 5 amino acids, wherein at least three of the amino acids are hydrophilic; and (iii) wherein D3 is a domain of about 4 amino acids, wherein at least two of the amino acids in D3 have an aromatic ring;

(b) modifying amino acids in 1, 2, or all 3 domains to produce a modified polypeptide; and (c) testing the modified polypeptide for altered binding to inorganic solid surfaces.

BRIEF DESCRIPTION OF THE FIGURES

Example 1

Figure Legends

DETAILED DESCRIPTION OF THE INVENTION

Figure 1:
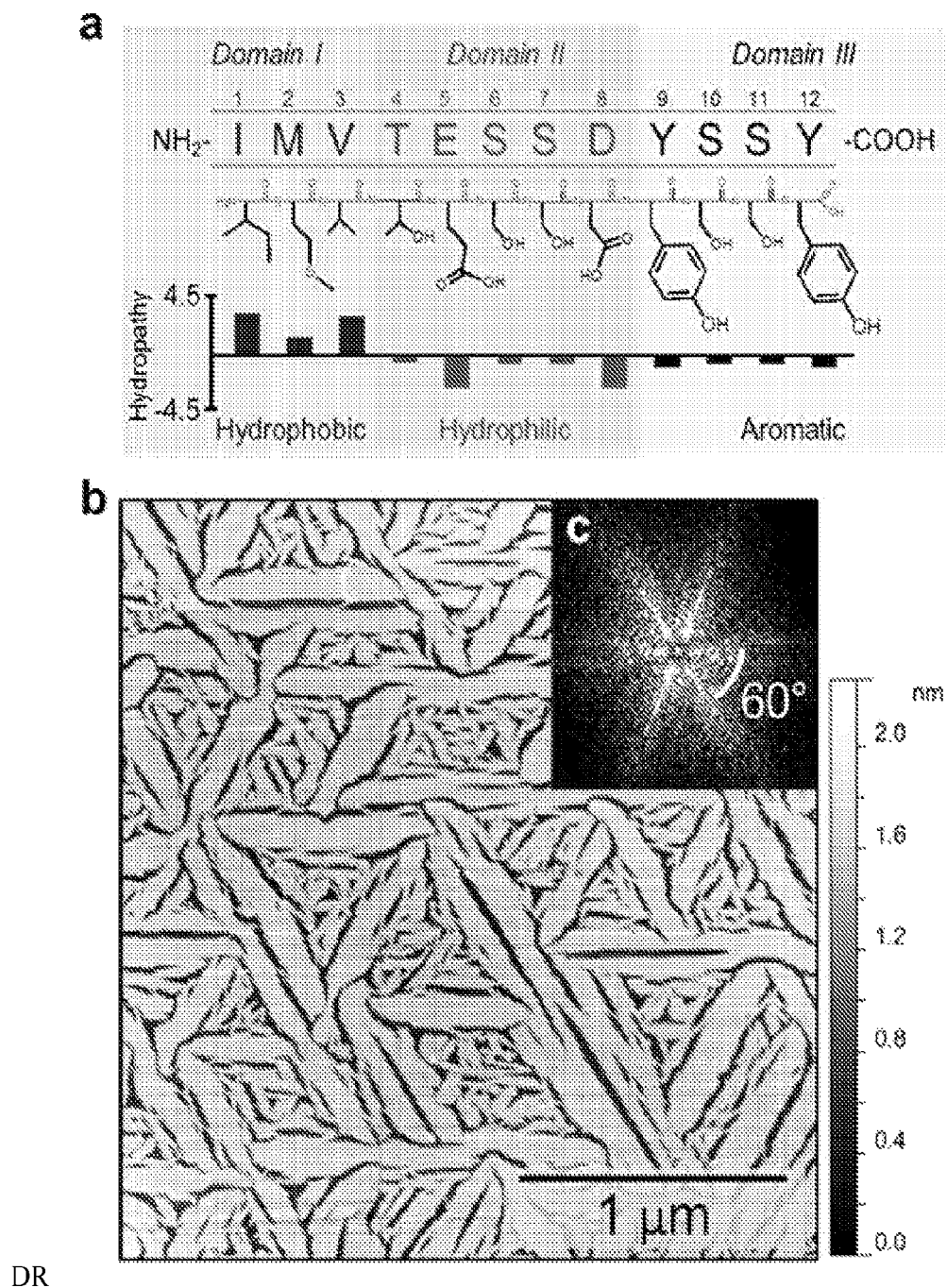
FIG. 1. Chemical properties of GrBP5 sequence and its self-assembled, ordered, nanostructure on graphite (0001) lattice. (a) The three chemically distinct domains of GrBP5. The mean hydropathy (defined by Kyte and Doolittle)[42] value of Domain-I is 3.53 (on an increasing scale from −4.5 to 4.5) and −1.86 for Domain-II, making the latter considerably more hydrophilic. (b) AFM image of GrBP5 on graphite showing ordering of the WT peptide over several micrometers displaying six-fold symmetrical self-assembled nanostructures, as observed in (c) the FFT of the AFM image.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (H is; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments within and between different aspects of the invention can be combined unless the context clearly dictates otherwise.

In a first aspect, the present invention provides polypeptide comprising an amino acid sequence according to the general formula I:

$$D1-D2-D3 \quad \text{(SEQ ID NO: 36)}$$

wherein D1 is a domain of about 3-5 amino acids, wherein at least two of the amino acids are hydrophobic and non-aromatic;

wherein D2 is a domain of about 5 amino acids, wherein at least three of the amino acids are hydrophilic;

wherein D3 is a domain of about 4 amino acids, wherein at least two of the amino acids in D3 have an aromatic ring;

wherein the polypeptide is capable of binding to an inorganic solid surface, such as graphite, graphene, $MoS_2$, $MoSe_2$, $WSe_2$, $WS_2$, or BN.

The polypeptides can be of any suitable length between 12 and 100 amino acid residues. In various embodiments, the polypeptides range in length between 12-90, 12-80, 12-70, 12-60, 12-50, 12-40, 12-30, 12-25, 12-20, 12-15, 12-14, 12-13, or 12 amino acids.

The polypeptides of the invention have been shown by the inventors to be capable of binding to inorganic solid surfaces, such as graphite, graphene, $MoS_2$, $MoSe_2$, $WSe_2$, $WS_2$, and BN, and to have a variety of activities related to diffusion across the surface and self-directed assembly on such inorganic atomically flat solid surfaces. Thus, the polypeptides can be used, for example, to control practical bio-solid interfaces and to prepare a wide variety of patterned arrays for a wide variety of uses. By using bio-combinatorial selection, the inventors have identified a large number of binding polypeptides, referred to as "graphene-binding polypeptides" (GrBPs); it will be understood that polypeptides disclosed here may have other binding specificities, as the polypeptides were derived by mutational analysis of polypeptides originally identified as graphene-binding polypeptides. The inventors have demonstrated herein that many such GrBPs, can self-assemble into long-range ordered nanostructures on single layer atomic materials (SLAM). Through the bio-combinatorial selection process disclosed herein, the inventors have discovered that the GrBPs of the invention possess 3 domains: hydrophobic, hydrophilic, and aromatic domains. As disclosed in more detail below, the 3-domain structure allows control of the surface chemistry of ordered peptide films, more flexibly and controllably, on graphite and graphene. For example, domain I (D1) can be changed from hydrophobic to hydrophilic by alteration of amino-acids, leading to arbitrarily change the hydrophobicity of peptide-coated graphite and graphene surfaces.

As demonstrated in the examples that follow, the polypeptides of the invention possess a broad area of activities relating to binding to, diffusing across (i.e. surface movement of the polypeptides), and assembling on inorganic solid surfaces, as well as possessing a variety of chemical activities (including but not limited to modifying inorganic surface hydrophobicity or contact angle), doping effects (including but not limited to injecting holes or electrons into the inorganic surface/single layer atomic materials (SLAM), enzymatic activities and additional functionalities.

The 3-domain structure of the polypeptides of the invention permits control of polypeptide self-assembly various material surfaces via rational design of amino-acid sequences. The alteration of amino acids in each domain enables us to control self-assembly of peptides on solid surfaces. For example, modification of primary amino acid sequence based on the 3-domain concept creates new polypeptides that can self-assemble into long-range ordered nanostructures on various atomic single layer materials, such as graphite, graphene, $MoS_2$, $MoSe_2$, $WSe_2$, $WS_2$, and BN. This technique can be applicable for other chalcogenides. In one non-limiting example (described in more detail in the examples that follow), the location of the charged amino acids in a starting polypeptide sequence (FIG. 1) is in domain 2. By changing the location of charged amino acids from domain 2 to domain 3 (M6: IMVTAS-SAYDDY (SEQ ID NO: 2), negatively charged), the resulting peptides can form ordered structures on $MoS_2$. In another non-limiting example, (M8: IMVTASSAYRRY (SEQ ID NO: 3), positively charged in domain 3) can form ordered structures on boron nitride (BN). The inventors have thus discovered, for the first time, such polypeptides forming ordered nanostructures on atomic single layers, graphene and $MoS_2$.

Based on these techniques, the electrical and optical properties of atomic single layer materials can be modified in a controlled manner, as demonstrated in the examples that follow. In one embodiment, the polypeptide nanostructures permit spatially doping charge carriers into inorganic surfaces, including but not limited to graphene and $MoS_2$. This is often called as spatial modulation doping in conventional semiconductor technology. Since single-layer graphene and $MoS_2$ are respectively zero-gap and direct-gap semiconductor, they are useful for electronics, where control of charge carrier density in semiconductor materials is essential for practical applications. The inventors have demonstrated that the polypeptides can be used to modify the carrier charge density with randomly attached adsorbates on graphene. Using ordered polypeptide nanowires (FIG. 12, for example), the spatially local carrier density of graphene was modified in a controlled manner, as described in the examples that follow. In the case of $MoS_2$, its optical properties have been modified using the polypeptides of the invention. Since MoS2 has bandgap, it can emit light. Using the polypeptides, the color of emitted light from $MoS_2$ can be modified by controlling the interaction between the polypeptides and $MoS_2$. This modulation doping of atomic single layers has never been achieved before the present invention. The present invention is thus of great value, for example, in nano-opto-electronic applications with bio-materials and biomolecular systems.

Any suitable hydrophobic, hydrophilic, or aromatic ring containing amino acid can be used, whether naturally occurring or non-naturally occurring. In one embodiment, the at least two amino acids in domain D3 that have an aromatic ring are selected from the group consisting of Y, F, and W. In another embodiment, the at least two hydrophobic amino acids in D1 are selected from the group consisting of I, L, A, and V. In a further embodiment, the at least three hydrophilic amino acids in D2 are selected from the group consisting of T, S, E, and D.

In another aspect, the present invention provides polypeptides comprising or consisting of the general formula II:

(SEQ ID NO: 1)
Z1-Z2-R1-R2-R3-T-R5-R6-R7-R8-R9-R10-R11-R12, wherein

Z1 is absent or is a molecular tag;

Z2 is absent or is any sequence of 1-88 amino acids;

R1 is selected from the group consisting of I, T, A, V, and L;

R2 is selected from the group consisting of M, Q, A, V, L, and I;

R3 is selected from the group consisting of V, S, T, I, L, and A;

R5 is selected from the group consisting of E, K, D, N, T, S and A;

R6 is selected from the group consisting of S and P;

R7 is selected from the group consisting of S and P;

R8 is selected from the group consisting of D, R, N, and A;

R9 is selected from the group consisting of W, F, F-phenyl, Amino-F, A, and Y;
R10 is selected from the group consisting of S, D, and R;
R11 is selected from the group consisting of S, D, and R; and
R12 is selected from the group consisting of W, F, A, and Y.

In one embodiment, Z1 is absent. In another embodiment, Z1 is present. As used herein, a "molecular tag" is any moiety that can be linked to polypeptide and which is optionally capable of further binding to a target of interest (directly or indirectly). Z1 can be present as part of a fusion protein with the remainder of the polypeptide, or may be otherwise bound to the polypeptide (covalently or non-covalently). In one embodiment, the molecular tag is a reporter molecule (including but not limited to fluorescent proteins, fluorescent dyes, etc.), and can be used to monitor location of the polypeptides, such as when bound to a surface. In another embodiment, the molecular tag is a chemical group of interest. In another embodiment, the molecular tag is capable of further binding to a target of interest (directly or indirectly). Non-limiting examples of such molecular tags include antibodies, epitope tags, protein domains, either member of a receptor/ligand pair or fragments thereof retaining binding activity, and other molecules with specific binding affinities to a target of interest. A non-limiting example of a binding pair is biotin/avidin; thus, in one non-limiting embodiment Z1 can comprise biotin. In another non-limiting embodiment, Z1 comprises dihydroxyphenylalanine (DOPA). In another non-limiting embodiment, Z1 comprises any tumor-specific molecular tag. In one embodiment of a tumor-specific molecular tag, Z1 comprises the peptide EPIHRSTLTALL (SEQ ID NO; 4). Other non-limiting binding pair examples include an antibody, fragment thereof, or epitope specific for a target of interest, peptides that bind to targets of interest (including but not limited to cell-specific binding peptides, anti-microbial peptides, peptides that bind to another solid, tumor cell-binding peptides, and other antigen/antibody pairs. Epitope tags, such as a his-tag, and antibodies directed against the epitope tag (or fragments thereof) are further examples of molecular tags. Many further such examples will be readily apparent to those of skill in the art. In one embodiment the molecular tag is a polypeptide present as a fusion with the polypeptide of the invention. Any molecular tag suitable for a given purpose can be used.

In one embodiment, Z2 is absent. In another embodiment, Z2 is present and is any sequence of 1-88 amino acids. While not being bound by any specific mechanism of action, the inventors believe that the N-terminus of the polypeptides of the invention are free for rational control of intermolecular interactions as well as further functionalization, and predictable display of specific chemistry. In various embodiments when Z2 is present, it is 1-80, 1-70, 1-10, 1-50, 1-40, 1-30, 1-20, 1-10, 1-9, 1-8, 1-7, 1-6, 1-5, 1-4, 1-3, 1-2, 2-80, 2-70, 2-10, 2-50, 2-40, 2-30, 2-20, 2-10, 2-9, 2-8, 2-7, 2-6, 2-5, 2-4, 2-3, 1, 2, or 3 amino acids. In one embodiment, Z2 is present and is 1, 2, or 3 hydrophilic amino acids; in another embodiment, Z2 is present as 1, 2, or 3 serine residues. In various further embodiments, Z2 is present as any 1, 2, or 3 amino acids (including amino acid analogues). In other embodiments, Z2 can be selected from the group consisting of: H, W, C, SS, and VV.

In another embodiment of the polypeptides according to general formula II:
Z1 and Z2 are as defined above;
R1 is selected from the group consisting of I, T, A, and L;
R2 is selected from the group consisting of M, Q, and I;
R3 is selected from the group consisting of V, S, T, and A;
R5 is selected from the group consisting of E, K, D, N, and A;
R6 is selected from the group consisting of S and P;
R7 is selected from the group consisting of S and P;
R8 is selected from the group consisting of D, R, N, and A;
R9 is selected from the group consisting of W, F, F-phenyl, Amino-F, A, and Y;
R10 is selected from the group consisting of S, D, and R;
R11 is selected from the group consisting of S, D, and R; and
R12 is selected from the group consisting of W, F, A, and Y.

In another embodiment of the polypeptides according to general formula II:
Z1 and Z2 are as defined above;
R1 is I;
R2 is selected from the group consisting of M and Q;
R3 is V;
R5 is selected from the group consisting of E, K, and A;
R6 is S;
R7 is S;
R8 is selected from the group consisting of D, R, and A;
R9 is selected from the group consisting of W and Y;
R10 is S;
R11 is S; and
R12 is selected from the group consisting of W and Y.

In a further preferred embodiment of any of the above embodiments, one, two, or all three of the following are true:
R1 is I;
R2 is M; and
R3 is V.

In a further preferred embodiment of any of the above embodiments, one, two, three, or all four of the following are true:
R5 is E;
R6 is S;
R7 is S; and
R8 is D.

In a further preferred embodiment of any of the above embodiments, one two, three, or all four of the following are true:
R5 is A;
R8 is A;
R10 is D or R; and
R11 is D or R. This embodiment is particularly useful for molybdenum binding and/or boron nitride binding polypeptides, as exemplified by the GrBP-5 and GrBP-8 mutants (see examples for details). In this embodiment, the polypeptides are of the general formula:
Z1 and Z2 are as defined above;
R1 is selected from the group consisting of I, T, A, V, and L;
R2 is selected from the group consisting of M, Q, A, V, L, and I;
R3 is selected from the group consisting of V, S, T, I, L, and A;
R5 is A;
R6 is selected from the group consisting of S and P;
R7 is selected from the group consisting of S and P;
R8 is A;
R9 is selected from the group consisting of W, F, F-phenyl, Amino-F, and Y;
R10 is selected from the group consisting of D, and R;
R11 is selected from the group consisting of D, and R; and R12 is selected from the group consisting of W, F, and Y.

In a further embodiment of the molybdenum binding polypeptides:
Z1 and Z2 are as defined above;
R1 is I;
R2 is M;
R3 is V;
R5 is A;
R6 is S;
R7 is S;
R8 is A;
R9 is Y;
R10 is selected from the group consisting of D, and R;
R11 is selected from the group consisting of D, and R; and
R12 is Y.

In a further preferred embodiment any of the above embodiments, one or more of the following is true:
R10 is S and R11 is S;
R9 is Y and R12 is Y;
R9 is F or W and R12 is F or W; and
R10 is D or R and R11 is D or R.

In another embodiment of the polypeptides according to general formula II:
Z1 is as defined above;
Z2 is any 1 or 2 amino acids;
R1 is I;
R2 is selected from the group consisting of M and Q;
R3 is V;
R5 is selected from the group consisting of E, K, and A;
R6 is S;
R7 is S;
R8 is selected from the group consisting of D, R, and A;
R9 is selected from the group consisting of W and Y;
R10 is S;
R11 is S; and
R12 is selected from the group consisting of W and Y.

Peptides according to this embodiment and the following two embodiments are shown to have enzymatic and other unique activities, as described in the examples that follow. In another embodiment:
Z1 is as defined above;
Z2 is selected from the group consisting of H, W, C, SS, and VV;
R1 is I;
R2 is selected from the group consisting of M and Q;
R3 is V;
R5 is selected from the group consisting of E, K, and A;
R6 is S;
R7 is S;
R8 is selected from the group consisting of D, R, and A;
R9 is selected from the group consisting of W and Y;
R10 is S;
R11 is S; and
R12 is selected from the group consisting of W and Y. In a further embodiment of the polypeptides according to general formula II:
Z1 is as defined above;
Z2 is selected from the group consisting of H, W, C, SS, and VV; and
R1 is I;
R2 M;
R3 is V;
R5 is E;
R6 is S;
R7 is S;
R8 is D;
R9 is Y;
R10 is S;
R11 is S; and
R12 is Y.

In another preferred embodiment, the polypeptide comprises or consists of a polypeptide selected from the group consisting of:

```
                                        (SEQ ID NO: 5)
IMVTESSDYSSY (GrBP5)

(SEQ ID NO: 6)
IMVTESSDASSA (GrBP5-M1)

(SEQ ID NO: 7)
IMVTESSDWSSW (GrBP5-M2);

(SEQ ID NO: 8)
IMVTKSSRFSSF (GrBP5-M3);

(SEQ ID NO: 9)
TQSTKSSRYSSY (GrBP5-M4);

(SEQ ID NO: 10)
IMVTESSRYSSY (GrBP5-M5);

(SEQ ID NO: 2)
IMVTASSAYDDY (GrBP5-M6);

(SEQ ID NO: 11)
IMVTASSAYRDY;

(SEQ ID NO: 3)
IMVTASSAYRRY (GrBP5-M8);

(SEQ ID NO: 12)
IMVTASSDYSSY (GrBP5-12);

(SEQ ID NO: 13)
HIMVTESSDYSSY (HGrBPS);

(SEQ ID NO: 14)
WIMVTESSDYSSY (WGrBPS);

(SEQ ID NO: 15)
VVIMVTESSDYSSY (VVGrBPS);

(SEQ ID NO: 16)
SSIMVTESSDYSSY (SSGrBPS);

(SEQ ID NO: 17)
LIATESSDYSSY (GrBP5 hydrophobic);

(SEQ ID NO: 18)
AQTTESSDYSSY (GrBP 5 hydrophilic);

(SEQ ID NO: 19)
IMVTASSAYSSY (GrBP 5 neutral);

(SEQ ID NO: 20)
Bio-IMVTESSDYSSY (Bio-GrBP5);

(SEQ ID NO: 21)
IMVTEPPDYSSY (Rigid GrBP5);

(SEQ ID NO: 22)
CIMVTESSDYSSY (Cys-GrBP5);

(SEQ ID NO: 23)
DOPA-IMVTESSDYSSY (DOPA-GrBP5);

(SEQ ID NO: 24)
IMVTESSD(Nonnatural F)SSY (AminoF-GrBP5);
```

```
IMVTESSD(F-Phenyl)SSY (F-Phenyl-GrBP5);              (SEQ ID NO: 25)

(SEQ ID NO: 26)
IMVTESSDYSSY (D-GrBP5),
where all residues are D amino acids;

(SEQ ID NO: 27)
EPIHRSTLTALL-SS-IMVTESSDYSSY (AntibodyBP-SS-GrBP5);

(SEQ ID NO: 28)
IMVTNSSNWSSW (GrBP5 neutral WSSW);

(SEQ ID NO: 29)
IMVTESSDFSSF;

(SEQ ID NO: 30)
TQSTESSDYSSY;
and (SEQ ID NO: 35)
IMVTDSSAYSSY (GRP5-M10).
```

The polypeptides of the invention can be made by any suitable technique, including but not limited to recombinant DNA technology and standard polypeptide synthetic techniques. The polypeptides may comprise D amino acids, L amino acids, or combinations thereof, and may further contain modifications as deemed appropriate for a given use.

In another embodiment, the present invention provides compositions, comprising two or more different polypeptides of the invention. As shown in the examples that follow, polypeptides of the invention that have different properties can be combined as appropriate for a given use to provide additional functionality to resulting surfaces/devices. In one non-limiting example, the composition comprises a combination of SSIMVTESSDYSSY (SEQ ID NO: 16) (SS-GrBP5) and one of the other polypeptides of the invention (including but not limited to GrBP5) that comprises a molecular tag. As shown in the examples that follow, SS-GrBP5 possesses anti-fouling properties; combinations of it with a tagged polypeptide of interest for a given purpose can be used to create sensors capable of selective detection of a target of the molecular tag in a complex solution (including but not limited to blood samples). In one embodiment, the polypeptides are not chemically bound to each other and may be present in any ratio suitable for a given purpose, including but not limited to between 10:1 and 1:10 of one polypeptide (such as SS-GrBP5) to another polypeptide (such as molecular tagged GrBP5); in various further embodiments, the polypeptides are present in a ratio of 9:1 to 1:9; 8:1 to 1:8; 7:1 to 1:7; 6:1 to 1:6; 5:1 to 1:5; 4:1 to 1:4; 3:1 to 1:3: 2:1 to 1:2; or 1:1. As will be understood by those of skill in the art, this embodiment includes any combination of two or more polypeptides disclosed herein. Thus, in various embodiments, the two or more polypeptides can be two or more polypeptides according to any of polypeptide formulae disclosed herein, or embodiments thereof, as well as:

```
                                                      (SEQ ID NO: 5)
IMVTESSDYSSY (GrBP5)

(SEQ ID NO: 6)
IMVTESSDASSA (GrBP5-M1)

(SEQ ID NO: 7)
IMVTESSDWSSW (GrBP5-M2);

(SEQ ID NO: 8)
IMVTKSSRFSSF (GrBP5-M3);

(SEQ ID NO: 9)
TQSTKSSRYSSY (GrBP5-M4);

(SEQ ID NO: 10)
IMVTESSRYSSY (GrBP5-M5);

(SEQ ID NO: 2)
IMVTASSAYDDY (GrBP5-M6);

(SEQ ID NO: 11)
IMVTASSAYRDY;

(SEQ ID NO: 3)
IMVTASSAYRRY (GrBP5-M8);

(SEQ ID NO: 12)
IMVTASSDYSSY (GrBP5-12);

(SEQ ID NO: 13)
HIMVTESSDYSSY (HGrBP5);

(SEQ ID NO: 14)
WIMVTESSDYSSY (WGrBP5);

(SEQ ID NO: 15)
VVIMVTESSDYSSY (VVGrBP5);

(SEQ ID NO: 16)
SSIMVTESSDYSSY (SSGrBPS);

(SEQ ID NO: 17)
LIATESSDYSSY (GrBP5 hydrophobic);

(SEQ ID NO: 18)
AQTTESSDYSSY (GrBP 5 hydrophilic);

(SEQ ID NO: 19)
IMVTASSAYSSY (GrBP 5 neutral);

(SEQ ID NO: 20)
Bio-IMVTESSDYSSY (Bio-GrBP5);

(SEQ ID NO: 21)
IMVTEPPDYSSY (Rigid GrBP5);

(SEQ ID NO: 22)
CIMVTESSDYSSY (Cys-GrBP5);

(SEQ ID NO: 23)
DOPA-IMVTESSDYSSY (DOPA-GrBP5);

(SEQ ID NO: 24)
IMVTESSD(Nonnatural F)SSY (AminoF-GrBP5);

(SEQ ID NO: 25)
IMVTESSD(F-Phenyl)SSY (F-Phenyl-GrBP5);

(SEQ ID NO: 26)
IMVTESSDYSSY (D-GrBP5);

(SEQ ID NO: 27)
EPIHRSTLTALL-SS-IMVTESSDYSSY (AntibodyBP-SS-GrBP5);

(SEQ ID NO: 28)
IMVTNSSNWSSW (GrBP5 neutral WSSW);

(SEQ ID NO: 29)
IMVTESSDFSSF;

(SEQ ID NO: 30)
TQSTESSDYSSY;
and (SEQ ID NO: 35)
IMVTDSSAYSSY (GRPS-M10)
``` and any modifications thereof, such as any of the recited polypeptides further comprising a molecular tag. As disclosed in the examples that follow, the different polypeptides disclosed herein possess different binding activities (i.e.: binding to different inorganic solids and/or different binding strengths to a given inorganic solid), aggregation, and/or diffusion properties, while some are shown to have anti-fouling capabilities or to be capable of modifying the wettability of the inorganic solid surface. Based on the teachings herein, one of skill in the art can determine which polypeptides to combine depending on the specific goal to be achieved.

In another embodiment, two or more polypeptides of the invention are provided as a fusion protein. In this embodiment, the fusion protein has a general formula of:

P1-Z-P2, wherein P1 and P2 are independently a polypeptide of the invention, and Z is an optional linker amino acid sequence between the polypeptides. In this embodiment, P1 and P2 can be the same polypeptide or different polypeptides. The linker amino acid sequence can include any number of residues between P1 and P2, or may be absent.

In a second aspect, the present invention provides isolated nucleic acid encoding the polypeptide of embodiment or combination of embodiments of the invention. The isolated nucleic acids can be used, for example, for recombinant production of the polypeptides of the invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a third aspect, the present invention provides recombinant expression vectors comprising the isolated nucleic acid of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The construction of expression vectors for use in transfecting prokaryotic and eukaryotic cells is well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a fourth aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the man skilled in the art.

In a fifth aspect, the present invention provides a structure, comprising:

(a) an inorganic solid surface; and (b) a polypeptide array bound to the solid surface, wherein the polypeptide array comprises the polypeptide of any embodiment or combination of embodiments of the invention. As described above, the polypeptides of the invention have been show by the inventors to be capable of binding to inorganic solid surfaces and capable of self-assembly into long-range ordered nanostructures on various atomic single layer materials, including but not limited to graphite, graphene, $MoS_2$, $MoSe_2$, $WSe_2$, $WS_2$, or BN, as well as other chalcogenides.

In a preferred embodiment, the inorganic solid surface is selected from the group consisting of graphite, graphene, $MoS_2$, $MoSe_2$, $WSe_2$, $WS_2$, and BN, or combinations there. In a further embodiment, the polypeptide array comprises a patterned array on the solid surface; such patterned array may include, but is not limited to, an ordered polypeptide film, a porous confluent film, peptide clusters, nanowires, quantum dots, metallic and insulator nanoparticles (NPs, such as Au and silica, glass), and nanoscale p-n junctions, or combinations of thereof.

In a further preferred embodiment, the inorganic solid surface is a single layer material.

In another further preferred embodiment, the inorganic solid surface is part of a device selected from the group consisting of protein chips, peptide-molecular circuits, field effect transistors, designer proteins, semiconductor structures, implantable medical devices (including but not limited to cardiovascular devices and bone-contacting devices), bio-fuel cells, and biosensors for any use (including but not limited to cancer detection, insulin monitoring, neural activity monitoring, etc.).

In one embodiment, the polypeptides comprise or consist of an amino acid sequence according to the general formula I:

D1-D2-D3, (SEQ ID NO: 36)

wherein D1 is a domain of about 3-5 amino acids, wherein at least two of the amino acids are hydrophobic and non-aromatic;

wherein D2 is a domain of about 5 amino acids, wherein at least three of the amino acids are hydrophilic;

wherein D3 is a domain of about 4 amino acids, wherein at least two of the amino acids in D3 have an aromatic ring;

wherein the polypeptide is capable of binding to an inorganic solid surface, such as graphite, graphene, $MoS_2$, $MoSe_2$, $WSe_2$, $WS_2$, or BN.

The polypeptides can be of any suitable length between 12 and 100 amino acid residues. In various embodiments, the polypeptides range in length between 12-90, 12-80, 12-70, 12-60, 12-50, 12-40, 12-30, 12-25, 12-20, 12-15, 12-14, 12-13, or 12 amino acids.

Any suitable hydrophobic, hydrophilic, or aromatic ring containing amino acid can be used, whether naturally occurring or non-naturally occurring. In one embodiment, the at least two amino acids in domain D3 that have an aromatic ring are selected from the group consisting of Y, F, and W. In another embodiment, the at least two hydrophobic amino acids in D1 are selected from the group consisting of I, L, A, and V. In a further embodiment, the at least three hydrophilic amino acids in D2 are selected from the group consisting of T, S, E, and D.

In another aspect, the present invention provides polypeptides comprising or consisting of the general formula II:

Z1-Z2-R1-R2-R3-T-R5-R6-R7-R8-R9-R10-R11-R12, (SEQ ID NO: 1)

Z1 is absent or is a molecular tag;
Z2 is absent or is any sequence of 1-88 amino acids;
R1 is selected from the group consisting of I, T, A, V, and L;
R2 is selected from the group consisting of M, Q, A, V, L, and I;
R3 is selected from the group consisting of V, S, T, I, L, and A;
R5 is selected from the group consisting of E, K, D, N, T, S and A;
R6 is selected from the group consisting of S and P;
R7 is selected from the group consisting of S and P;
R8 is selected from the group consisting of D, R, N, and A;
R9 is selected from the group consisting of W, F, F-phenyl, Amino-F, A, and Y;
R10 is selected from the group consisting of S, D, and R;
R11 is selected from the group consisting of S, D, and R; and
R12 is selected from the group consisting of W, F, A, and Y.

In one embodiment, Z1 is absent. In another embodiment, Z1 is present. As used herein, a "molecular tag" is any moiety that can be linked to polypeptide and which is optionally capable of further binding to a target of interest (directly or indirectly). Z1 can be present as part of a fusion protein with the remainder of the polypeptide, or may be otherwise bound to the polypeptide (covalently or non-covalently). In one embodiment, the molecular tag is a reporter molecule (including but not limited to fluorescent proteins, fluorescent dyes, etc.), and can be used to monitor location of the polypeptides, such as when bound to a surface. In another embodiment, the molecular tag is a chemical group of interest. In another embodiment, the molecular tag is capable of further binding to a target of interest (directly or indirectly). Non-limiting examples of such molecular tags include antibodies, epitope tags, protein domains, either member of a receptor/ligand pair or fragments thereof retaining binding activity, and other molecules with specific binding affinities to a target of interest. A non-limiting example of a binding pair is biotin/avidin; thus, in one non-limiting embodiment Z1 can comprise biotin. In another non-limiting embodiment, Z1 comprises DOPA. In another non-limiting embodiment, Z1 comprises the peptide EPIHRSTLTALL (SEQ ID NO: 4), a tumor-specific molecular tag. Other non-limiting binding pair examples include an antibody, fragment thereof, or epitope specific for a target of interest, peptides that bind to targets of interest (including but not limited to cell-specific binding peptides, anti-microbial peptides, peptides that bind to another solid, tumor cell-binding peptides, and other antigen/antibody pairs. Epitope tags, such as a his-tag, and antibodies directed against the epitope tag (or fragments thereof) are further examples of molecular tags. Many further such examples will be readily apparent to those of skill in the art. In one embodiment the molecular tag is a polypeptide present as a fusion with the polypeptide of the invention. Any molecular tag suitable for a given purpose can be used.

In one embodiment, Z2 is absent. In another embodiment, Z2 is present and is any sequence of 1-88 amino acids. In various embodiments when Z2 is present, it is 1-80, 1-70, 1-10, 1-50, 1-40, 1-30, 1-20, 1-10, 1-9, 1-8, 1-7, 1-6, 1-5, 1-4, 1-3, 1-2, 2-80, 2-70, 2-10, 2-50, 2-40, 2-30, 2-20, 2-10, 2-9, 2-8, 2-7, 2-6, 2-5, 2-4, 2-3, 1, 2, or 3 amino acids. In one embodiment, Z2 is present and is 1, 2, or 3 hydrophilic amino acids; in another embodiment, Z2 is present as 1, 2, or 3 serine residues. In various further embodiments, Z2 is present as any 1, 2, or 3 amino acids (including amino acid analogues). In other embodiments, Z2 can be selected from the group consisting of: H, W, C, SS, and VV.

In another embodiment of the polypeptides according to general formula II:
Z1 and Z2 are as defined above;
R1 is selected from the group consisting of I, T, A, and L;
R2 is selected from the group consisting of M, Q, and I;
R3 is selected from the group consisting of V, S, T, and A;
R5 is selected from the group consisting of E, K, D, N, and A;
R6 is selected from the group consisting of S and P;
R7 is selected from the group consisting of S and P;
R8 is selected from the group consisting of D, R, N, and A;
R9 is selected from the group consisting of W, F, F-phenyl, Amino-F, A, and Y;
R10 is selected from the group consisting of S, D, and R;
R11 is selected from the group consisting of S, D, and R; and
R12 is selected from the group consisting of W, F, A, and Y.

In another embodiment of the polypeptides according to general formula II:
Z1 and Z2 are as defined above;
R1 is I;
R2 is selected from the group consisting of M and Q;
R3 is V;

R5 is selected from the group consisting of E, K, and A;
R6 is S;
R7 is S;
R8 is selected from the group consisting of D, R, and A;
R9 is selected from the group consisting of W and Y;
R10 is S;
R11 is S; and
R12 is selected from the group consisting of W and Y.

In a further preferred embodiment of any of the above embodiments, one, two, or all three of the following are true:
R1 is I;
R2 is M; and
R3 is V.

In a further preferred embodiment of any of the above embodiments, one, two, three, or all four of the following are true:
R5 is E;
R6 is S;
R7 is S; and
R8 is D.

In a further preferred embodiment of any of the above embodiments, one two, three, or all four of the following are true:
R5 is A;
R8 is A;
R10 is D or R; and
R11 is D or R. This embodiment is particularly useful for molybdenum binding and/or boron nitride binding polypeptides, as exemplified by the GrBP-5 and GrBP-8 mutants (see examples for details). In this embodiment, the polypeptides are of the general formula:
Z1 and Z2 are as defined above;
R1 is selected from the group consisting of I, T, A, V, and L;
R2 is selected from the group consisting of M, Q, A, V, L, and I;
R3 is selected from the group consisting of V, S, T, I, L, and A;
R5 is A;
R6 is selected from the group consisting of S and P;
R7 is selected from the group consisting of S and P;
R8 is A;
R9 is selected from the group consisting of W, F, F-phenyl, Amino-F, and Y;
R10 is selected from the group consisting of D, and R;
R11 is selected from the group consisting of D, and R; and
R12 is selected from the group consisting of W, F, and Y.

In a further embodiment of the molybdenum binding polypeptides:
Z1 and Z2 are as defined above;
R1 is I;
R2 is M;
R3 is V;
R5 is A;
R6 is S;
R7 is S;
R8 is A;
R9 is Y;
R10 is selected from the group consisting of D, and R;
R11 is selected from the group consisting of D, and R; and
R12 is Y.

In a further preferred embodiment any of the above embodiments, one or more of the following is true:
R10 is S and R11 is S;
R9 is Y and R12 is Y;
R9 is F or W and R12 is F or W; and R10 is D or R and R11 is D or R.

In another embodiment of the polypeptides according to general formula II:
Z1 is as defined above;
Z2 is any 1 or 2 amino acids;
R1 is I;
R2 is selected from the group consisting of M and Q;
R3 is V;
R5 is selected from the group consisting of E, K, and A;
R6 is S;
R7 is S;
R8 is selected from the group consisting of D, R, and A;
R9 is selected from the group consisting of W and Y;
R10 is S;
R11 is S; and
R12 is selected from the group consisting of W and Y.

Polypeptides according to this embodiment and the following two embodiments are shown to have enzymatic and other unique activities, as described in the examples that follow. In another embodiment:
Z1 is as defined above;
Z2 is selected from the group consisting of H, W, C, SS, and VV;
R1 is I;
R2 is selected from the group consisting of M and Q;
R3 is V;
R5 is selected from the group consisting of E, K, and A;
R6 is S;
R7 is S;
R8 is selected from the group consisting of D, R, and A;
R9 is selected from the group consisting of W and Y;
R10 is S;
R11 is S; and
R12 is selected from the group consisting of W and Y. In a further embodiment of the polypeptides according to general formula II:
Z1 is as defined above;
Z2 is selected from the group consisting of H, W, C, SS, and VV; and
R1 is I;
R2 is M;
R3 is V;
R5 is E;
R6 is S;
R7 is S;
R8 is D;
R9 is Y;
R10 is S;
R11 is S; and
R12 is Y.

In another preferred embodiment, the polypeptide comprises or consists of a polypeptide selected from the group consisting of:

```
                            (SEQ ID NO: 5)
IMVTESSDYSSY (GrBP5)

(SEQ ID NO: 6)
IMVTESSDASSA (GrBP5-M1)

(SEQ ID NO: 7)
IMVTESSDWSSW (GrBP5-M2);

(SEQ ID NO: 8)
IMVTKSSRFSSF (GrBP5-M3);

(SEQ ID NO: 9)
TQSTKSSRYSSY (GrBP5-M4);
```

```
IMVTESSRYSSY (GrBP5-M5);                          (SEQ ID NO: 10)

IMVTASSAYDDY (GrBP5-M6);                          (SEQ ID NO: 2)

IMVTASSAYRDY;                                     (SEQ ID NO: 11)

IMVTASSAYRRY (GrBP5-M8);                          (SEQ ID NO: 3)

IMVTASSDYSSY (GrBP5-12);                          (SEQ ID NO: 12)

HIMVTESSDYSSY (HGrBP5);                           (SEQ ID NO: 13)

WIMVTESSDYSSY (WGrBP5);                           (SEQ ID NO: 14)

VVIMVTESSDYSSY (VVGrBP5);                         (SEQ ID NO: 15)

SSIMVTESSDYSSY (SSGrBP5);                         (SEQ ID NO: 16)

LIATESSDYSSY (GrBP5 hydrophobic);                 (SEQ ID NO: 17)

AQTTESSDYSSY (GrBP 5 hydrophilic);                (SEQ ID NO: 18)

IMVTASSAYSSY (GrBP 5 neutral);                    (SEQ ID NO: 19)

Bio-IMVTESSDYSSY (Bio-GrBP5);                     (SEQ ID NO: 20)

IMVTEPPDYSSY (Rigid GrBP5);                       (SEQ ID NO: 21)

CIMVTESSDYSSY (Cys-GrBP5);                        (SEQ ID NO: 22)

DOPA-IMVTESSDYSSY (DOPA-GrBP5);                   (SEQ ID NO: 23)

IMVTESSD(Nonnatural F)SSY (AminoF-GrBP5);         (SEQ ID NO: 24)

IMVTESSD(F-Phenyl)SSY (F-Phenyl-GrBP5);           (SEQ ID NO: 25)

IMVTESSDYSSY (D-GrBP5);                           (SEQ ID NO: 26)

EPIHRSTLTALL-SS-IMVTESSDYSSY (AntibodyBP-SS-GrBP5); (SEQ ID NO: 27)

IMVTNSSNWSSW (GrBP5 neutral WSSW);                (SEQ ID NO: 28)

IMVTESSDFSSF;                                     (SEQ ID NO: 29)

TQSTESSDYSSY;
and                                               (SEQ ID NO: 30)

IMVTDSSAYSSY (GRPS-M10).                          (SEQ ID NO: 35)
```

The 3-domain structure of the polypeptides of the invention permits control of polypeptide self-assembly various material surfaces via rational design of amino-acid sequences. The alteration of amino acids in each domain enables us to control self-assembly of peptides on solid surfaces. For example, modification of primary amino acid sequence based on the 3-domain concept creates new polypeptides that can self-assemble into long-range ordered nanostructures on various atomic single layer materials, such as $MoS_2$, $WSe_2$, and BN. This technique can be applicable for other chalcogenides. In one non-limiting example (described in more detail in the examples that follow), the location of the charged amino acids in a starting polypeptide sequence (FIG. 1) is in domain 2. By changing the location of charged amino acids from domain 2 to domain 3 (M6: IMVTASSAYDDY (SEQ ID NO: 2), negatively charged), the resulting peptides can form ordered structures on $MoS_2$. In another non-limiting example, (M8: IMVTASSAYRRY (SEQ ID NO: 3), positively charged in domain 3) can form ordered structures on boron nitride (BN). The inventors have thus discovered, for the first time, such polypeptides forming ordered nanostructures on atomic single layers, graphene and $MoS_2$.

Based on these techniques, the electrical and optical properties of atomic single layer materials can be modified in a controlled manner, as demonstrated in the examples that follow. In one embodiment, the polypeptide nanostructures permit spatially doping charge carriers into inorganic surfaces, including but not limited to graphene and $MoS_2$. This is often called as spatial modulation doping in conventional semiconductor technology. Since single-layer graphene and $MoS_2$ are respectively zero-gap and direct-gap semiconductor, they are useful for electronics, where control of charge carrier density in semiconductor materials is essential for practical applications. The inventors have demonstrated that the polypeptides can be used to modify the carrier charge density with randomly attached adsorbates on graphene. Using ordered polypeptide nanowires (FIG. 12, for example), the spatially local carrier density of graphene was modified in a controlled manner, as described in the examples that follow. In the case of $MoS_2$, its optical properties have been modified using the polypeptides of the invention. Since MoS2 has bandgap, it can emit light. Using the polypeptides, the color of emitted light from $MoS_2$ can be modified by controlling the interaction between the polypeptides and $MoS_2$. This modulation doping of atomic single layers has never been achieved before the present invention. The present invention is thus of great value, for example, in nano-opto-electronic applications with bio-materials and biomolecular systems.

In another embodiment, the polypeptides comprising two or more different polypeptides of the invention. As shown in the examples that follow, polypeptides of the invention that have different properties can be combined as appropriate for a given use to provide additional functionality to resulting surfaces/devices. In one non-limiting example, the composition comprises a combination of SSIMVTESSDYSSY (SEQ ID NO: 16) (SS-GrBP5) and one of the other polypeptides of the invention (including but not limited to GrBP5) that comprises a molecular tag. As shown in the examples that follow, SS-GrBP5 possesses anti-fouling properties; combinations of it with a tagged polypeptide of interest for a given purpose can be used to create sensors capable of selective detection of a target of the molecular tag in a complex solution (including but not limited to blood samples). In one embodiment, the polypeptides are not chemically bound to each other and may be present in any ratio suitable for a given purpose, including but not limited to between 10:1 and 1:10 of one polypeptide (such as SS-GrBP5) to another polypeptide (such as molecular tagged GrBP5); in various further embodiments, the polypeptides are present in a ratio of 9:1 to 1:9; 8:1 to 1:8; 7:1 to 1:7; 6:1 to 1:6; 5:1 to 1:5; 4:1 to 1:4; 3:1 to 1:3; 2:1 to 1:2; or 1:1. As will be understood by those of skill in the art, this embodiment includes any combination of two or more polypeptides disclosed herein. Thus, in various embodiments, the two or more polypeptides can be two or more polypeptides according to general formulae I or II above, or embodiments thereof, as well as

| | |
|---|---|
| IMVTESSDYSSY (GrBP5) | (SEQ ID NO: 5) |
| IMVTESSDASSA (GrBP5-M1) | (SEQ ID NO: 6) |
| IMVTESSDWSSW (GrBP5-M2); | (SEQ ID NO: 7) |
| IMVTKSSRFSSF (GrBP5-M3); | (SEQ ID NO: 8) |
| TQSTKSSRYSSY (GrBP5-M4); | (SEQ ID NO: 9) |
| IMVTESSRYSSY (GrBP5-M5); | (SEQ ID NO: 10) |
| IMVTASSAYDDY (GrBP5-M6); | (SEQ ID NO: 2) |
| IMVTASSAYRDY; | (SEQ ID NO: 11) |
| IMVTASSAYRRY (GrBP5-M8); | (SEQ ID NO: 3) |
| IMVTASSDYSSY (GrBP5-12); | (SEQ ID NO: 12) |
| HIMVTESSDYSSY (HGrBPS); | (SEQ ID NO: 13) |
| WIMVTESSDYSSY (WGrBPS); | (SEQ ID NO: 14) |
| VVIMVTESSDYSSY (VVGrBPS); | (SEQ ID NO: 15) |
| SSIMVTESSDYSSY (SSGrBPS); | (SEQ ID NO: 16) |
| LIATESSDYSSY (GrBP5 hydrophobic); | (SEQ ID NO: 17) |
| AQTTESSDYSSY (GrBP 5 hydrophilic); | (SEQ ID NO: 18) |
| IMVTASSAYSSY (GrBP 5 neutral); | (SEQ ID NO: 19) |
| Bio-IMVTESSDYSSY (Bio-GrBP5); | (SEQ ID NO: 20) |
| IMVTEPPDYSSY (Rigid GrBP5); | (SEQ ID NO: 21) |
| CIMVTESSDYSSY (Cys-GrBP5); | (SEQ ID NO: 22) |
| DOPA-IMVTESSDYSSY (DOPA-GrBP5); | (SEQ ID NO: 23) |
| IMVTESSD(Nonnatural F)SSY (AminoF-GrBP5); | (SEQ ID NO: 24) |
| IMVTESSD(F-Phenyl)SSY (F-Phenyl-GrBP5); | (SEQ ID NO: 25) |
| IMVTESSDYSSY (D-GrBP5); | (SEQ ID NO: 26) |
| EPIHRSTLTALL-SS-IMVTESSDYSSY (AntibodyBP-SS-GrBP5); | (SEQ ID NO: 27) |
| IMVTNSSNWSSW (GrBP5 neutral WSSW); | (SEQ ID NO: 28) |
| IMVTESSDFSSF; | (SEQ ID NO: 29) |
| TQSTESSDYSSY; | (SEQ ID NO: 30) |
| IMVTDSSAYSSY (GRP5-M10); | (SEQ ID NO: 35) | and any modifications thereof, such as any of the recited polypeptides further comprising a molecular tag. As disclosed in the examples that follow, the different polypeptides disclosed herein possess different binding activities (i.e.: binding to different inorganic solids and/or different binding strengths to a given inorganic solid), aggregation, and/or diffusion properties, while some are shown to have anti-fouling capabilities or to be capable of modifying the wettability of the inorganic solid surface. Based on the teachings herein, one of skill in the art can determine which polypeptides to combine depending on the specific goal to be achieved.

In various non-limiting embodiments:

M6: IMVTASSAYDDY (SEQ ID NO: 2) (or M6 with a molecular tag) can form ordered structures on $MoS_2$;

M8: IMVTASSAYRRY (SEQ ID NO: 3) (or M8 with a molecular tag) can form ordered structures on boron nitride (BN);

GrBP5, SS-GrBP5, M2, M4, and M5 (with or without a molecular tag) can form ordered structures on graphene;

Inorganic surface wettability can be controlled using polypeptide arrays of M1, M2, M3, M4, M5, M6, M7, M8, (with or without a molecular tag), or combinations thereof;

Use of any of the polypeptides (or combinations thereof) with a molecular tag to form chemically addressable polypeptide nanowires on an inorganic surface on which the polypeptide(s) used form ordered structures. By controlling the growth conditions, through both time and concentration of polypeptide(s), it is possible to form variety of polypeptide nanostructures, i.e., 0-D clusters, 1-D wires and 2-D films, with defined number density and highly precise spacing at nanoscale dimensions. Attachment of the molecular tag to such arrays can be used as the basis for organizing other metallic nanoparticles for optical, electrical or magnetic nanodevices fabricated on inorganic solids; and Providing a mixed monolayer of SS-GrBP5 combined with GrBP-5 (with a molecular tag) on graphene to produce a sensor capable of selective detection of a target of the molecular tag in a complex solution. Numerous other non-limiting embodiments are disclosed in the examples that follow. As discussed above, the structures of the invention permit the electrical and optical properties of atomic single layer materials to be modified in a controlled manner. In one embodiment, the polypeptide nanostructures (including but not limited to nanowires quantum dots, and metallic and insulator nanoparticles (NPs, such as Au and silica, glass)) permit spatially doping charge carriers into inorganic surfaces, including but not limited to graphite, graphene, $MoS_2$, $MoSe_2$, $WSe_2$, $WS_2$, and BN. Since single-layer graphene and $MoS_2$ are respectively zero-gap and direct-gap semi-conductor, they are useful for electronics, where control of charge carrier density in semiconductor materials is essential for practical applications. In another embodiment, the surface comprises $MoS_2$, Since MoS2 has bandgap, it can emit light; the structures of the invention provide for modified color of emitted light from $MoS_2$ by controlling the interaction between the polypeptides and $MoS_2$. Other non-limiting embodiments are described in the examples that follow.

The self-assembled polypeptides, SAPs, discovered here offer opportunities for new fundamental studies of ordered bio-molecular surface structures and their atomistic details via computational modeling and more detailed and quantitative experimental structural analysis. Biologically engineered inorganic solid surfaces created by SAPs may enable future peptide-based hybrid molecular technologies such as protein chips, peptide-molecular circuits, and designer multifunctional proteins and enzymes genetically engineered to perform diverse, addressable functions. Further, the inventors have shown that the polypeptides can self-assemble into long range ordered structures, such as nanowires, quantum dots, and/or metallic and insulator nanoparticles (NPs, such as Au and silica, glass), on single-layer inorganic solid surfaces, can form nano-scale electronic p-n junctions on inorganic solid surfaces, and can modulate the electrical conductivity and photoluminescence of inorganic solid surfaces such as single-layer $MoS_2$. Thus, the structures of the present invention can realize diverse and complex electronics of two dimensional materials, such as bio-nano electronics.

Surface functionalization of solid surfaces with biological materials has been done by synthetic chemicals linked with proteins or other biological materials. However, these conventional techniques have difficulties in forming long-range ordered structures on solid surfaces and their covalent bonding to solid surfaces easily distract the inherent physical properties of solid surfaces. This is more critical in the case of atomic single layers because of their extremely small thickness and volume. The polypeptides of the invention interact with surfaces through pi-pi coupling with aromatic rings rather than such distractive covalent bonds. Furthermore, the rational design of amino acid sequence based on the three domain concept allows control of the assembly and surface (physical) topology, surface chemistry, and interaction of the polypeptides with the surface, leading to doping effects.

In a sixth aspect, the present invention provides methods for making the structures of the invention, comprising contacting an inorganic solid surface with one or more polypeptides of the invention under conditions suitable to promote self-assembly of the polypeptides into a patterned array on the surface. Such patterned array may include, but is not limited to, an ordered polypeptide film, a porous confluent film, peptide clusters, nanowires, quantum dots, metallic and insulator nanoparticles (NPs, such as Au and silica, glass), nanoscale p-n junctions, and combinations thereof. Any suitable conditions can be used to promote self-assembly of the polypeptides on the inorganic solid surface, and will depend at least on the polypeptide(s) used, the inorganic solid surface used, and the structure to be prepared. It is well within the level of skill in the art to determine appropriate conditions, based on the extensive teachings herein. For example, the use of different pH and buffer conditions can be used to modify polypeptide binding to the inorganic solid surface, surface diffusion, and/or self-assembly, as shown in the examples that follow.

In a preferred embodiment, the inorganic solid surface is selected from the group consisting of graphite, graphene, $MoS_2$, $MoSe_2$, $WSe_2$, $WS_2$, or BN, or combinations there. In a further preferred embodiment, the inorganic solid surface is a single layer material. In another further preferred embodiment, the inorganic solid surface is part of a device selected from the group consisting of protein chips, peptide-molecular circuits, field effect transistors, designer proteins, semiconductor structures, implantable medical devices (including but not limited to cardiovascular devices and bone-contacting devices), bio-fuel cells, and biosensors for any use (including but not limited to cancer detection, insulin monitoring, neural activity monitoring, etc.).

In a seventh aspect, the present invention provides methods for designing polypeptides that bind to inorganic solid surfaces, comprising:
(a) providing a polypeptide according to the general formula D1-D2-D3 (SEQ ID NO: 36),
  (i) wherein D1 is a domain of about 3 amino acids, wherein at least two of the amino acids are hydrophobic and non-aromatic;
  (ii) wherein D2 is a domain of about 5 amino acids, wherein at least three of the amino acids are hydrophilic; and
  (iii) wherein D3 is a domain of about 4 amino acids, wherein at least two of the amino acids in D3 have an aromatic ring;

(b) modifying amino acids in 1, 2, or all 3 domains to produce a modified polypeptide; and
(c) testing the modified polypeptide for altered binding to inorganic solid surfaces.

The methods of this aspect of the invention utilize the polypeptides designed herein, and their 3-domain structure, as the basis for design of modified polypeptides that can be used to produce polypeptides with altered inorganic solid surface binding characteristics of interest. The polypeptides of this aspect are as described herein. Modifying amino acids in the peptides can be accomplished using any suitable technique, such as through replacement with a different amino acid during chemical synthesis, or by modifying a coding region using standard techniques where recombinant production is desired. Any suitable methods for testing binding of the polypeptides to inorganic solid surfaces can be used, including but not limited to those disclosed in the examples that follow.

In one non-limiting embodiment, at least one amino acid is modified in D1 to alter D1 from hydrophobic to hydrophilic. In one embodiment, one or both of the hydrophobic amino acids in D1 are modified to hydrophilic amino acids. In this embodiment, one can change the hydrophobicity of peptide-coated surfaces in a controlled manner.

In another non-limiting embodiment, at least one amino acid modification is made in D2 and at least one amino acid modification is made in D3, such that a charged residue is only found in D3. Such peptides can form ordered structures on boron nitride (BN) or $MoS_2$, as described herein. For example, in one non-limiting embodiment, at least two amino acid modifications are made in D3, such that D3 comprises or consists of at least two amino acids having an aromatic ring and at least two charged amino acids.

As demonstrated in the examples, the ability to control electronic and optical properties of a man-made matter (single layer atomic materials, the latest in nanotechnology) using bio-combinatorially selected and rationally engineered represents for the first time, the opening of a new area of technology with tremendous potential in practical engineering and medicine. By doing so, it is demonstrated that inanimate matter can now be manipulated to change its intrinsic physical and chemical functionalities using an animate (biological) entity, a simple sequence design of a peptide. The extraordinary potential posed by this invention is schematically described below:

Gene→coding DNA/RNA sequence→Amino acid sequence of the peptide (GEPI)→Molecular structure→Molecular physical binding & assembly accompanied by chemical doping→Manipulating functions of single layer atomic materials—Molecular materials and devices with genetically designed functions.

Since the polypeptide (containing just 12 amino acids in the examples, and hence several hundred atoms) and the single layer material (several hundred atoms) are comparable in size, GEPI can affect the structure and, hence, the intrinsic function of SLAM, and vice versa, i.e., surface atomic structures of the inorganic SLAM material, including chemistry and crystallographic symmetry, affects/controls the conformation on the polypeptide on the surface and its function (i.e., assembly and displayed chemistry).

The surface-bound polypeptides may further bind to other entities, including but not limited to DNA, RNA, and proteins, for use in diagnostic and therapeutic applications.

The results demonstrated herein also show that quantum dots (QDs) can be directed assembled on, for example, peptide nanowires described. Similarly, metallic and insulator nanoparticles (NPs, such as Au and silica, glass) can also be directed assembled. Clearly, these further demonstrate the significance of the invention, since NPs and QDs add enormously to the functionality of these GEPIU/SLAM systems.

Example 1

Controlling Self-Assembly of Engineered Peptides on Graphite by Rational Mutation In organisms, interfaces in hard tissues are controlled by proteins via molecular recognition of specific mineral faces in, e.g., bones, spicules, shells, and teeth,[1-3] where they initiate nucleation and regulate growth of specific phases to form intricate solid architectures.[4-6] Inspired by biology, self-assembly of proteins onto solid surfaces is an enabling methodology for developing molecular surface coatings for a wide range of biological applications, e.g., biocompatible implants,[7] controlled biofilms,[8] and, more recently, the development of molecular biosensors.[9] In these applications, protein functions on solids, such as molecular recognition[10] and self-assembly,[11] derives from inherently rich chemistry and complex molecular conformations coded by their amino acid sequences. Understanding the relationship between protein sequences and surface functions during self-assembly would establish them as highly programmable molecular constructs to tailor structure and chemistry of bio-solid interfaces. To this end, unique 2D organizations of proteins have been exploited on solid surfaces using, e.g., bacterial surface-layer proteins,[12] linear amyloid structures[13-15] and ordered films of de novo designed peptides.[16,17] However, the correlation between amino acid sequences and detailed 2D molecular ordering remains largely unknown, due to complex biomolecule-solid and intermolecular interactions that accompany surface growth processes.

As a novel approach, we demonstrate that short dodecapeptides selected by phage display are capable of self-assembly on graphite and form long-range ordered biomolecular nanostructures. Using atomic force microscopy and contact angle studies, we identify three amino-acid domains along the primary sequence that steer peptide ordering and lead to nanostructures with uniformly displayed residues. The peptides are further engineered via simple mutations to control fundamental interfacial processes, including initial binding, surface aggregation and growth kinetics, and intermolecular interactions. Tailoring short peptides via their primary sequence offers versatile control over molecular self-assembly, resulting in well-defined surface properties essential in building engineered, chemically rich, bio-solid interfaces.

Results

In this molecular self-assembly study, we utilize GrBP5 (IMVTESSDYSSY (SEQ ID NO: 5), FIG. 1a), the strongest solid binding member of the biocombinatorially selected sixty different sequences, designated as the wild-type (WT) peptide. A combinatorial library of ~$10^9$ random 12-mer peptides fused to the minor coat protein (pIII) of M13 phage was used to select sequences with affinity to graphite flakes. Four selection rounds were carried out in the panning experiment, where each round consisted of (i) Panning the phage library against graphite powder, (ii) Rinsing unbound phage, (iii) Elution of specifically bound phages and (iv) Amplification of the enriched selection library. Affinity of the final selected clones was then quantified by spectrophotometric absorbance of depleted phage solutions after long exposure to graphite (see SI, Supplementary Methods S1-S3). We first characterize assembly of WT GrBP5 on highly ordered pyrolytic graphite (HOPG) substrate, incubated with 2 μM peptide solution in distilled water for three hours and scanned with an atomic force microscope (AFM) in air. The images reveal the unique capability of GrBP5 to form uniformly ordered molecular structures over several micrometers in dimension on the HOPG surface (FIG. 1b). The peptide film displays highly ordered nanostructures that display six-fold symmetry; seen as discrete maxima in the fast Fourier transform (FFT) power spectra taken by using the AFM image (FIG. 1c). The symmetry in the peptide film is likely to be guided by the molecular recognition of the underlying (0001) hexagonal graphite lattice, leading to preferred growth along specific crystallographic directions during the assembly process. The measured height of ~1.4 nm implies that the film is monomolecular thick, well below the longest dimension of a stretched single peptide (with a stretched end-to-end distance of ~4.2 nm). The considerably short height implies that peptides conform into a more compact, folded, structure during molecular ordering on graphite.

Figure 2A:
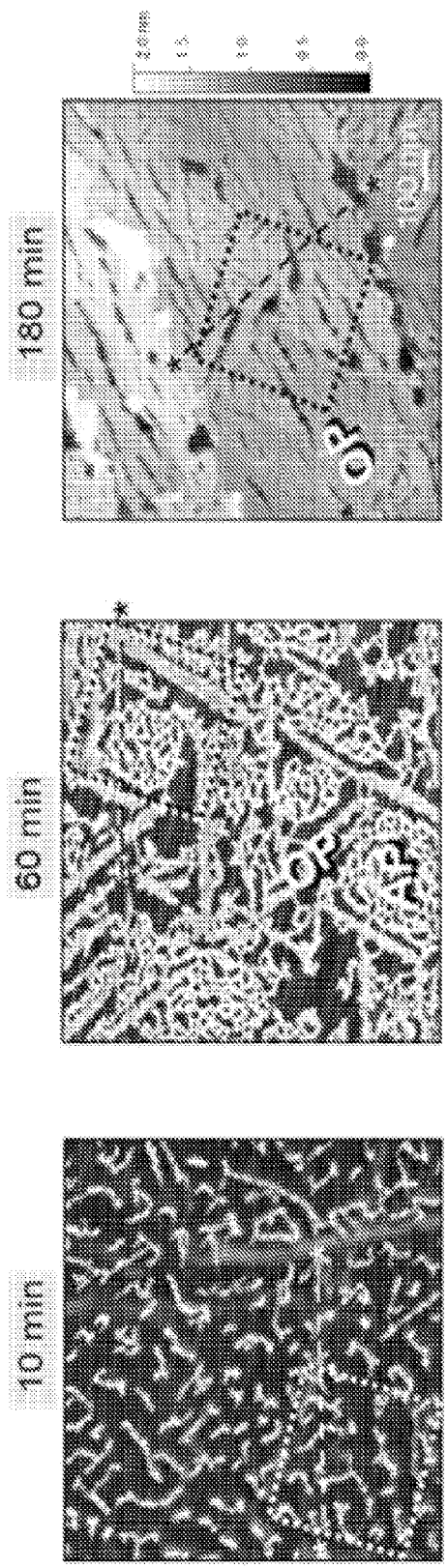
FIG. 2. Time-lapsed AFM of GrBP5 assembly. (a) Height contrast AFM images, for 10, 60 and 180 minutes, display structural evolution beginning with (left) discrete peptide clusters; (middle) growth of both amorphous (AP), and ordered (OP) phases as respectively labeled; and (right) complete OP monolayer. (b) Psuedo-3D representations of boxed regions showing height contrast among the phases formed: discrete (red), higher AP (yellow) and flat OP (orange), which are labeled below (c) on cross-sections of height taken across *---* in (a). Inset (d) shows lateral growth of OP including a cross sectional height taken between two peaks of AP peptides on either side. (e) Plot of percent total disordered/ordered peptide vs total coverage showing ordering transition and (f) Schematic of peptide self-assembly process highlighting surface phenomena: (i) Aggregation involving binding, diffusion, and clustering processes and (ii) Ordering involving self-assembly.
Figures 2B, 2C, 2D:
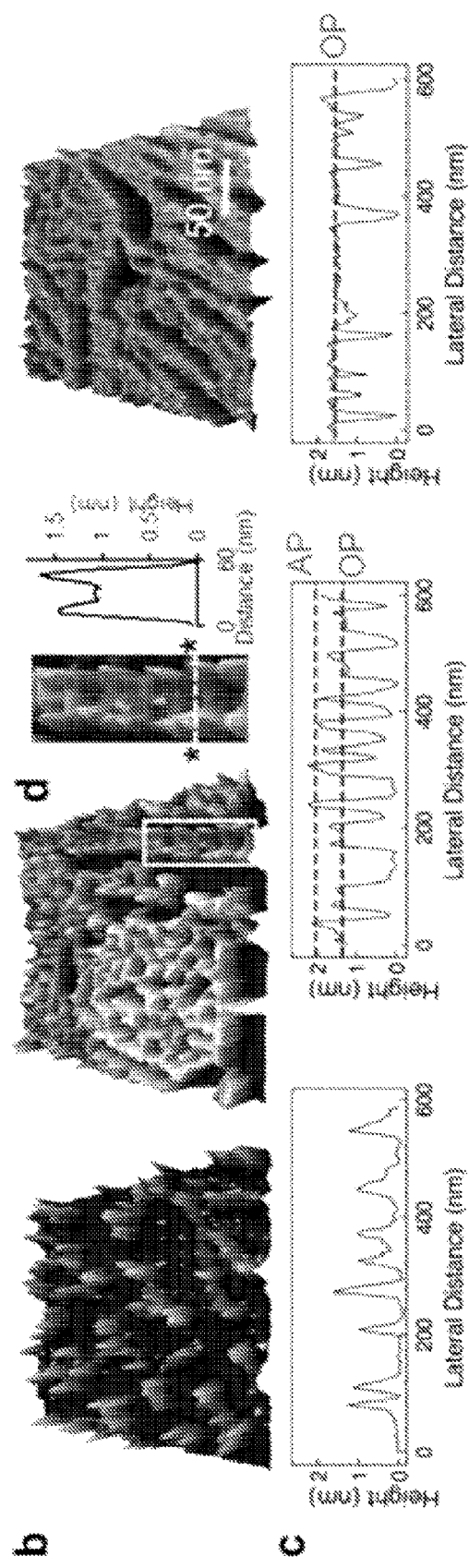

To understand the formation of peptide nanostructures, graphite surfaces were exposed to GrBP5 in a time-lapsed series of experiments (FIGS. 2a and b). Initially, upon 10 minutes of exposure to HOPG, peptides form discrete clusters ~10-50 nm in diameter with an average height of ~1.2 nm. At 60 minutes, two distinct phases are present, revealing that surface bound peptides undergo a dynamic morphological transformation from an amorphous (disordered) to an ordered state. The thicker, amorphous phase (AP) is ~1.8 nm in height, and the thinner, flat, ordered phase (OP) is ~1.3 nm in height. Phase-lag imaging by AFM signify a large difference between AP and OP structures (not shown). In the AP, surface-bound peptides likely crowd together randomly to form a topologically rough, disordered and porous structure (FIG. 2a, 60 min) By 180 minutes, the disordered phase has fully transformed into a flat ~1.3-nm thick OP monolayer with ordered morphology covering the HOPG. Pseudo three-dimensional renderings of the AFM images (FIG. 2b) better highlight the higher topography of disordered molecules among the ordered regions, showing a distinctive color for the OP (red strips) from the higher AP regions (yellow porous film). As seen in FIG. 2d, growing OP edges are dotted with peaks (in yellow, separated by ~30-nm average distance), suggesting that loosely ordered peptides are captured and incorporated into growing OP structures (also confirmed by in situ AFM experiments, not shown).

Figures 2E, 2F:
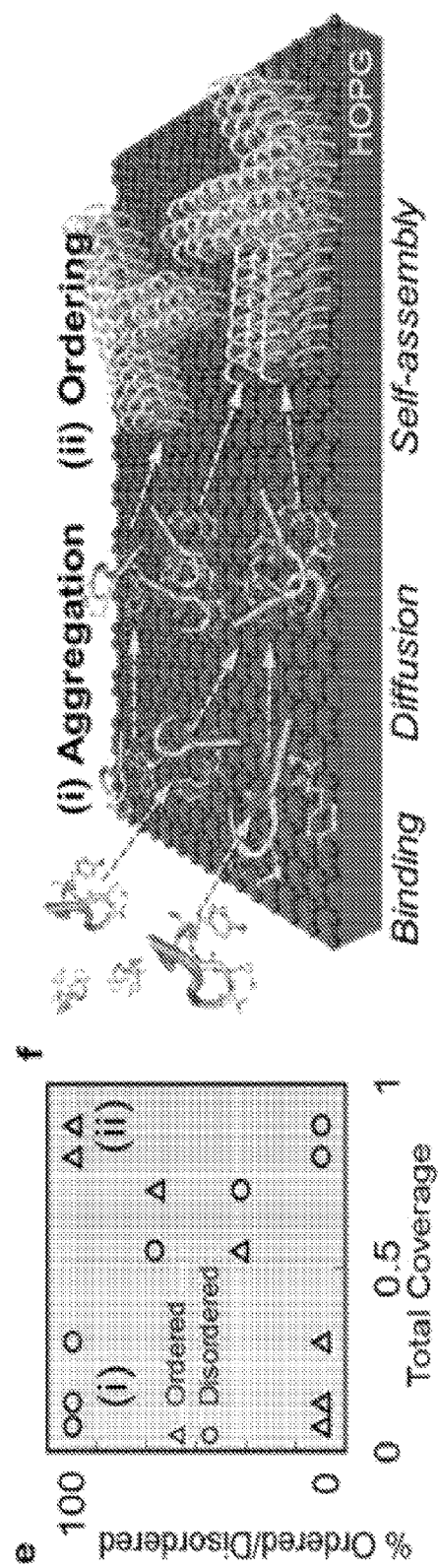

In contrast to the previous observations of peptide assembly on other atomically flat solid surfaces in the literature,[21,25,27] we discovered in this work that the two phases formed by the peptides coexist until an eventual full ordering of a GrBP5 monolayer. This unique disordered-to-ordered peptide phase transformation takes place at about 60% total surface coverage as shown in FIG. 2e, where percent total coverage of disordered and ordered peptides are plotted against total surface coverage (See SI, Supplementary Methods S4). Depicted in FIG. 2f, the assembly process of GrBP5 can be divided into two broad regimes: (i) Surface aggregation, comprised of binding to and clustering of peptides on graphite, and (ii) A gradual densification and ordering process, accompanied by a phase transformation that occurs at ~60% total peptide coverage.

To demonstrate that the surface processes of GrBP5 self-assembly can be interrogated through rational mutations of the peptide, we first classify the sequence into three chemically distinct domains, as depicted in FIG. 1a: (I)

hydrophobic (IMV), (II) hydrophilic (TESSD) and (III) aromatic (YSSY). Aromatic residues such as tyrosine (Y) are known to strongly interact with graphitic surfaces through a coupling of π-electrons.[28,29] Two of the four residues at the C-terminus of GrBP5 are aromatic-containing tyrosines (Y), defining YSSY as Domain-III. Located at the C-terminus of the peptide, this aromatic domain may function as an anchor for initial binding and possible diffusion during the aggregation regime of GrBP5 on graphite. On the other hand, intermolecular interactions necessary for long-range order may be driven by the amphiphilic tail comprised of hydrophobic Domain-I and hydrophilic Domain-II. Domain-I contains three purely aliphatic residues isoleucine (I), methionine (M) and valine (V), located at the N-terminus, while the Domain-II spans residues 4-8: threonine (T), glutamic acid (E), two serines (S), and aspartic acid (D) in the center of the peptide. The prevalence of amphiphilic motifs in many self-assembling molecular systems[13,14,30] leads us to assume that the tail component of the peptide may play a key role in the AP to OP ordering transformation. Overall, therefore, we hypothesize that each domain can be correlated to the observed framework of the three regimes in the interfacial processes, i.e., binding, diffusion and self-assembly (FIG. 1f) which were then individually addressed using five mutants (labeled M1 through M5) generated specifically for this purpose.

Figure 3:
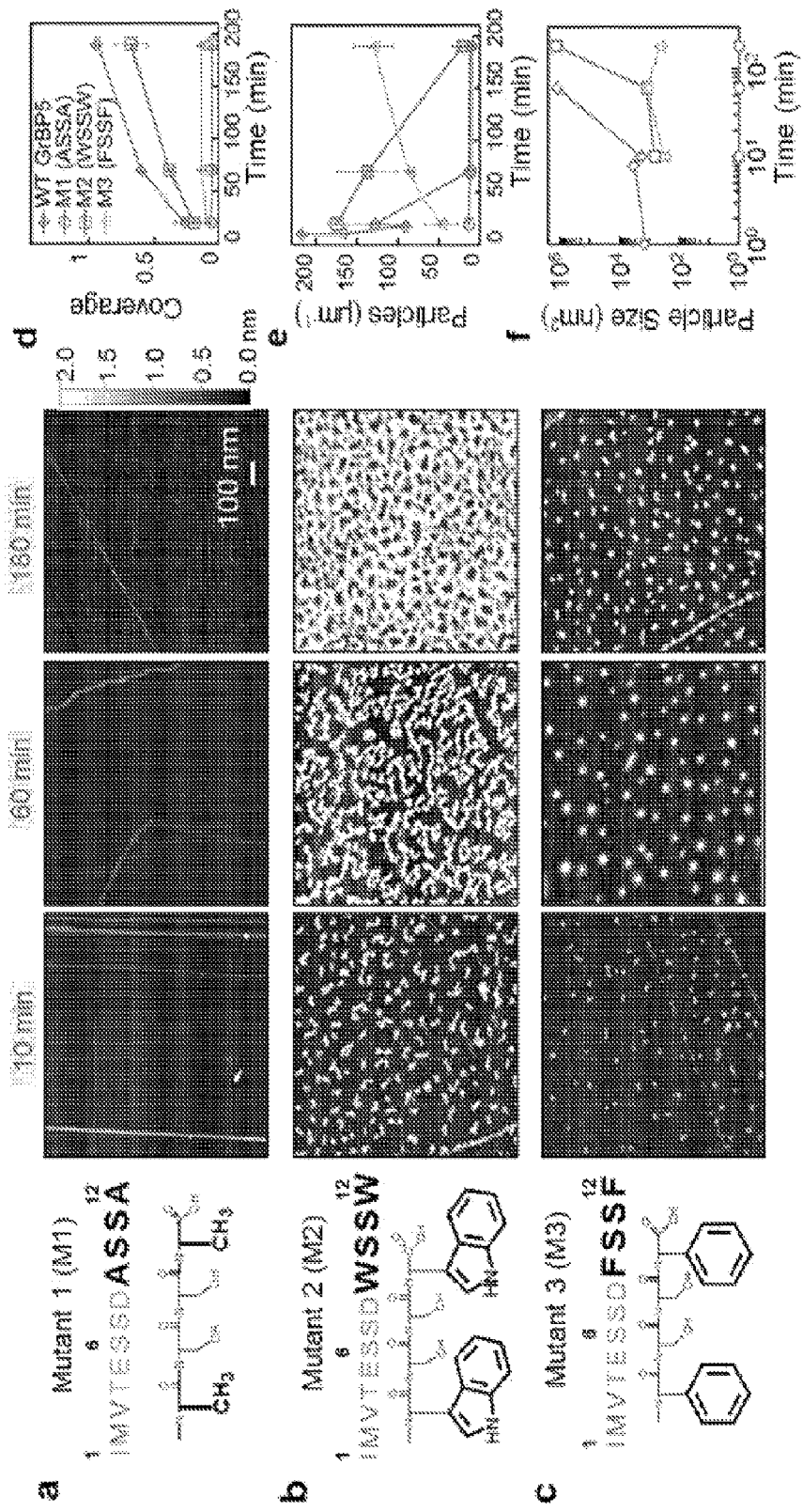
FIG. 3. Time-lapse behavior of the peptides with Domain-III mutations. (a) In Mutant 1 the aromatic residues, Tyrosine (Y), of GrBP5 are eliminated and replaced by Alanine (A) resulting in no bound molecules on surface. (b) Tryptophan and (c) Phenylalanine replace WT-Tyrosine in Mutants 2 (M2) and 3 (M3), respectively. The resultant peptides, respectively, are either strongly bound to the surface forming percolated, but finely porous, film (M3) or weakly bound peptides forming isolated islands, each over the course of 3 hours. (d) Fractional coverage trends from time-lapse AFM of WT, M1, M2, and M3; (e) Particle count of each of the peptides; and (f) Average particle size over time; Error bars represent standard deviation of 3 different images from the sample surface, totaling an area of 16 µm².

To test the function of the presumed binding domain, first the aromatic content of Domain-III was knocked out by replacing both of the tyrosine residues at the C-terminus with alanine, A. This mutant peptide, named M1 (IMVTESSDASSA (SEQ ID NO: 6)), is expected to maintain minimal interactions with graphite by displaying only methyl groups. Not unexpectedly, AFM analysis demonstrates that the HOPG surfaces remain bare even after exposure to 1 μM of M1 for up to 3 hours (FIG. 3a). From this simple mutation, the binding capability of GrBP5 to graphite is largely eliminated, indicating that the roles of hydrophobic residues in Domain-I and hydrophilic residues in Domain-II are not sufficient to promote an interaction with graphite. More importantly, these results show that Domain-III (YSSY (SEQ ID NO: 31)), provides anchoring of the peptide to the surface, and can be addressed independently of the remaining sequence to alter peptide binding and, possibly, surface diffusion leading to aggregation.

To examine the binding characteristics of the peptide further, the tyrosine residues in Domain-III were replaced with either tryptophan (W) or phenylalanine (F), two other natural amino acids containing aromatic moieties. It is possible that peptides containing W, which contains an extra indole-ring, provides a more conformal and stable i-interaction with graphite surfaces, giving it a higher affinity over Y. On the other hand, peptides including F, lacking an OH⁻ group, may have a weaker affinity towards graphite. Thus, the designed two mutant sequences, M2 (IMVTESSDWSSW (SEQ ID NO: 7)) and M3 (IMVTESSDFSSF (SEQ ID NO: 8)) may have different binding and aggregation from those of GrBP5. Systematic time-lapsed AFM experiments show that the type of aromatic residues in the anchoring domain significantly influences the formation of peptide nanostructures on graphite (FIGS. 3b and c). M2 and M3 display either a highly porous disordered film or only fine peptide clusters, respectively. The effect of aromatic residues on binding, as well as unbinding, is evident when the initial deposition rates of peptides, D, are quantified and compared among samples prepared at the earliest exposure times: 5 seconds for WT, 10 min for M2 and M3 (See SI, Supplementary Methods S7). Such an analysis reveals that WT peptides arrive at the surface with an estimated D of ~4235±43 $s^{-1}$, while M2 arrives at ~73±9 $s^{-1}$ and M3 at 22±8 $s^{-1}$ over a 1 $\mu m^2$ area (FIG. 3d). Thus, there is a ~60× discrepancy in initial binding between WT and M2, while M3 remains the slowest.

In addition to binding, the anchoring domain may also have a fundamental role in cluster formation during the initial aggregation stages of interfacial processes on solid surfaces. Measuring the number and size of peptide cluster features on graphite over time provides means to quantitatively track peptide surface kinetics in response to Domain-III mutations. In this scheme, surface aggregation is manifested as a decrease in the number density of clusters while the cluster size increases on the average. AFM analyses of early adsorption by WT and M2 reveal that, as total area coverage increases over time, the number of WT clusters decreases at a rate of ~1 $s^{-1}$ compared to a rate of ~1.3×10⁻² $s^{-1}$ for M2 over an area of 1 $\mu m^2$; a 75-fold difference (determined from the initial slope from FIG. 3e). While the number of clusters decreases, as expected, the average cluster size increases over time for both WT and M2 peptides (FIG. 3f); clusters of WT grow 24× faster than those of M2. These observations signify that WT has a higher aggregation rate than M2. In contrast, the number of clusters in M3 increases over time while the size remains the same, implying limited diffusion and, hence, lack of aggregation. The ~58× discrepancy in deposition rate between WT and M2 might explain the higher aggregation rate of WT over M2. The relative binding and aggregation rates of mutant peptides can, therefore, be ranked in decreasing order as: WT, highest binding and aggregation; M2, low binding and low aggregation; M3, low binding and no aggregation; and M1, no binding.

Figure 4:
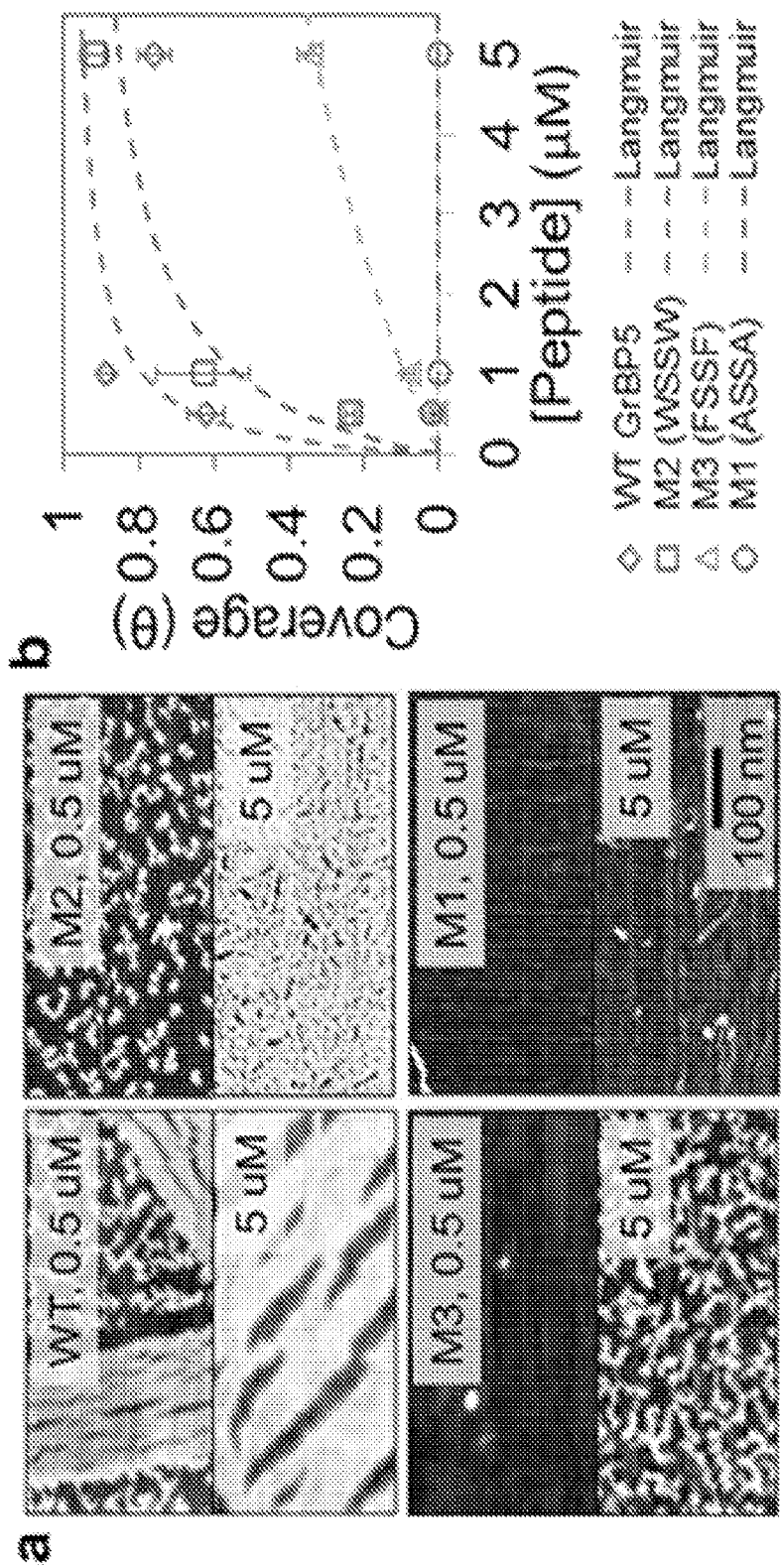
FIG. 4. Quantification of graphite affinity for aromatic mutants. (a) AFM images of HOPG exposed to 0.5 and 5.0 µM of WT, M1, M2, and M3 peptides for 3 hours. (b) Graph of surface coverage for each peptide plotted against concentration, and fitted using a Langmuir adsorption model for affinity constant, K. Error bars represent standard deviation of 3 different images from the sample surface, totaling an area of 16 µm².

The aggregation behavior of peptides is likely to be the key in determining their final, ordered nanostructures on graphite. This phenomenon was further studied by exposing graphite samples to three concentrations of peptide solutions for 3 hours each, as shown in FIG. 4. Upon this incubation period, WT formed long-range ordered self-assembled peptide nanostructures in all three conditions, i.e., 0.1, 1.0 and 5.0 μM. The mutant M2, with the second highest rate of aggregation, remains disordered at 0.1 μM and 1.0 μM concentrations; interestingly, however, at 5.0 μM it forms very finely ordered structures after 3 hours of incubation (See FIG. 4). Since the density of peptide clusters increases monotonically with total surface coverage, a critical density of clusters is likely required for ordering. This is apparent for the WT peptide, where the film undergoes transformation from AP to OP at ~60% total surface coverage (FIG. 2e). At 60%, half of the adsorbed WT peptide exists in the ordered phase, indicating threshold coverage for transformation. M2, on the other hand, remains entirely disordered at the same total surface coverage. Since M2 eventually orders at near 100% coverage, it likely undergoes transformation at a higher total coverage than WT. We speculate that the slower aggregation kinetics of M2 impedes peptide clusters from crowding on the surface and results in finer AP features, defining the small dimension of the ordered features observed at 5 μM. On the other hand, M3 remains too sparsely clustered at all three concentrations used here, never reaching a coverage threshold and remaining discretely bound even after 3 hours and at the highest concentrations. The trends in peptide aggregation rates were also verified by quantifying differences in values of peptide affinity constants, K, which are quantitatively estimated using Langmuir-like treatments (FIG. 4, and Supplementary Methods S9). Here, the Y-containing WT displayed the highest K of 3.78 µM$^{-1}$, while the WSSW mutant had a K of 1.17 µM$^{-1}$; an affinity to graphite of about one third of the WT value. Lastly, the mutant M3 shows a significant loss of affinity with a low K of ~0.1 µM$^{-1}$. The high K of WT peptide may be an indication that the highly ordered structures are the most stable on graphite surfaces due to favorable intermolecular interactions as well as their strong surface binding.

To probe the domain that directs the ordering seen in the WT GrBP5 on graphite, Domain-I at the N-terminus was mutated by modifying its hydrophobic nature. For this purpose, both negative and positive sequence knock-outs were prepared. In the design of a negative knock-out sequence, we replaced IMV with three similarly sized hydrophilic amino acids: threonine (T), glutamine (Q) and serine (S). The resulting sequence of mutant M4, therefore, is entirely hydrophilic. In contrast to the highly ordered structures of WT peptide on the surface (FIG. 5a), the M4 peptide forms highly porous and disordered structures (FIG. 5b). Next, the positive knock-out mutant M5 was designed to restore the hydrophobic characteristics of Domain-I and, therefore, the amphiphilic nature of the overall tail, presuming this mutant might allow the formation of ordered structures on graphite. Here IMV was replaced with three other aliphatic amino acids; leucine (L), isoleucine (I) and alanine (A) which results in slightly higher hydropathy than that of WT. As expected, the mutant M5 is also found to bind strongly to graphite (not shown), and, upon assembly, maintains ordering similar to that by WT (FIGS. 5a and c). This result, therefore, proves that the hydrophobic nature of Domain-I, and the amphiphilic tail it forms with Domain-II, are essential for long-range order of the dodecapeptide on graphite.

Figure 5:
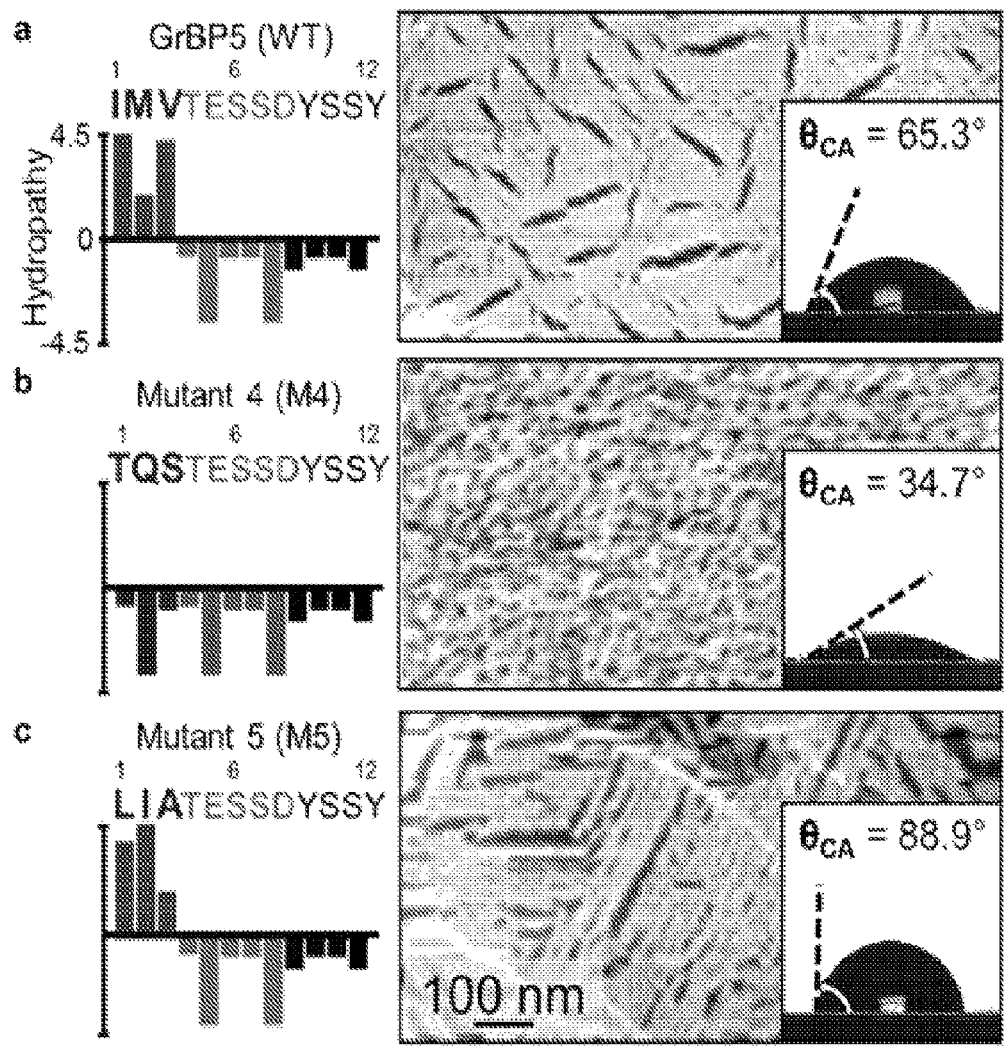
FIG. 5. Chemical properties of Domain-I mutants and their assembly behavior. (Left column) Domain-I mutant sequences and hydropathy values; (Right column) AFM images of hydropathic mutants on HOPG, and (insets) contact angle measurements of imaged surfaces. (a) WT GrBP5 forms long-range ordered nanometer-scale structure and a high contact angle, $\theta_{CA}$, of 65.3°. (b) Hydrophilic mutant M4 does not form an observable long range order and displays a low contact angle of 34.7°; while (c) Hydrophobic mutant M5 forms an ordered peptide film, similar to that of WT, with a much greater $\theta_{CA}$ of 88.9°.

These hydropathic mutations can also be utilized to control the chemical characteristics of the graphite surface, such as wettability. For this, contact angle ($\theta_{CA}$) of aqueous droplets were measured on HOPG coated with confluent peptide films, each at a comparable surface coverage (FIG. 5 insets, see Methods and Materials). The ordered WT and M5 films display an average contact angle of 65.3±0.8° and 88.9±0.7°, respectively, indicating that peptides with hydrophobic Domain-I exposed display surfaces with low wettability. In contrast, graphite covered by disordered peptides, e.g., the case of M4, exhibit a significant drop in $\theta_{CA}$ with a contact angle of 34.7±1.2°, forming a wetting surface. A simple knock out of hydrophobic Domain-I in M4, therefore, considerably lowers $\theta_{CA}$ as compared to those in WT and M5. These results demonstrate that the chemical properties of graphite surface are tunable by rational amino acid mutations, governed by specific peptide conformations brought about by the self-assembly processes.

Discussion

Figure 6:
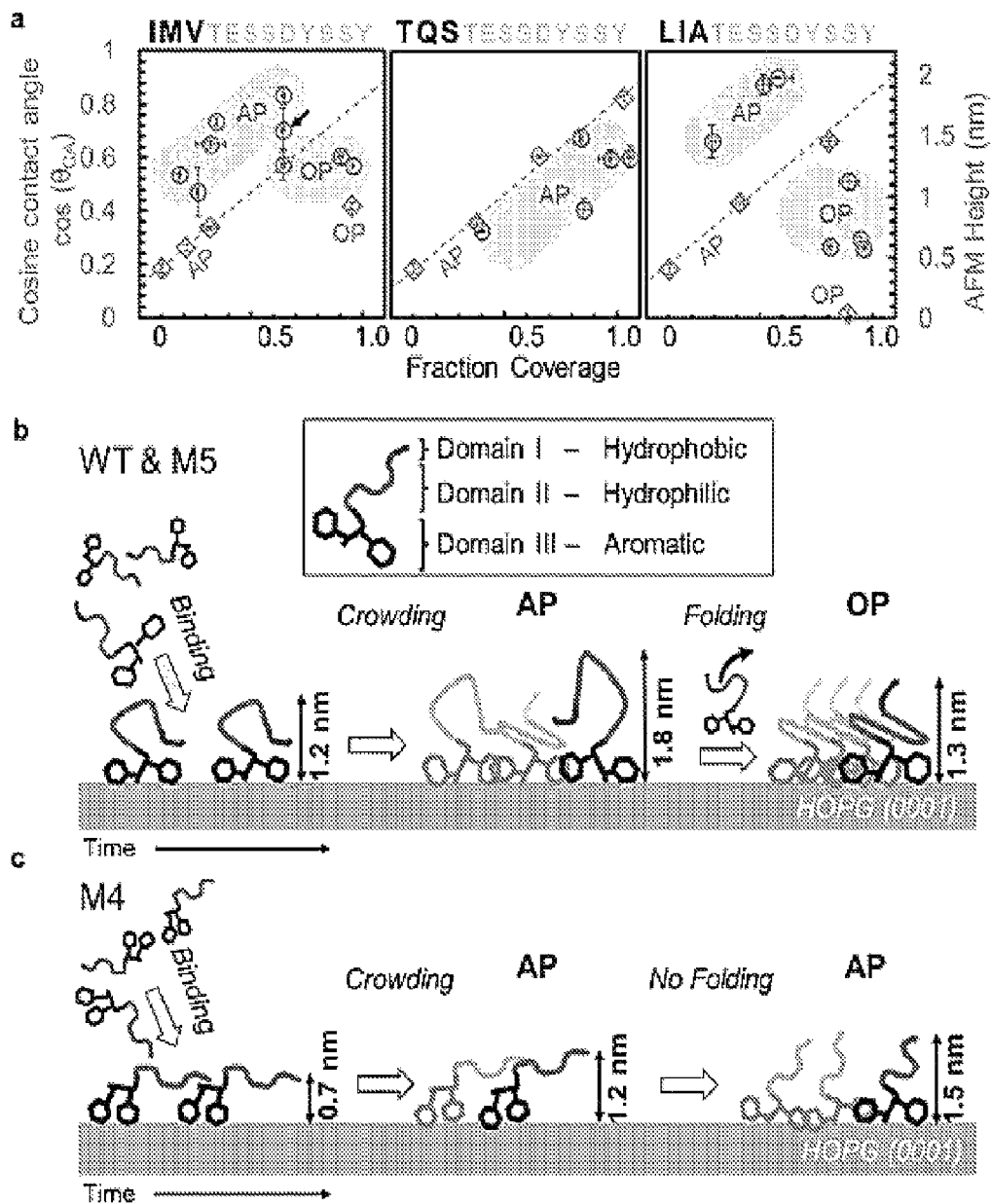
FIG. 6. Behavior of peptides during molecular self-assembly. (a) AFM height (red) and cosine of contact angle, $\cos(\theta_{cA})$, (blue) both plotted against surface coverage, respectively. Data from AP and OP images labeled accordingly. Blue dotted lines represent guides for the AP of peptides to demonstrate their shared linear behavior, i.e., chemistry, as defined by Cassie's Law.[42] Black arrow in WT indicates heights averaged from an image containing both AP and OP. Horizontal error bars represents standard deviation from 3 different analyzed images on the sample surface, totaling an area of 16µ². Vertical error bars are the standard deviation from two droplets on duplicate samples (b) A schematic of WT and M5 self-assembly mechanism where peptides undergo binding and diffusion via Domain-III, first aggregating randomly to form rough AP and, finally, rearranging Domains-I and -II while folding into OP. (c) Mechanism of M4 in the absence of hydrophobic Domain-I; here there is neither retraction in height nor change in surface chemistry.

The correlation between sequence and self-assembly, as established, provides key insight into the transformation from disordered to ordered nanostructures of the peptide, GrBP5, on graphite. An analysis of the amphiphilic behavior of our peptides, manifested by a change in concurrent wetting angle and film height over time, permits us to propose a unique transition in the molecular conformation during assembly on the solid surface. Contact angle measurements of samples scanned by AFM containing AP peptide reveal that the $\theta_{CA}$ values for WT, M4 and M5 decrease linearly with surface coverage, becoming hydrophilic. The linear trend of cos($\theta_{CA}$) shown in FIG. 6a (blue dotted line) for all three peptides implies that the AP displays chemistries, and conformations, are similar in both discrete and confluent states.[32] As seen in FIG. 5, ordered films present a shift to greater hydrophobicity. In the low coverage regime, the terminal hydrophobic amino acid domain of the WT peptide is likely first buried towards graphite while hydrophilic residues are exposed to water, as depicted in FIG. 6b. When coverage reaches a certain threshold, however, a drastic shift is observed from hydrophilic towards more hydrophobic values (black arrow in FIG. 6a). This phenomenon suggests that the hydrophobic domain emerges from its buried state and is, then, exposed to water, effectively switching the amphiphile's conformation. The plausible changes in the molecular structure of peptides between the disordered and ordered states are concurrent with the height changes of the peptides, as determined by AFM (FIG. 5a). Here, the height of WT and M5 peptide films exhibit a drastic contraction by 33% and 50%, respectively. The range of height changes observed for the OP is only ~0.1 nm, while it is ~1.0 nm for the AP. Thus, the switch in surface wetting properties, accompanied by a physical molecular contraction, leads us to believe that amphiphilic peptides undergo folding to reach their energetically favored, and uniform, final state in the ordered phase on the surface. The purely hydrophilic M4 peptide, by contrast, exhibits no folding, or ordering, that can be measured by AFM or contact angle, as plotted in FIG. 6a and schematically illustrated in FIG. 6c.

Conclusion

Detailed investigation of the molecular self-assembly of a graphite-binding peptide, GrBP5, on graphite studied by AFM imaging revealed a strong correlation between the amino acid composition and sequence to the resulting self-assembled nanostructures. Formation of peptide nanostructures on graphite involves first the formation of a disordered film that eventually transforms into an ordered structure. This is accompanied by height changes in the film as well as various wetting characteristics, as determined by contact angle measurements. Analysis of the sequence reveals three distinct chemical domains which play a role in the binding, diffusion, and assembled organization of the peptide on graphite: aromatic, hydrophilic, and hydrophobic. Mutations of the aromatic domain at the C-terminus significantly modifies the binding characteristics of GrBP5. Tyrosine (Y) residues replaced by alanine (A) largely eliminates the ability for the peptide to bind to graphite, while replacing tyrosine with tryptophan (W) or phenylalanine (F) tunes the peptide's affinity to graphite from strong to weak or moderate binding, respectively. Mutation of the tail at the N-terminus from hydrophobic to hydrophilic eliminates the amphiphilic character of the peptide, disrupting intermolecular interactions on the surface, and prevents bound peptides from forming long range ordered nanostructures. Disordered and ordered nanostructures of peptide mutants on graphite display either hydrophilic or hydrophobic domains, respectively, effectively tuning the contact angle and, thus, giving the film wetting or non-wetting characteristics.

A wide-range of surface phenomena exhibited by peptides during assembly, e.g., binding, clustering, and ordering, share large similarities with well-established epitaxial growth processes of atomic systems on surfaces, e.g., in molecular beam epitaxy (MBE),[33,34] the foundation for modern semiconducting devices. As demonstrated (FIGS. 3 and 4), the growth behavior of peptides can be controlled by varying the peptide concentration and incubation time, which effectively changes their rate of arrival to the surface and growth on graphite. Unique to peptides, however, a simple sequence of amino acids, as found here, can be further engineered to contain programmable segments for independently controlling multiple surface and intermolecular interactions. The ability to address peptide domains provides an opportunity for the predictable control over biomolecular self-assembly in the formation of complex, novel nanoarchitectures i.e., nanoislands (M2), nanowires (WT), and amorphous and ordered confluent films (M5 and WT, respectively). The SAPs, with the capability to form ordered nanostructures with controlled surface chemistry, therefore, have the potential to be the foundation of future peptide-based hybrid molecular technologies such as protein chips,[35,36] peptide-molecular circuits,[37] and designer multi-functional proteins[38] and enzymes,[39] that can be genetically engineered to perform diverse, addressable functions.

Methods

Peptide Synthesis.

Peptides were prepared on an automated solid-phase peptide synthesizer (CS336X, CSBio Inc., Menlo Park, Calif.) employing standard batch wise Fmoc chemistry procedures as reported previously.[21] Peptides were verified by MALDI-TOF mass spectrometry. The monomeric state of peptides in solution was also verified via size-exclusion chromatography (See SI, Supplementary Methods S12).

Sample Preparation for Microscopy.

For ex situ imaging, it was essential to prevent the reorganization of peptide structures during the drying process. We found that removing incubation solutions by applying a flash freeze and freeze-dry technique, common in biological electron microscopy specimen preparation,[40,41] preserved surfaces adequately. Freshly cleaved HOPG surfaces are mounted on a nickel specimen puck (Ted Pella, Inc., Redding, Calif.) and incubated with 50 µL peptide under experimental conditions in a modified scintillation vial. The vial contains a centered hollow glass column which elevates the sample to minimize contact with warm elements during the freeze-dry process. When incubation is finished, the vial is immediately placed in a −80 C deep freezer which freezes within 10-15 seconds. Samples are then immediately placed inside a glass jar and surrounded with crushed ice. The jar is placed in a liquid $N_2$ bath and transferred to a standard freeze-drier (Virtis Benchtop K, SP Industries, Inc., Warminster, Pa.) and immediately placed in a vacuum with a −80 C condensing plate to sublime frozen incubation solutions. The drying rate was ~6 µL/hr. All images in this study, except for FIG. 1a, were prepared using this method. Surfaces in FIG. 1a were prepared by wicking incubation solution with a KimWipe. For verification, we performed extensive time and concentration experiments using our 5 mutants and found (see FIGS. 2-3) agreement in coverage, height and density trends. In all, ~60 samples were prepared in this study for reproducibility.

Atomic Force Microscopy.

A Digital Instruments (Veeco, Santa Barbara, Calif.) Multimode Nanoscope IIIa scanning probe microscope equipped with high frequency NanoSensors PPP-NCHR (NanoandMore USA, Lady's Island, S.C., USA) non-contact probes, with a 42 N/m spring constant, at a 4V amplitude set point.

AFM Image Processing.

Large 'wavy' topographic features coming from HOPG surfaces observed by AFM were removed by image subtraction to allow large area coverage analysis of peptides. Specifically, GWYDDION (Czech Metrology Institute, Czech Republic) image filters and simple image operations were applied to the raw AFM data. First, images were corrected for tilt by a first order plane subtraction while fast scan lines were normalized by aligning their median z-offset. Next, an erosion filter was applied to AFM images using a neighborhood of 10-15 pixels, where peptide features are removed to create a secondary image containing only the topography of the bare surface. This secondary image is then directly subtracted from the original AFM image, yielding a background subtracted image for surface coverage analysis. To quantify surface coverage values, IMAGEJ (NIH, Bethesda, Md., USA) is used to determine the threshold depth in the image where full lateral surface features are measured. This threshold is then used to form a binary image.

To calculate coverage values for mixed images comprised of both disordered and ordered peptides (e.g., FIG. 2e), a particle analyzer was used to distinguish peptide features via SPIP (Image Metrology A/S, Denmark). Ordered peptides generally occupy higher area coverage over disordered peptides and can be quantified separately for independent coverage values based on particle size.

Height measurements of discretely bound, amorphous and ordered phases of peptide in FIG. 5 were measured by AFM height image histogram analysis. Peaks in the histogram arise from a predominant number of pixels at certain heights. For peptides on HOPG, bare surface pixels form a prominent peak due to the atomically flat nature of graphite. Particles observed on the surface, likely clustered or monomeric peptides, are tip convoluted and fail to reflect the true maximum height of interest in the histogram so image filtering is necessary. To address this, dilation filtering was used to enhance the total number of pixels representing the maximum heights of bound particles. This is reflected by an upward shift in peptide peak height on the histogram, where overall height is measured with respect to the bare graphite peak from the original image. These values agree with individual cross sectional measurements. In confluent films, no filtering was used since pixels mainly come from the flat film and form a dominant peak. For images with two phases present, height was measured from each phase independently.

Contact Angle Study.

For coverage normalized $\theta_{CA}$ values, 50 mm² HOPG samples were freshly cleaved and immediately incubated with 80 µL of appropriate peptide solution in water ranging from 10 mins to 7 hrs. The drop was then wicked off using a tissue and the sample was dried under a gentle stream of $N_2$. Samples were equilibrated in air for 30 min prior to contact angle measurements. Static sessile contact angles were measured by an FTA1000B Goniometer (First Ten Angstroms, Inc., Portsmouth, Va.) with a digital camera and auto-capture software system by the vendor after 2 µL of peptide solution is dropped, performed in duplicate for each surface. The peptide solutions were placed on graphite with the same concentrations as used for their original assembly to prevent desorption. The samples were then dried with nitrogen and measured for coverage by AFM. AFM images were obtained from at least four different locations (4 µm×0.5 µm sized scans each) on all samples by the methods described above. (See SI, Supplementary Methods S11)

S1. Supplementary Methods: Combinatorial Selection of Graphite Binding Peptides by Phage Display The Ph.D-12 phage display library, based on a combinatorial library of random 12-mer peptides fused to the minor coat protein(pIII) of M13 phage (New England BioLabs), was used to select peptide sequences against graphite powder (crystalline, ~300 mesh, 99%, 10129, Alfa Aesar). The 12-mer phage display library has an estimated diversity of 2.7×10⁹ different random clones. To enrich the graphite binding clones, four selection rounds were carried out in the panning experiment. Prior to exposing powders to the phage library, graphite was cleaned by exposure to increasingly polar solvents in the presence of ultrasonication first in a methanol/acetone mixture, then in isopropanol, and lastly in DI water. The graphite powder was then dried under vacuum. 10 mg of graphite powder was exposed to a volume of 10 µL of phage display library and incubated in potassium phosphate/sodium carbonate buffer (PC, 55 mM $KH_2PO_4$, 45 mM $Na_2CO_3$ and 200 mM NaCl, pH 7.4), containing 0.1% detergent (combination of 20% (w/v) tween 20 and 20% (w/v) tween 80) for 30 min. on a rotator at room temperature and then washed twice before overnight incubation. Following overnight incubation, to remove the non-specifically- or weakly-bound phage, the graphite powder was then washed ten times using PC buffer with increasing detergent concentrations from 0.1% to 0.5% (v/v), at pH 7.2. The bound phage were then eluted from the surface in a stepwise manner by applying an elution buffer consisting of 0.2 M Glycine-HCl pH 2.2 (Sigma Aldrich, St. Louis, Mo.) for 15 min. Eluted phage were then transferred to an early log phase *E. coli* ER2738 culture (~OD: 0.5) and amplified for 4.5 h. The amplified phage were isolated by polyethylene glycol (PEG) precipitation. Purification of phage includes three main PEG-NaCl (20% (w/v) PEG-8000 (Sigma) and 2.5 M NaCl (Sigma)) steps followed by re-suspension of phage precipitate in PC buffer with decreased volume. In the first step, 1:6 ratio PEG-NaCl (~40 mL) was added into supernatant that is recovered after centrifugation of *E. coli* and incubated overnight at 40° C. to precipitate phage. Following, phage pellet was obtained by centrifugation and re-suspended in 5 mL PC. In the second and third steps, the same procedure was followed with decreased incubation times (2 hours and 10 min) and PC buffer volume (1 mL and 200 µL) In the subsequent three selection rounds, graphite powder was exposed to the phage obtained from each previous round to enrich the phage pool in favor of the strongest-binding clones. Following the four rounds of panning, amino acid sequences of the 60 phage selected clones were amplified and identified by DNA sequencing. The single-stranded DNA of selected phage plaques were isolated by a QIAprep Spin M13 Kit (Qiagen, Valencia, Calif.) and amplified via PCR in the presence of dye-labeled terminators (Big dye terminator v3.1, Applied Biosystems, Carlsbad, Calif.). PCR products were purified by Shephadex G-50 column precipitation. A 96 gIII primer or 5'-OH CCC TC TAGTTA GCG TAA CG-3' (SEQ ID NO: 32) primer was used for the amplification of ssDNA. The selected sequences of DNA from clones were analyzed by an Applied Biosystems 310 Avant genetic analyzer.

S2. Supplementary Methods: Characterization of Graphite Binding Affinity by Spectrophotometric Quantification of Phage The selected clones, following sequencing, were then tested individually for their binding affinities. To measure clone binding affinity, we adopted spectrophotometry to quantify both the amplified phage starting solutions as well as their depletion due to reaction with graphite powder. Phage concentrations in the range 10¹⁰-10¹² pfu/ml can be accurately determined by analyzing the broad optical absorption peak located from 260 nm to 280 nm, with a slight maximum at 269 nm. Since this peak reflects the nucleotide content of the particular phage, a molar extinction coefficient (9.006×10³ M-1cm-1) has been previously derived (3). This treatment was modified to reflect the genome size of M13KE used in our study, 7222 bp, as calculated below.

$$\text{Phage particles/ml} = \frac{(\text{Measured } A269 - \text{Measured } A320) \times 6 \times 10^{16}}{7222 \, (\text{Number of nucleotides in phage genome})}$$

To quantify the relative binding strength of all selected clones, both phage concentration and powder weight were optimized to maximize the absorbance change upon phage reaction with graphite. First, a phage working concentration was found by forming an optimization curve (via absorbance of 10¹⁰, 10¹¹ and 10¹² pfu/ml phage solutions) and choosing the greatest value from the linear regime, 10¹² pfu/mL. Next, analogously, graphite powders of incremental weights (0.5, 1.0, 2.0 and 5.0 mg) were each exposed to 10¹² pfu/ml phage solution to form a second optimization curve, establishing a working powder weight of 5 mg. Using these conditions, all selected clones were individually exposed to 5 mg of graphite powder in PC buffer and incubated for 24 hours on a rotator at room temperature to allow phage-inorganic powder surface interactions to occur. After incubation, the reacted graphite powder was pelleted by centrifugation at 5,000 rpm for 3 min and the supernatant (unbound phage) was used for spectrophotometric measurements. Relative binding affinities were calculated from the measured absorption intensities of depleted (unbound) phage solutions as a percentage of the original absorption intensity from starting solutions. Each experimental set was performed in triplicates and repeated twice, including a positive control of only 10¹² pfu/ml selected phage clones with no graphite powder and a negative control that has no random insertion sequence (M13KO7 purchased from NEB, N0315S). Finally, the graphite binding peptides (GrBPs) were categorized and grouped as strong, moderate and weak binders.

S3. Supplementary Methods: Verification of Clone Affinity by Atomic Force Microscopy (AFM)

The strongest (GrBP5: IMVTESSDYSSY (SEQ ID NO: 5)) and weakest (GrBP6: THPLPIHANELT (SEQ ID NO: 34)) selected binders were verified quantitatively via AFM imaging and Langmuir modeling on highly ordered pyrolytic graphite (HOPG). Peptide sequences were synthesized and characterized for their affinity by drop coating HOPG samples with various concentrations of peptide for three hours. Samples were then scanned with high resolution tapping force AFM and coverage was quantified to form curves. From this analysis, GrBP5 was found to have an equilibrium constant (Keq) of 2.23 µM-1, which was about five-fold greater than 0.43 µM-1 Keq of GrBP6. Interestingly, while GrBP6 contains His residues that may be involved with graphite binding, it lacks the cooperative interactions of GrBP5 that forms more highly covered ordered surfaces. The hydrophilic central region of GrBP5 may be related to the evolution of the three domains of GrBP5 from the phage screening process. It is likely that the central hydrophilic region of the peptide (IMVTESSDYSSY (SEQ ID NO: 5)) allows a higher chance for selection, since soluble phages are preferable in the aqueous screening media.

S7. Supplementary Methods: Quantification of Deposition Rate D

The deposition rate of peptides onto the surface is defined by the relation: $D(t)=s*F(t)$, where $D(t)$ is the deposition rate, s is the sticking coefficient of the peptide, and $F(t)$ is the flux rate of peptides hitting the surface, resulting from their bulk diffusion in solution. Since peptides used in this study are chemically similar, their size and hydrodynamic properties should result in similar F(t) trends. Therefore, measuring D(t) should directly reflect their surface affinity from varied s values of different peptide sequences. The adsorption probability s is also a measure of peptide lifetime on the surface, including both binding and unbinding events. To quantify peptide arrival rates over time in our study, coverage values at 10 minutes were divided by assuming a peptide surface area of 3.14 nm$^2$ with a radius of roughly 1 nm, established by molecular simulations to be detailed elsewhere. Coverage values were measured over ten separate 1 μm2 regions on the surface using the methods outlined previously. Counts were then calculated as per second intervals. Errors in the main text were derived by taking the error in coverage from FIG. 3d by the area of peptides, as was done to calculate the F value.

S8. Supplementary Methods: Quantification of Particle Density Change Over Time

The change in number density of particles over time was determined by quantifying the number of features in each image over time. Methods described previously were used to measure the population of particles, defined as isolated features on the surface, over a combined minimum scanning area of 16 μm$^2$ (3-4 2 μm×2 μm AFM images). For WT-GrBP5, images at 1 hour were already interconnected so earlier adsorption times, below 10 mins, were required for measurable coarsening rates. Rates were measured from the linear region of the curves, which was up to ~900 secs. for WT-GrBP5 and 10800 secs. for Mutant 2.

S9. Supplementary Methods: Determining Peptide Binding Affinity (K) on HOPG by AFM WT GrBP5 and its five mutants were assessed for affinity towards HOPG by exposing surfaces to 0.5, 1.0 and 5.0 μM concentrations of 50 μL of each peptide for 3 hours. After three hours, samples were immediately flash frozen in a −80° C. freezer (observed to take ~10 seconds) and freeze-dried using the protocol described in the M&M section of the main text. The results permit surface coverage quantification, and yield exponential behaviors which can be modeled and quantified by fitting to an adsorption model for an affinity constant K. To extract K values, the binding affinities of peptides to graphite were estimated from a relationship between the observed surface coverage of peptides by AFM and the peptide concentrations used for incubation. Here, we employed a simple adsorption equation based on reference 4 which allows us to approximate the binding affinity.

$$\theta = \theta_{max} \times \frac{K \times C}{1 + U \times C}$$

θ is coverage of peptides, $\theta_{max}$ is maximal coverage of peptides, C is concentration of peptide solution, and K is binding affinity constant.

S10. Supplementary Methods: Peptide Synthesis

Synthesis was carried out on a preloaded support resin using HBTU activation chemistry, while 20% piperidine in DMF was employed to afford the Fmoc deprotection and monitored by UV absorbance at 301 nm. Following solid-phase synthesis, the peptides were cleaved off the support and side chain deprotected by stirring the resin-bound peptide in a cocktail (containing either 87.5:5:5:2.5 TFA/thioanisole/H$_2$O/phenol/ethanedithiol or 94:1:2.5:2.5 TFA/triisopropylsilane/H$_2$O/EDT, depending on the peptide) under N2 atmosphere for 2-3 hrs. The resin was removed by filtration, and each of the peptides was precipitated with cold ether to yield crude peptide product that was lyophilized (Virtis Benchtop K, SP Industries, Inc., Warminster, Pa.). Peptides were reconstituted using various ratios of DI H2O and acetonitrile. Purification by reverse-phase HPLC for peptides employed, first, an isocratic (0% B for 2 min) and, then, a linear gradient of 1%/min for analytical and 0.5%/min for semiprep scales at 1 and 10 mL/min flow rates, respectively. Retention times spanned 30-50 mins depending on the peptide in semi-preparative HPLC. Analytical peaks were isolated by auto-threshold collection (Waters Deltaprep 600, analytical mode) and peptides were verified by MALDI-TOF mass spectrometry with reflectron (RETOF-MS) on an Autoflex II (Bruker Daltonics, Billerica, Mass.) mass spectrometer in positive-ion mode. The observed M/Z fractions were subsequently collected manually from a scaled semi-preparative separation (Waters Deltaprep 600, semiprep. mode).

S11. Supplementary Methods: Pendant Drop Analysis of Peptide Solutions

Pendant drop shape analysis, used to determine the liquid-air interfacial tension of solutions, relies on the distortion, by gravity, of a drop suspended from a syringe needle of a known diameter. By using the Young-Laplace equation interfacial tension is derived from the total volume of the drop, its vertical size, contact angle with the needle, and liquid density. In this case all of the geometric parameters were automatically obtained from the drop images using vendor-provided software (First Ten Angstroms, Inc, Portsmouth, Va.) and the density of the liquid is assumed to be that of water. The results indicate no statistically significant differences in the interfacial tensions of various peptide solutions used in our experiments.

S12. Supplementary Methods: Size-Exclusion Chromatography of GrBP5

Solution state of GrBP5 was characterized by size-exclusion chromatography (7.8×300 mm, Ultrahydrogel 250, Waters Corporation, Milford, Mass.), at a constant 1 mL/min flow rate using DI Water. DI water alone showed characteristic solvent front. Peptide calibration solution (Bruker Daltonics, Billerica, Mass.), demonstrated mass range and resolution of the SEC column, while GrBP5 solution showing one major peak in generally 1200-1400 mass region of the calibration solution (data not shown). Minor peak existed as ~10% of total peak area while GrBP5 peak is quantified as ~90%, making up the majority of the solution.

REFERENCES FOR EXAMPLE 1

1. Lowenstam, H.; Weiner, S., *On Biomineralization*. Oxford University Press: Oxford, 1989.
2. Sarikaya, M.; Aksay, I., *Biomimetics: Design & Processing of Materials*. AIP:College Park, 1996.
3. Mann, S., *Biomineralization: Principles and Concepts in Bioinorganic Materials Chemistry*. Oxford University Press: Oxford, 2001.
4. Addadi, L.; Weiner, S., Interactions between Acidic Proteins and Crystals—Stereochemical Requirements in Biomineralization. *Proc. Natl. Acad. Sci. USA* 1985, 82, 4110-4114.
5. Mann, S., Molecular Recognition in Biomineralization. *Nature* 1988, 332 (6160), 119-124.
6. Cha, J. N.; Shimizu, K.; Zhou, Y.; Christiansen, S. C.; Chmelka, B. F.; Stucky, G. D.; Morse, D. E., Silicatein Filaments and Subunits From a Marine Sponge Direct the Polymerization of Silica and Silicones in vitro. *Proc. Natl. Acad. Sci. USA* 1999, 96, 361-365.
7. Ratner, B. D.; Hoffman, A. S.; Schoen, F. J.; Lemons, J. E., *Biomaterials Science, Second Edition An Introduction to Materials in Medicine.* 2nd ed.; Elsevier Academic Press: San Diego, 2004.
8. Chen, C. S.; Mrksich, M.; Huang, S.; Whitesides, G. M.; Ingber, D. E., Geometric Control of Cell Life and Death. *Science* 1997, 276, 1425-1428.
9. Templin, M. F.; Stoll, D.; Schrenk, M.; Traub, P. C.; Vohringer, C. F.; Joos, T. O., Protein Microarray Technology. *Trends Biotechnol.* 2002, 20, 160-167.
10. Pauling, L., Molecular architecture and Biological Reactions. *Chem. Eng. News* 1946, 24, 1375-1377.
11. Bradley, D. E., Ultrastructure of Bacteriophages and Bacteriocins. *Bacteriol Rev.* 1967, 31, 230-314.
12. Gyorvary, E. S.; Stein, O.; Pum, D.; Sleytr, U. B., Self-assembly and Recrystallization of Bacterial S-layer Proteins at Silicon Supports Imaged in Real Time by Atomic Force Microscopy. *J. Microsc. (Oxf)* 2003, 212, 300-306.
13. Sneer, R.; Weygand, M. J.; Kjaer, K.; Tirrell, D. A.; Rapaport, H., Parallel β-Sheet Assemblies at Interfaces. *Chemphyschem* 2004, 5, 747-750.
14. Zhang, F.; Du, H. N.; Zhang, Z. X.; Ji, L. N.; Li, H. T.; Tang, L.; Wang, H. B.; Fan, C. H.; Xu, H. J.; Zhang, Y., et al., Epitaxial Growth of Peptide Nanofilaments on Inorganic Surfaces: Effects of Interfacial Hydrophobicity/Hydrophilicity. *Angew. Chem. Int. Edit.* 2006, 45, 3611-3613.
15. Harper, J. D.; Wong, S. S.; Lieber, C. M.; Lansbury, P. T., Observation of Metastable A-β Amyloid Protofibrils by Atomic Force Microscopy. *Chem. Biol.* 1997, 4, 119-125.
16. Brown, C. L.; Aksay, I. A.; Saville, D. A.; Hecht, M. H., Template-Directed Assembly of a de novo Designed Protein. *J. Am. Chem. Soc.* 2002, 124, 6846-6848.
17. Grigoryan, G.; Kim, Y. H.; Acharya, R.; Axelrod, K.; Jain, R. M.; Willis, L.; Drndic, M.; Kikkawa, J. M.; DeGrado, W. F., Computational Design of Virus-Like Protein Assemblies on Carbon Nanotube Surfaces. *Science* 2011, 332, 1071-1076.
18. Sarikaya, M.; Tamerler, C.; Jen, A. K. Y.; Schulten, K.; Baneyx, F., Molecular Biomimetics: Nanotechnology through Biology. *Nat. Mater.* 2003, 2, 577-585.
19. Whaley, S. R.; English, D. S.; Hu, E. L.; Barbara, P. F.; Belcher, A. M., Selection of Peptides with Semiconductor Binding Specificity for Directed Nanocrystal Assembly. *Nature* 2000, 405, 665-668.
20. Sano, K. I.; Shiba, K., A Hexapeptide Motif that Electrostatically Binds to the Surface of Titanium. *J. Am. Chem. Soc.* 2003, 125, 14234-14235.
21. So, C. R.; Kulp, J. L.; Oren, E. E.; Zareie, H.; Tamerler, C.; Evans, J. S.; Sarikaya, M., Molecular Recognition and Supramolecular Self-Assembly of a Genetically Engineered Gold Binding Peptide on Au{111}. *ACS Nano* 2009, 3, 1525-1531.
22. Wang, S. Q.; Humphreys, E. S.; Chung, S. Y.; Delduco, D. F.; Lustig, S. R.; Wang, H.; Parker, K. N.; Rizzo, N. W.; Subramoney, S.; Chiang, Y. M., et al., Peptides with Selective Affinity for Carbon Nanotubes. *Nat. Mater.* 2003, 2, 196-200.
23. Naik, R. R.; Brott, L. L.; Clarson, S. J.; Stone, M. O., Silica-precipitating peptides isolated from a combinatorial phage display peptide library. *J. Nanosci. Nanotechnol.* 2002, 2, 95-100.
24. Brown, S., Metal-recognition by repeating polypeptides. *Nat. Biotechnol.* 1997, 15, 269-272.
25. So, C. R.; Tamerler, C.; Sarikaya, M., Adsorption, Diffusion, and Self-Assembly of an Engineered Gold-Binding Peptide on Au(111) Investigated by Atomic Force Microscopy. *Angew. Chem. Int. Edit.* 2009, 48, 5174-5177.
26. Hnilova, M. et al. Effect of Molecular Conformations on the Adsorption Behavior of Gold-Binding Peptides. *Langmuir* 2008, 24, 12440-12445.
27. Kowalewski, T.; Holtzman, D. M., In situ atomic force microscopy study of Alzheimer's β-amyloid peptide on different substrates: New insights into mechanism of (3-sheet formation. *Proc. Natl. Acad. Sci. USA* 1999, 96, 3688-3693.
28. Xie, H.; Becraft, E. J.; Baughman, R. H.; Dalton, A. B.; Dieckmann, G. R., Ranking the Affinity of Aromatic Residues for Carbon Nanotubes by Using Designed Surfactant Peptides. *J. Pept. Sci.* 2008, 14, 139-151.
29. Tomasio, S. M.; Walsh, T. R., Modeling the Binding Affinity of Peptides for Graphitic Surfaces. Influences of Aromatic Content and Interfacial Shape. *J. Phys. Chem. C* 2009, 113, 8778-8785.
30. Whitehouse, C.; Fang, J. Y.; Aggeli, A.; Bell, M.; Brydson, R.; Fishwick, C. W. G.; Henderson, J. R.; Knobler, C. M.; Owens, R. W.; Thomson, N. H., et al., Adsorption and Self-Assembly of Peptides on Mica Substrates. *Angew. Chem. Int. Edit.* 2005, 44, 1965-1968.
31. Sowerby, S. J.; Petersen, G. B.; Holm, N. G., Primordial Coding of Amino Acids by Adsorbed Purine Bases. *Origins Life Evol. B* 2002, 32, 35-46.
32. Schwartz, D. K., Mechanisms and Kinetics of Self-Assembled Monolayer Formation. *Annu. Rev. Phys. Chem.* 2001, 52, 107-137.
33. Barth, J. V.; Costantini, G.; Kern, K., Engineering Atomic and Molecular Nanostructures at Surfaces. *Nature* 2005, 437, 671-679.
34. Jensen, P.; Barabasi, A. L.; Larralde, H.; Havlin, S.; Stanley, H. E., Deposition, Diffusion and Aggregation of Atoms on Surfaces—a Model for Nanostructure Growth. *Phys. Rev. B* 1994, 50, 15316-15329.
35. Zhu, H.; Bilgin, M.; Bangham, R.; Hall, D.; Casamayor, A.; Bertone, P.; Lan, N.; Jansen, R.; Bidlingmaier, S.; Houfek, T., et al., Global Analysis of Protein Activities using Proteome Chips. *Science* 2001, 293, 2101-2105.
36. Langer, R.; Peppas, N. A., Advances in Biomaterials, Drug Delivery, and Bionanotechnology. *Aiche. J.* 2003, 49, 2990-3006.
37. Joachim, C.; Gimzewski, J. K.; Aviram, A., Electronics using Hybrid-Molecular and Mono-Molecular Devices. *Nature* 2000, 408, 541-548.
38. Baneyx, F.; Mujacic, M., Recombinant Protein Folding and Misfolding in *Escherichia Coli.* *Nat. Biotechnol.* 2004, 22, 1399-1408.
39. Siegel, J. B.; Zanghellini, A.; Lovick, H. M.; Kiss, G.; Lambert, A. R.; Clair, J. L. S.; Gallaher, J. L.; Hilvert, D.; Gelb, M. H.; Stoddard, B. L., et al., Computational Design of an Enzyme Catalyst for a Stereoselective Bimolecular Diels-Alder Reaction. *Science* 2010, 329, 309-313.
40. Gross, H., *Cryotechniques in Biological Electron Microscopy.* 1 ed.; Springer: New York, 1987.
41. Engel, A., Biological Applications of Scanning Probe Microscopes. *Annu. Rev. Biophys. Bio.* 1991, 20, 79-108.
42. Kyte, J. & Doolittle, R. F. A Simple Method for Displaying the Hydropathic Character of a Pro-tein. *J. Mol. Biol.* 1982, 157, 105-132.

43. Cassie, A. B. D. & Baxter, S. Wettability of Porous Surfaces. *T Faraday Soc.* 1944, 40, 0546-0550.

SUPPLEMENTAL REFERENCES

1. S. Donatan, H. Yazici, H. Bermek, M. Sarikaya, C. Tamerler, M. Urgen, *Mat. Sci. and Eng. C,* 29, 14 (2009).
2. M. Gungormus, H. Fong, I. W. Kim, J. S. Evans, C. Tamerler, M. Sarikaya, *Biomacromol.,* 9, 966 (2008).
3. C. F. Barbas, D. R. Burton, J. K. Scott, G. J. Silverman, *Cold Spring Harbor Laboratory Press,* 2001.
4. I. Langmuir, *J. Am. Chem. Soc.,* 38, 2221 (1917).

Example 2

Controlling the Surface Chemistry of Graphite by Engineered Self-Assembled Peptides Abstract The systematic control over surface chemistry is a long-standing challenge in biomedical and nano-technological applications for graphitic materials. As a novel approach, we utilize graphite-binding dodecapeptides that self-assemble into dense domains to form monolayer thick long-range ordered films on graphite. Specifically, the peptides are rationally designed through their amino acid sequences to predictably display hydrophilic and hydrophobic characteristics while maintaining their self-assembly capabilities on the solid substrate. The peptides are observed to maintain a high tolerance for sequence modification, allowing the control over surface chemistry via their amino acid sequence. Furthermore, through a single step co-assembly of two different designed peptides, we predictably and precisely tune the wettability of the resulting functionalized graphite surfaces from 44 to 83 degrees. The modular molecular structures and predictable behavior of short peptides demonstrated here give rise to a novel platform for functionalizing graphitic materials that offers numerous advantages, including non-invasive modification of the substrate, biocompatible processing in an aqueous environment, and simple fusion with other functional biological molecules.

Introduction

Controlling interfacial properties of materials through surface functionalization of solid substrates has been a major challenge in medicine and nanotechnology for the last two decades.[1,2] The precise display of function and chemistry is particularly critical for engineering bio-inorganic interfaces, where the orientation and density of the immobilized molecules may have direct bearing on the performance of the resulting assembly, such as, for example, the specific activity of immobilized enzymes.[3] Biocombinatorially selected (through phage or cell-surface display) and genetically engineered solid-binding peptides offer a versatile platform for bridging the bio/inorganic divide.[4-7] These strong-binding ($k_d$~50 nM to 1 µM), material-specific 7-14 amino acid long sequences possess a wealth of chemical diversity and modular capacity through mutation and targeted chemical modification, providing unique opportunities for tuning binding, chemical properties and display.[8,9] Rather than covalent bonding, prevalent in synthetic linkers, such as silanes, thiols, and phosphanates,[10,11] short peptides bind through weak forces at multiple positions at the peptide/solid interface with the advantage of assembling and functioning in aqueous solutions.[12,13] As biocompatible coatings, therefore, solid-binding peptides are particularly well suited for applications in medical and biological fields because they are produced and function under biological conditions, and have not shown any toxicity in cell culture studies.[7,14,15]

Graphite, graphene and carbon nano-tubes (CNT) have been employed for both biomedical and nanotechnological applications due to their anti-microbial activity,[16] high conductivity, optical transparency, and surface sensitive properties.[17-20] These graphitic materials have been employed for biosensing applications in particular due to their excellent electronic properties, resulting from delocalized π bonds on the surface.[21-23] A number of functionalization routes through covalent bonding, i.e. the introduction of carboxylic groups, have been employed to control the interface with graphitic materials.[24,25] In parallel, however, to preserve the intrinsic properties of these materials, methods of non-covalent functionalization via π-π stacking using aromatic chemistry have been used to assemble functional molecules.[26,27]

A non-invasive approach using peptides could present a biocompatible alternative to controlling the surface properties of graphite. Here, we demonstrate precise control over the hydropathy of graphite through single-step self-assembly of peptides and their engineered mutants. The graphite binding peptides are modular and can be designed to self-assemble into stable monomolecular films on graphite, exposing predictable surface chemistry through the display of specific amino acids. The highly oriented pyrolytic graphite (HOPG) has an atomically flat surface which is ideally suited to demonstrate, using atomic force microscopy and contact angle measurements, the display of tailored chemistries on graphite through controlling the binding and assembly of the designed peptides, in the absence of roughness effects.[28]

Figure 7:
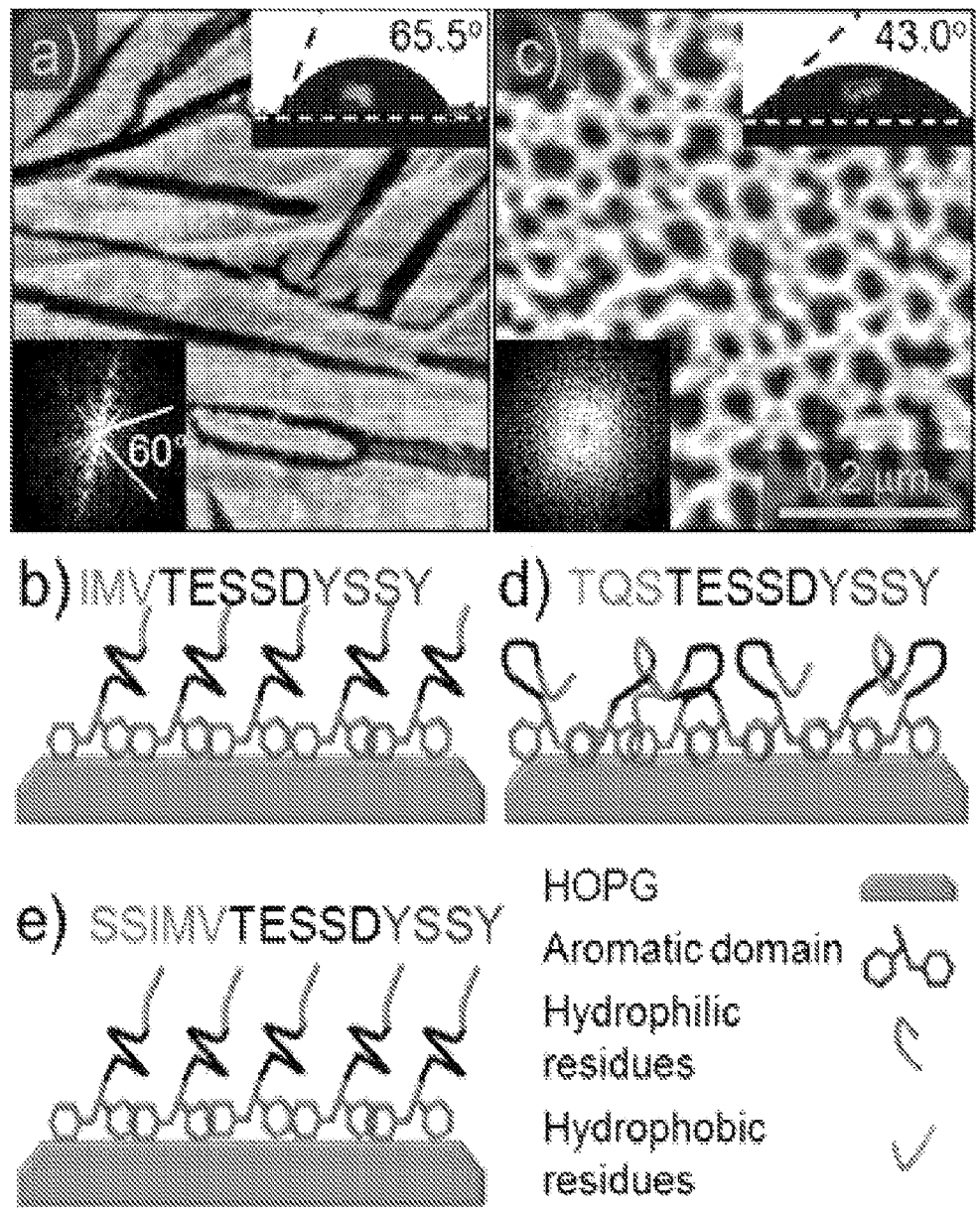
FIG. 7. (a) Atomic force microscopy (AFM) image of the peptide GrBP5-WT on graphite with (b) Corresponding sequence (N- to C-terminus) and its schematics. (c) AFM image of GrBP5-Phil mutant on graphite with (d) Corresponding sequence and its schematics. Insets show the contact angles and the Fast Fourier Transforms (FFT) of the images that highlights the presence (spots or lines) or the lack of ordering (featureless). Schematics in (b), (d) and (e) illustrate the hypothetical conformation of the peptides within the film which produce the observed contact angles, binding through the aromatic region, and displaying either the ordered hydrophobic or disordered hydrophilic residues.

The dodecapeptide used in this work, GrBP5-WT (Sequence: IMVTESSDYSSY (SEQ ID NO: 5), affinity constant: $K_a$=3.78 µM$^{-1}$)[36] is unique among graphite- and CNT-binding peptide sequences, as it forms long-range ordered, uniform, and crystallographic molecular nanostructures on HOPG (FIG. 7a), which can be controlled through sequence mutation. The abbreviation WT denotes the original, unmodified, sequence of the peptide, which we call "wild type". We have found that the self-assembly of GrBP5-WT arises from a combination of binding through the aromatic rings of tyrosine residues at the C-terminus, and ordering through intermolecular interactions among hydrophobic tail domains (FIG. 7b). The formation of ordered morphology, apparent from FIG. 7a, and evidenced by the FFT, seems to be a result of both lattice matching with the underlying HOPG, which results in six-fold symmetry, and assembly conditions, such as concentration, which, along with intermolecular interactions, determines the size of features.[36] Replacing the hydrophobic residues at the N-terminus with hydrophilic ones, therefore, inhibits formation of the ordered phase (OP) and causes the peptide film to remain in the amorphous phase (AP) because of the lack of intermolecular interactions (FIGS. 7c and 7d). Furthermore, it was found that an ordered film of GrBP5-WT displays hydrophobic property on the graphite surface (FIG. 7a). These findings motivated us to hypothesize that ordered structures of GrBP5-WT leave the N-terminus amino-acids free for rational control of intermolecular interactions as well as further functionalization, and predictable display of specific chemistry. Based on this hypothesis, we aim here to demonstrate that the wettability of graphite can be controlled by varying the N-terminal sequence of the GrBP5-WT peptide. Specifically, we design two mutants (i.e., variants of the WT peptide) which exhibit hydrophobic or hydrophilic properties while retaining their ordered structure and predictable display capability. The hydrophobic mutant GrBP5-Phob is produced by substitution of the three N-terminal amino-acids of the wild type with a more hydrophobic LIA sequence (Table 1). The hydrophilic hybrid mutant SS-GrBP5 (FIG. 7e, Table 1), on the other hand, is designed by the addition of two hydrophilic serine residues to the N-terminus of the wild type peptide.

TABLE 1

Peptide sequences, weights, and hydropathy indices

| Peptide | Sequence | Mol. Mass | G.R.A.V.Y.[a] |
|---|---|---|---|
| GrBP5-WT | IMVTESSDYSSY (SEQ ID NO: 5) | 1381.4 | −0.242 |
| GrBP5-Phob | LIATESSDYSSY (SEQ ID NO: 17) | 1335.3 | −0.283 |
| GrBP5-Phil | TQSTESSDYSSY (SEQ ID NO: 30) | 1354.3 | −1.542 |
| SS-GrBP5 | SSIMVTESSDYSSY (SEQ ID NO: 16) | 1555.6 | −0.321 |

[a]Grand average hydropathy index

To characterize the wettability of the peptide-functionalized graphite surfaces, freshly prepared HOPG substrates were incubated in 1 μM aqueous peptide solutions (Table 1) for several time intervals, resulting in samples of peptide films on the graphite surface that range from sparse to near-confluent monolayers. The wettability of these films was quantified by contact angle goniometry, and the coverage was determined by atomic force microscopy (AFM) (See supporting information for detailed procedures). The plot of coverage vs. contact angle values exhibits a coinciding linear correlation below 70% coverage for all peptides (FIG. 2a). Above 70%, they also display linear relationships but with slopes that vary greatly with sequence (FIG. 8a).

To quantitatively compare the wettability of different peptides, we applied Cassie's Law,[37] which describes the contact angle, cos θ, of a macroscopic droplet on a chemically heterogeneous surface via the relation: $\cos \theta = \phi_g \cos \theta_g + \phi_p \cos \theta_p$ ($\phi_{g,p}$: coverage and $\theta_{g,p}$: contact angle for graphite and peptides, respectively). By fitting this equation to the experimental data, effective contact angles are extrapolated for fully covered surfaces of each peptide, $\theta_p$, (Table 2). Between 0 and 70% coverage, all peptides display little difference in $\theta_p$ (about 28°±4°). The $\theta_p$ values above 70% coverage of GrBP5-WT and GrBP5-Phob, however, are drastically different.

TABLE 2

Projected contact angles of a theoretical 100% peptide-covered sample for each peptide and phase, and corresponding measured roughness values.

| Peptide | θ AP (0≤70% coverage) | AP Roug./ nm | θ OP (>70% coverage) | OP Rough./ nm |
|---|---|---|---|---|
| GrBP5-WT | 30.0° ± 2.5° | 0.92 | 64.0° ± 1.0° | 0.39 |
| GrBP5-Phob | 23.0° ± 11.5° | 0.53 | 87.0° ± 0.5° | 0.36 |
| GrBP5-Phil | 32.0° ± 12.0° | 0.72 | No Order | No Order |

TABLE 2-continued

Projected contact angles of a theoretical 100% peptide-covered sample for each peptide and phase, and corresponding measured roughness values.

| Peptide | θ AP (0≤70% coverage) | AP Roug./ nm | θ OP (>70% coverage) | OP Rough./ nm |
|---|---|---|---|---|
| SS-GrBP5 | 25.5° ± 5.5° | 1.20 | 36.0° ± 1.0° | 0.34 |

These results are also reflected in the corresponding AFM experiments (FIG. 8b) where peptides are observed to form one of the two phases on the surface: either a long-range ordered phase (OP) at high coverage, exhibiting six-fold symmetry, or a sparse amorphous phase (AP) at low coverage without recognizable crystallographic symmetry in the formed film. There is an effective transition threshold from AP to OP at about 70% coverage. Ordered peptide films also exhibit more uniform and narrow distributions of thickness as measured by AFM, which is apparent from the average roughness values in Table 2. Only GrBP5-Phil, with no hydrophobic tail, remained disordered under all incubation conditions.

The similarity in the $\theta_p$ contact angles of all peptides in the AP below 70% coverage may indicate that the exposed amino acid domain is conserved among mutants and is predominantly hydrophilic. This is most likely due to the random alignment of peptides displaying polar residue- and a serine-rich domain in the central portion of the peptide (Table 1). Conversely, the contrast between the contact angle contribution of GrBP5-WT (64.0°) and GrBP5-Phob (87.0°) in the OP implies that the three amino-acids at the N-terminus are uniformly exposed towards the solution, since they are the only ones that differ between the two peptide sequences.

Figure 8:
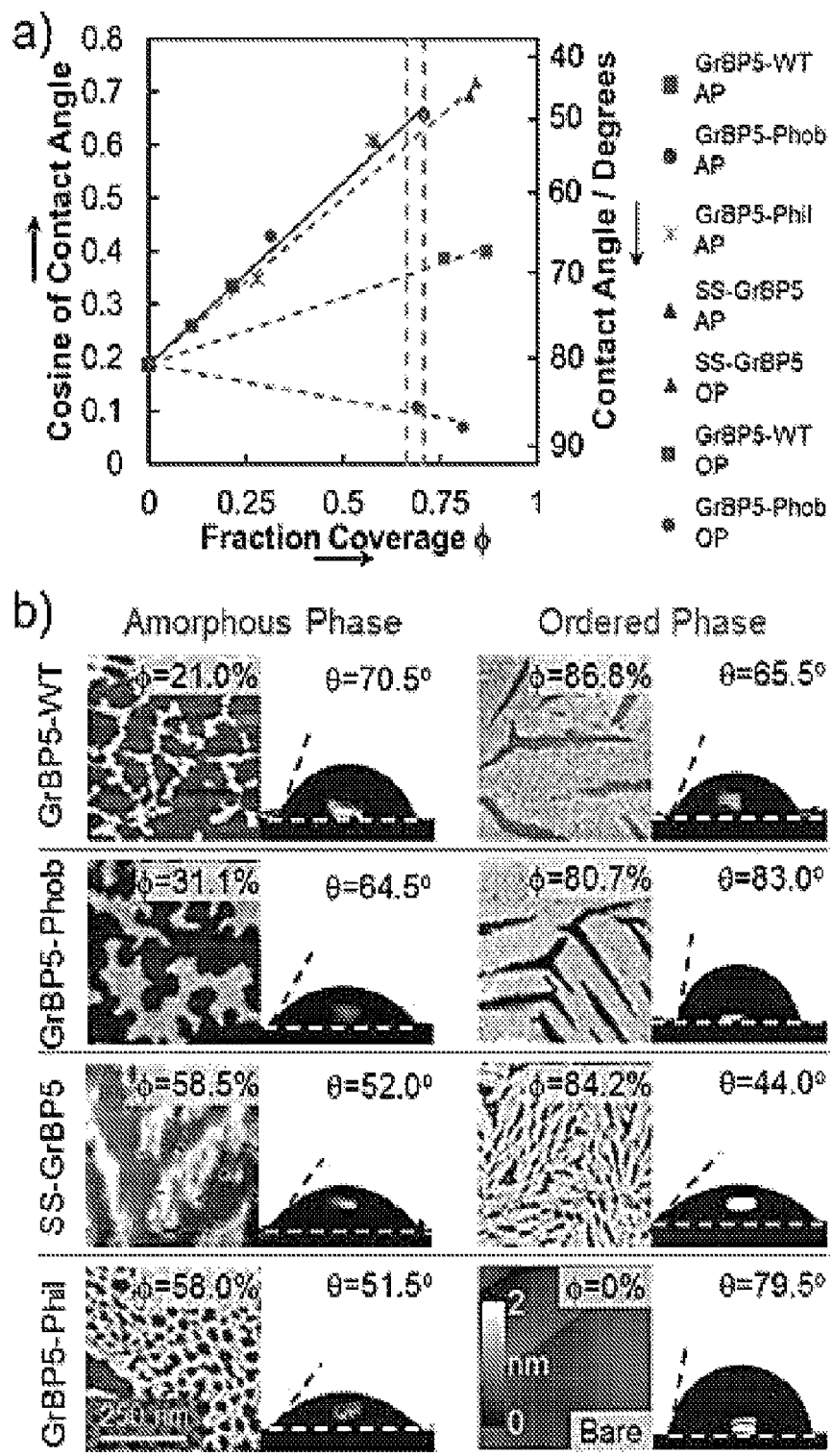
FIG. 8. (a) Plot of contact angle θ versus fraction coverage φ of peptides on graphite. The blue lines indicate linear trends above 70% coverage; the red line represents the linear trend for all peptides below 70% coverage. The change in slope between ordered (OP) and amorphous (AP) trend lines indicates the change in the displayed chemistry. The grey lines indicate the AP to OP transition region (b) AFM images showing typical examples of AP and OP structures, as well as the corresponding coverage and contact angles.

Remarkably, both the binding and ordering capabilities of the peptides were retained in the SS-GrBP5 mutant (FIG. 8). Even in the ordered state, the SS-GrBP5 mutant has a contact angle contribution close to that of the AP (Table 2), indicating that hydrophilic residues are displayed in both of its phases of the peptide films. The difference in the contribution of the two phases, about 9°, confirms a transition from AP to OP, seen clearly in FIG. 8, on surfaces functionalized by SS-GrBP5.

Figure 9:
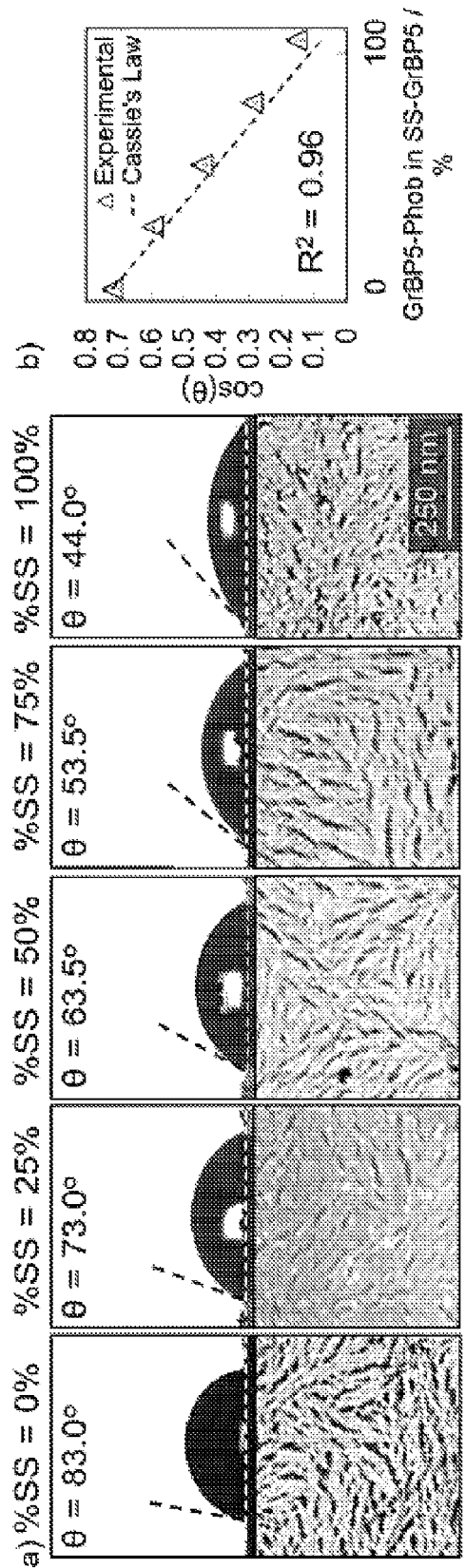
FIG. 9. (a) Contact angles and AFM images of ordered co-assembled peptide monolayer containing SS-GrBP5 and GrBP5-Phob. Coverage for all surfaces is greater than 80%. (b) Plot of cosine of the contact angle versus % of GrBP5-Phob mixed in SS-GrBP5 shows agreement with the trend predicted by Cassie's Law.

The uniform display of N-terminal residues by self-assembling peptides forming confluent ordered films on graphite results in a wide range of wettability values. It is, therefore, plausible to further tune the contact angle through a simultaneous high coverage, single-step, co-assembly of peptides with varying wettability. We chose the two mutants that retained their assembly capabilities and exhibited the widest range of $\theta_p$, i.e., 36.0° and 87.0°, to achieve precise control over the wettability of graphite surfaces at a constant coverage. For this, 1 μM aqueous solutions of GrBP5-Phob and the SS-GrBP5 were mixed in appropriate proportions and incubated on HOPG for 3 hours, assuming the complete solubility of the two peptides solutions. The AFM images and contact angle versus fraction coverage dependencies are shown in FIG. 9. While the peptide coverage of these films remained at around 80%, the contact angles of functionalized surfaces varied from 44.0° to 83.0°. The linear nature of the plot and the uniformity of the AFM images indicate that GrBP5-Phob is homogeneously dispersed within the film formed by SS-GrBP5. Moreover, by adding a third term to Cassie's equation, we were able to predict the cosine of the contact angle resulting from a given mixed monolayer based on the $\theta_p$ values from Table 2 (FIG. 9). The agreement between the prediction and the data is quite close (Coefficient of determination, based on sum of squares of error is $R^2=0.96$). The small discrepancy in the predicted and measured values could result from a slight variation in the binding affinities of the two peptides, whereby SS-GrBP5 is present on the surface in slightly higher proportion than the GrBP5-Phob under the same incubation conditions.

Controlling surface wettability through self-assembled peptides provides a novel approach for engineering biomolecule/graphite interfaces. Mixed self-assembled peptide films prepared in water can be used, for example, in the development of bio-sensors with optimized chemical properties and biocompatibility. The intermolecular interactions among different peptides in the ordered phase can be tailored to form novel, complex nanostructures with spatially controlled structural and biofunctional properties. Furthermore, the ease with which displayed amino acid domains are introduced into short peptides permits development of biomolecular constructs with designer proteins,[38,39] peptide domains,[13,40] and chemical groups[5,7] to further control functionality of graphitic surfaces. This inherently biocompatible and non-covalent molecular immobilization approach is suitable for a variety of potential applications of graphite, and graphitic materials, in nanobiotechnology.

Supporting Information

1) Normalization of peptide coverage and application Cassie's Law. Young's equation indicates that the surface energy varies linearly with the cosine of the contact angle:

$$\cos\theta = \frac{\gamma_{SV} - \gamma_{SL}}{\gamma_{LV}}$$

It is possible to model the contact angle of a more complex surface by linear addition of the weighted contributions of their constituents, as is shown by Cassie's law.

$$\cos\theta = \phi_1 \cos\theta_1 + \phi_2 \cos\theta_2$$

where $\phi_n$ and $\theta_n$ are the coverage and surface energy associated with each constituent respectively, it is possible, therefore, to normalize the contact angles with respect to coverage of each peptide, and to extrapolate the hydropathy of a theoretical fully covered surface, as long as the two displayed phases have uniform and distinct properties and no superhydrophobic effect is taking place.

Samples of varying coverage were prepared to contain either the ordered or disordered phases as determined by AFM and subjected to contact angle measurement. The relationship between the coverage and cosine of the contact angle was linear over the range of coverages produced, indicating that no superhydrophobicity was occurring, justifying the assumptions of Cassie's law.

2) Liquid surface tension data. Interfacial tension was calculated from at least 3 pendant drop shapes. The results indicated that there was no significant difference in the interfacial energies of various peptide solutions and that the contact angle measurements, therefore, could be compared directly.

REFERENCES FOR EXAMPLE 2

1. Chen, D.; Wang, G.; Li, J. H. Interfacial bioelectrochemistry: Fabrication, properties and applications of functional nanostructured biointerfaces. *J. Phys. Chem. C* 2007, 111, 2351-2367.
2. Nel, A. E.; Madler, L.; Velegol, D.; Xia, T.; Hoek, E. M. V.; Somasundaran, P.; Klaessig, F.; Castranova, V.; Thompson, M. Understanding Biophysicochemical Interactions at the Nano-bio Interface. *Nat. Mater.* 2009, 8, 543-557.
3. Cha, T.; Guo, A.; Zhu, X. Y. Enzymatic Activity on a Chip: The Critical Role of Protein Orientation. *Proteomics* 2005, 5, 416-419.
4. Tamerler, C.; Khatayevich, D.; Gungormus, M.; Kacar, T.; Oren, E. E.; Hnilova, M.; Sarikaya, M. Molecular Biomimetics: GEPI-Based Biological Routes to Technology. *Biopolymers* 2010, 94, 78-94.
5. Shiba, K. Exploitation of Peptide Motif Sequences and their Use in Nanobiotechnology. *Curr. Opin. in Biotechnol.* 2010, 21, 412-425.
6. Peelle, B. R.; Krauland, E. M.; Wittrup, K. D.; Belcher, A. M. Design Criteria for Engineering Inorganic Material-Specific Peptides. *Langmuir* 2005, 21, 6929-6933.
7. Meyers, S. R.; Khoo, X. J.; Huang, X.; Walsh, E. B.; Grinstaff, M. W.; Kenan, D. J. The Development of Peptide-Based Interfacial Biomaterials for Generating Biological Functionality on the Surface of Bioinert Materials. *Biomaterials* 2009, 30, 277-286.
8. Sarikaya, M.; Tamerler, C.; Jen, A. K. Y.; Schulten, K.; Baneyx, F. Molecular Biomimetics: Nanotechnology Through Biology. *Nat. Mater.* 2003, 2, 577-585.
9. Wei, J. H.; Kacar, T.; Tamerler, C.; Sarikaya, M.; Ginger, D. S, Nanopatterning Peptides as Bifunctional Inks for Templated Assembly. *Small* 2009, 5, 689-693.
10. Ulman, A. Formation and Structure of Self-Assembled Monolayers. *Chem. Rev.* 1996, 96, 1533-1554.
11. Gawalt, E. S; Avaltroni, M. J.; Koch, N.; Schwartz, J. Self-Assembly and Bonding of Alkanephosphonic Acids on the Native Oxide Surface of Titanium. *Langmuir* 2001, 17, 5736-5738.
12. Hnilova, M.; Oren, O. O.; Seker, U. O. S.; Wilson, B. R.; Collino, S.; Evans, J. S.; Tamerler, C.; Sarikaya, M. Effect of Molecular Conformations on the Adsorption Behavior of Gold-Binding Peptides. *Langmuir* 2008, 24, 12440-12445.
13. Tamerler, C.; Sarikaya, M. Molecular Biomimetics: Nanotechnology and Bionanotechnology Using Genetically Engineered Peptides. *Phil. Trans. R. S. A* 2009, 367 1705-1726.
14. Khatayevich, D.; Gungormus, M.; Yazici, H.; So, C.; Cetinel, S.; Ma, H.; Jen, A.; Tamerler, C.; Sarikaya, M. Biofunctionalization of Materials for Implants Using Engineered Peptides. *Acta Biomater.* 2010, 6, 4634-4641.
15. Yuca, E.; Karatas, A. Y.; Seker, U. O, S.; Gungormus, M.; Dinler-Doganay, G.; Sarikaya, M.; Tamerler, C. In Vitro Labeling of Hydroxyapatite Minerals by an Engineered Protein. *Biotechnol. Bioeng.* 2011, 108, 1021-1030.
16. Hu, W. B.; Peng, C.; Luo, W. J.; Lv, M.; Li, X. M.; Li, D.; Huang, Q.; Fan, C. H. Graphene-Based Antibacterial Paper. *ACS Nano* 2010, 4, 4317-4323.
17. Balandin, A. A.; Ghosh, S.; Bao, W. Z.; Calizo, I.; Teweldebrhan, D.; Miao, F.; Lau, C. N. Superior Thermal Conductivity of Single-Layer Graphene. *Nano Lett.* 2008, 8, 902-907.
18. Castro Neto, A. H.; Guinea, F.; Peres, N. M. R.; Novoselov, K. S.; Geim, A. K. The Electronic Properties of Graphene. *Rev. Mod. Phys.* 3 2009, 81, 109-162.
19. Dai, H. J. Carbon Nanotubes: Synthesis, Integration, and Properties. *Acc. Chem. Res.* 2002, 35, 1035-1044.
20. Novoselov, K. S.; Geim, A. K.; Morozov, S. V.; Jiang, D.; Zhang, Y.; Dubonos, S. V.; Grigorieva, I. V.; Firsov, A.

A. Electric Field Effect in Atomically Thin Carbon Films. *Science* 2004, 306, 666-669.
21. Gorton, L. *Biosensors and modern biospecific analytical techniques*; Elsevier Science: Amsterdam, Netherlands, 2005.
22. Du, D.; Zou, Z. X.; Shin, Y. S.; Wang, J.; Wu, H.; Engelhard, M. H.; Liu, J.; Aksay, I. A.; Lin, Y. H. Sensitive Immunosensor for Cancer Biomarker Based on Dual Signal Amplification Strategy of Graphene Sheets and Multienzyme Functionalized Carbon Nanospheres. *Anal. Chem.* 2010, 82, 2989-2995.
23. Lin, Y. H.; Lu, F.; Tu, Y.; Ren, Z. F. Glucose Biosensors Based on Carbon Nanotube Nanoelectrode Ensembles. *Nano Lett.* 2004, 4, 191-195.
24. Li, D.; Muller, M. B.; Gilje, S.; Kaner, R. B.; Wallace, G. G. Processable Aqueous Dispersions of Graphene Nanosheets. *Nat. Nanotechnol.* 2008, 3, 101-105.
25. Niyogi, S.; Bekyarova, E.; Itkis, M. E.; McWilliams, J. L.; Hamon, M. A.; Haddon, R. C. Solution Properties of Graphite and Graphene. *J. Am. Chem. Soc.* 2006, 128, 7720-7721.
26. Choi, E. Y.; Han, T. H.; Hong, J. H.; Kim, J. E.; Lee, S. H.; Kim, H. W.; Kim, S. O, Noncovalent Functionalization of Graphene with End-Functional Polymers. *J. Mater. Chem.* 2010, 20, 1907-1912.
27. Ghosh, A.; Rao, K. V.; Voggu, R.; George, S. J. Non-Covalent Functionalization, Solubilization of Graphene and Single-Walled Carbon Nanotubes with Aromatic Donor and Acceptor Molecules. *Chem. Phys. Lett.* 2010, 488, 198-201.
28. Yu, X.; Wang, Z. Q.; Jiang, Y. G.; Zhang, X. Surface Gradient Material: From Superhydrophobicity to Superhydrophilicity. *Langmuir* 2006, 22, 4483-4486.
29. Yang, H.; Fung, S.; Sun, W.; Mikkelsen, S.; Pritzker, M.; Chen, P. Ionic-Complementary Peptide-Modified Highly Ordered Pyrolytic Graphite Electrode for Biosensor Application. *Biotenol. Prog.* 2008, 24, 964-971.
30. Cui, Y.; Kim, S. N.; Jones, S. E.; Wissler, L. L.; Naik, R. R.; McAlpine, M. C. Chemical Functionalization of Graphene Enabled by Phage Displayed Peptides. *Nano Lett.* 2010, 10, 4559-4565.
31. Wang, Q. H.; Hersam, M. C. Room-Temperature Molecular-Resolution Characterization of Self-Assembled Organic Monolayers on Epitaxial Graphene. *Nat. Chem.* 2009, 1, 206-211.
32. Kim, S. N.; Kuang, Z.; Slocik, J. M.; Jones, S. E.; Cui, Y.; Farmer, B. L.; McAlpine, M. C.; Naik, R. R. Preferential Binding of Peptides to Graphene Edges and Planes. *J. Am. Chem. Soc.* 2011, 133, 14480-14483.
33. Kase, D.; Kulp, J. L.; Yudasaka, M.; Evans, J. S.; Iijima, S.; Shiba, K. Affinity Selection of Peptide Phage Libraries Against Single-Wall Carbon Nanohorns Identifies a Peptide Aptamer with Conformational Variability. *Langmuir* 2004, 20, 8939-8941.
34. Tomasio, S. M.; Walsh, T. R. Modeling the Binding Affinity of Peptides for Graphitic Surfaces. Influences of Aromatic Content and Interfacial Shape. *J. Phys. Chem. C* 2009, 113, 8778-8785.
35. Han, T. H.; Lee, W. J.; Lee, D. H., Kim, J. E., Choi, E., Kim, S. O. Peptide/Graphene Hybrid Assembly into Core/Shell Nanowires. *Adv. Mater.* 2010, 22, 2060-2064.
36. So, C. R.; Hayamizu, Y.; Yazici, H.; Gresswell, C.; Khatayevich, D.; Tamerler, C.; Sarikaya M. Controlling Self-Assembly of Engineered Peptides on Graphite by Rational Mutation. *ACS Nano* 2012, 6, 1648-1656
37. Cassie, A. B. D.; Baxter, S. Wettability of Porous Surfaces. *Trans. Faraday Soc.* 1944, 40, 0546-0550.
38. Kacar, T.; Zin. M. T.; So, C. R.; Wilson, B. R.; Ma, H.; Gul-Karaguler, N.; Jen, A. K-Y.; Sarikaya, M.; Tamerler, C. Directed Self-Immobilization of Alkaline Phosphatase on Micro-Patterned Substrates Via Genetically Fused Metal-Binding Peptide. *Biotechnol. Bioeng.* 2009, 103, 696-705.
39. Hall Sedlak, R.; Hnilova, M.; Gachelet, E.; Przybylal, L.; Dranow, D.; Gonen, T.; Sarikaya, M.; Tamerler, C.; Traxler, B. An Engineered DNA-Binding Protein Self-assembles Metallic Nanostructures. *Chembiochem.* 2010, 11, 2108-2112.
40. Hnilova, M.; Khatayevich, D.; Carlson, A.; Oren, E. E.; Gresswell, C.;, S. Zheng; Ohuchi, F.; Sarikaya, M.; Tamerler, C. Single-Step Fabrication of Patterned Gold Film Array by an Engineered Multi-Functional Peptide. *J. Colloid Interface Sci.* 2012, 365, 97-102.

Example 3

Spatially Modulated Biomolecular Doping of Single-Layer Graphene by Self-Assembled Peptide Nanostructures Abstract We show that two-dimensional supramolecular patterns of engineered dodecapeptides modify the electrical conductivity of graphene via biomolecular doping. Observed conductivity of graphene field effect transistors covered by self-assembled peptides indicates a formation of electronic junctions. Peptides also modify the carrier mobility in the graphene. While ordered peptides maintain the carrier mobility of graphene, randomly adsorbed peptides significantly reduce it. Engineered peptides have significant promise as novel molecular tools to link electronics of single layer atomic materials with biology.

Introduction

Self-assembly of biomolecules on nanomaterials potentially offers a novel bottom-up technology to form bio-nano hybrid systems toward development of bio-nanoelectronic devices[5,6]. In particular, proteins are auspicious building blocks for the assembly of hierarchical structures due to their diversity of conformation and chemistry based on simple amino acid sequences. Graphene can be an ideal platform for the self-assembly because of the atomically flat two-dimensional (2D) surface and rich physical properties, e.g., linear energy dispersion[7,8], high carrier mobility[9], and high mechanical strength[10]. Recent studies on graphene electronics have been focused on the surface functionalization modifying electronic characteristics of graphene directly through interactions with adsorbed molecules, i.e. chemical doping[11,12]. Although not yet explored, doping strategies via molecular self-assembly may be extended to proteins having both characteristics of the doping and their spatial control by using their exquisite nanostructures. Even more intriguing is the ability to control interfaces between biomolecule and the single layer atomic material via the molecular recognition of graphene by engineered peptides. Interface control is the key to develop novel bioelectronic sensors with high sensitivity and intricate spatial configurations at the nanoscale. For design of the bio/nano interfaces, one needs to probe electrical interactions that arise between the peptides and graphene, where the conformation and chemistry of the peptides are expected to play the most significant role.

Peptides can be a versatile molecular tool to address the challenge of self-assembly and molecular doping on graphene as they are simpler (shorter in size and simpler in chemistry) than natural proteins, and yet they have a wide-range of chemistry and molecular conformations inherent in their amino acid sequences. Engineered peptides have been shown to self-assemble into supramolecular structures on atomically flat surfaces, such as on mica, Au(111) and graphite[1-4]. These peptides exhibit long-range ordered structures template and directed by the atomic lattice of the underlying surfaces, indicating that peptides have a potential to directly functionalize graphene via molecular recognition to solid surfaces. Similar to the epitaxial crystal growth[16], peptides forms ordered nanostructures on solid surfaces through a series of surface phenomena: binding, diffusion, and ordering[4]. Unlike randomly immobilized biomolecules on solid surfaces, long-range ordered peptides preserve the sufficient energy balance essential among their binding, diffusion, and conformational changes. Recently, peptides have been demonstrated to modify graphene conductivity, although they do not form ordered structures on a graphene[17]. Uniform alignment and conformations of peptides in their ordered structures could be the key to controllably modify electrical properties of bio/nano interfaces.

In this work, we use to form supramolecular ordered structures and investigate its effect on the electronic properties of the graphene. We demonstrate that dodecapeptides of the present invention self-assemble into 2D supramolecular network modifying electric properties of graphene that are correlated to their morphology on the graphene. The abrupt boundaries of ordered peptide supramolecules create electronic junctions via spatial biomolecular doping, manifested as a self-assembled electronic network. We also utilize GrBP5 mutants without the ability to form ordered structures on the graphene, as control experiments. While ordered peptides of GrBP5 do not change the mobility of graphene, randomly absorbed mutant peptides significantly reduce it. The biomolecular doping of graphene, spatially defined by peptide supramolecular nanostructures, represents the first step in integrating biology with nano-electronics towards realizing fully self-assembled bio-nanoelectronics systems.

Results

To study the self-assembly of GrBP5 on graphene, mechanically exfoliated graphene are incubated with peptides in degased DI water (500 nM for 20 minutes, Supplementary Method). After the incubation, the sample is quickly dried by nitrogen blow. Atomic force microscopy (AFM) imaging revealed that peptides self-assemble into ordered structures, "supramolecular nanowires", (FIG. 10a) with six-fold symmetry on single-layer graphene (FIG. 10b). The longitudinal length of nanowires ranges up to micrometers, while the observed average thickness is 1.10 nm with a minimal width of about 12.00 nm (FIGS. 10c and 10d). Since the length of the straightened (non-folded) GrBP5 molecule is about 3 nm, the observations suggest that the peptides have folded into packed conformation forming a monomolecular thickness throughout their self-assembled nanostructures, similar to that seen with graphite. It is also worth to mention that there are no peptides observed on $SiO_2$, indicating that peptides bind specifically to the graphene.

Figure 11:
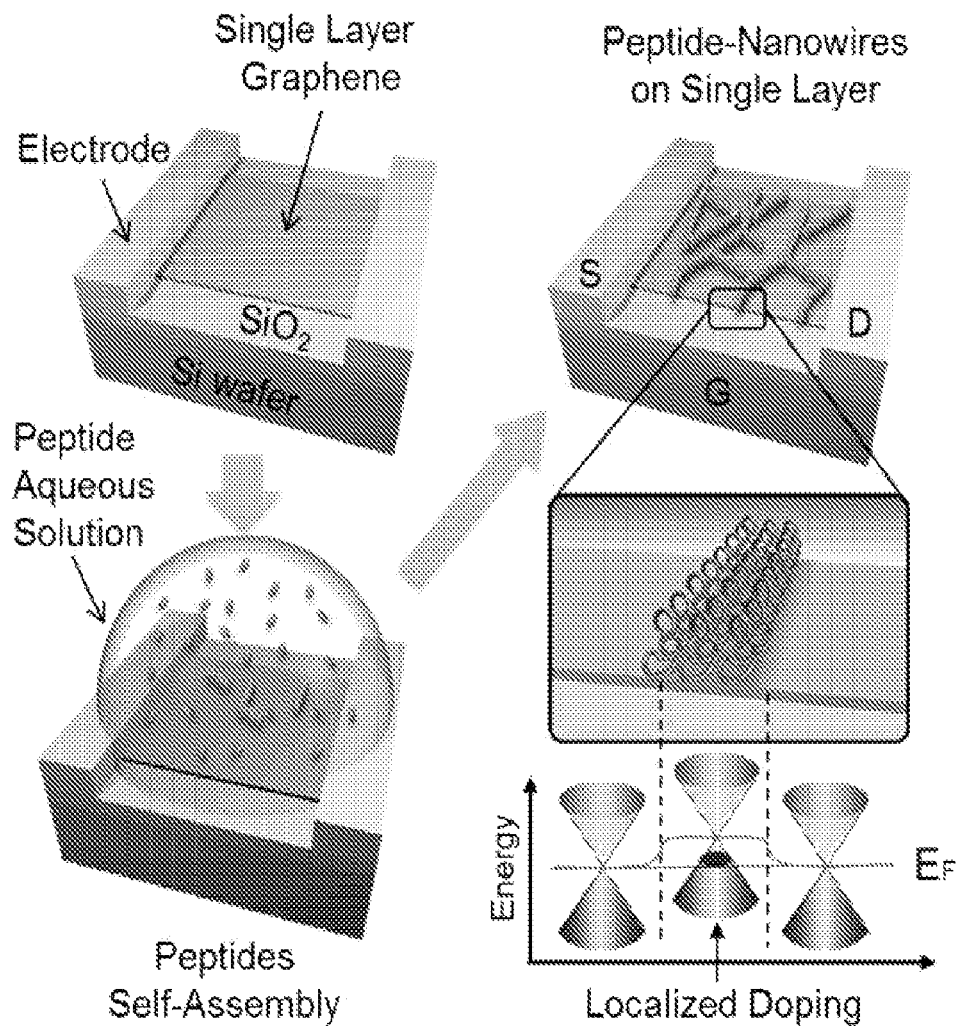
FIG. 11. Schematics of supramolecular peptides on a graphene field effect transistor (GFET). A mechanically exfoliated single layer graphene on 300 nm-thick $SiO_2$ has a micro-soldered source (S) and drain (D) contacts, and backgate (G) of highly-doped Si. A droplet of peptide solution is placed on the GFET, which is followed by peptide self-assembly into supramolecular structures on the surface. The FET is then gently dried by Nitrogen gas. The energy profile illustrates our hypothesis that peptide nanowires modify local electronic states of the underlying graphene, forming molecular electronic junctions.

Peptide self-assembly may provide a novel way to modify electrical properties of graphene, where ordered peptides locally dope graphene with charge carriers. To verify this hypothesis, investigation was geared towards correlating the assembled morphologies of the peptides and the measured conductivities of the graphene field effect transistor (GFET). As depicted in FIG. 11, special care was taken for reliable characterization of graphene conductivity induced by the ordered peptides. First, GFETs are fabricated by direct soldering of indium contacts to an exfoliated graphene on a $SiO_2$/Si wafer[19]. We employed this resist-free process instead of a conventional lithography, because of the difficulty to completely remove residues from the resists that disrupt peptide self-assembly into long-range ordered structures. Second, we directly place a droplet of peptide aqueous solution on GFETs to prevent contamination. In the solution process, water molecules are known to significantly change the conductivity of the graphene on $SiO_2$ in the presence of oxygen[20]. To prevent the water effect, we utilize deoxygenated DI water prepared by bubbling with nitrogen or argon gases (Supplementary Method). All the conductivity measurements, therefore, have been performed in argon atmosphere to eliminate the water effect.

In this work, we characterized conductivities of more than ten GFETs before and after the peptide incubation. Each GFET has various morphologies of peptides controlled by the incubation time and concentration of peptide solutions. AFM images exhibit a gradual growth of supramolecular peptides from disordered islands to nanowires with increasing coverage (FIG. 12a), and conductivities of GFETs are clearly modulated by peptides (FIG. 12b). The gate-voltage was cyclically swept over a range from 0V to maximum, from maximum to minimum, and back to 0V. All as-prepared GFETs have symmetric conductivity curves with a charge neutral point (CNP) at around 20V, i.e., the voltage with minimum conductivity. GFETs with peptide coverage of 26, 40, and 48% display two distinct dips in their conductivities. As coverage increases, the left-dip gradually disappears and the right-dip becomes dominant. At 88% coverage, the CNP shifts up to +85V, indicating significant hole doping by peptides. The observation of two dips is unique in our supramolecular peptides on graphene compared with previous reports on the chemical doping of graphene[21], where a CNP monotonically shifts without displaying another dip. In these published cases, potassium atoms or organic molecules randomly deposit on graphene surface. On the other hand, two minima in conductivity have also been observed in GFETs with micro-patterned chemical dopants[22,23] where graphene is selectively covered partially by dopants and other regions remain uncovered. Based on these previous findings, our observations indicate that the two conductivity minima, on the left and the right, can be attributed to uncovered and peptide-covered regions in graphene, respectively. This result suggests formation of electronic junctions in graphene, where charge carriers of holes accumulate underneath peptides via biomolecular doping. The first time observation that there are two minima (i.e., electronic junction) in graphene functionalized by self-assembled peptides is highly significant as they form without the use of a top-down technique such as lithography shown in the literature. Additionally, the conductivity shows no hysteresis over the cyclic sweep of the gate voltage, which indicates that: (1) Peptides are rigidly immobilized and stable even under the electric field, and (2) In our measurement conditions, water effects were not observed, which usually appears as a hysteresis in the cyclic measurement of the conductivity.

Figure 12:
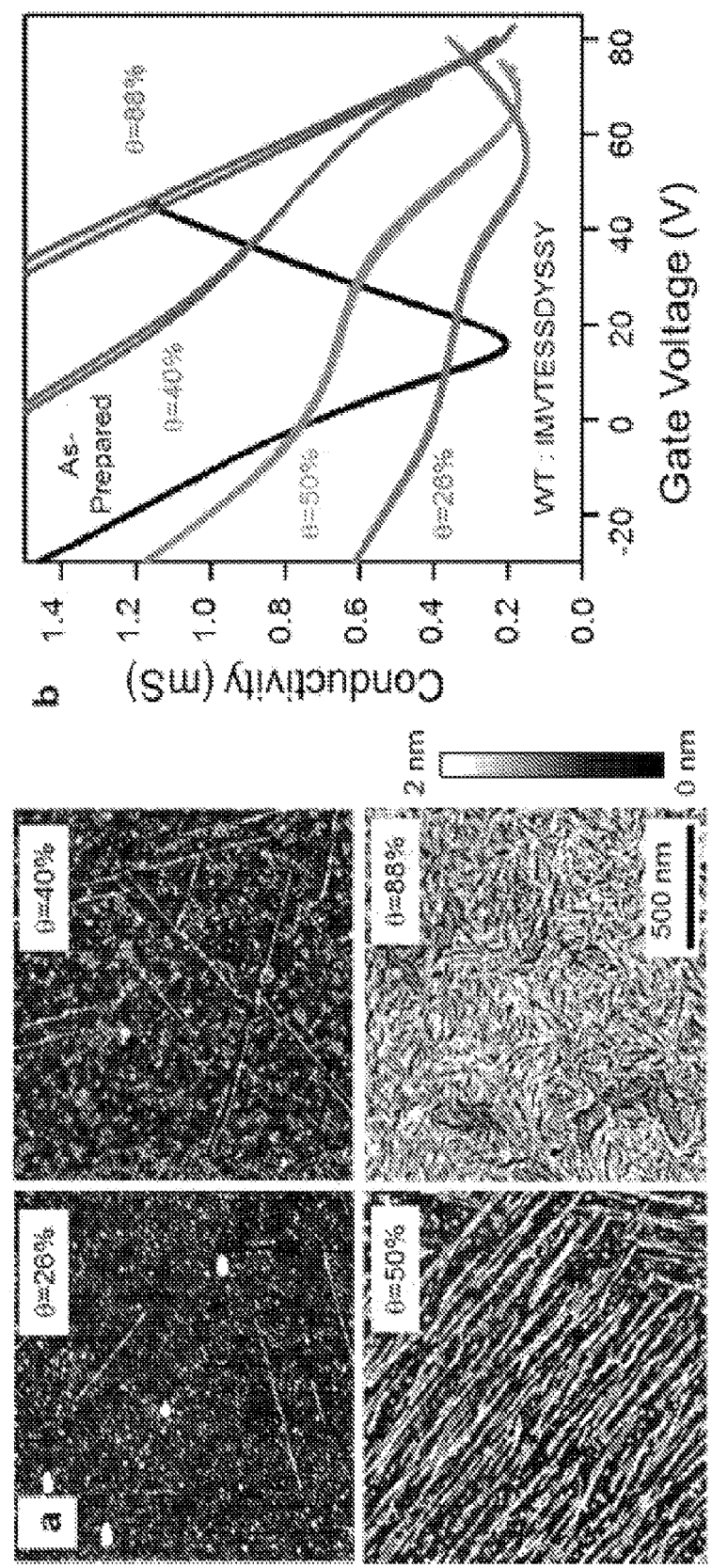
FIG. 12. GrBP5:WT with ordered nanostructures on graphene FETs and their corresponding conductivity characteristics. (a) AFM images of peptides on GFETs with various peptide coverages from 26% to 88%, and corresponding color scale. As the coverage increases, peptides form ordered structures "peptide nanowires". (b) The conductivity vs. backgate voltage curves for an as-prepared GFET (black) and graphene FETs with different peptide coverages corresponding to the AFM images in (a): purple, 26%; blue, 40%; green, 50%; red, 88%.
Figure 13:
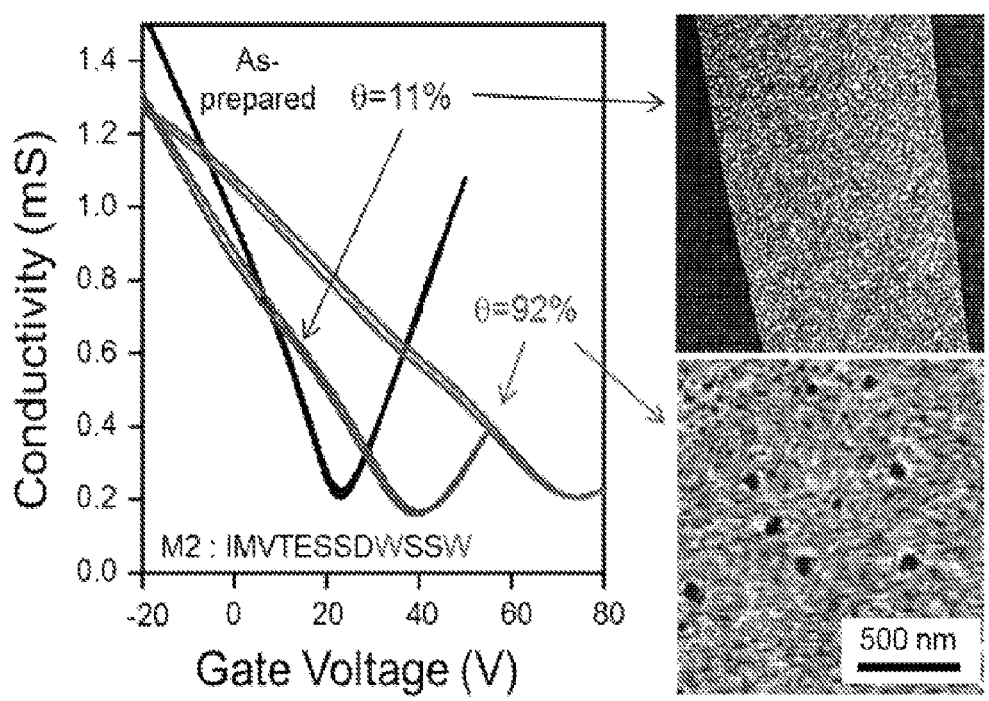
FIG. 13. AFM images of GrBP5:M2 on graphene FETs and their corresponding conductivity characteristics. The conductivity vs. backgate voltage curves for an as prepared GFET (black) and graphene FETs with different peptide coverages corresponding to the AFM images: blue, 11%; red, 92%. M2 is randomly absorbed on graphenes without forming ordered structures.

AFM images in FIG. 12 show that disordered (islands) and ordered peptides (nanowires) coexist at low coverage of 26 and 40%, while nanowires are dominant at 48% coverage, a possible threshold. Here, a question arises as to which of the structures (random islands or ordered nanowires) of the peptides mainly contribute to the formation of two dips observed in the graphene conductivity. To address this question, we performed a control experiment with a mutant peptide, M2, which only forms disordered, or random, nanostructures on graphene. The mutant M2 has slightly modified sequence (IMVTESSDWSSW (SEQ ID NO: 7)), where two tyrosines (Y) in the anchoring domain of the wild-type GrBP5 sequence (WT) are replaced by tryptophans (W). In a previous study, it was found that the two tyrosines play an essential role in the binding of the peptide to graphite substrate and that the mutant M2 has random adsorption on graphite due to relatively small surface diffusion caused by the two tryptophans[4]. In this work, AFM studies show that M2 is again randomly absorbed on graphene (FIG. 13). In the subsequent conductivity measurement of GFETs with M2, a single dip, rather than two dips, was observed and the CNP shifts up to 75V as the coverage increases to 92%. This result conclusively confirms that the random adsorption of peptides does not form abrupt boundaries between the covered and uncovered regions, resulting in an averaged doping of the graphene with holes. Thus, one could conclude that the observed two dips in FIG. 12 are originated from the ordered peptides creating abrupt boundaries at the edges of the ordered nanostructures.

Figure 14:
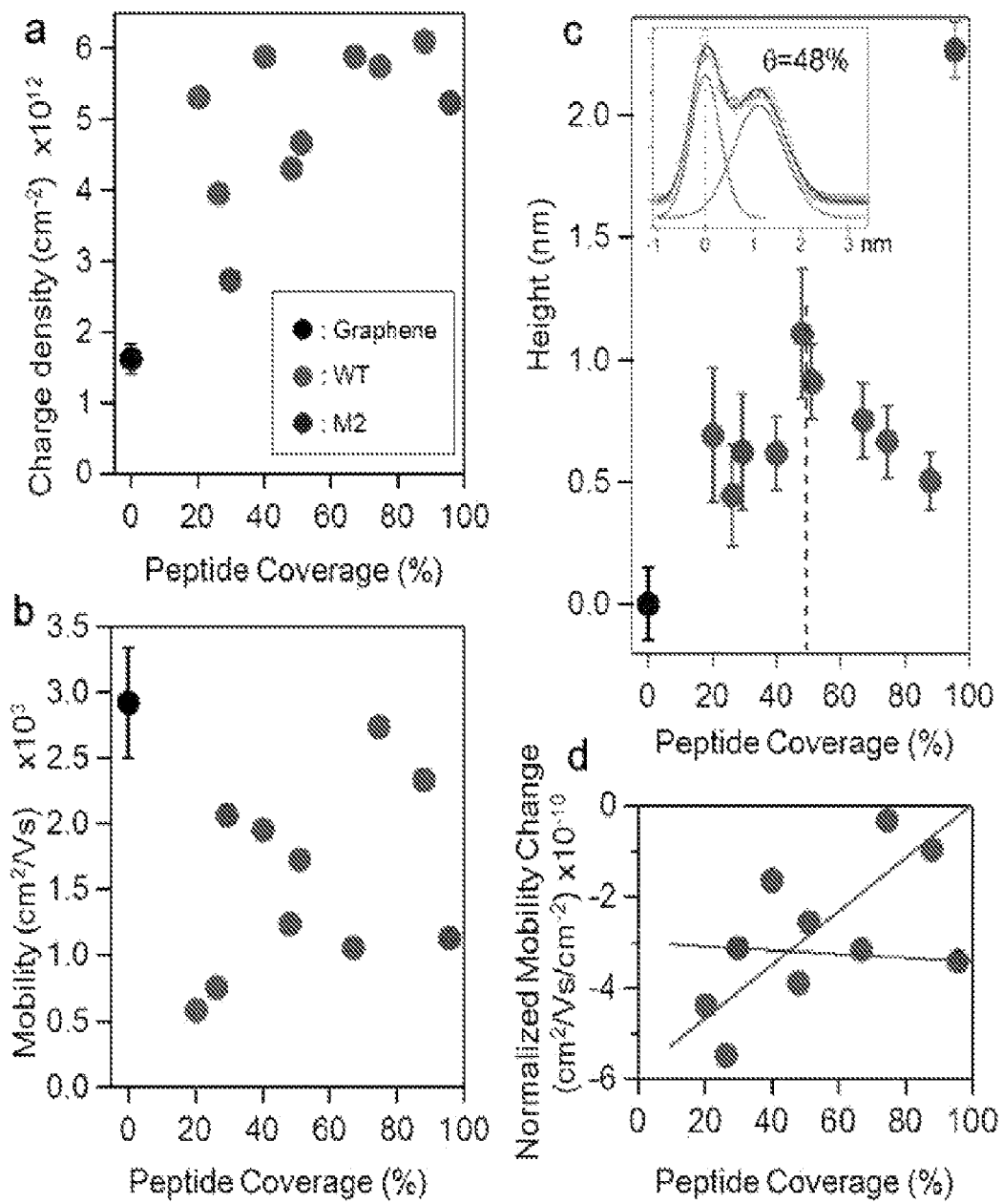
FIG. 14. Charge densities and mobilities estimated from FIGS. 3 and 4. Red and blue marks are data points of WT and M2, respectively. (a) Charge density vs. peptide coverage, showing monotonic increase of charge density in the both peptides, as the peptide coverage increases. (b) Field-effect mobility vs. peptide coverage, showing a recovery of field-effect mobility of WT as the peptide coverage increases. On the other hand, M6 shows monotonic decrease. The black mark is the averaged mobility of the all as-prepared GFETs. The error bar is the standard deviation of the mobility. (c) Height of peptides vs. the peptide coverage, showing contraction of WT peptides above the threshold coverage. The error bars show the standard deviations of the peptide height distribution. The inset shows a height histogram of WT peptides with 48% coverage. The graphene surface is centered at 0 nm. (d) Normalized mobility change by the carrier density over the peptide coverage. Fitted lines are plotted to show the intersection between WT and M2.

To interrogate the effects of the peptides more quantitatively, we determine the charge carrier density and mobility from FIG. 12 (b) and FIG. 13 (Supplementary Methods). From the shifts of CNPs, the charge carrier density induced by peptides onto graphene can be estimated over a range of coverage (FIG. 14a). First to notice is that both the WT and M2 show monotonic increase of the hole density as the peptide coverage on the graphene surface increases. WT has slightly higher carrier density than that of M2; this effect might be caused either by relatively strong interactions of WT peptides with graphene or high density of WT peptides on graphene. In contrast, the mobility of the graphene vs. the peptide coverage shows clear distinct effects between WT and M2 (FIG. 14b). The mobility was estimated from the slope of the linear region on the left side of conductivity curves. In the case of WT, the mobility decreases from 2,900 $cm^2/Vs$ of as-prepared GFETs to 500 $cm^2/Vs$ at the low coverage of 20%. This observation indicates that peptide islands may induce charge impurities into graphene. Such a reduction in mobility has been previously observed by the depositing potassium atoms[21], self-assembled monolayers[25], and micelles[26] on graphene. As the coverage of peptides increases, the mobility recovers gradually. This trend implies that the growth of ordered structures significantly reduces the carrier scattering in graphene. Enhancements of the carrier mobility have been recently observed by several studies employing high dielectric media on graphene, such as a high-κ material[26] and ionic solutions[27], where the dielectric media partially screens charge impurities in graphene. Our observations with the WT peptides can also be interpreted as being caused by the screening effect from the densely-packed peptides, which are uniformly aligned on the graphene substrate. In contrast, the mobility change by M2 shows a monotonic decrease as the coverage of disordered peptides increases. This observation is similar to the reduction of the mobility by deposited materials, as seen in previous studies[21], 24, 25 indicating that randomly adsorbed peptides induce charge impurities which results in carrier scattering even at the high coverage regime.

This trend has meaningful correlations with the peptide morphology on the graphene. Analyzing the AFM images closely, one notices that the height of peptides vs. the coverage (FIG. 14c) shows a tendency that is different in WT than in M2. While M2 shows a monotonic increase of the height as the coverage increases, WT reveals threshold coverage at around 50%, above which value the height and its standard deviation decreases. The non-monotonic change of the height and its distribution could be an indication that WT forms ordered nanostructures with a close-packed organization. In contrast, the monotonic change in the M2 could indicate that M2 peptides form random conformations resulting in crowding, rather than ordering, on the surface. In FIG. 14d, the mobility change caused by peptide vs. the peptide coverage is plotted. The mobility change is calculated by $\Delta\mu=(\mu_o-\mu_p)/n$, where $\mu_o$, $\mu_p$, and n are the mobility of as-prepared GFETs, mobility modified by peptides, and charge carrier density induced by peptides, respectively. The mobility change is normalized by the carrier density over the peptide coverage, which roughly provides us information of how highly an induced carrier by peptides reduces the mobility of holes in a graphene. This mobility change shows a similar threshold of the coverage to the one in the height change. While M2 shows a nearly-constant change of mobilities over the peptide coverage, WT shows a monotonic change of the mobility reduction. Interestingly, the fitted line of WT intersects the one of M2 at around the threshold coverage of 50%. The reduction of mobilities by WT is higher than M2 in the low coverage regime, but it becomes less in the high coverage regime. These observations suggest that the electrical interactions of WT peptides with the graphene cause the carrier scattering more than M2 at the low coverage regime, but the scattering becomes weaker once WT peptides form ordered structures above the threshold coverage.

Although there is no experimental work evaluating electrical interactions of every amino acid to the graphene in a quantitative manner, both of the aromatic and charged amino acids are promising candidates with meaningful effects on the graphene conductivity as suggested by previous works including carbon nanotubes[28-30]. Our peptides in this work have two aromatic amino acids (W and Y) and two charged amino acids (D and E). W and Y have isoelectric points (IP) of 5.7 and 5.9, respectively, which possibly cause moderate electric interactions with graphene in the neutral condition of water. On the other hand, charged amino acids, aspartic acid (D) and glutamic acid (E), have respectively 2.8 and 3.2, and their electrical interactions can be stronger than the aromatic amino acids. In our previous work, we found that the aromatic amino acids are the binding site to the graphite. Thus, the distance of the aromatic residues of W and Y to the graphene could be similar. However the distance of the charged amino acids could be varied by the conformation of peptides significantly, which might be the major difference between WT and M2. Ordered structures of peptides may periodically place these charged amino acids, leading the less carrier scattering.

Our approach demonstrated here to modify local electronic properties of graphenes by self-assembled peptides can be used in a wide range of potential fundamental research and practical implementations. For example, a supramolecular array of peptides can provide two-dimensional scaffolds for functional proteins in forming nanoscale bioelectronic circuits on graphenes without a significant disturbance of the carrier mobility, which may facilitate new applications in biosensing or bioenergy generation[5,6]. The change of the graphene mobility by absorbed peptides can be useful to detect conformation changes of peptides or proteins on graphenes.

REFERENCES FOR EXAMPLE 3

1. Kowalewski, T. and Holtzman, D. M. In situ atomic force microscopy study of Alzheimer's β-amyloid peptide on different substrates: New insights into mechanism of β-sheet formation. *Proc. Natl. Acad. Sci. USA* 96, 3688 (1999).
2. Zhang, F. et al. Epitaxial growth of peptide nanofilaments on inorganic surfaces: effects of interfacial hydrophobicity/hydrophilicity. *Angew. Chem. Int. Edit.* 45, 3611 (2006).
3. So, C. R. et al. Molecular recognition and supramolecular self-assembly of a genetically engineered gold binding peptide on Au {111}. *ACS Nano,* 3, 1525 (2009).
4. So, C. R. et al. Controlled self-assembly of peptides on graphite via rational mutation. (2011).
5. Katz, E. and Willner I. Integrated nanoparticle-biomolecule hybrid systems: synthesis, properties, and applications. *Angew. Chem. Int. Edn* 43, 6042 (2004).
6. Offenhäusser, A. and Rinaldi, R. *Nanobioelectronics: for electronics, biology, and medicine* (Springer-Verlag, New York, 2009).
7. Novoselov, K. S. et al. Electric field effect in atomically thin carbon films. *Science* 306, 666 (2004).
8. Zhang, Y., Tan, J. W., Stormer, H. L. and Kim, P. Experimental observation of the quantum Hall effect and Berry's phase in graphene. *Nature* 438, 201 (2005).
9. Bolotin, K. I. et al. Ultrahigh electron mobility in suspended graphene. *Solid State Commun.* 146, 351 (2008).
10. Lee, C., Wei, X., Kysar, J. W. and Hone, J. Measurement of the elastic properties and intrinsic strength of monolayer graphene, *Science* 321, 385 (2008).
11. Schedin, F. et al. Detection of individual gas molecules adsorbed on graphene. *Nature Materials* 6, 652 (2007).
12. Dong, X. et al. Doping single-layer graphene with aromatic molecules. *Small* 5, 1422 (2009).
13. Wang, Q. H. and Hersam, M. C. Room-temperature molecular-resolution characterization of self-assembled organic monolayers on epitaxial graphene. *Nat. Chem.* 1, 206 (2009).
14. Pollard, A. J. et al. Supramolecular assemblies formed on an epitaxial graphene superstructure, *Angew. Chem. Int. Ed.* 49, 1794 (2010).
15. Wang, X., Tabakman, S. M. and Dai, H. Atomic layer deposition of metal oxides on pristine and functionalized. *J. Am. Chem. Soc.* 130, 8152 (2008).
16. Barth, J. V., Costantini, G. and Kern, K. Engineering atomic and molecular nanostructures at surfaces. *Nature* 437, 671 (2005).
17. Cui, Y. et al. Chemical functionalization of graphene enabled by phage displayed peptides. *Nano Lett.* 10, 4559 (2010).
18. Sarikaya, M. et al. Molecular biomimetics: nanotechnology through biology. *Nat. Mater.* 2, 577 (2003).
19. Girita, C. O. and Zettl, A., Soldering to a single atomic layer. *Appl. Phys. Lett.* 91, 193512 (2007).
20. Levesque, P. L. et al. Probing charge transfer at surfaces using graphene transistors. *Nano Lett.* 11, 132 (2011).
21. Chen, J. H. et al. Charged-impurity scattering in graphene. *Nat. Phys.* 4, 377 (2008).
22. Farmer, D. B., Lin, Y. M., Afzali-Ardakani, A. and Avouris, P. Behavior of a chemically doped graphene junction. *Appl. Phys. Lett.* 94, 213106 (2009).
23. Cheng, H. C. et al. high-quality graphene p-n junctions via resist-free fabrication and solution-based noncovalent functionalization. *ACS Nano* 5, 2051 (2011).
24. Lee, B. et al. Modification of electronic properties of graphene with self-assembled monolayers. *Nano Lett.* 10, 2427 (2010).
25. Shih, C. J., et al. Understanding surfactant/graphene interactions using a graphene field effect transistor: relating molecular structure to hysteresis and carrier mobility. *Langmuir* 22, 8579 (2012).
26. Chen, F.; Xia, J.; Ferry, D. K.; Tao, N. Dielectric screening enhanced performance in graphene FET. *Nano Lett.* 2009, 9, 2571.
27. Chen, F.; Xia, J.; Tao, N. Ionic screening of charged-impurity scattering in graphene. *Nano Lett.* 2009, 9, 1621.
28. Allen, B. L.; Kichambare, D. P.; Star, A. Carbon nanotube field-effect-transistor-based biosensors. *Adv. Mater.* 2007, 19, 1439.
29. Tomasio, S. M. and Walsh, T. R. Modeling the binding affinity of peptides for graphitic surfaces. influences of aromatic content and interfacial shape, *J. Phys. Chem. C* 113, 8778 (2009).
30. Rajesh, C., Majumder, C., Mizuseki, H. and Kawazoe, Y. A theoretical study on the interaction of aromatic amino acids with graphene and single walled carbon nanotube. *J. Chem. Phys.* 130, 124911 (2009).

Supplemental Information for Example 3

S1. Peptide Synthesis

Peptide synthesis was carried out on a preloaded support resin using HBTU activation chemistry, while 20% piperidine in DMF was employed to afford the Fmoc deprotection and monitored by UV absorbance at 301 nm. Following solid-phase synthesis, the peptides were cleaved off the support and side chain deprotected by stirring the resin-bound peptide in a cocktail under $N_2$ atmosphere for 2-3 hours. This cocktail contained either TFA/thioanisole/$H_2O$/phenol/ethanedithiol (87.5:5:5:2.5) or TFA/triisopropylsilane/$H_2O$/EDT (94:1:2.5:2.5), depending on the peptide. The resin was removed by filtration, and each of the peptides was precipitated with cold ether to yield crude peptide product that was lyophilized (Virtis Benchtop K, SP Industries, Inc., Warminster, Pa.). Peptides were reconstituted using various ratios of DI water and acetonitrile. Purification by reverse-phase HPLC for peptides employed, first, an isocratic (0% B for 2 min) and, then, a linear gradient of 1%/min for analytical and 0.5%/min for semiprep scales at 1 and 10 mL/min flow rates, respectively. Retention times spanned 30-50 mins depending on the peptide in semi-preparative HPLC. Analytical peaks were isolated by auto-threshold collection (Waters Deltaprep 600, analytical mode) and peptides were verified by MALDI-TOF mass spectrometry with reflectron (RETOF-MS) on an Autoflex II (Bruker Daltonics, Billerica, Mass.) mass spectrometer in positive-ion mode. The observed M/Z fractions were subsequently collected manually from a scaled semi-preparative separation (Waters Deltaprep 600, semiprep. mode).

S2. Sample Preparation for Atomic Force Microscope Measurements

Graphene was mechanically exfoliated from natural graphite flakes (3763, Asbury Carbons) on a Si wafer with 300 nm $SiO_2$ (1). The number of graphene layers was confirmed by Raman spectroscopy and atomic force microscope (AFM). Single-layer $MoS_2$ was also mechanically exfoliated from a bulk $MoS_2$ (Moly Disulfide, SPI Supplies). Single $MoS_2$ layers were confirmed by AFM and photoluminescence (PL) measurements. After exfoliation, samples were incubated with peptides in DI water. A sample for FIG. 10B was incubated under the condition of 500 nM peptide concentration for 20 minutes. All samples for FIG. 10F were prepared under the condition of 1 μM for 1 hour. After the incubation, samples were gently dried with nitrogen blow.

Figure 24:
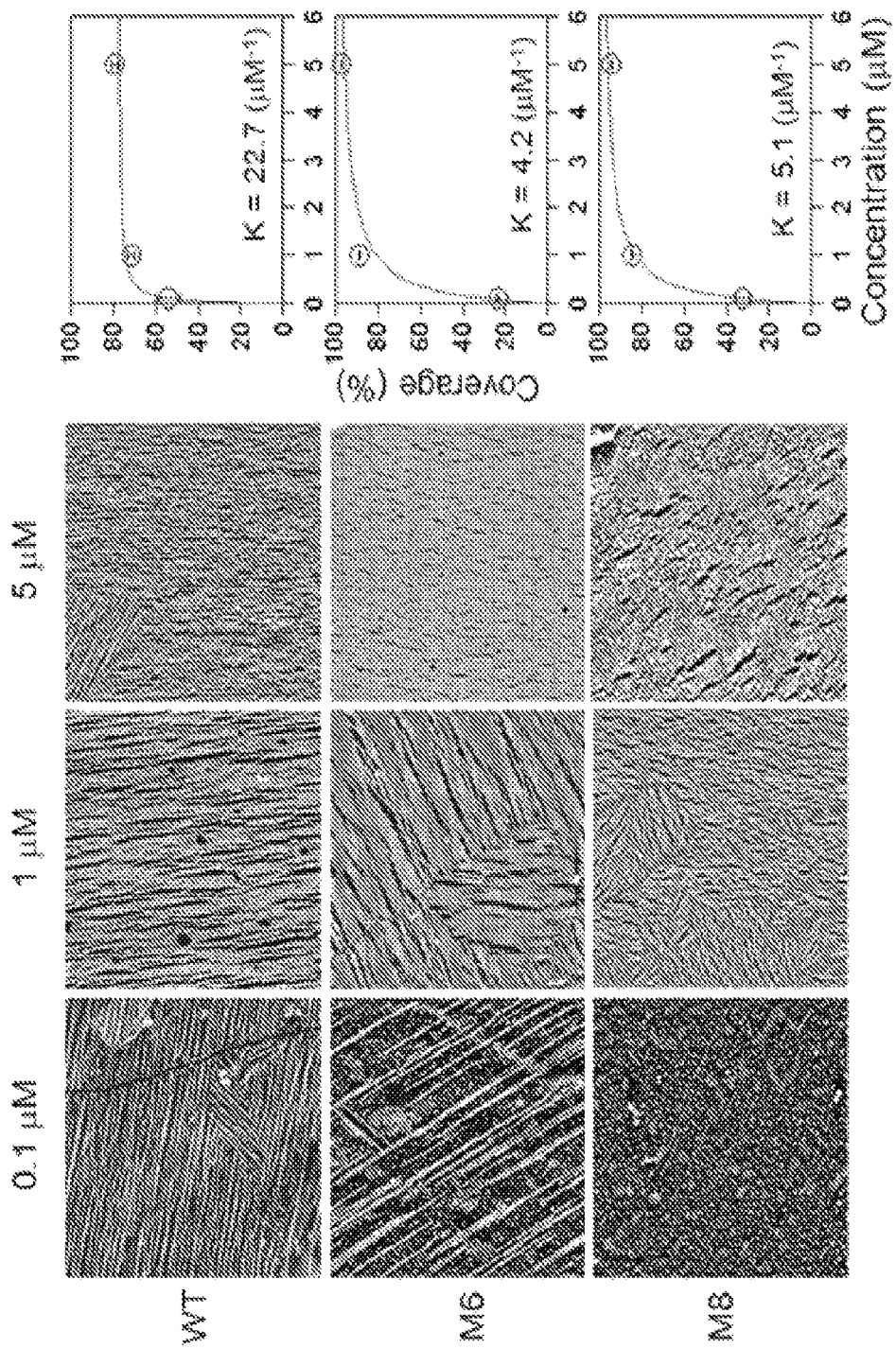
Figure 25:
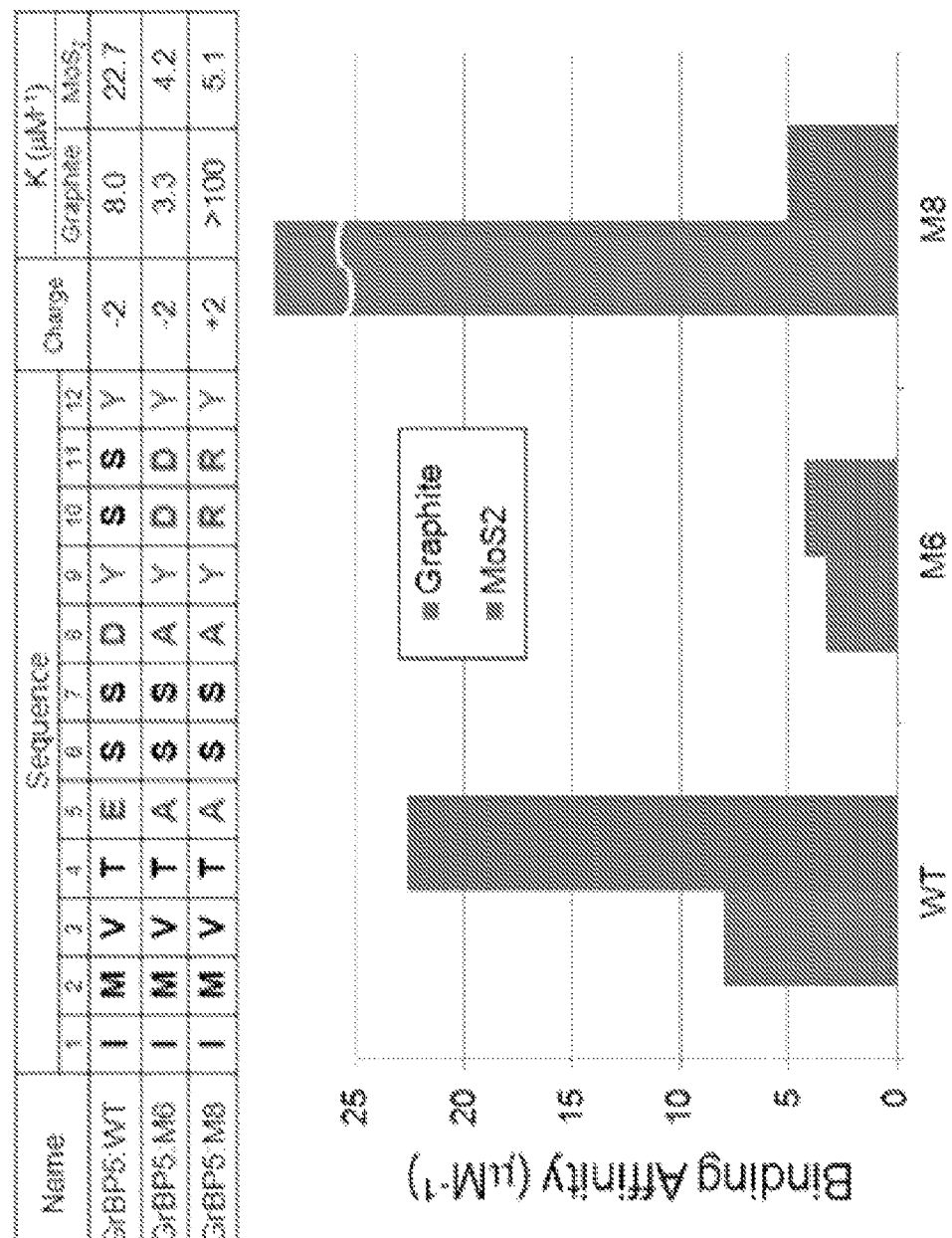
FIG. 25. AFM images of peptides on surfaces of bulk $MoS_2$ and the plots of coverage of peptides vs. incubation concentration of peptides.

S3. Characterization of GrBP5 and its Mutants, M6 and M8, on Bulk Graphite and $MoS_2$ To roughly estimate binding affinities of each peptide (WT, M6 and M8) to surfaces, we characterized peptides on bulk graphite and $MoS_2$ by AFM. Flakes of graphite and $MoS_2$ (same suppliers in the section 2) on Si wafers with 300 nm-thick $SiO_2$ were incubated with peptides in DI wafer for 3 hours. The concentrations of peptides were 0.1, 1, and 5 μM. After the incubation, samples were gently dried under Nitrogen gas. Interestingly, the results show all peptides capable of forming long-range ordered nanowires at 0.1 μM on both graphite and $MoS_2$, except for M8 on graphite, which instead forms fiber-like structures with loose alignment (data not shown for graphite; $MoS_2$ data shown in FIG. 24). At higher concentrations, all peptides show domains with aligned structures inside, except for M8 on graphite with randomly distributed domains. The distinctive behavior of M8 on graphite was also observed in its binding affinity. The binding affinities of peptides to graphite and $MoS_2$ were estimated from a relationship between the observed surface coverage of peptides by AFM and the peptide concentrations used for incubation. (FIG. 25) Here, we employed a simple adsorption equation which allows us to roughly estimate the binding affinity, as described in Example 1 Supporting information.

The binding affinities obtained by fitting the adsorption equation with experimental data show that M8 has the exceptionally large binding affinity to graphite. On the other hand, other peptides, WT and M6, have relatively weak binding affinities. In fact, aligned peptide nanowires on graphite were already observed in previous reports, which characterized surface morphology of peptides on graphite at various conditions (14,16). These report suggested that binding, diffusion and intermolecular interactions of peptides play important roles during their self-assembly process into long-range ordered structures. It also suggested that strong interactions between peptides and the surface results in suppressed surface-diffusion rates and, therefore, inhibits peptide self-assembly into ordered structures. In light of such findings, our observations indicate that M8 has strong interactions with graphite surfaces and therefore an apparent suppressed surface diffusion. On the other hand, WT and M6 may have optimal interactions with the surface, readily forming self-assembled structures. Also notable is the contrast in peptide binding specificity to particular materials that arises from modified primary amino acid sequences. While M6 has weak but comparable binding affinities to both graphite and $MoS_2$, WT and M8 show opposing trends in binding affinity to graphite and $MoS_2$. While WT binds strongly to $MoS_2$, M8 binds weakly. In the case of graphite, however, this tendency is reversed. The opposing material selectivity may be due to the difference in electric potential of graphite and $MoS_2$ at the interface between surface and peptide solution. WT and M8, with their opposing mean charge, might therefore show contrasting tendencies in their material selectivity. At the same time, they may have a higher sensitivity to the electric potential of surfaces over M6. Although these hypotheses need to be further investigated, the significant effect on peptide binding affinity after rational modification of the amino acid sequence sheds light on tuning supramolecular peptide self-assembly on multiple materials.

S4. Fabrication of Field Effect Transistors (FET) and Electrical Characterization Graphene was exfoliated from natural graphite flakes (3763, Asbury Carbons) on a doped Si wafer, covered with 300 nm $SiO_2$, by the conventional mechanical exfoliation method (1). Single layers of graphene were identified by Raman spectroscopy and AFM. In this study, the cleanliness of graphene surfaces was vital in order to observe supramolecular assembly of peptides. In conventional lithographic fabrication of graphene FETs (GFET), resists often remain on graphene surfaces even after rigorous cleaning processes. Such contamination was found to cause undesired doping effects in the ASL and also disrupt the self-assembly of peptides. To avoid such contamination, we utilized microsoldering of Indium (24). After the mechanical exfoliation of graphene, we immediately formed indium electrodes on graphene. The Indium electrodes were also manually covered by PMMA (495, MicroChem Corp.) to minimize their electrochemical disturbance to graphene and self-assembly of peptides during incubation. Peptides were immobilized by placing 20 μL droplets of peptide solution at various concentrations onto a GFET chip. Samples were kept under humidity control (>80%) to prevent drying during their incubation. Then, GFETs were rinsed with DI water promptly and dried with nitrogen flow. The details of the incubation conditions for the imaged GFETs in FIG. 12 are as follows; Sample 1: θ=26%, 50 nM for 20 minutes; Sample 2: θ=40%, 50 nM for 60 minutes; Sample 3: θ=50%, 200 nM for 90 minutes; Sample 4: θ=88%, 500 nM for 20 minutes.

Electric measurements were carried out on two-probe measurements with a semiconductor characterization system (4200-SCS, Keithley) and a probe station (Singatone Corp., Gilroy, Calif.). The conductivity of GFETs in FIG. 12 was normalized using the dimensions of GFETs. The typical size of the graphene sheet between two electric contacts is 40 μm in width and 20 μm in length. All electrical measurement was performed under Argon atmosphere to eliminate instability caused by moisture. In gate response measurements, the typical source-drain voltage was 5 mV. In our study, contact resistance of indium electrodes was small compared with resistance of graphene, because of the large contact area, typically 40 μm by 10 μm. Typically, resistance of GFET is in the order of kilo ohms, while contact resistance is sub ohms Plots of sheet resistance vs. gate voltages also show small contribution of contact resistance (not shown). Before the incubation with peptides, as-prepared GFETs shows charge neutral point (CNP) at around 20V on average. The CNPs depends on a sample and range from 15V to 25V (not shown). During the conductivity measurement, the gate voltages were cyclically swept from minimal to maximal voltage, and then, to minimal voltage again. Even after incubation with peptides, GFETs did not show hysteresis in cyclic gate voltage measurements. It is worth to note that GFETs incubated with DI water showed shifts of CNP (10V after 10-minuites incubation). However, GFETs incubated with degassed DI water (bubbled with Ar gas for 30 minutes) did not show significant CNP shifts. It indicates that oxygen dissolved in water might cause doping. In this work, we used degassed peptide solution (bubbled with Ar gas for 30 minutes) in the incubation with GFETs to eliminate excessive doping.

In the case of $MoS_2$, due to the difficulty of mechanically exfoliating large single-layer flakes, we employed electron beam lithography to fabricate electrodes over the previous micro-soldering approach. For the lithography, we used PMMA (495, MicroChem. Corp.) as a resist, and exposed it using a scanning electron microscope (SEM7000, JEOL). After development in MIBK:IPA 1:3 solution (developer, Microchem) for 3 min, we sputtered Ti/Pt (5 nm/25 nm) as electrodes, and lifted off by boiled acetone and isopropyl alcohol. All FET devices were cleaned by following three cleaning processes; 1) Rinsing with boiled acetone for 30 minutes, 2) Cleaning with UV/ozone (UV/Ozone Pro-Cleaner, BioForce Nanosciences Inc.) for 1 minute, 3) Current induced annealing (ref) under argon gas atmosphere. We confirmed that we can regenerate the conductivity of all three FET devices using this cleaning process even after the incubation with peptides. In this study, we utilized a same FET platform to directly compare modification of $MoS_2$ conductivity by peptides, M6 and M8. All peptides were incubated with the $MoS_2$ FET under a condition of 1 µM for 1 hour. After the incubation, peptide solution was gently dried by nitrogen. The conductivity measurement was performed under argon gas. Source-drain voltage was 100 mV for gate response measurements.

S5. Estimation of Charge Carrier Density and Field-Effect Mobility

The charge carrier density in single-layer graphene was estimated from $V_{cnp}$ observed in FIG. 12 using a simple relationship $$n = C_i \times V_{cnp}/e,$$

where n is charge carrier density, $C_i$ is the capacitance between the channel and the back gate per unit area $$\left(C_i = \varepsilon_2 \varepsilon_r / d; = \varepsilon_r = 3.9, d = 300 \text{ nm}\right),$$

$V_{cnp}$ is the gate voltage corresponding to charge neutral point, and e is electron charge (1, 25). To analyze how peptides impact the carrier mobility of graphene, we roughly estimated field effect mobility. From the conductivity of GFETs in FIG. 12, we extracted the field effect mobility using the expression $$\mu = [dI_{ds}/dV_s] \times [L/(WC_iV_{ds})],$$

where L is the channel length, W is the channel width, and $V_{ds}$ is source-drain voltage (20). $dI_{ds}/dV_g$ were extracted from slopes of conductivity curves in FIG. 12B. We fitted a linear region in left sides of the conductivity curves with a line to estimate the slope.

S6. Height Analysis of Peptides on a Graphene and Graphene FETs

Various peptide nanostructures observed in this study exhibited a height distribution dependent on their lateral size. We analyzed an AFM image with peptide nanostructures on graphene using a particle analysis module in SPIP (Image Metrology A/S). The AFM image shows peptide nanowires to have a linear shape and lateral length of greater than a micron, as well as particle-like islands with a lateral diameter of less than 100 nm. An increase of lateral size from islands to nanowires correlates monotonically with the height of the nanostructures (not shown). This tendency was also observed in the peptide morphology on actual GFET devices (not shown).

S7. Height Analysis of Peptides on Graphene and $MoS_2$

Figure 10:
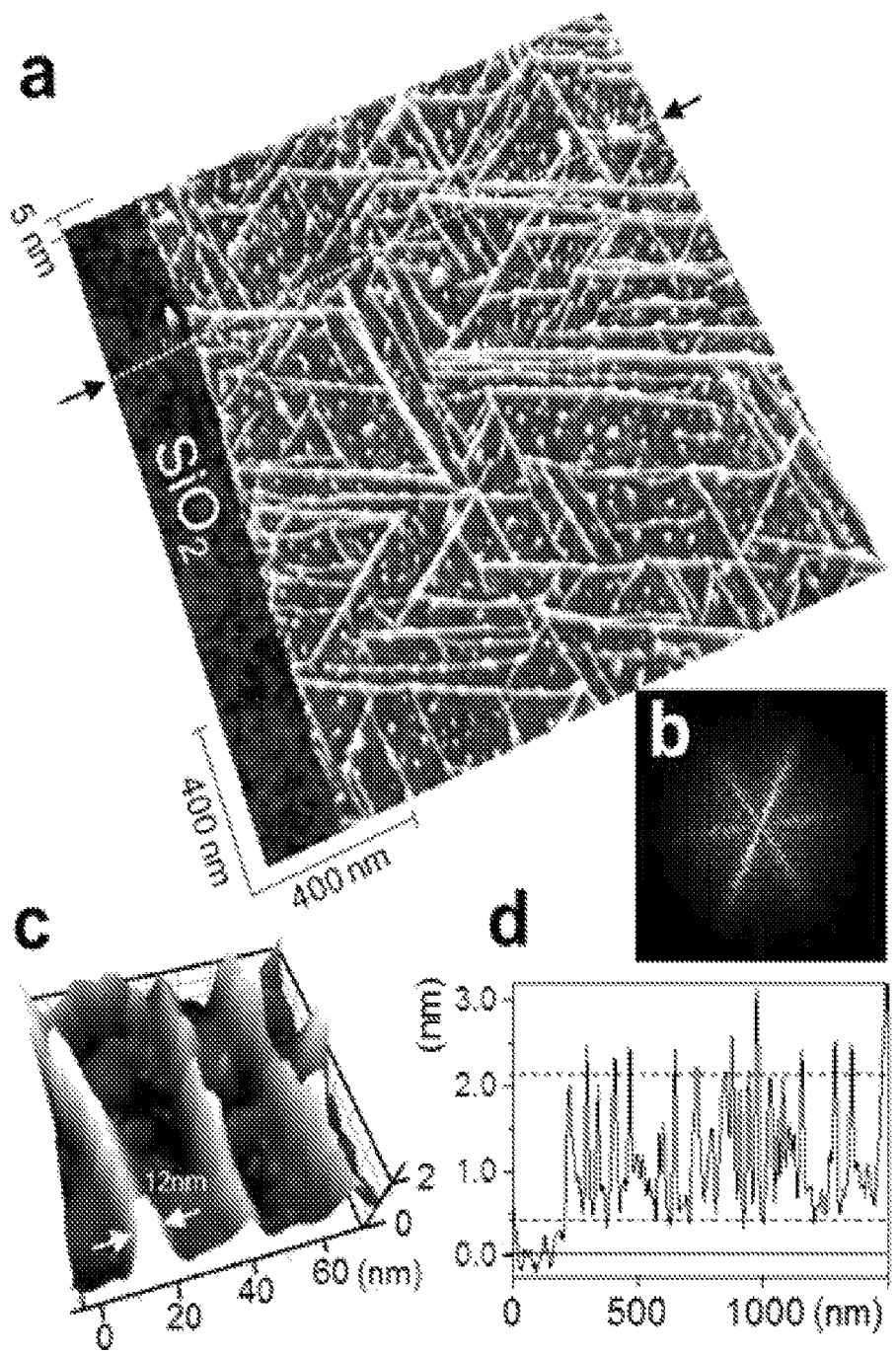
FIG. 10. Self-assembled peptide nanostructures on a graphene. (a) A 3-dimensional AFM image of GrBP5:WT on graphene. (b) Fast Fourier transform of (a) showing 6-fold symmetry of the peptide self-assembly. (c) A magnified region in (a). (d) A line profile of the AFM image as indicated with a dashed line in (a) showing thicknesses of the graphene and self-assembled peptides.

To quantitatively compare the thickness of peptide structures on ASLs, we further analyzed the height histograms of AFM images in FIG. 10. AFM images and their corresponding height histograms for peptides WT, M6 and M8 on graphene and $MoS_2$ were obtained using SPIP (not shown). Each histogram was fitted with Gaussian peaks to derive the average thickness of peptide structures. In this analysis, most images are best fit with three Gaussian peaks, except for WT on a graphene. The presence of three individual peaks in the histogram may indicate that AFM images contain distributions of structures on ASL surfaces with two general phases, disordered and ordered. In the case of WT on graphene, the AFM image does not contain disordered peptides. The fitting results clearly show that peptides have a similar thickness of 1 nm on both graphene and $MoS_2$, with the exception of M8 on $MoS_2$, which has a thickness of 1.7 nm. This observation implies that the distinct effects of M6 and M8 on the PL and conductivity of $MoS_2$ in FIG. 13 originates from a conformational difference between M6 and M8 on $MoS_2$.

S8. Raman Measurements for Graphene and Peptide Modified Graphene

Mechanically exfoliated single-layer graphene on Si wafers were verified by a Raman microscope. Recently, the doping of graphene by organic molecules has been characterized by Raman spectroscopy (13). We characterized Raman spectra of graphene before and after incubation with the GrBP5:WT peptide (not shown). Raman spectroscopy was performed using a Renishaw Raman microscope with the 514 nm excitation laser. The excitation power was 100 µW. The Si peak at 520 cm$^{-1}$ was used as a reference for wavenumber calibration. Ten graphene samples were used for the Raman characterization of the peptide doping effect. The well characterized graphene samples were then incubated with 1 µM peptide solutions of GrBP5:WT for 1 hour. GrBP5:WT shows 5 cm$^{-1}$ shift in the G-band and 1 cm$^{-1}$ shift in the 2D-band after the incubation on the average. In the previous report (13), organic molecules act as hole dopants showed positive shift in both 2D and G band. GrBP5:WT also demonstrated positive peak shifts in both 2D- and D-band, and it supports the results of the conductivity measurements (FIG. 3) showing hole doping by peptides.

Supplemental References for Example 3

1. K. S, Novoselov et al., Electric field effect in atomically thin carbon films. *Science* 306, 666 (2004).
2. Y. Zhang, J. W. Tan, H. L. Stormer, P. Kim, Experimental observation of the quantum Hall effect and Berry's phase in graphene. *Nature* 438, 201 (2005).
3. K. I. Bolotin et al., Ultrahigh electron mobility in suspended graphene. *Solid State Commun.* 146, 351 (2008).
4. A. Splendiani et al., Emerging photoluminescence in monolayer $MoS_2$. *Nano Lett.* 10, 1271 (2010).
5. K. F. Mak et al., Atomically thin $MoS_2$: a new direct-gap semiconductor. *Phys. Rev. Lett.* 105, 136805 (2010).
6. K. S, Novoselov et al., Two-dimensional atomic crystals. *Proc. Natl. Acad. Sci. U.S.A.* 102, 10451 (2005).
7. B. Radisavljevic, A. Radenovic, J. Brivio, V. Giacometti, A. K is, Single-layer $MoS_2$ transistors. *Nat. Nanotech.* 6, 147 (2011).
8. Q. H. Wang, M. C. Hersam, Room-temperature molecular-resolution characterization of self-assembled organic monolayers on epitaxial graphene. *Nat. Chem.* 1, 206 (2009).

9. A. J. Pollard et al., Supramolecular assemblies formed on an epitaxial graphene superstructure, *Angew. Chem. Int. Ed.* 49, 1794 (2010).
10. X. Wang, S. M. Tabakman, H. Dai, Atomic layer deposition of metal oxides on pristine and functionalized. *J. Am. Chem. Soc.* 130, 8152 (2008).
11. F. Schedin et al., Detection of individual gas molecules adsorbed on graphene. *Nature Materials* 6, 652 (2007).
12. J.-H. Chen et al., Charged-impurity scattering in graphene. *Nat. Phys.* 4, 377 (2008).
13. X. Dong et al., Doping single-layer graphene with aromatic molecules. *Small* 5, 1422 (2009).
14. T. Kowalewski, D. M. Holtzman, In situ atomic force microscopy study of Alzheimer's β-amyloid peptide on different substrates: New insights into mechanism of b-sheet formation. *Proc. Natl. Acad. Sci. USA* 96, 3688 (1999).
15. C. So et al., Molecular recognition and supramolecular self-assembly of a genetically engineered gold binding peptide on Au{111}. *ACS Nano,* 3, 1525 (2009).
16. C. So et al., The molecular mechanism of self-assembled peptides on graphite. (2011)
17. S. Brown, M. Sarikaya, E. A. Johnson, A genetic analysis of crystal growth. *J. Mol. Biol.* 299, 725-735 (2000).
18. S. R. Whaley et al., Selection of peptides with semiconductor binding specificity for directed nanocrystal assembly. *Nature* 405, 665 (2000).
19. M. Sarikaya et al., Molecular biomimetics: nanotechnology through biology. *Nat. Mater.* 2, 577 (2003).
20. D. B. Farmer, Y. M. Lin, A. Afzali-Ardakani, P. Avouris, Behavior of a chemically doped graphene junction. *Appl. Phys. Lett.* 94, 213106 (2009).
21. H. C. Cheng et al., high-quality graphene p-n junctions via resist-free fabrication and solution-based noncovalent functionalization. *ACS Nano* 5, 2051 (2011).
22. C. Rajesh, C. Majumder, H. Mizuseki, Y. Kawazoe, A theoretical study on the interaction of aromatic amino acids with graphene and single walled carbon nanotube. *J. Chem. Phys.* 130, 124911 (2009).
23. S. Regot, et al., Distributed biological computation with multicellular engineered networks. *Nature* 469, 207 (2011).
24. C. O. Girit, A. Zettl, Soldering to a single atomic layer. *Appl. Phys. Lett.* 91, 193512 (2007).
25. J. Yan, Y. Zhang, P. Kim, A. Pinczuk, Electric field effect tuning of electron-phonon coupling in graphene. *Phys. Rev. Lett.* 98, 166802 (2007).

Example 4

Biofunctionalized Peptide Nanowires on Graphite for the Self-Assembly of Hierarchical Nanostructures Abstract Peptide GrBP5 has been shown above to have a strong affinity to graphite and form high aspect ratio nanostructures that are symmetrically aligned along specific crystal orientations of the surface. More importantly, explicit domains of amino acids along the primary sequence of the GrBP5 dodecapeptide (IMVTESSDYSSY (SEQ ID NO: 5)) govern peptide-surface and peptide-peptide interactions, resulting in growth of structures where the N-terminus of peptides are uniformly exposed from the substrate into the solution. Utilizing GrBP5, here we demonstrate two accomplishments: Formation of discrete nm-wide, micron-long peptide nanowires (PNWs) on graphite, and targeted assembly of quantum dots (QDs) on these functional molecular scaffolds.

Results

Figure 15:
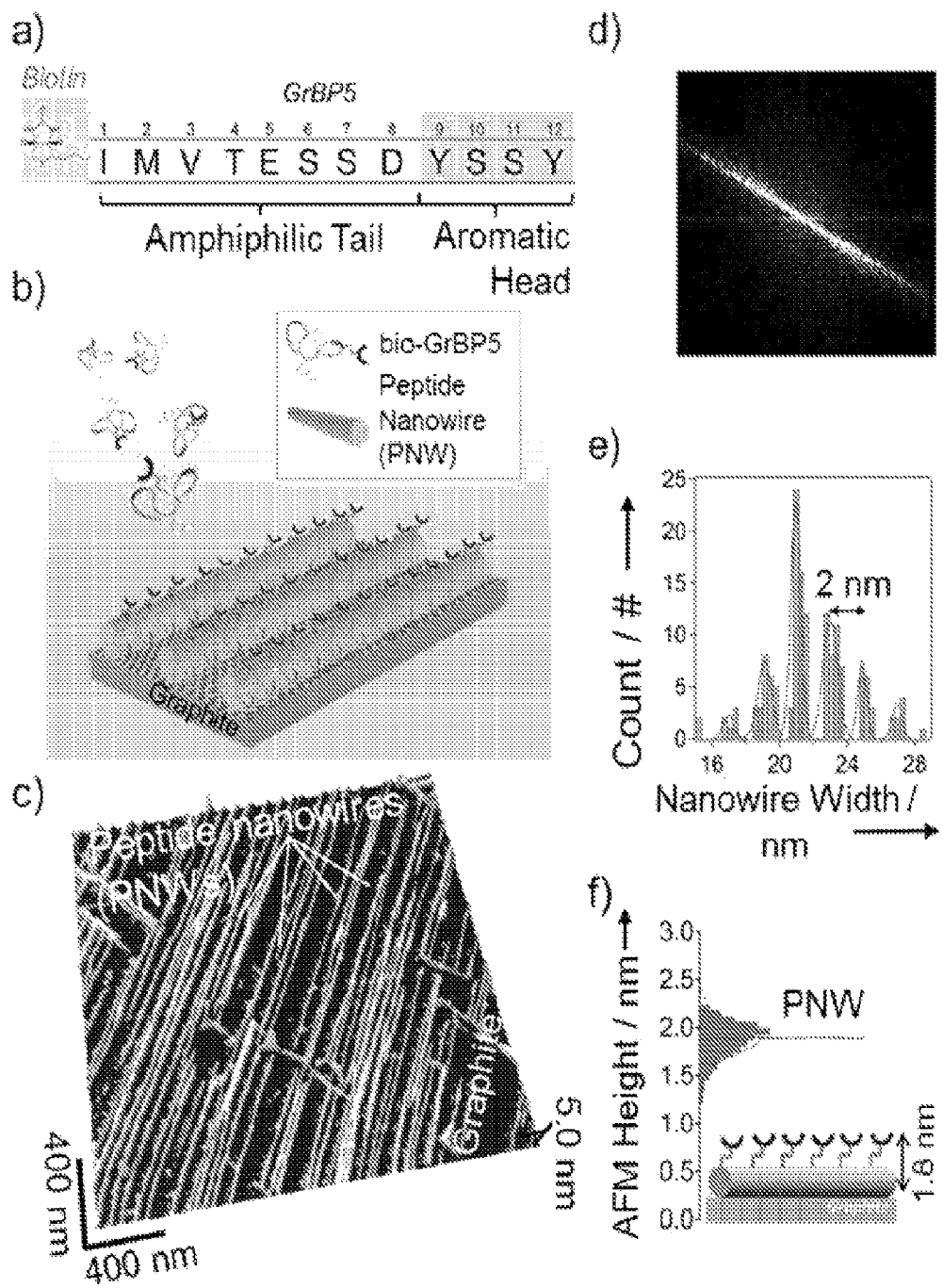
FIG. 15. Design of bio-GrBP5 and AFM characterization of peptide nanowires. a) Amino acid sequence of GrBP5 identifying the biotin, amphiphilic tail and aromatic head regions from N- to C-terminus (left to right). b) Schematic depicting the molecular self-assembly of individual peptides in water to form peptide nanowires on graphite, displaying functional biotin. c) 3 μm×3 μm AFM image of self-assembled peptide nanowires with d) FFT showing largely uniaxial growth of wires, e) distribution of measured wire widths with 2 nm intervals and f) histogram of cross section measurements from C showing uniform height at ~1.8 nm for PNWs. Height and width measurements are from at least n=100 measurements.

We first attach biological functionality into GrBP5 by appending biotin to its N-terminus (bio-GrBP5: FIG. 15a). Discrete nano-sized clusters of bio-GrBP5 that form at low concentrations, over time, transform into high aspect ratio nanowires of uniform orientation. As we demonstrate here, utilizing highly specific biotin-streptavidin (SA) interactions, it is then possible to target SA-functionalized entities such as quantum dots onto nanowires.

By controlling peptide deposition conditions, e.g., time and concentration, discrete molecular nanowires can be assembled at ultralow concentrations (10s of nM) which display biotin on graphite, as schematically displayed in FIG. 15b. Upon exposure to these conditions, long spanning peptide nanowires (PNWs) are successfully formed using 50 nM peptides (suspended in deionized water) as imaged by AFM in FIG. 15c. The PNWs are oriented uniaxially, as seen by Fast Fourier Transform (FFT) in FIG. 15d, with a minimum width of ~17 nm (FIG. 15e) and lengths spanning at least 4 µm, spaced ~16 nm apart. The maximum height of PNWs, measured by AFM, is ~1.8±0.4 nm (FIG. 15f), This value, on the average, is higher than the structures formed by WT GrBP5, i.e., without the biotin, by about 3 Å[11a] roughly the same size of free molecular biotin (~6×9×2 Å) and may indicate that biotin is displayed by the NWs. Interestingly, as seen in FIG. 1e, PNW widths are measured to increase at 2 nm intervals, suggesting that new wires grow co-axially along existing wires. This also reveals the size for single peptide nanowires without the convoluting effects of the AFM tip.

Figure 16:
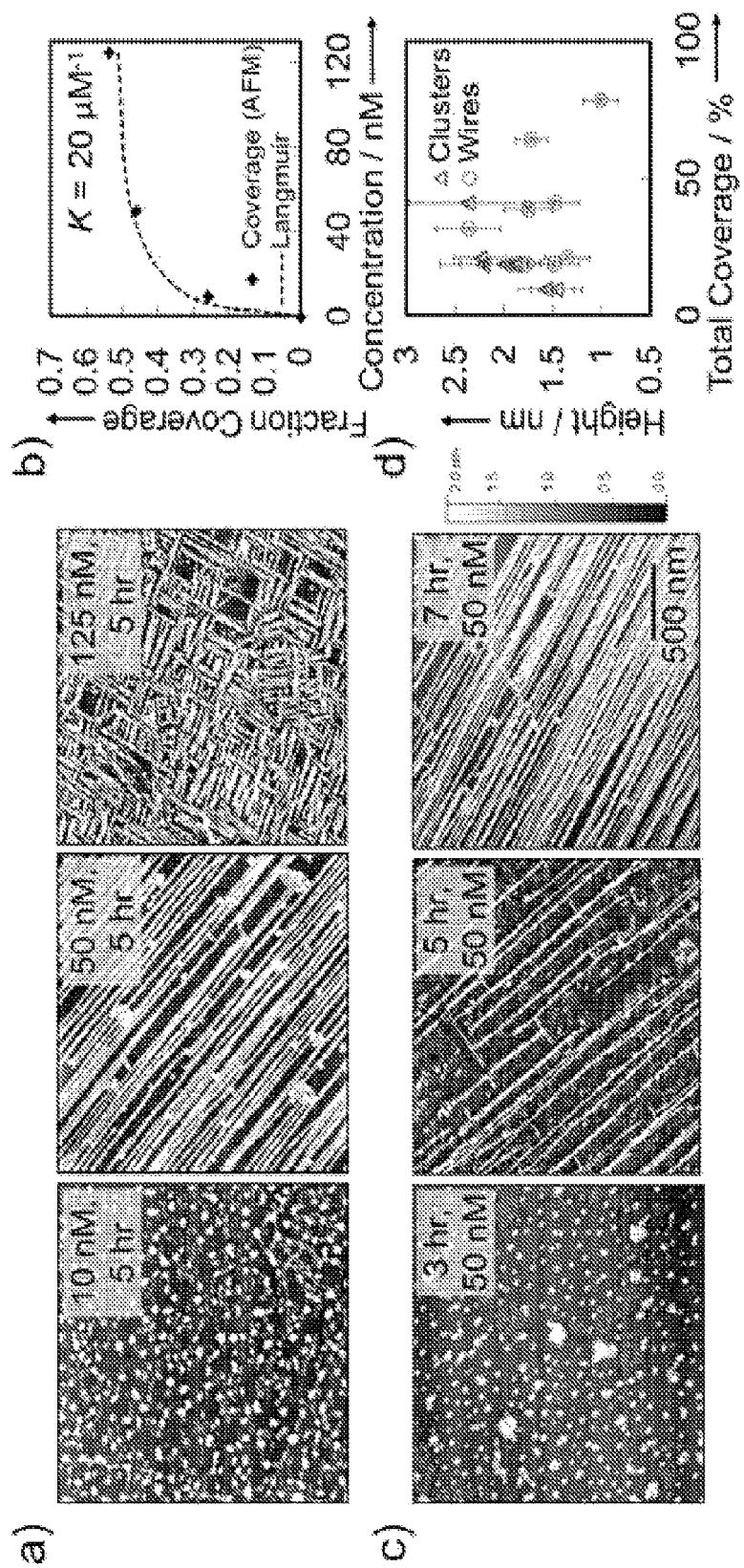
FIG. 16. Optimization of peptide nanowire growth conditions. a) 2 μm×2 μm AFM images of graphite surfaces exposed to peptide solutions of various concentrations for 5 hrs showing particles, wires, and confluent films (left to right). b) Quantification of surface coverage from images in (a) and fitting to a Langmuir model. c) Time-lapse AFM images showing transformation from discrete particles (3 hrs) to sparse wires (5 hrs) and denser wires (7 hrs). d) Quantification of peptide heights from AFM images with various surface coverages, showing clusters (red) increasing with coverage and wires (blue) mostly below 1.8 nm. Error bars represent standard deviation from at least n=40 measurements per datapoint.

A variety of peptide nanostructures form at 10, 50 and 125 nM concentrations upon 5 hours of incubation time under ambient conditions, as shown in FIG. 16a. From these quasi-equilibrium states, peptide affinity (K) can be calculated by surface coverage measurements (FIG. 16b), yielding a value of 20 µM$^{-1}$. While assembly at 125 nM solution yields confluent ordered films, similar to previous observations[11a], the lowest concentration yields sparse peptide clusters, ~1.5 nm in height, and 20-30 nm in diameter. The height of the clusters are reminiscent of the disordered phase from previous studies of GrBP5 film formation,[11a] seen immediately preceding the ordering transition. Interestingly, isolated high aspect ratio nanowires form at 50 nM with uniform spacing, signifying a threshold concentration for wire formation.

To understand the transition from discrete peptide clusters to individual molecular wires, we perform time-lapsed AFM of the adsorption process using the solutions containing 50 nM concentrations at different time spans (3, 5 and 7 hours, FIG. 16c). In previous observations of the confluent film formation, the transition from disorder to order was observed to correspond with a decrease in height of the assembled peptide by up to ~50%. During the particle-to-wire transition observed here, a similar trend occurs with a less abrupt height change of ~30% as peptide coverage increases (FIG. 16d). Concurrent with the NW formation, the spacing narrows from ~50 nm to ~16 nm upon 5 and 7 hours of assembly, respectively. Thus, at low concentrations, peptides initially exist as discrete clusters that reach a certain height and size, and eventually grow over time to form nanowires likely templated by the graphite surface lattice.

Figure 17:
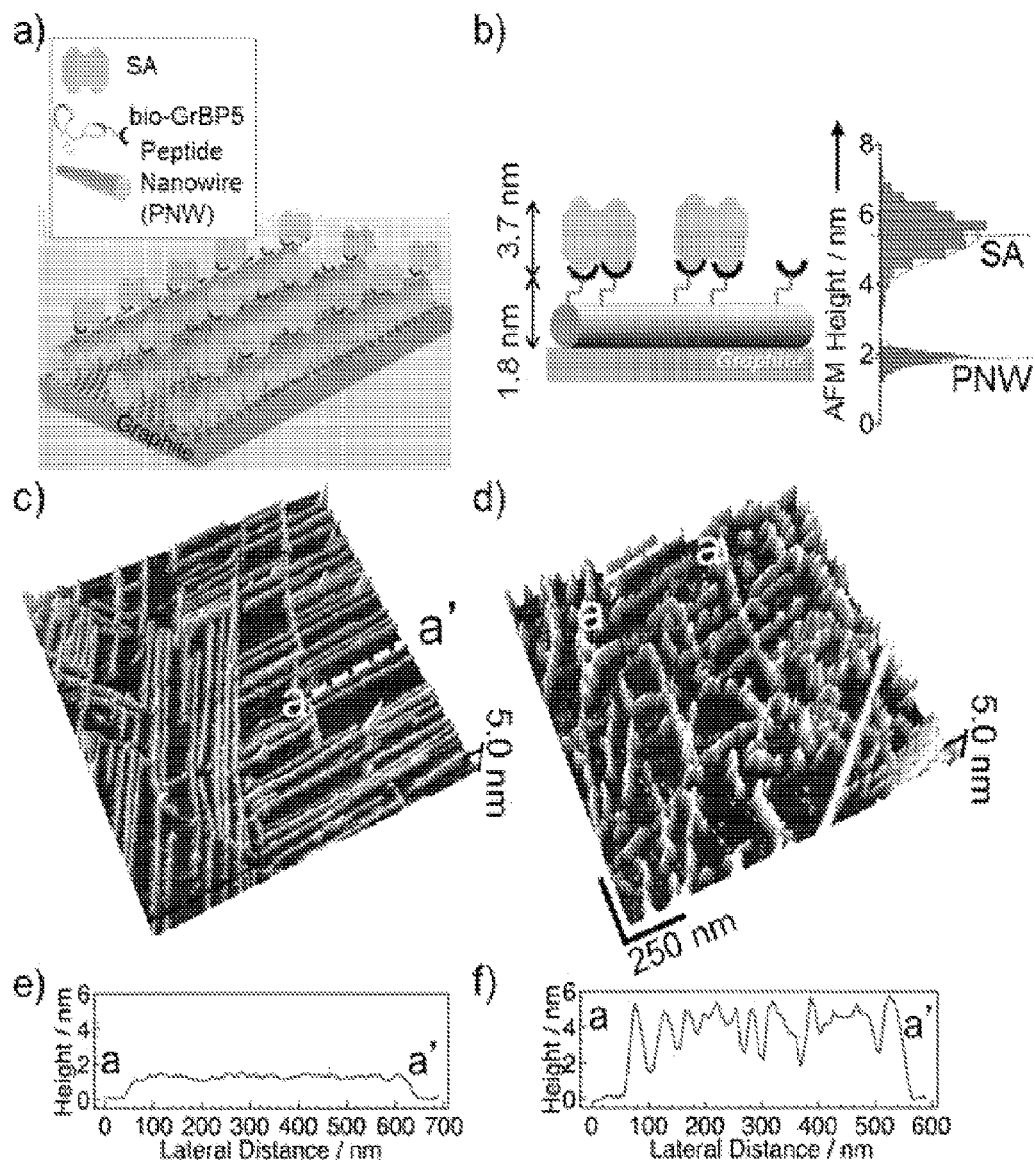
FIG. 17. Characterization of biotin display by PNWs. a) Schematic of fabricated bio-GrBP5 wires displaying biotin and immobilized streptavidin proteins, b) Side profile of PNW on graphite with immobilized SA and their respective heights, observed in AFM height histogram on the right. c) Pseudo-3D AFM image of bare PNW on graphite and d) PNWs after incubation with SA solution showing wires coated with SA. Both images have the same z-scale. e) and f) respective AFM cross sections showing difference in height. Height measurements are from at least n=100 measurements.

Functional peptide nanowires offer a novel molecular scaffold to immobilize biomolecules via specific recognition of its accessible tail, which is programmable through the known peptide sequence. To demonstrate this, here we first utilize available biotin from peptide NW formation and, taking advantage of the highly specific biotin-SA interaction, incubate SA proteins to assess the functionality of biotin displayed on the nanowires (depicted in FIG. 17a). To immobilize SA, functional nanowires are first formed on graphite (FIG. 17c), followed by exposure to a solution of SA in buffer for 1 minute. As seen in FIG. 17d, nanowires are uniformly coated with SA and are spaced roughly 30 nm apart on the wire. The observed height of coated bio-GrBP5 PNWs significantly increased from 1.8±0.4 nm to 5.8±0.9 nm, indicating that SA molecules are bound to the nanowires. The average height of immobilized SA on NWs is, therefore, ~4 nm, in good agreement with the dimension characterized by protein crystallography (45×45×53 Å).[13] Thus, these results indicate that protein dimension, and structure of SA could be largely preserved when bound to PNWs.

Figure 18:
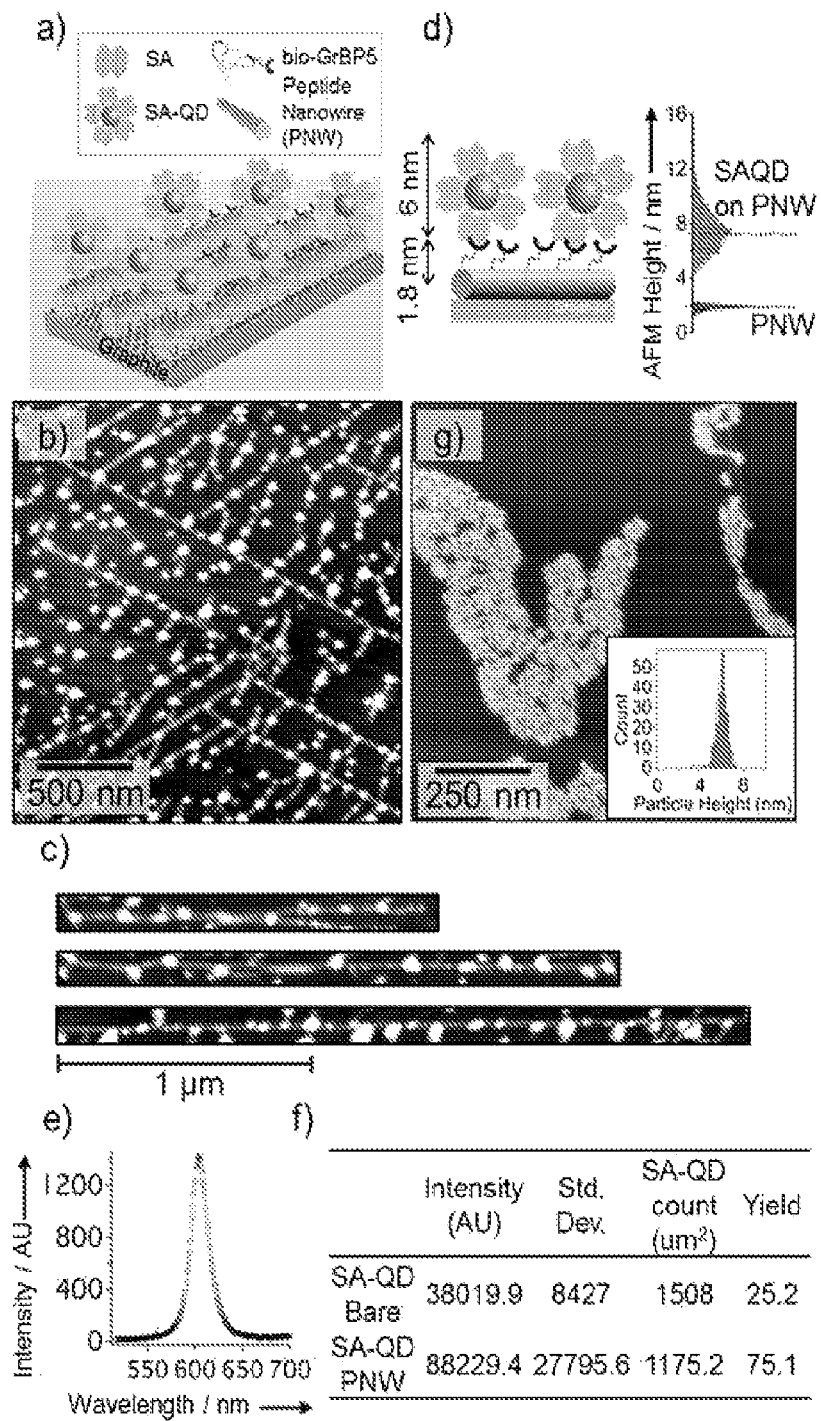
FIG. 18. Targeted immobilization of SA-QD on PNWs. a) Schematic of hierarchical QD assembly on self-assembled nanowires b) AFM image of particles targeted onto micron-length PNWs assembled on graphite with individual wires highlighted in c). d) Side profile of SA-QD on PNW showing observed heights and histogram from image (b). e) Representative photoluminescence measurement under excitation with laser showing emission at 605 nm from QD on PNWs and f) Table summarizing photoluminescence measurements of SA-QDs both with and without PNWs, indicating a 3× higher yield per particle when immobilized on PNWs. g) SA-QD on graphite without PNWs. Height measurements are from at least n=100 measurements.

To demonstrate further utility, chemically functionalized self-assembled PNWs allow targeted assembly of nanoparticles onto patterns on graphite. SA-coated quantum dots (SA-QDs) are widely employed in both nanotechnology and nanomedicine.[4a, 14] We used SA-QDs here to demonstrate the functionality of bio-GrBP5 as a molecular scaffold through the highly ordered NW architecture. Upon exposure to SA-QD solution, particles target bio-GrBP5 wires and self-organize into 2D patterns via specific biotin-SA molecular recognition. SA-QD decorated NWs span several micrometers on the surface, represented in FIG. 18b with the longest measuring 3-μm or longer (FIG. 18c). AFM height measurements of the PNW-immobilized particles averaged ~7.5 nm; this is indicative of the presence of PNWs (~1.8 nm in height) underlying immobilized SA-QD particles (FIG. 18d). The resulting 5.7 nm increase in height, on the average, over the measured height of bare PNWs (~L8 nm) agrees well with the literature values of free standing SA-QDs which reportedly varies from 4.7±0.7 nm to 5.5±0.6 nm[4a,15]. As indicated in the histogram in FIG. 18g, the height of SA-QDs adsorbed onto bare graphite is determined to be about 6 nm in height, also in agreement with SA-QD measurements on PNWs. In the absence of PNWs, however, SA-QDs aggregate uncontrollably on the graphite substrate forming large, mostly irregular, 2D islands (FIG. 18g). As further confirmation of QDs on PNWs, immobilized QDs are excited by a 514 nm laser to measure their photoluminescence (PL) (See FIGS. 18e and 18f, Supporting Information). The PL spectrum shows a large peak at the expected emission wavelength of 605 nm for the specific Cd—Se QDs used (FIG. 18e). To estimate the PL yield per QD, the integrated intensity of the emission peak is divided by the number of particles determined by AFM analysis (Supporting Information Methods); the resulting values are listed in FIG. 18f. The yield from SA-QD particles on wires is found to be, on average, ~3× greater than their emission on bare graphite, indicating that the increased distance between QDs and graphite by PNWs may effectively suppress the quenching of the PL signal.

In conclusion, we demonstrate a method to form chemically addressable peptide nanowires on graphite which then can be used as a molecular scaffold for the hierarchical assembly of quantum dots. Specifically, at low peptide concentrations (a few nM) discrete PNWs form on atomically flat graphite through a transformation of peptide nanoclusters into elongated nanostructures, guided by the surface lattice. In fact, by controlling the growth conditions, through both time and concentration, it is possible to form variety of peptide nanostructures, i.e., 0-D clusters, 1-D wires and 2-D films, with defined number density and highly precise spacing at nanoscale dimensions. Furthermore, bio-functional moieties, such as biotin, can be attached to the N-terminus of the peptides and which then become available for interaction with the protein SA and SA-functionalized QDs upon self-assembly on graphite. Chemically addressable nanowires, via functionalization of the GrBP5 tail, can be used as the basis for organizing other metallic nanoparticles, e.g., via Cysteine- or Histidine-tags, for future optical, electrical or magnetic nanodevices fabricated on graphite and graphene.

REFERENCES FOR EXAMPLE 4

[1] a) M. Grzelczak, J. Vermant, E. M. Furst, L. M. Liz-Marzan, *ACS Nano* 2010, 4, 3591; b) S. Srivastava, N. A. Kotov, Soft Matter 2009, 5, 1146.

[2] Z. Y. Tang, N. A. Kotov, *Adv. Mater.* 2005, 17, 951.

[3] a) I. W. Hamley, *Nanotechnology* 2003, 14, R39; b) Y. Lin, A. Boker, J. B. He, K. Sill, H. Q. Xiang, C. Abetz, X. F. Li, J. Wang, T. Emrick, S. Long, Q. Wang, A. Balazs, T. P. Russell, *Nature* 2005, 434, 55; c) S. O. Kim, H. H. Solak, M. P. Stoykovich, N. J. Ferrier, J. J. de Pablo, P. F. Nealey, *Nature* 2003, 424, 411; d) W. A. Lopes, H. M. Jaeger, *Nature* 2001, 414, 735.

[4] a) H. Bui, C. Onodera, C. Kidwell, Y. Tan, E. Graugnard, W. Kuang, J. Lee, W. B. Knowlton, B. Yurke, W. L. Hughes, *Nano Lett.* 2010, 10, 3367; b) H. Yan, J. Sharma, R. Chhabra, Y. Liu, Y. G. Ke, *Angew. Chem. Int. Edit.* 2006, 45, 730; c) J. D. Le, Y. Pinto, N. C. Seeman, K. Musier-Forsyth, T. A. Taton, R. A. Kiehl, *Nano Lett.* 2004, 4, 2343; d) T. H. LaBean, H. Y. Li, S. H. Park, J. H. Reif, H. Yan, *J. Am. Chem. Soc.* 2004, 126, 418.

[5] a) Y. Huang, C. Y. Chiang, S. K. Lee, Y. Gao, E. L. Hu, J. De Yoreo, A. M. Belcher, *Nano Lett.* 2005, 5, 1429; b) T. Scheibel, R. Parthasarathy, G. Sawicki, X. M. Lin, H. Jaeger, S. L. Lindquist, *Proc. Natl. Acad. Sci. U.S.A.* 2003, 100, 4527; c) G. Grigoryan, Y. H. Kim, R. Acharya, K. Axelrod, R. M. Jain, L. Willis, M. Drndic, J. M. Kikkawa, W. F. DeGrado, *Science* 2011, 332, 1071; d) R. A. McMillan, C. D. Paavola, J. Howard, S. L. Chan, N. J. Zaluzec, J. D. Trent, *Nat. Mater.* 2002, 1, 247; e) S. Sotiropoulou, Y. Sierra-Sastre, S. S. Mark, C. A. Batt, *Chem. Mater.* 2008, 20, 821.

[6] L. Adler-Abramovich, D. Aronov, P. Beker, M. Yevnin, S. Stempler, L. Buzhansky, G. Rosenman, E. Gazit, *Nat. Nanotechnol.* 2009, 4, 849.

[7] C. Whitehouse, J. Y. Fang, A. Aggeli, M. Bell, R. Brydson, C. W. G. Fishwick, J. R. Henderson, C. M. Knobler, R. W. Owens, N. H. Thomson, D. A. Smith, N. Boden, *Angew. Chem. Int. Edit.* 2005, 44, 1965.

[8] H. Y. Bai, K. Xu, Y. J. Xu, H. Matsui, *Angew. Chem. Int. Edit.* 2007, 46, 3319.

[9] Z. H. Su, Y. A. Lin, G. H. Xiao, E. Balizan, G. Kaur, Z. W. Niu, Q. A. Wang, *Langmuir* 2011, 27, 1398.

[10] a) Q. Gu, C. D. Cheng, R. Gonela, S. Suryanarayanan, S. Anabathula, K. Dai, D. T. Haynie, *Nanotechnology* 2006, 17, R14; b) N. Nuraje, I. A. Banerjee, R. I. MacCuspie, L. T. Yu, H. Matsui, *J. Am. Chem. Soc.* 2004, 126, 8088.

[11] a) C. R. So, Y. Hayamizu, H. Yazici, C. Gresswell, D. Khatayevich, C. Tamerler, M. Sarikaya, *ACS Nano* 2012, 6, 1648; b) C. R. So, J. L. Kulp, E. E. Oren, H. Zareie, C. Tamerler, J. S. Evans, M. Sarikaya, *ACS Nano* 2009, 3, 1525; c) F. Zhang, H. N. Du, Z. X. Zhang, L. N. Ji, H. T. Li, L. Tang, H. B. Wang, C. H. Fan, H. J. Xu, Y. Zhang, J. Hu, H. Y. Hu, J. H. He, *Angew. Chem. Int. Edit.* 2006, 45, 3611; d) C. L. Brown, I. A. Aksay, D. A. Saville, M. H. Hecht, *J. Am. Chem. Soc.* 2002, 124, 6846.

[12] J. V. Barth, J. Weckesser, G. Trimarchi, M. Vladimirova, A. De Vita, C. Z. Cai, H. Brune, P. Gunter, K. Kern, *J. Am. Chem. Soc.* 2002, 124, 7991.

[13] A. L. Weisenhorn, F. J. Schmitt, W. Knoll, P. K. Hansma, *Ultramicroscopy* 1992, 42, 1125.

[14] A. M. Belcher, C. B. Mao, C. E. Flynn, A. Hayhurst, R. Sweeney, J. F. Qi, G. Georgiou, B. Iverson, *Proc. Natl. Acad. Sci. U.S.A.* 2003, 100, 6946.

[15] T. Q. Vu, V. P. Pattani, C. F. Li, T. A. Desai, *Biomed. Microdevices* 2008, 10, 367.

Supplemental Information for Example 4

Immobilization of Streptavidin and Streptavidin-Quantum Dots on Peptide Nanowires bio-GrBP5 peptide nanowires were first formed on graphite and verified under an AFM. Next, either streptavidin (from *Streptomyces avidinii*, 50677, Sigma-Aldrich, St. Louis, Mo.) or streptavidin-Qdot conjugates (SA-QDs) were introduced to the same surface for immobilization on nanowires. For this, a 1 μM solution of SA or Cd—Se Qdot 605-streptayidin conjugate (Q10101MP, Life Technologies Co., Grand Island, N.Y.) was diluted 1:1 with deionized water at room temperature for a 500 nM solution of SA or SA-QD. On a pre-assembled surface with bio-GrBP5 peptide nanowires, 500 nM SA or SA-QD solution was incubated on graphite at room temperature for 1 minute. Excess SA or SA-QD solution was removed after 1 minute by pipette. In order to prevent salt formation from the buffer, 100 μL of deionized water was drop incubated on graphite after SA or SA-QD incubation and removed by pipetting. After this rinsing step, the remaining liquid on graphite surface was dried off with a stream of nitrogen.

Photoluminescence Measurements.

For photoluminescence measurements, a Raman microscope (InVia, Renishaw, Hoffman Estates, Ill.) equipped with an inverted optical microscope (DMIRBE, Leica Microsystems, Wetzlar, Germany) was used. The excitation source used was an Argon Ion laser at 514 nm wavelength with a spot size of less than 1 μm (using a 100× objective). Laser output power was 10 mW, set to 10% power by microscope software prior to data acquisition.

Example 5

Selective Detection of Proteins via Self-Coassembled Mixed Peptide Functionalized Graphene Bio-Sensors Abstract In the present study we demonstrate selective detection of a model protein against a background of serum protein using a graphene sensor functionalized via co-assembled, multifunctional, self-assembling peptides, which simultaneously display the probe and prevent non-specific adsorption. In particular we demonstrate a graphene field effect transistor sensor which can detect streptavidin against a background of serum bovine albumin at less than 50 ng/ml. We have also developed a regeneration protocol, which allows us to utilize each sensor for over 12 experiments. This peptide based functionalization platform is particularly well suited to biological applications due to the ease of fusion of peptides with proteinaceous probes, and biocompatible nature. This system can be applied to a variety of bio-sensing problems, such as the detection of cancer markers under clinical conditions.

Introduction

Detection of molecular recognition events ex situ has been a well-established approach to drug discovery, and molecular biology research since the 1960s.[1] More recently, it has been applied in clinical research and practice for diagnosing and monitoring of diseases, including several types of cancer, through the detection of biomarkers in blood, tissues, or urine of the patient. [2] Among the techniques used to detect such markers are the surface plasmon resonance spectroscopy (SPR),[3, 4] quartz crystal microbalance (QCM),[5] various immunoassays, including electrochemical assays, and others.[6-9] The applicability of these techniques to clinical practice remains limited, however, since the markers are present in very low concentrations, against a background of serum or tissue proteins. In the last several years, single layer material field effect transistor (SLaM-FET) sensors have been employed for ultrasensitive detection of molecular binding.[10, 11] Graphene and carbon nano-tubes in particular have been used successfully to achieve very low detection limit,[12-15] with some designs reported to detect femtogram per milliliter concentrations of analyte.[16] Such sensitivity is possible due to graphene's excellent electronic properties, resulting from delocalized it bonds on the surface, and a band gap which is very sensitive to doping.[17-19]

Figure 19:
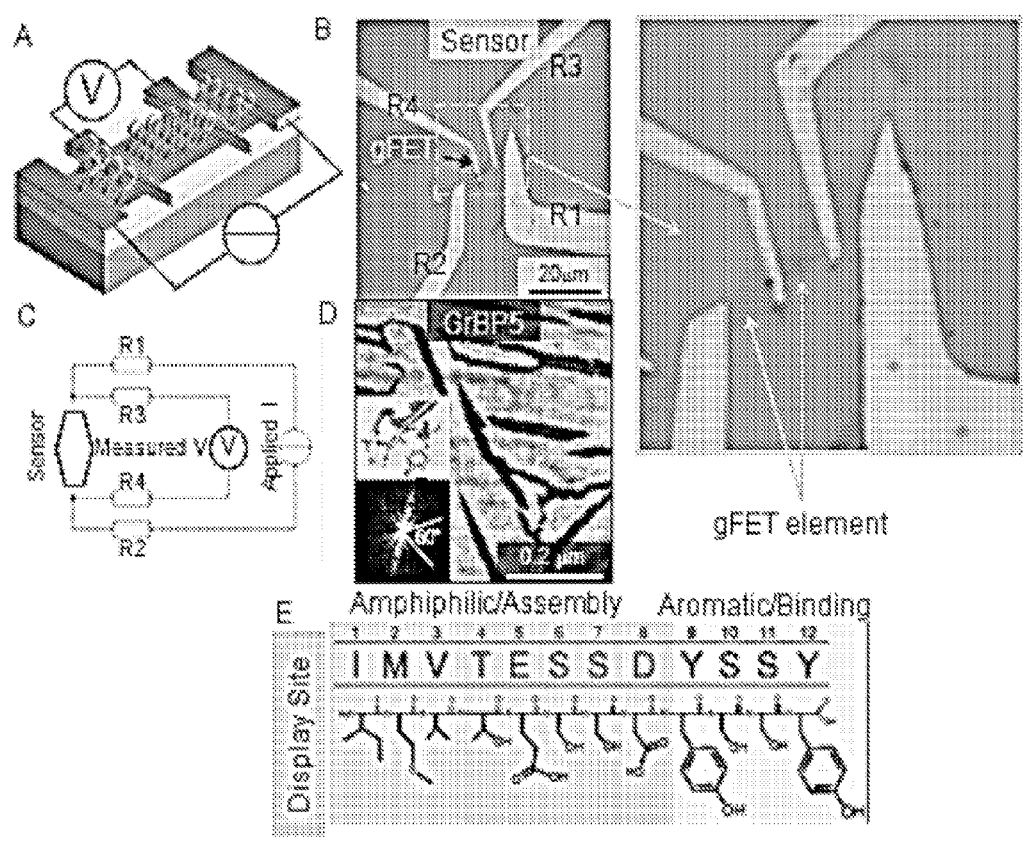
FIG. 19. A) Schematic illustration of the four-probe bio-functionalized graphene sensor; B) Optical microscopy image of the sensor device; C) Equivalent circuit; D) Monolayer of GrBP5-WT assembled on graphite (AFM); E) GrBP5-WT sequence and property/function map.

In order to capture the target, probes must be immobilized on the sensor surface in a predictable, non-perturbative fashion. A number of functionalization routes through covalent bonding, i.e. the introduction of carboxylic groups, have been employed to control the interface with graphitic materials.[20, 21] However, to preserve the intrinsic properties of these materials, methods of non-covalent functionalization via π-π it stacking using aromatic chemistry have been used.[22, 23] In addition to these successful chemical functionalization techniques, non-invasive approaches using peptides have been demonstrated as a biocompatible alternative to controlling the surface properties of graphitic materials. Biocombinatorially selected through phage or cell-surface display, engineered solid-binding peptides offer a versatile platform for bridging the bio/inorganic divide. [24-26] These strong-binding (kd 50 nM to 1 μM), material-specific 7-14 amino acid long sequences possess a wealth of chemical diversity and modular capacity through mutation and targeted chemical modification, providing unique opportunities for tuning binding, chemical properties, and display.[27, 28] Instead of covalent bonding, prevalent in synthetic linkers, short peptides bind through weak forces at multiple positions at the peptide/solid interface enabling them to assemble and function in aqueous solutions.[29, 30] Solid-binding peptides are particularly well suited for applications in medical and biological fields because they are produced and function under biological conditions, and have not shown any toxicity in cell culture studies.[31, 32] Various graphite,[33] graphene-,[34-36] and CNT-binding [37, 38] peptide sequences and poly amino acids have been identified in literature through combinatorial display and other means. They have been employed for applications such as bioinorganic nano-structure formation,[39] as well as non-specific control of surface chemistry.[33] The dodecapeptide GrBP5-WT (Sequence: IMVTESSDYSSY (SEQ ID NO: 5), affinity constant: Ka=3.78 μM-1) is unique among graphite- and CNT-binding peptide sequences identified so far, as it forms long-range ordered, uniform, and crystallographic molecular nanostructures on graphitic materials (FIG. 19D), which can be controlled through sequence mutation. GrBP5-WT is modular and can be designed to expose predictable surface chemistry through the display of specific amino acids. Moreover, it has been shown that two mutants of GrBP5-WT can be simultaneously assembled to display a combination of properties. Multi-functionality is critical to the application of a biomarker sensor in clinical practice, since in addition to possessing sensitivity, it must be capable of discriminating for the target against a background of proteins present in the sample. It is necessary to simultaneously impart the targeting and the anti-fouling capabilities to the sensor. In the present study, we demonstrate selective detection of a model protein against a background of serum protein using a graphene sensor functionalized via co-assembled, multi-functional, self-assembling peptides, which simultaneously display the probe and prevent non-specific adsorption. In particular we employ a 4-probe graphene field effect transistor (gFET) sensor (FIG. 19A, B, C), functionalized using simultaneously co-assembled mutants of GrBP5-WT, displaying biotin, or hydrophilic residues at the N-terminus (Table 3) to detect streptavidin (SA) against a background of bovine serum albumin (BSA). We also developed a regeneration protocol, which allows us to utilize a single sensor for over 12 experiments. Through this study we establish a methodology for single-step bio-functionalization of graphitic sensors toward sensitive detection of biomolecules, which can be applied to a variety of analytes in complex solutions.

TABLE 3

Peptide sequences weights and hydropathy indices

| Molecule | Sequence | Mol. Mass | G.R.A.V.Y.[a] |
|---|---|---|---|
| GrBP5-WT | IMVTESSDYSSY (SEQ ID NO: 5) | 1381.4 | −0.242 |
| Bio-GrBP5 | bioIMVTESSDYSSY (SEQ ID NO: 20) | 1624.3 | Aprox. −0.185 |
| SS-GrBP5 | SSIMVTESSDYSSY (SEQ ID NO: 16) | 1555.6 | −0.321 |

Materials and Methods

Sensor Construction

Graphene was prepared by exfoliation method [18] on SiO2 wafers, which were pre-treated with acidic piranha solution (75% sulfuric acid, 25% hydrogen peroxide). Orientation markers were made via indium micro-soldering, [42] and a PMMA coating was applied to the wafer by spin-coating for 1 min at 1000 RPM. The patterns (FIG. 19 A,B) were made via electron beam lithography on JOEL 7000 SEM (JOEL Ltd., Japan). The pattern was developed and then extended by hand to lengthen the electrodes. The electrodes were made by sputtering 2 nm of titanium as adhesion layer, followed by 46 nm of platinum, and 2 nm of titanium, as insulating layer using Gatan Precision Etching Coating System Model 682 (Gatan Inc., USA). The PMMA was removed in boiling acetone, and the device annealed in a tube furnace under a 60% argon/40% hydrogen atmosphere at 450 Co for 1 hour. The terminals of indium solder were added at the ends of the electrodes. The contacts were current-annealed under nitrogen atmosphere by cycling currents of up to 1 mA at up to 60 volts through the device using Agilent U2722A USB Modular Source Measure Unit (Agilent. USA), until the resistance of the device remained constant between cycles. The devices were re-cleaned between experiments by boiling in acetone for 1 hour, followed by current-annealing.

Peptides and Proteins

The peptides were produced by solid-state synthesis using a CSBio 336 s automated peptide synthesizer (CSBio, USA) on Wang resin via Fmoc chemistry and HBTU activation. The crude peptides were purified by reverse phase high performance liquid chromatography to >98% purity (Gemini 10 µm C18 110A column) The purified peptides were verified by mass spectroscopy (MS) using a MALDI-TOF mass spectrometer (Bruker Daltonics Inc., USA). The amino acid sequences and the physio-chemical properties of the peptides used in the study are shown in Table 3. Streptavidin and bovine serum albumin were purchased from Sigma-Aldrich, USA, and used as received. All of the solutions were prepared with deionized water.

Experimental Setup

The device was connected to the Agilent U2722A USB Modular Source Measure Unit (Agilent, USA) in a four probe configuration, with current kept constant between R1 and R2 terminals, and voltage measured between R3 and R4 terminals (FIG. 19C). A 20 µl drop of water was placed on the sensor and the resistance was allowed to equilibrate. The device was maintained in a hydration chamber at 100% humidity to prevent evaporation. Analyte was added to the static drop on the sensor in the appropriate concentrations, so that the total volume of the drop never exceeded 35 µl. Data was collected from two distinct devices and each experiment was reproduced at least once. See supporting information for additional data.

Atomic Force Microscopy

To complement the biosensor results, certain states of each experiment were reproduced on highly-oriented pyrolytic graphite (HOPG) and imaged by atomic force microscopy (AFM). The peptide solutions, at concentrations identical to those used for sensing experiments, were placed on HOPG and allowed to bind for a similar amount of time (10-90 minutes). The samples were washed by dilution, dried and immediately imaged using a Digital Instruments Nanoscope-IIIa Multimode AFM (Veeco, USA) under tapping mode. The images were taken in at least 3 different areas of the sample. The similarity between peptide binding to HOPG and peptide binding to graphene was demonstrated by AFM (not shown).

Results and Discussion

Figure 20:
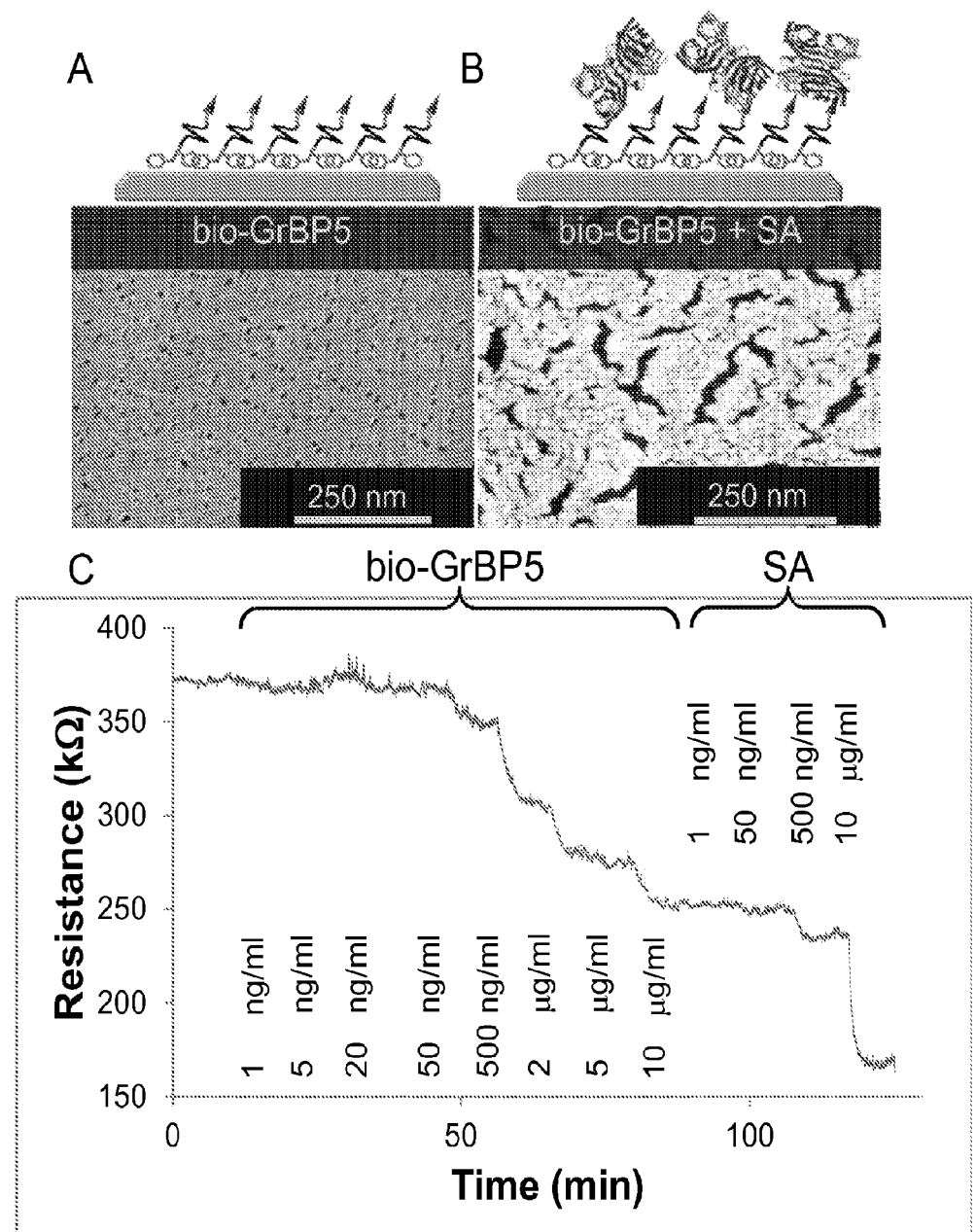
FIG. 20. A) AFM image and schematic of 10 mg/ml bio-GrBP5 self-assembled on graphite; B) AFM image and schematic of 10 mg/ml streptavidin captured by the bio-GrBP5 monolayer; C) Corresponding sensogram of sequential addition of increased concentrations of bio-GrBP5 followed by the sequential addition of increased concentrations of streptavidin.

In order to test the capabilities of the graphene field effect transistor sensor, as well as to ensure that our peptide-based functionalization scheme appropriately displayed the probe, we created a biotin-graphite binding peptide (bio-GrBP5) fusion sequence (Table 3). By sequential introduction of increasing concentrations of the peptide to the sensor, we were able to determine the ultimate sensitivity of our system, and to create a dense, uniform monolayer of self-assembled biotinilated peptide (FIG. 20A, C). We then introduced streptavidin to the system in sequentially increasing concentrations to determine if the sensitivity significantly diminishes with distance from the sensor. The AFM images (FIG. 20B), along with the sensogram (FIG. 20C) demonstrate binding of streptavidin to the biotinilated sensor. The height difference of about 2 nm is observed between the peptide only and the SA added surfaces. Moreover, we found that the sensitivity of our device is between 20 and 50 ng/ml, both in the bare and functionalized state. As a control, we also tested the binding of SA to the un-functionalized sensor, finding that no detectable binding occurs in the range of concentrations used (not shown). The differences in morphology in the two AFM images indicates that there is a certain amount of instability introduced into the peptide by the analyte, however, the coverage remains above 85% after two hours of testing, which is well beyond the time required for measurements.

Figure 21:
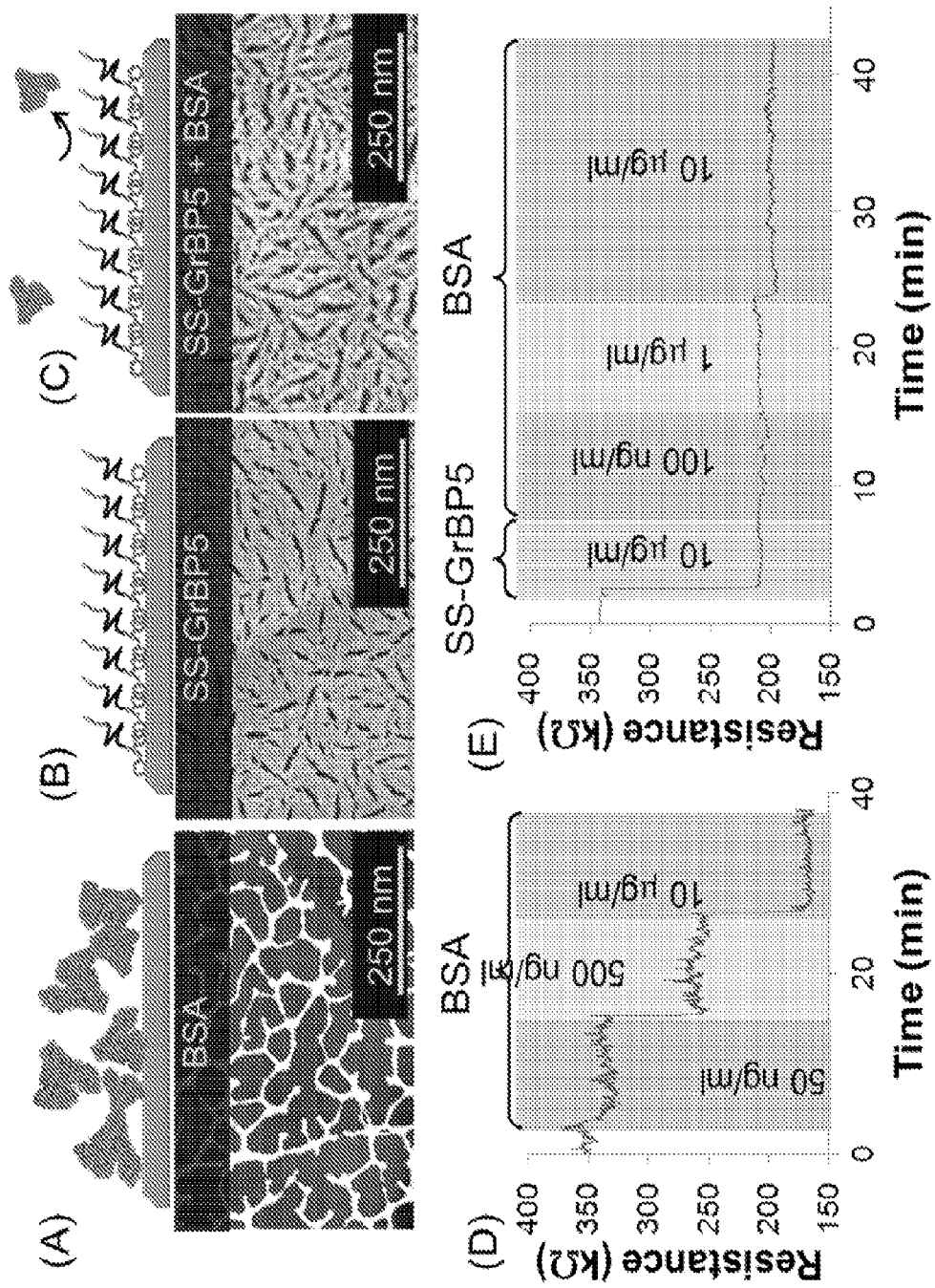
FIG. 21. A) AFM image and schematic of 10 mg/ml BSA Adsorption to bare graphite; B) AFM image and schematic of 10 mg/ml SS-GrBP5 on graphite; C) AFM image and schematic of 10 mg/ml BSA adsorption blocked by SS-GrBP5—functionalized graphite; D) Sensogram of sequentially increasing concentrations of BSA added to bare sensor; E) Sensogram of sequentially increasing concentrations of BSA added to SS-GrBP5 functionalized sensor.

Non-specific adsorption of background proteins is a major concern when testing for biomarkers in clinically relevant samples. Serum albumin (BSA) constitutes about 50% of the blood serum proteins, and is, therefore, a good model protein to serve as the background against which SA may be detected. FIG. 21A demonstrates the adsorption of BSA on graphite after washing (corresponding sensogram FIG. 21D). The protein is present on the entire surface and agglomerates into fibers as the result of drying. The sensogram shows robust detection of binding at 50 ng/ml, followed by increased binding with overall resistance shift of almost 200 kΩ at 10 µg/ml, which is higher than any observed in other experiments, probably due to the formation of a multi-layer film. In order to prevent non-specific adsorption of BSA, we employed the SS-GrBP5 mutant (Table 3), identified in an earlier study as one capable of assembling into ordered monolayers and presenting hydrophilic chemistry (36' contact angle at 100% coverage).[41] Such a contact angle value is similar to those achieved in literature by self-assembled monolayer polyethylene glycol anti-fouling systems (about 32°).[32, 43, 44] The contact angle value has been strongly linked to anti-fouling properties in a variety of systems.[45] We, therefore, hypothesized that our self-assembled peptide monolayers, which are dense and exhibit similar contact angles, would also be anti-fouling. To test this hypothesis, we assembled SS-GrBP5 peptide (FIG. 21B) on the sensor surface, and introduced BSA to the system (FIGS. 21C and 21E). The binding of BSA was significantly impaired by the SS-GrBP5 mutant, resulting in no detectable binding at less than 10 µg/ml concentrations of BSA. The AFM image of the surface after incubation with 10 µg/ml BSA for 90 minutes (FIG. 21C) shows a small amount of protein present sparsely on the surface and very low degradation of the underlying peptide monolayer. The added stability, as compared to the bio-GrBP5 mutant, is likely the result of the more amphiphilic nature of the SS-GrBP5 monolayer, which remains robustly oriented between the hydrophobic graphite and water. As a control experiment, we introduced BSA to a monolayer of bio-GrBP5 (not shown). The sensogram show significant binding of BSA.

Figure 22:
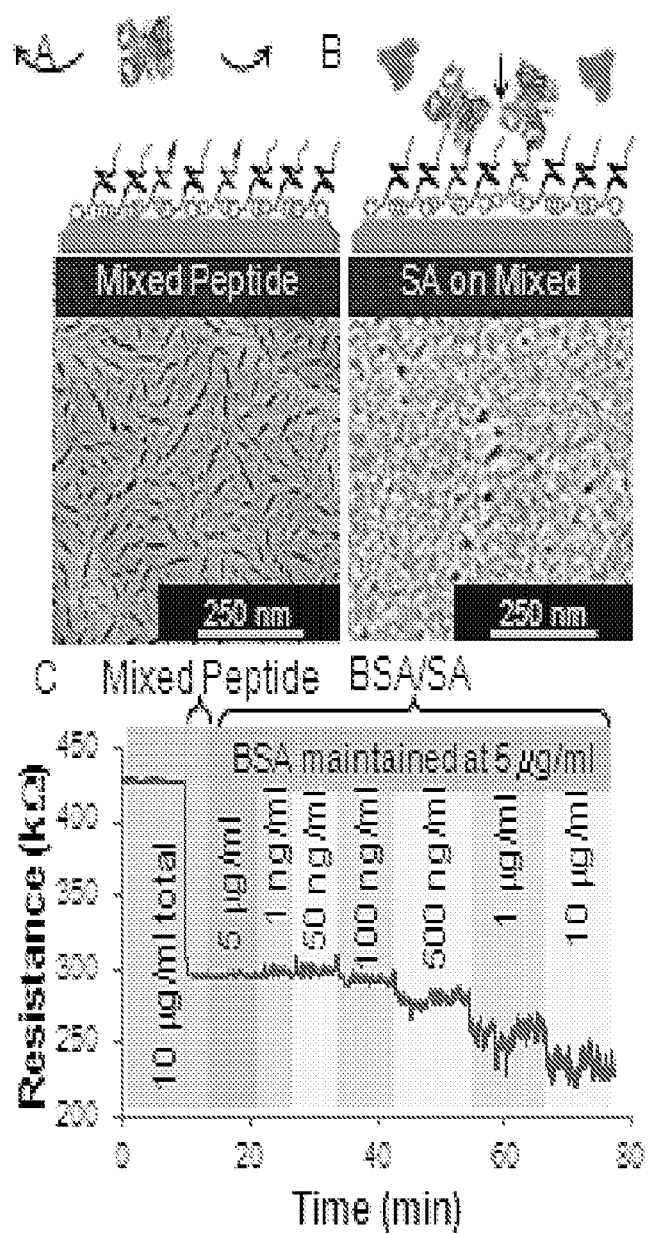
FIG. 22. A) AFM image and schematic of mixed peptide monolayer on graphite B) AFM image and schematic of selective detection of streptavidin against a BSA background; C) corresponding sensogram, where 25% bio-GrBP5, 75% ss-GrBP5 peptide mixture is introduced first, followed by BSA, which shows no binding, and finally, streptavidin, which is captured selectively.
Figure 23:
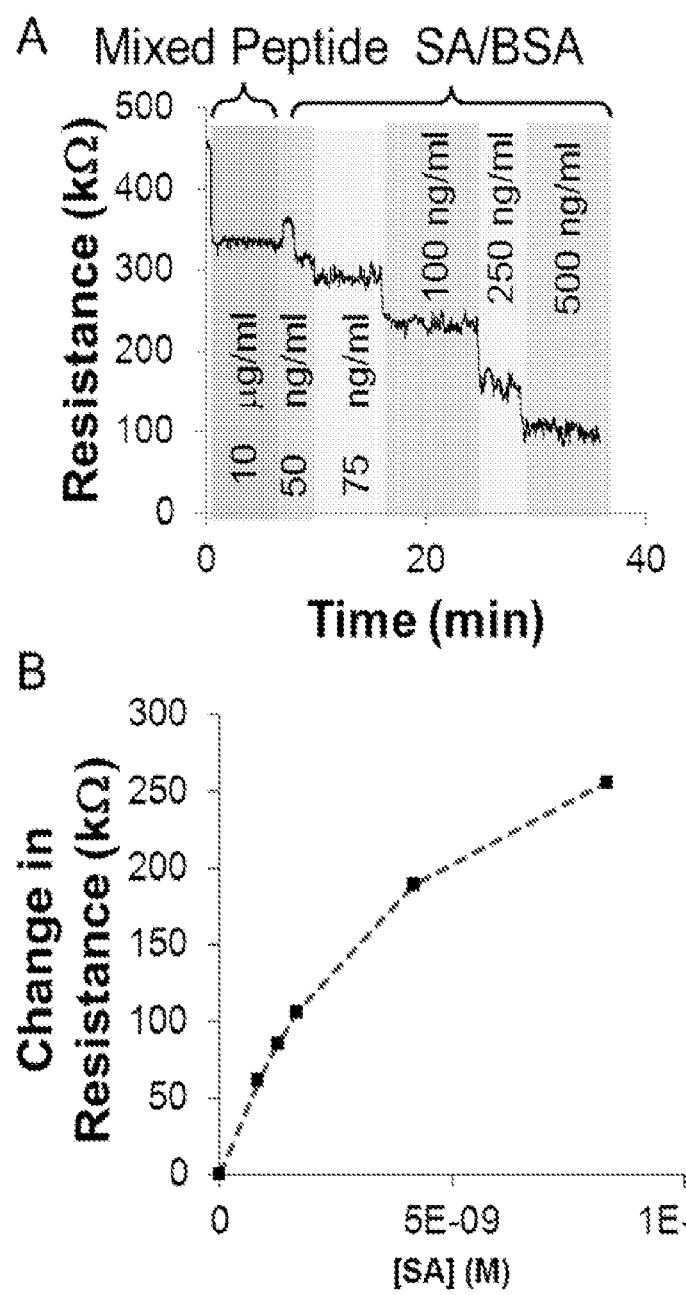
FIG. 23. A) Sensogram of formation of the mixed peptide monolayer (25% bio-GrBP5, 75% SS-GrBP5), followed by washing and re-stabilization (cut at grey), followed by the sequential addition of increased concentrations of bio-GrBP5 in a 5 mM BSA Solution; B) Corresponding response versus concentration plot fitted with Langmuir isotherm FIG. 24. AFM images of peptides on surfaces of bulk $MoS_2$ and the plots of coverage of peptides vs. incubation concentration of peptides. The size of each AFM image is 2 μm by 2 μm.

By combining the anti-fouling properties of SS-GrBP5 with the biotinylated probe peptide, we created a sensor capable of selective detection of streptavidin in a bovine serum albumin solution. A mixed peptide monolayer consisting of 25% bio-GrBP5 and 75% SS-GrBP5 was formed in a single step from a solution with an overall concentration of 10 µg/ml. The AFM of the resulting monolayer (FIG. 22A) shows that the peptides self-assembled into the dense, ordered structure with no discernible segregation, leading to the likely conclusion that the peptides are miscible. Guided by the results in FIG. 21, we introduced 5 µg/ml BSA to the sensor and detected no binding (FIG. 22C). We then introduced sequentially increasing concentrations of SA to the sensor, while maintaining the levels of BSA, and were able to reliably detect streptavidin at 100 ng/ml, although some signal was present at even lower concentrations (FIG. 22C). The AFM image of the graphite surface at the final conditions (FIG. 22B) showed less coverage by SA than the biotin-only surface (FIG. 20B). The overall stability of the bio-GrBP5 appears to have been improved by co-assembly with SS-GrBP5, displaying very high coverage and density. SS-GrBP5 also seems to retain its anti-fouling function despite a 25% reduction in coverage, owing to the fact that the overall order of the monolayer is maintained by the self-assembling sequence of bio-GrBP5 inclusion. Since the above experiment was carried out under the stop-flow conditions, some of the streptavidin may have been deactivated by the excess bio-GrBP5 still left in solution. To eliminate this variable and to find the region of linear response for our sensor, we repeated the experiment, washing the sensor by dilution after immobilizing bio-GrBP5, prior to introducing streptavidin. FIG. 23 shows the sensogram, and the corresponding signal versus concentration plot for the experiment. The Langmuir fit shows a KD value of about 1.5 nM-9, which is higher than the established literature values. [46] This may indicate that biotin is not as readily accessible on the co-assembled surface, possibly because it is surrounded by a large numbers of the anti-fouling SS-GrBP5 peptides, which are slightly larger that bio-GrBP5.

The sensor devices used in this study were regenerated and reused. We observed some sensor degradation over the course of about 12 experiments, with the noise levels increasing from near 2 kΩ to about 10 kΩ. However, it seems that the sensitivity of the device is not significantly affected between trials, meaning that it can be used to produce comparable data several times. This is a significant feature for practical application of graphene based sensors, and represents another advantage of peptide functionalization over covalent approaches.

Conclusions

In this study, we demonstrated a system for simultaneous passivation and functionalization of the graphene sensor using the GrBP5 modular graphite-binding peptide family, allowing for selective detection of streptavidin against a serum albumin background. The same system can be extended to other, more efficient sensor architectures, and other single layer materials systems, such as the semi-conducting MoS2 or WS2, through rational mutation of the GrBP5-WT peptide. Our ability to control the groups displayed by the peptide monolayers, as well as the possibility of creating mixed monolayers, allows for the construction of multi-functional sensors capable of selective detection of multiple probes in a complex environment. Since a variety of short peptidic probes have been identified for many disease biomarkers through phage and cell-surface display, the next step for this technology would be to create a diagnosis and monitoring system via genetic fusion of the two sequences. However, the system is not limited to clinical applications. Specific ligand receptor interactions are of critical importance to all areas of molecular biology. Using our system, a selective biosensor can be created for many of the ligand-receptor pairs under investigation, by displaying one of the constituents on the graphene surface in a predictable and robust fashion. More broadly, this study adds another tool to the peptide-based bionanotechnology toolkit, taking advantage of Nature's way of putting together materials at the nano-scale.

REFERENCES FOR EXAMPLE 5

[1] Yalow R S, Berson S A. IMMUNOASSAY OF ENDOGENOUS PLASMA INSULIN 1N MA N. Journal of Clinical Investigation. 1960; 39:1157-75.

[2] Ludwig J A, Weinstein J N. Biomarkers in cancer staging, prognosis and treatment selection. Nature Reviews Cancer. 2005; 5:845-56.

[3] Vaisocherova H, Yang W, Zhang Z, Cao Z Q, Cheng G, Piliarik M, et al. Ultralow fouling and functionalizable surface chemistry based on a zwitterionic polymer enabling sensitive and specific protein detection in undiluted blood plasma. Analytical Chemistry. 2008; 80:7894-901.

[4] Chou S F, Hsu W L, Hwang J M, Chen C Y. Development of an immunosensor for human ferritin, a nonspecific tumor marker, based on surface plasmon resonance. Biosensors & Bioelectronics. 2004; 19:999-1005.

[5] Di Natale C, Macagnano A, Martinelli E, Paolesse R, D'Arcangelo G, Roscioni C, et al. Lung cancer identification by the analysis of breath by means of an array of non-selective gas sensors. Biosensors & Bioelectronics. 2003; 18:1209-18.

[6] Yu X, Munge B, Patel V, Jensen G, Bhirde A, Gong J D, et al. Carbon nanotube amplification strategies for highly sensitive immunodetection of cancer biomarkers. Journal of the American Chemical Society. 2006; 128:11199-205.

[7] Liu X, Dai Q, Austin L, Coutts J, Knowles G, Zou J H, et al. A one-step homogeneous immunoassay for cancer biomarker detection using gold nanoparticle probes coupled with dynamic light scattering. Journal of the American Chemical Society. 2008; 130:2780-+.

[8] Mani V, Chikkaveeraiah B V, Patel V, Gutkind J S, Rusling J F. Ultrasensitive Immunosensor for Cancer Biomarker Proteins Using Gold Nanoparticle Film Electrodes and Multienzyme-Particle Amplification. Acs Nano. 2009; 3:585-94.

[9] Liu G D, Lin Y Y, Wang J, Wu H, Wai C M, Lin Y H. Disposable electrochemical immunosensor diagnosis device based on nanoparticle probe and immunochromatographic strip. Analytical Chemistry.

[10] Curreli M, Zhang R, Ishikawa F N, Chang H K, Cote R J, Zhou C, et al. Real-Time, Label-Free Detection of Biological Entities Using Nanowire-Based FETs. Ieee Transactions on Nanotechnology. 2008; 7:651-67.

[11] Alam M M, Wang J, Guo Y Y, Lee S P, Tseng H R. Electrolyte-gated transistors based on conducting polymer nanowire junction arrays. Journal of Physical Chemistry B. 2005; 109:12777-84.

[12] Ohno Y, Maehashi K, Matsumoto K. Label-Free Biosensors Based on Aptamer-Modified Graphene Field-Effect Transistors. Journal of the American Chemical Society. 2010; 132:18012-3.

[13] Stine R, Robinson J T, Sheehan P E, Tamanaha C R. Real-Time DNA Detection Using Reduced Graphene Oxide Field Effect Transistors. Advanced Materials. 2010; 22:5297-300.

[14] Someya T, Small J, Kim P, Nuckolls C, Yardley J T. Alcohol vapor sensors based on single-walled carbon nanotube field effect transistors. Nano Letters. 2003; 3:877-81.

[15] Page T R, Hayamizu Y, So C R, Sarikaya M. Electrical detection of biomolecular adsorption on sprayed graphene sheets. Biosensors & Bioelectronics. 2012; 33:304-8.

[16] Zhang B, Li Q, Cui T H. Ultra-sensitive suspended graphene nanocomposite cancer sensors with strong suppression of electrical noise. Biosensors & Bioelectronics. 2012; 31:105-9.

[17] Castro Neto A H, Guinea F, Peres N M R, Novoselov K S, Geim A K. The electronic properties of graphene. Reviews of Modern Physics. 2009; 81:109-62.

[18] Novoselov K S, Geim A K, Morozov S V, Jiang D, Zhang Y, Dubonos S V, et al. Electric field effect in atomically thin carbon films. Science. 2004; 306:666-9.

[19] Balandin A A, Ghosh S, Bao W Z, Calizo I, Teweldebrhan D, Miao F, et al. Superior thermal conductivity of single-layer graphene. Nano Letters. 2008; 8:902-7.

[20] Li D, Muller M B, Gilje S, Kaner R B, Wallace G G. Processable aqueous dispersions of graphene nanosheets. Nature Nanotechnology. 2008; 3:101-5.

[21] Niyogi S, Bekyarova E, Itkis M E, McWilliams J L, Hamon M A, Haddon R C. Solution properties of graphite and graphene. Journal of the American Chemical Society. 2006; 128:7720-1.

[22] Choi E Y, Han T H, Hong J H, Kim J E, Lee S H, Kim H W, et al. Noncovalent functionalization of graphene with end-functional polymers. Journal of Materials Chemistry. 2010; 20:1907-12.

[23] Ghosh A, Rao K V, Voggu R, George S J. Non-covalent functionalization, solubilization of graphene and single-walled carbon nanotubes with aromatic donor and acceptor molecules. Chemical Physics Letters. 2010; 488:198-201.

[24] Shiba K. Exploitation of peptide motif sequences and their use in nanobiotechnology. Current Opinion in Biotechnology. 2010; 21:412-25.

[25] Tamerler C, Khatayevich D, Gungormus M, Kacar T, Oren E E, Hnilova M, et al. Molecular Biomimetics: GEPI-Based Biological Routes to Technology. Biopolymers. 2010; 94:78-94.

[26] Peelle B R, Krauland E M, Wittrup K D, Belcher A M. Design criteria for engineering inorganic material-specific peptides. Langmuir. 2005; 21:6929-33.

[27] Sarikaya M, Tamerler C, Jen A K Y, Schulten K, Baneyx F. Molecular biomimetics: nanotechnology through biology. Nature Materials. 2003; 2:577-85.

[28] Wei J H, Kacar T, Tamerler C, Sarikaya M, Ginger D S. Nanopatterning Peptides as Bifunctional Inks for Templated Assembly. Small. 2009; 5:689-93.

[29] Hnilova M, Oren E E, Seker U O S, Wilson B R, Collino S, Evans J S, et al. Effect of Molecular Conformations on the Adsorption Behavior of Gold-Binding Peptides. Langmuir. 2008; 24:12440-5.

[30] Tamerler C, Sarikaya M. Molecular biomimetics: nanotechnology and bionanotechnology using genetically engineered peptides. Philosophical Transactions of the Royal Society a-Mathematical Physical and Engineering Sciences. 2009; 367:1705-26.

[31] Meyers S R, Khoo X J, Huang X, Walsh E B, Grinstaff M W, Kenan D J. The development of peptide-based interfacial biomaterials for generating biological functionality on the surface of bioinert materials. Biomaterials. 2009; 30:277-86.

[32] Khatayevich D, Gungormus M, Yazici H, So C, Cetinel S, Ma H, et al. Biofunctionalization of materials for implants using engineered peptides. Acta Biomaterialia. 2010; 6:4634-41.

[33] Yang H, Fung S Y, Sun W, Mikkelsen S, Pritzker M, Chen P. Ionic-complementary peptide-modified highly ordered pyrolytic graphite electrode for biosensor application. Biotechnology Progress. 2008; 24:964-71.

[34] Cui Y, Kim S N, Jones S E, Wissler L L, Naik R R, McAlpine M C. Chemical Functionalization of Graphene Enabled by Phage Displayed Peptides. Nano Letters. 2010; 10:4559-65.

[35] Wang Q H, Hersam M C. Room-temperature molecular-resolution characterization of self-assembled organic monolayers on epitaxial graphene. Nature Chemistry. 2009; 1:206-11.

[36] Kim S N, Kuang Z F, Slocik J M, Jones S E, Cui Y, Farmer B L, et al. Preferential Binding of Peptides to Graphene Edges and Planes. Journal of the American Chemical Society. 2011; 133:14480-3.

[37] Kase D, Kulp J L, Yudasaka M, Evans J S, Iijima S, Shiba K. Affinity selection of peptide phage libraries against single-wall carbon nanohorns identifies a peptide aptamer with conformational variability. Langmuir. 2004; 20:8939-41.

[38] Tomasio S M, Walsh T R. Modeling the Binding Affinity of Peptides for Graphitic Surfaces. Influences of Aromatic Content and Interfacial Shape. Journal of Physical Chemistry C. 2009; 113:8778-85.

[39] Han T H, Lee W J, Lee D H, Kim J E, Choi E Y, Kim S O. Peptide/Graphene Hybrid Assembly into Core/Shell Nanowires. Advanced Materials. 2010; 22:2060-+.

[40] So C R, Hayamizu Y, Yazici H, Gresswell C, Khatayevich D, Tamerler C, et al. Controlling Self-Assembly of Engineered Peptides on Graphite by Rational Mutation. Acs Nano. 2012; 6:1648-56.

[41] Khatayevich D, So C R, Hayamizu Y, Gresswell C, Sarikaya M. Controlling the Surface Chemistry of Graphite by Engineered Self-Assembled Peptides. Langmuir. 2012; 28:8589-93.

[42] Girit C O, Zettl A. Soldering to a single atomic layer. Applied Physics Letters. 2007; 91.

[43] Harder P, Grunze M, Dahint R, Whitesides G M, Laibinis P E. Molecular conformation in oligo(ethylene glycol)-terminated self-assembled monolayers on gold and silver surfaces determines their ability to resist protein adsorption. Journal of Physical Chemistry B. 1998; 102:426-36.

[44] Faucheux N, Schweiss R, Lutzow K, Werner C, Groth T. Self-assembled monolayers with different terminating groups as model substrates for cell adhesion studies. Biomaterials. 2004; 25:2721-30.

[45] Menzies K L, Jones L. The Impact of Contact Angle on the Biocompatibility of Biomaterials. Optometry and Vision Science. 2010; 87:387-99.

[46] Holmberg A, Blomstergren A, Nord O, Lukacs M, Lundeberg J, Uhlen M. The biotin-streptavidin interaction can be reversibly broken using water at elevated temperatures. Electrophoresis. 2005; 26:501-10.

Example 6

Self-Assembled Peptides Modulating Electrical Properties of Single-Layer Two-Dimensional Materials Abstract Single atomic layers of two-dimensional materials, such as graphene and $MoS_2$, are attractive as a novel platform to integrate heterogeneous nano-scale components towards a diversity of applications in the next generation electronics. Furthermore, the controllability of their electrical property via chemical doping with heterogeneous molecules attached on the surface gains increased interest. There have been various studies in the assembly of nano-materials on graphene, such as nano-particles, organic molecules, and bio-molecules. In order to realize more complex electronics with the two-dimensional materials, it is crucial to assemble sophisticated nano-structures forming discrete electronic junctions on a single layer of two-dimensional materials. However, such organic molecules can form only confluent monolayer film on graphene. Furthermore, there has been no study of molecular self-assembly on MoS2 single layers. Here we demonstrate that bio-combinatorially selected and rationally designed peptides can self-assemble into long range ordered structures, i.e., nanowires, on single-layer graphene and $MoS_2$. The self-assembled peptides form nano-scale electronic p-n junctions in graphene. Furthermore, peptides modulate the electrical conductivity and photoluminescence of single-layer $MoS_2$. Self-assembled peptides can potentially realize diverse and complex electronics of two dimensional materials, such as bio-nano electronics.

Graphene has attracted wide interests due to its rich physics and extraordinarily high carrier mobility. Recently, single-layer $MoS_2$, another two-dimensional material, has been found to have a direct band gap exhibiting appreciable photoluminescence and attractive switching property in a field effect transistor. Of particular interest in those single layer materials is energy-band engineering via chemical doping, in which the charge carrier density is varied by adsorbed chemical substances. Whereas there has been no report of chemical doping in single-layer $MoS_2$, chemical doping in graphene has been reported using adsorbed gases or molecules as dopants. In principle, the chemical doping is capable of forming spatially abrupt electronic junctions with nano-scale patterns of dopants on single layer materials. Aiming to form electronic junctions for realization of more sophisticated graphene-based electronics, lithographic, imprinting, and micro-drawing techniques have been utilized to fabricate patterned dopants on graphene. In contrast to those top-down processes, molecules self-assembled into long-range ordered nanostructures could offer a scalable bottom-up approach to create nano-scale electronic junctions on graphene. However, those molecules that have been utilized as dopants have established only confluent films on surfaces, mainly due to their simple molecular structures. Hence, we need to find more complex molecules having broad chemical diversity able to form discrete nanostructures, i.e., two-dimensional patterns of ordered molecules, on single layer materials. Furthermore, the complex molecules need the ability of doping effect with single layer materials.

Utilizing GrBP5 as a starting point, we rationally designed its derivatives by simple substitutions of several amino acids in the primary sequence. The challenging task in the new design is to create a peptide capable of forming ordered structures on $MoS_2$. Our strategy of the rational design is to control the peptide self-assembly and their doping effect through smart control of the location and the sign of charged amino acids. The GrBP5 contains charged and aromatic amino acids (colored in FIG. 26a). The charged amino acids, Aspartate (D) and Glutamate (E), are negatively charged under the condition of pH 7. Based on previous studies indicating a strong binding affinity of aromatic amino acids to graphite surfaces via pi-electrons, we assumed that YSSY (SEQ ID NO: 31) containing two Tyrosines (Y) could be the binding site to graphene. When peptides bound on a graphene, the separation between charged amino acids and aromatic amino acids in the sequence could be monotonically related to the actual distance of the charged amino acids from the graphene surface. Based on the above assumption, we synthesized GrBP5 mutant6 (M6), which was designed to have a stronger electric interaction with graphene than GrBP5 wild type (WT), due to the negatively charged amino acids in the middle of two tyrosines. In the same manner, M8 has been synthesized to have opposite charges (FIG. 26a).

Figure 26:
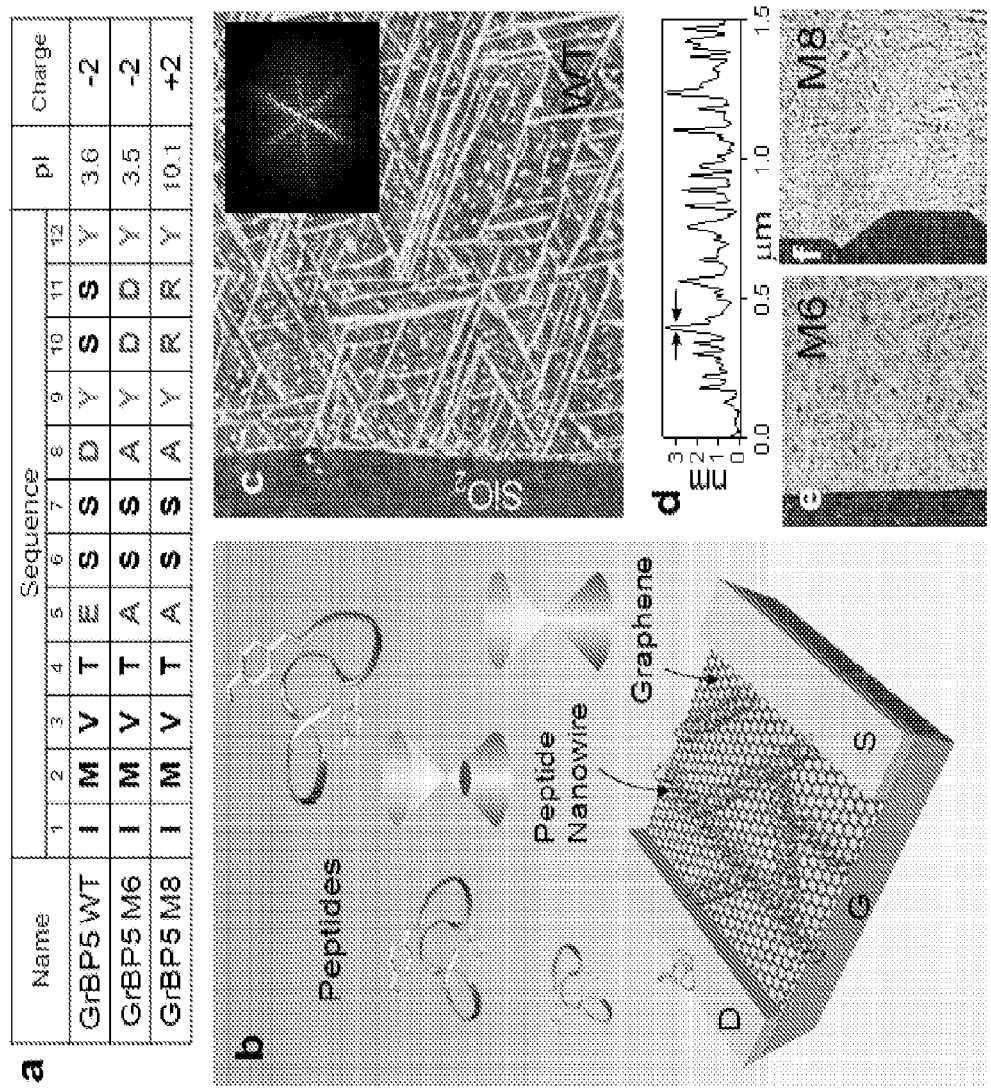
FIG. 26. Self-assembly of GrBP5 and it derivatives. (a) Amino acid sequence of GrBPs with corresponding isoelectric point (pI) and the net charge. (b) a schematic exhibiting the concept of peptides enabled electronic junctions in graphene. (c) AFM image of GrBP5 on graphene showing long range ordering over a micron with FFT displaying six-fold symmetry. Graphene was mechanically exfoliated on $SiO_2$. (d) a line profile of (c). (e) and (f) AFM images of M6 and M8 respectively.

FIG. 26b depicts the concept of peptide enabled p-n junctions in graphene, where peptides self-assemble into discrete nanostructures on a graphene field effect transistor (FET). Peptides nanostructures can locally dope the underneath graphene with charge carriers, while a back-gate can electrostatically tune the charge density in the whole system. Among our GrBPs, it was found that only WT exhibited long range ordered structures on graphene. The image of the atomic force microscope (AFM) shows that WT forms long range ordered structures, like nanowires, on a graphene (FIG. 26c). The fast Fourier transform (inset in FIG. 26c) of the AFM image reveals the ordered structure of WT has 6-fold symmetry. The thickness of the self-assembled peptides is 1.5 nm on average. The minimal width of peptide nanowires is about 10 nm (FIG. 26d). The maximal lateral length of the peptide nanowires is 750 nm. While the WT revealed ordered structures on single-layer graphene, M6 and M8 formed isolated islands with high coverage (FIGS. 26 e and f).

Figure 27:
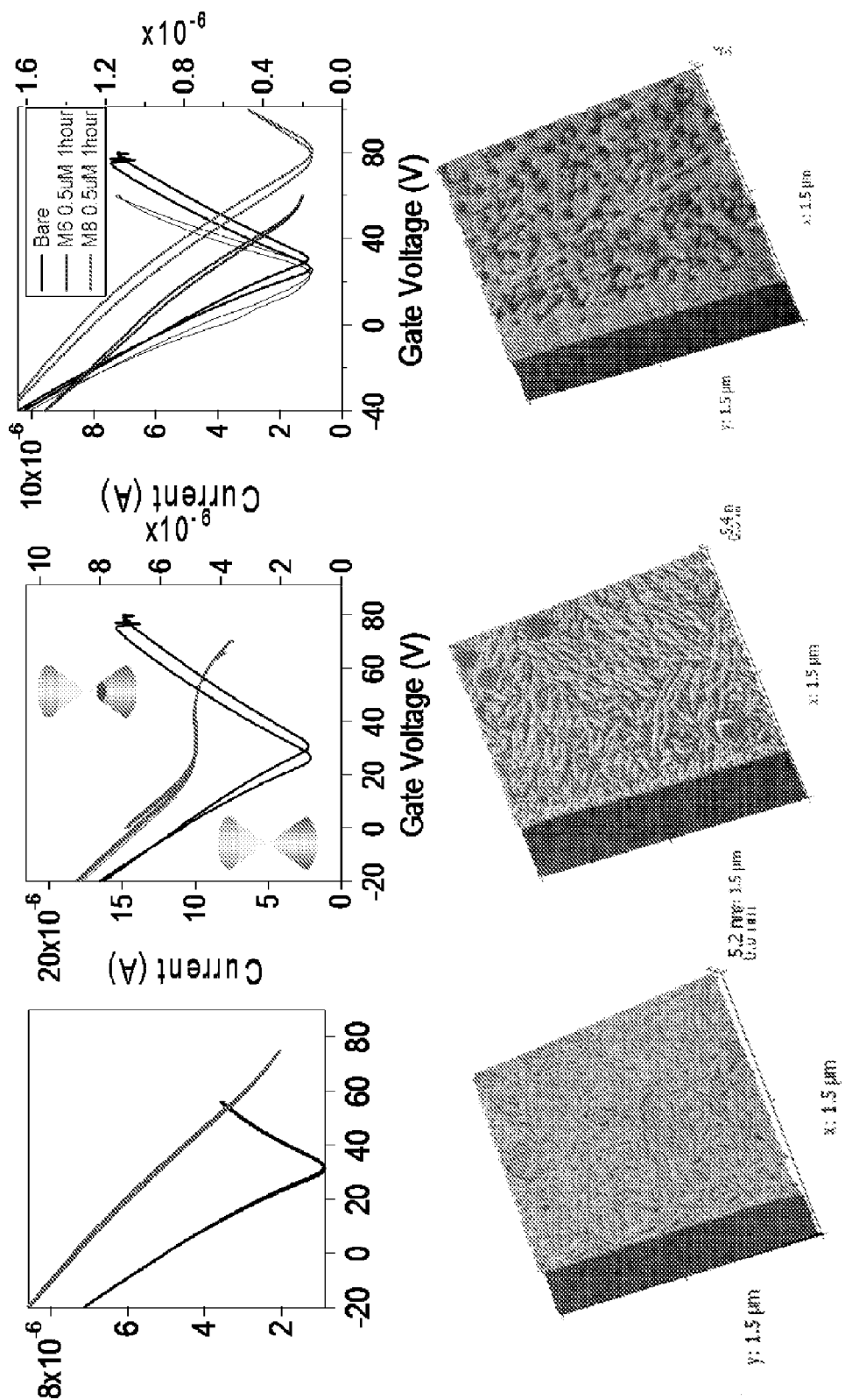
FIG. 27. Conductivity measurements of graphene FET and AFM images.

The conductivity of graphene was clearly modulated by peptides. Two-terminal indium electrodes were contacted on a mechanically exfoliated graphene by micro-soldering technique to persevere the cleanness of graphene, which is essential for the peptide self-assembly. All electrical measurement was performed under Argon gas atmosphere to eliminate instability caused by moisture. To investigate the correlation between the morphology of peptide nanostructures on graphene and the graphene conductivity, we utilized various concentrations of the GrBP5 WT from 50 nM to 500 nM to tune the peptides self-assembly and the coverage on graphene. The conductivity of graphene with 500 nM WT shows significant peak shift in the gate response (FIG. 27a). The bare graphene shows charge neutral point (CNP) at 30V typically. After the peptide incubation, the peak is shifted to 80V indicating hole doping via the peptides. Interestingly, the field-effect mobility of holes in graphene shows slight change from 3500 to 2500 $cm^2V^{-1} s^{-1}$ after peptides incubation. The observation of a weak disruption in the mobility is consistent with previous reports on the chemically doped graphene with organic molecules. The AFM image of the actual FET device shows highly covered graphene surface by ordered peptides (FIG. 27c). The peptides formed a number of nanowires with a close separation. When a graphene FET was incubated with 50 nM GrBP5, the conductivity of graphene revealed double peaks in the gate response (FIG. 27d). Each CNP peak at 30V and 80V can be attributed to bare graphene region and peptide coated region based on the original location of those bare and peptide coated graphene in FIG. 27c. Supporting this interpretation, the AFM image shows well-defined peptide nanowires on graphene (FIG. 27e). The energy separation between n- and p-type regions is estimated as 200 meV, which is sufficiently larger than thermal energy at room temperature. The formation of PN junction enabled by peptides is scalable and very simple because we use only aqueous droplet on a graphene FET. Other derivatives, M6 and M8, also modulated the graphene conductivity via doping. M6 shows hole doping in the gate response. Not as expected, the M8, which has opposite charges from M6 and WT, did not dope graphene with electrons but holes. It is probably because of the absence of the water molecules.

Similar to graphene, the interaction of peptides with single layer $MoS_2$ is highly correlated with the peptide sequence. Interestingly, on $MoS_2$, only M6 formed long range ordered structures like nanowires (FIG. 28a), but not WT. The single layer $MoS_2$ was prepared in the same manner as graphene. The number of the layers was confirmed by both the AFM and PL. The width and height of the nanowires are 11 nm and 1.5 nm, respectively (FIG. 26g). The WT and M8 forms only isolated islands with high coverage (FIGS. 26h and i). It indicates that the location of the charged amino acids in the sequence is highly correlated with the surface behavior of peptides on graphene including binding, diffusion and self-assembly. To investigate the peptide effect on an optical process in $MoS_2$, we performed PL measurements before and after peptide incubation. We focus here M6 and M8 since M6 is the only peptide forming ordered structures and M8 is its pair with opposite sign of charges. While WT shows the large peak shift of 9 meV in the PL among our peptides. On the other hand, M8 does not show any peak shift. Note that the peak width of the both peptide case is broadened from 64 meV to 76 meV after peptide incubation.

Figure 28:
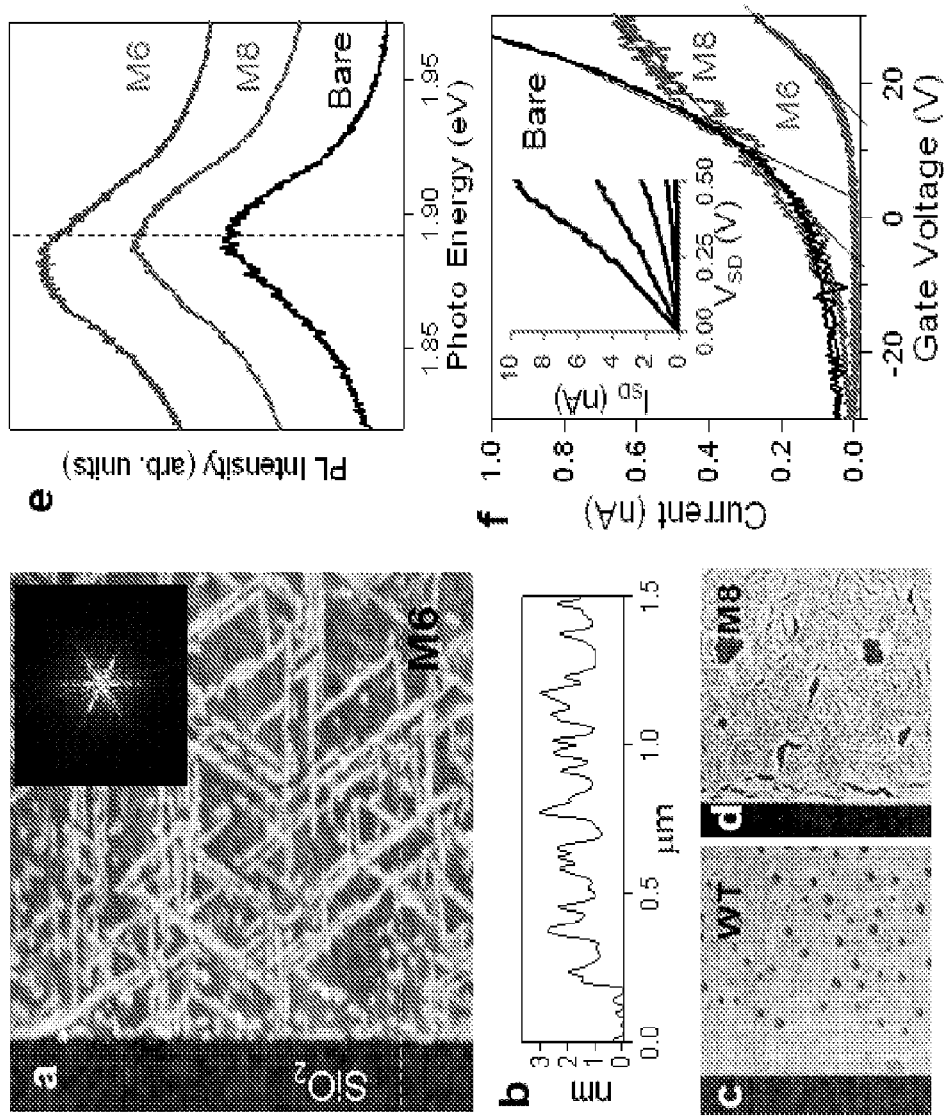
FIG. 28. AFM image of M6 mutant on $MoS_2$ showing (a) self-assembled peptide nanowire nanostructure, with (b) height profile. Ordering is not seen with (c) M8 mutant or (d) the WT peptide on $MoS_2$. Modification of photoluminescence and conductivity characteristics of single layer $MoS_2$ with designed peptides M6 and M8. (e) Photoluminescence spectra of single layer $MoS_2$ before (black) and after incubation with peptides M6 (blue) and M8 (red), respectively. The excitation wavelength and power were 514 nm and 10 W, respectively. The inset shows an optical image of a single-layer $MoS_2$. (f) The source-drain current versus backgate voltage curves of single layer MoS2 FETs before (black) and after incubation with peptide M6 (blue) and M8 (red). The source-drain voltage was 0.1 V. The inset shows the plot of source-drain current vs. source-drain voltage with various backgate voltages of −20, −10, 0, 10, and 20V; the observed current increases as the gate voltage is increased.
Figure 29:
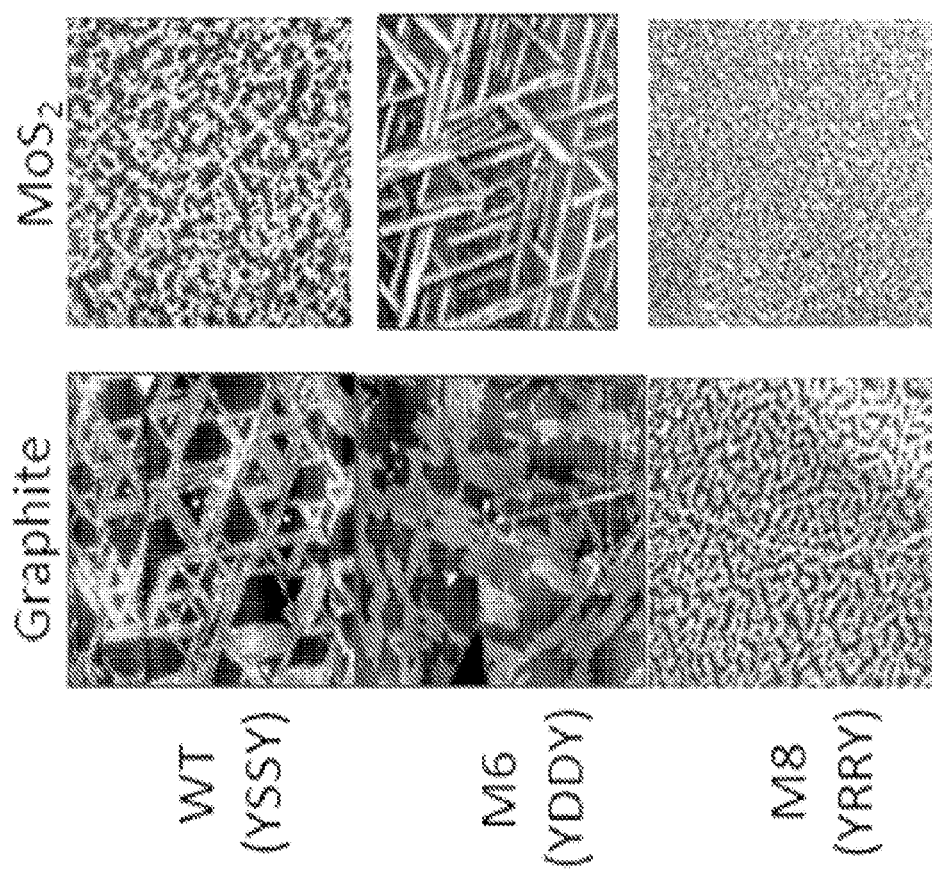
FIG. 29. Self-assembly characteristics of the peptides on graphite and MoS2 samples. All images were recorded using an atomic force microscope with samples containing 1 micromolar per milliliter peptides after 1 hour incubation time at pH 7.4 and room temperature. The first row: Assembled structures of WT GrBP5 on graphite (ordered) and on MoS2 (not ordered). The second row, assembled structures of mutant M6 (with DD replacing SS in YSSY in WT), loosely ordered on graphite and highly ordered on MoS2. Third row, assembly of mutant M8 (i.e., RR replacing SS in YSSY in WT), disordered both on graphite and on MoS2. These results show the specificity of the WT and the two mutants to each of these potential SLAM substrates.
Figure 30:
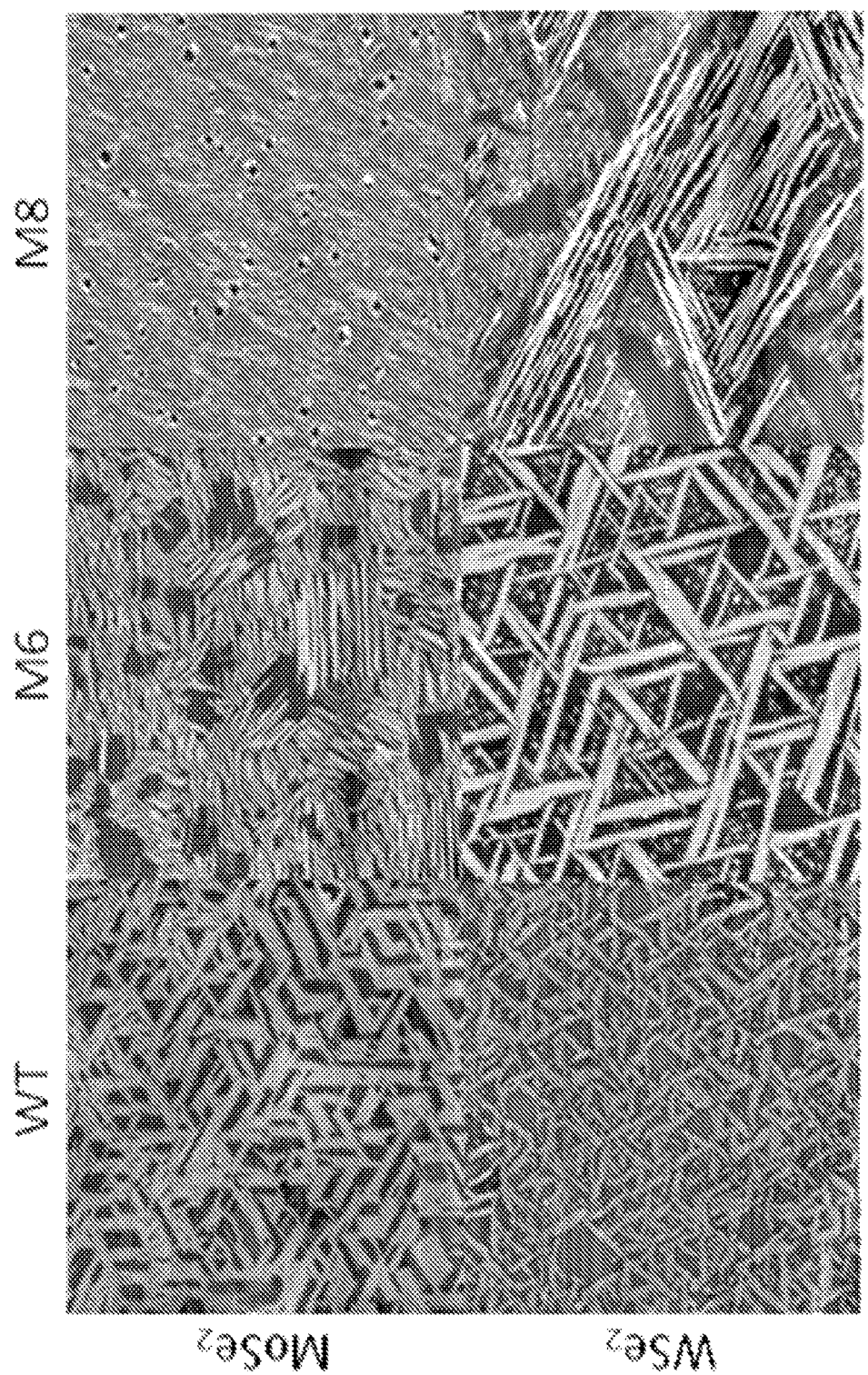
FIG. 30. Self-assembly characteristics of the peptides on MoSe2 and WSe2 samples. All images were recorded using an atomic force microscope with samples containing 1 micromolar per milliliter peptides after 1 hour incubation time at pH 7.4 and room temperature. The first column: Assembled structures of WT GrBP5 on MoSe2 (ordered, wide domains) and on WSe2 (ordered, small domains). The second column, assembled structures of mutant M6 (with DD replacing SS in YSSY in WT), highly ordered on both substrates with different patterns, commensurate with their crystal structures. Third row, assembly of mutant M8 (i.e., RR replacing SS in YSSY in WT), loosely ordered on MoSe2 while ordered on WSe2. These results show the specificity of the WT and the mutant to each of these potential SLAM substrates which similar surface crystal structures but with different lattice parameters.
Figure 31:
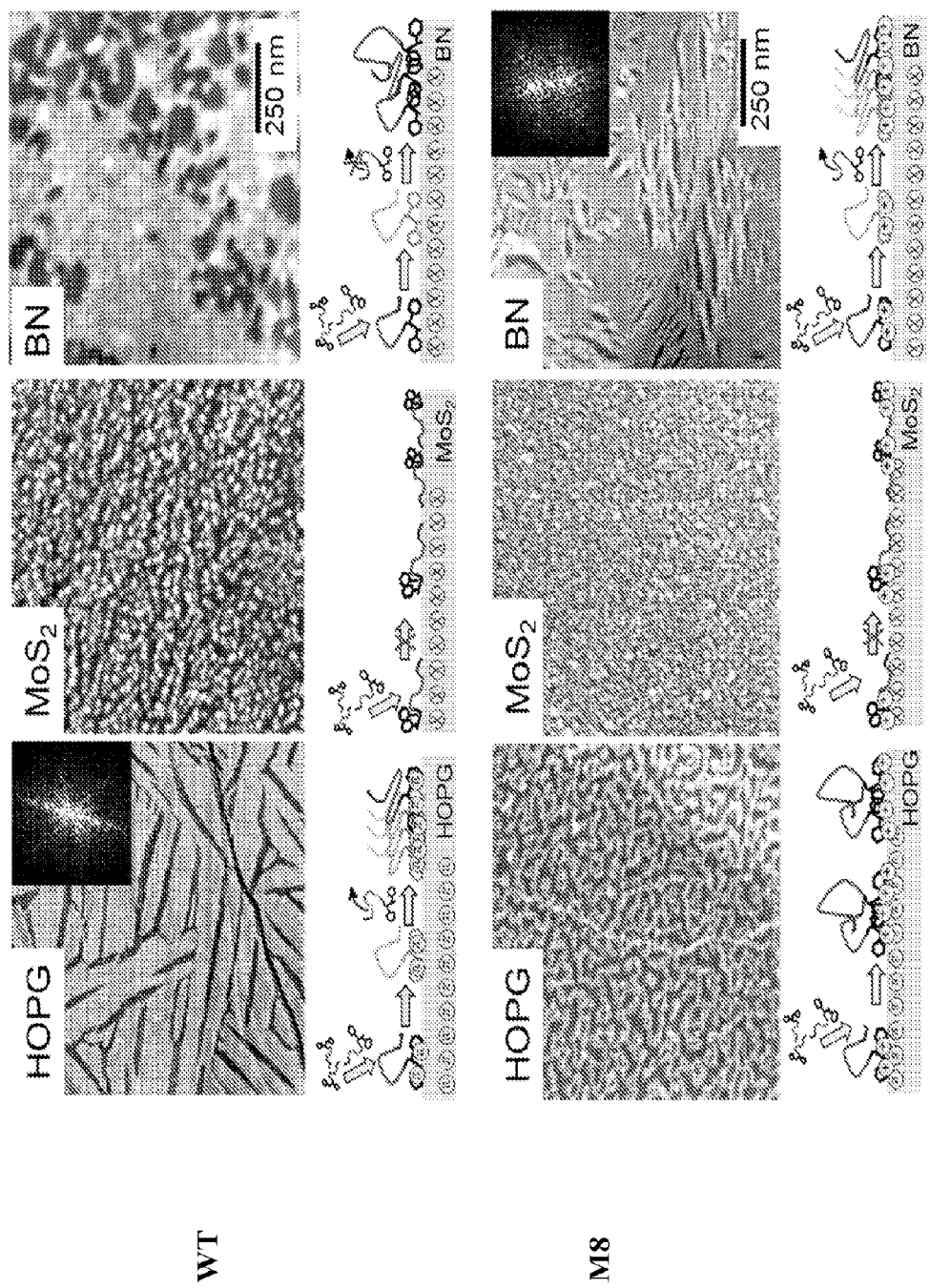
FIG. 31. Additional information of peptides assembling onto single layer atomic materials including new one, BN, demonstrating the universality of the SAP/SLAM concept. All images were recorded using an atomic force microscope with samples containing 1 micromolar per milliliter peptides after 1 hour incubation time at pH 7.4 and room temperature. The first row: Assembled structures of WT GrBP5 on HOPG (highly ordered pyrolytic graphite with ordered WT nanostructures), MoS2 (disordered, wide domains) and on BN (partially bound and not ordered). The second row, assembled structures of mutant M8 (i.e., RR replacing SS in YSSY in WT), disordered on HOPG, disordered on MoS2 while partially ordered on BN. These results show the specificity of the WT and the M8 mutant to each of these potential SLAM substrates which different surface crystal structures. Schematics below the AFM images depict possible folding of the peptides on each of these substrates.
Figure 32:
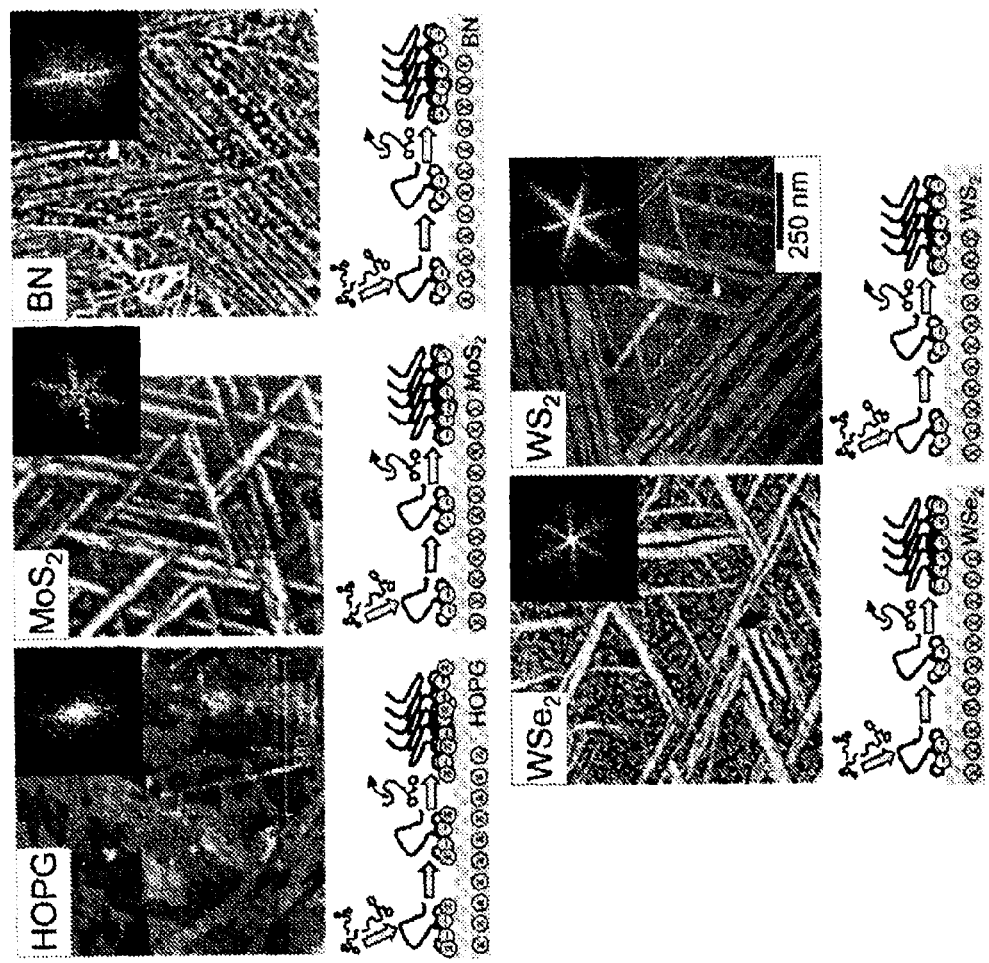
FIG. 32. The examples of assembly of one of the mutant peptides, M6, onto five different single layer atomic materials, demonstrating the universality of the SAP/SLAM concept. All images were recorded using an atomic force microscope with samples containing 1 micromolar per milliliter peptides after 1 hour incubation time at pH 7.4 and room temperature. In each of the 5 examples, M6 mutant binds onto the substrate, diffuses and then, through intermolecular interactions, assemble in a variety of peptide nanostructures forming crystallographic patterns each of which is unique to the substrate while the peptide used is the same. The schematics below the AFM images depict possible folding of the peptides on each of these substrates.

Conductivity measurements performed by single layer $MoS_2$ transistors shows a consistent result with the PL measurement. Due to the difficulty to produce a large sheet of mechanically exfoliated MoS2, we employed electron beam lithography to fabricate electrodes on the single layer $MoS_2$, instead of the micro-soldering. In the gate response, M6 shows significant doping effect as the threshold voltage is shifted from −10V to 15V (FIG. 28f). M8 does not show the threshold voltage shift. It corresponds to the peak shifts in PL. However both peptides show similarly slower slope than the bare graphene, which indicates decrease of the hole mobility. This is related with the observation of the peak broadening in the PL measurement.

Methods

Peptide Synthesis.
Peptides were prepared on an automated solid-phase peptide synthesizer (CS336X, CSBio Inc., Menlo Park, Calif.) employing standard batch wise Fmoc chemistry procedures as reported previously.[16] Peptides were verified by MALDI-TOF mass spectrometry as well as size-exclusion chromatography to verify peptide mass and dispersion in water. (See SI appendix, S7)
Sample Preparations.
Graphenes were mechanically exfoliated on a Si wafer with 300-nm thick SiO2 and incubated with 50 μL peptide under experimental condition. When incubation is finished, the substrate is gently dried with nitrogen gas. All samples in this study were prepared using this method.

We used a mechanically exfoliated graphene on a Si-wafer with 300 nm-thick SiO2. The exfoliated graphene was incubated with an aqueous solution of peptides (0.25 μM concentration for 20 minutes). After the incubation, the sample was gently dried by nitrogen gas.
Atomic Force Microscopy.
A Digital Instruments (Veeco, Santa Barbara, Calif.) Multimode Nanoscope Ma scanning probe microscope equipped with high frequency NanoSensors PPP—NCHR (NanoandMore USA, Lady's Island, S.C., USA) non-contact probes, with a 42 N/m spring constant, at a 4V amplitude setpoint.
Conductivity Measurements.
Room Temperature
Photoluminescence Measurements.
Room Temperatures

REFERENCES FOR EXAMPLE 6

1. H. A. Lowenstam and S. Weiner, On Biomineralization (Oxford University Press, Oxford, UK, 1989).
2. M. Sarikaya, Biomimetics: Materials fabrication through biology, Proc. Natl. Acad. Sci. USA, 96, 14183 (1999).
3. S. Mann, Molecular recognition in biomineralization, Nature, 332, 119 (1988).
4. I Weissbuch, L. Addadi, M. Lahav, and L. Leiserowitz, Molecular recognition at crystal interfaces, Science 253, 637 (1991).
5. M. Sarikaya, C. Tamerler, A. K. Y. Jen, K. Schulten, F. Baneyx, Molecular biomimetics: nanotechnology through biology. Nat. Mater., 2, 577 (2003).
6. S. W. Lee, C. B. Mao, C. E. Flynn, A. M. Belcher, Ordering of Quantum Dots Using Genetically Engineered Viruses. Science, 296, 892 (2002).
7. M. B. Dickerson, K. H. Sandhage, and R. R. Naik, Protein- and Peptide-Directed Syntheses of Inorganic Materials. Chem. Reviews, 108, 4935 (2008).
8. K. Sano, H. Sasaki, and K. Shiba, Utilization of the Pleiotropy of a Peptidic Aptamer To Fabricate Heterogeneous Nanodot-Containing Multilayer Nanostructures. J. Am. Chem. Soc., 128, 1717 (2006).
9. C. L. Chen and N. L. Rosi, Peptide-Based Methods for the Preparation of Nanostructured Inorganic Materials. Angew. Chem. Intl. Ed., 49, 1924 (2010).
10. C. Toniolo, A. Bianco, M. Maggini, G. Scorrano, M. Prato et al., A Bioactive Fullerene Peptide. J. Med. Chem. 37, 4558 (1994).
11. D. Pantarotto, C. D. Partidos, R. Graff, J. Hoebeke, J-P., Briand, M. Prato, A. Bianco, Synthesis, Structural Characterization, and Immunological Properties of Carbon Nanotubes Functionalized with Peptides. J. Am. Chem. Soc. 125, 6160 (2003).
12. D. Kase, J. L. Kulp, M. Yudasaka, J. S. Evans, S. Iijima, K. Shiba, Affinity Selection of Peptide Phage Libraries against Single-Wall Carbon Nanohorns Identifies a Peptide Aptamer with Conformational Variability. Langmuir 20, 8939 (2004).
13. B. L. Allen, P. D. Kichambare, A. Star, Carbon Nanotube Field-Effect-Transistor-Based Biosensors. Adv. Mater. 9, 1439 (2006).
14. K. S, Novoselov, A. K. Geim, S. V. Morozov, D. Jiang, Y. Zhang, S. V. Dubonos, I. V. Grigorieva, A. A. Firsov, Science 306, 666 (2004).
15. Y. Zhang, J. W. Tan, H. L. Stormer, P. Kim, Experimental observation of the quantum Hall effect and Berry's phase in graphene. Nature 438, 201 (2005).
16. K. I. Bolotin, K. J. Sikes, Z. Jiang, M. Klima, G. Fudenberg, J. Hone, P. Kim, H. L. Stormer, Ultrahigh electron mobility in suspended graphene. Solid State Commun 146, 351 (2008).
17. M. Y. Han, B. Oezyilmaz, Y. Zhang, P. Kim, Energy Band Gap Engineering of Graphene Nanoribbons. Phys. Rev. Lett. 98, 206805 (2007).
18. Y. Zhang, T.-Ta Tang, C. Girit, Z. Hao, M. C. Martin, A. Zettl, M. F. Crommie, Y. R. Shen, F. Wang, Direct observation of a widely tunable bandgap in bilayer graphene. Nature 459, 820 (2009).
19. X. Dong, D. Fu, W. Fang, Y. Shi, P. C., L.-J. Li, Doping Single-Layer Graphene with Aromatic Molecules. Small 5, 1422 (2009).
20. A. Das, S. Pinsana, B. Chakraborty, S. Piscanec, S. K. Saha, U. V. Waghmare, K. S. Novoselov, H. R. Krishnamurthy, A. K. Geim, A. C. Ferrari, A. K. Sood, Monitoring dopants by Raman scattering in an electrochemically top-gated graphene transistor, Nature Nanotech. 3, 210 (2008).
21. G. P. Smith, Filamentous fusion phage: novel expression vectors that display cloned antigens on the virion surface. Science, 228, 1315 (1985).
22. S. Brown, Engineered iron oxide adhesion mutants of the *Escherichia coli* phage-lambda receptor, Proc. Natl. Acad. Sci. U.S.A. 89, 8651 (1992).
23. See supporting on-line material.
24. S. D. M. Tomasio and T. R. Walsh, Atomistic modeling of the interaction between peptides and carbon nanotubes. Molecular Physics, 105, 221 (2007).
25. C. Rajesh, C. Majumder, H. Mizuseki, and Y. A. Kawazoe, A theoretical study on the interaction of aromatic amino acids with graphene and single walled carbon nanotube. J. Chem. Phys. 130, 124911 (2009).
26. C. So, C. Tamerler and M. Sarikaya, Adsorption, Diffusion, and Self-Assembly of an Engineered Gold-Binding Peptide on Au(111) Investigated by Atomic Force Microscopy. Angew Chem. Intl. Ed. 48, 5174 (2009).
27. C. So, J. L. Kulp, E. E., Oren, H. Zareie, C. Tamerler, J. S. Evans, and M. Sarikaya, Molecular Recognition and Supramolecular Self-Assembly of a Genetically Engineered Gold Binding Peptide on Au {111}. ACS Nano, 3, 1525 (2009).
28. C. H. Lui, L. Liu, K. F. Mak, G. W. Flynn, T. F. Heinz, Ultraflat graphene, Nature 462, 339 (2009).
29. G. M. Whitesides, J. P. Mathias, and C. T. Seto, Molecular self-assembly and nanochemistry: a chemical strategy for the synthesis of nanostructures. Science 254, 1312 (1991).
30. L. A. Bumm, J. J. Arnold, M. T. Cygan, T. D. Dunbar, T. P. Burgin, L. D. Jones, J. M. Tour, and P. S. Weiss, Are single molecular wires conducting? Science, 271, 1705 (1996).

Example 7

Using the methods demonstrated in the various examples above, various mutations of the WT GrBP5 have been shown capable of binding and ordering on variety of single layer atomic materials (SLAMs) with different physical characteristics, such as crystal structure and conducting. These include: semiconducting, metallic and insulator characteristics.

Representative SLAMs include:
  Metallic: Graphene or doped graphene
  Semiconductors: MoS2, MoSe2, WS2, WSe2, -- Insulator: BN.

Exemplary of such ordering are provided in FIGS. 29-32. One such study involved analysis of M8 (IMVTASSAYRRY) (SEQ ID NO:3) on BN (Boron Nitride). Similar to the assembly of specific peptides on other atomically flat materials or single layer materials, here assembly of M8 on BN is shown as observed by atomic force microscopy imaging. The assembly of the peptide M8 was accomplished using a 1 mM/ml upon 1 hr of incubation (followed by rinsing and drying). Despite the fact that M8 peptide does not form long range ordered structures on any of the other four substrates, except partial ordering on WSe2, this peptides assembly on BN is much more prominent. Having basic amino acid Arginine "RR" replacing the two Serine residues at the same position, while removing the acidic residues E and D (and replacing them with Alanine) makes this peptide more positively charged and results in the binding and assembly of the peptide on BN. In summary, the M8 mutation is specific for BN substrate. Similar studies were done for other mutants on other inorganic solid surfaces (See FIGS. 29-32 and Figure Legends). A summary of exemplary studies on the polypeptides is shown in Table 4 below. Each peptide has been tested for binding activity to one or more SLAM, as well as diffusion, assembly, chemical activity (such as modifying SLAM hydrophobicity or contact angle), and electrical activity (such as doping effects, including but not limited to injecting holes or electrons into the SLAM. The presence of such activities is noted by a "Y", or "YY" (for very strong activity), the absence of such activity is noted by a "N", and a "?" indicates that the activity has not been tested.

TABLE 4

| Peptide | Sequence | Binding | Diffusing | Assembling | Chemical | Electronic |
|---|---|---|---|---|---|---|
| GrBP5-WT | IMVTESSDYSSY (SEQ ID NO: 5) | Y | Y | YY | Y | Y |
| GrBP5-M1 | IMVTESSDASSA (SEQ ID NO: 6) | N | N | N | N | N |
| GrBP5-M2 | IMVTESSDWSSW (SEQ ID NO: 7) | Y | Y | N | Y | Y |
| GrBP5-M3 | IMVTKSSRFSSF (SEQ ID NO: 8) | Y | N | N | Y | |
| GrBP5-M4 | TQSTKSSRYSSY (SEQ ID NO: 9) | Y | Y | N | Y | Y |
| GrBP5-M5 | IMVTESSRYSSY (SEQ ID NO: 10) | Y | Y | Y | Y | Y |
| GrBP5-M6 | IMVTASSAYDDY (SEQ ID NO: 2) | Y | Y | Y | Y | YY |
| GrBP5-M8 | IMVTASSAYRRY (SEQ ID NO: 3) | Y | Y | N | Y | YY |
| GrBP5-M10 | IMVTDSSAYSSY (SEQ ID NO: 35) | Y | Y | ? | Y | Y |
| GrBP5-12 | IMVTASSDYSSY (SEQ ID NO: 12) | Y | Y | ? | Y | Y |
| HGrBP5 | HIMVTESSDYSSY (SEQ ID NO: 13) | Y | Y | Y | YY | Y |
| WGrBP5 | WIMVTESSDYSSY (SEQ ID NO: 14) | Y | Y | Y | YY | Y |
| SSGrBP5 | SSIMVTESSDYSSY (SEQ ID NO: 16) | Y | Y | YY | Y | Y |
| VVGrBP5 | VVIMVTESSDYSSY (SEQ ID NO: 15) | Y | Y | ? | Y | Y |
| GrBP5 hydrophobic | LIATESSDYSSY (SEQ ID NO: 17) | Y | Y | Y | YY | Y |
| GrBP 5 hydrophilic | AQTTESSDYSSY (SEQ ID NO: 18) | Y | Y | N | YY | Y |
| GrBP 5 neutral | IMVTASSAYSSY (SEQ ID NO: 19) | Y | ? | ? | ? | Y |
| Bio-GrBP5 (Biotin) | Bio-IMVTESSDYSSY (SEQ ID NO: 20) | Y | Y | YY | YY | Y |
| Rigid GrBP5 | IMVTEPPDYSSY (SEQ ID NO: 21) | Y | ? | ? | ? | Y |
| Cys-GrBP5 | CIMVTESSDYSSY (SEQ ID NO: 22) | Y | Y | Y | YY | Y |
| DOPA-GrBP5 | DOPA-IMVTESSDYSSY (SEQ ID NO: 23) | Y | Y | Y | YY | Y |
| AminoF-GrBP5 | IMVTESSD(NonnaturalF)SSY (SEQ ID NO: 24) | Y | ? | ? | ? | ? |
| F-Phenyl-GrBP5 | IMVTESSD(F-Phenyl)SSY (SEQ ID NO: 25) | Y | ? | ? | ? | ? |

TABLE 4-continued

| Peptide | Sequence | Binding | Diffusing | Assembling | Chemical | Electronic |
|---|---|---|---|---|---|---|
| D-GrBP5 | IMVTESSDYSSY (SEQ ID NO: 26) | Y | Y | YY | Y | Y |
| AntibodyBP-SS-GrBP5 | EPIHRSTLTALL-SS-IMVTESSDYSSY (SEQ ID NO: 27) | Y | Y | Y | YY | N |

We claim:

1. A polypeptide consisting of the general formula

Z1-Z2-R1-R2-R3-T-R5-R6-R7-R8-R9-R10 (SEQ ID NO: 1), wherein

Z1 is absent or is a molecular tag;
Z2 is absent or is any sequence of 1-88 amino acids;
R1 is selected from the group consisting of I, T, A, V, and L;
R2 is selected from the group consisting of M, Q, A, V, L, and I;
R3 is selected from the group consisting of V, S, T, I, L, and A;
R5 is selected from the group consisting of E, K, D, N, T, S and A;
R6 is selected from the group consisting of S and P;
R7 is selected from the group consisting of S and P;
R8 is selected from the group consisting of D, R, N, and A;
R9 is selected from the group consisting of W, F, F-phenyl, Amino-F, A, and Y;
R10 is selected from the group consisting of S, D, and R;
R11 is selected from the group consisting of S, D, and R; and
R12 is selected from the group consisting of W, F, A, and Y.

2. The polypeptide of claim 1, wherein:
R1 is selected from the group consisting of I, T, A, and L;
R2 is selected from the group consisting of M, Q, and I;
R3 is selected from the group consisting of V, S, T, and A;
R5 is selected from the group consisting of E, K, D, N, and A;
R6 is selected from the group consisting of S and P;
R7 is selected from the group consisting of S and P;
R8 is selected from the group consisting of D, R, N, and A;
R9 is selected from the group consisting of W, F, F-phenyl, Amino-F, A, and Y;
R10 is selected from the group consisting of S, D, and R;
R11 is selected from the group consisting of S, D, and R; and
R12 is selected from the group consisting of W, F, A, and Y.

3. The polypeptide of claim 1, wherein one, two, or all three of the following are true:
R1 is I;
R2 is M; and
R3 is V.

4. The polypeptide of claim 1, wherein one, two, three, or all four of the following are true:
R5 is E;
R6 is S;
R7 is S; and
R8 is D.

5. The polypeptide of claim 1, wherein one, two, three, or all four of the following are true:
R5 is A;
R8 is A;
R10 is D or R; and
R11 is D or R.

6. The polypeptide of claim 1, wherein:
R1 is I;
R2 is selected from the group consisting of M and Q;
R3 is V;
R5 is selected from the group consisting of E, K, and A;
R6 is S;
R7 is S;
R8 is selected from the group consisting of D, R, and A;
R9 is selected from the group consisting of W and Y;
R10 is S;
R11 is S; and
R12 is selected from the group consisting of W and Y.

7. The polypeptide of claim 1, wherein
R1 is selected from the group consisting of I, T, A, V, and L;
R2 is selected from the group consisting of M, Q, A, V, L, and I;
R3 is selected from the group consisting of V, S, T, I, L, and A;
R5 is A;
R6 is selected from the group consisting of S and P;
R7 is selected from the group consisting of S and P;
R8 is A;
R9 is selected from the group consisting of W, F, F-phenyl, Amino-F, and Y;
R10 is selected from the group consisting of D, and R;
R11 is selected from the group consisting of D, and R; and
R12 is selected from the group consisting of W, F, and Y.

8. The polypeptide of claim 1, wherein
R1 is I;
R2 is M;
R3 is V;
R5 is A;
R6 is S;
R7 is S;
R8 is A;
R9 is Y;
R10 is selected from the group consisting of D, and R;
R11 is selected from the group consisting of D, and R; and
R12 is Y.

9. The polypeptide of claim 1, wherein at least one of the following is true:
R10 is S and R11 is S;
R9 is Y and R12 is Y;
R9 is F or W and R12 is F or W; and
R10 is D or R and R11 is D or R.

10. The polypeptide of claim 1, wherein Z2 is present, and wherein Z2 is between 1 and 5 amino acids in length.

11. The polypeptide of claim 10, wherein Z2 is between 1 and 2 amino acids in length.

12. The polypeptide of claim 11, wherein Z2 is selected from the group consisting of H, W, C, SS, and VV.

13. The polypeptide of claim 1, wherein the polypeptide comprises an amino acid sequence selected from the group consisting of:

IMVTESSDYSSY (GrBP5) (SEQ ID NO: 5)

IMVTESSDASSA (GrBP5-M1) (SEQ ID NO: 6)

IMVTESSDWSSW (GrBP5-M2); (SEQ ID NO: 7)

-continued

IMVTKSSRFSSF (GrBP5-M3); (SEQ ID NO: 8)

TQSTKSSRYSSY (GrBP5-M4); (SEQ ID NO: 9)

IMVTESSRYSSY (GrBP5-M5); (SEQ ID NO: 10)

IMVTASSAYDDY (GrBP5-M6); (SEQ ID NO: 2)

IMVTASSAYRDY; (SEQ ID NO: 11)

IMVTASSAYRRY (GrBP5-M8); (SEQ ID NO: 3)

IMVTASSDYSSY (GrBP5-12); (SEQ ID NO: 12)

HIMVTESSDYSSY (HGrBP5); (SEQ ID NO: 13)

WIMVTESSDYSSY (WGrBP5); (SEQ ID NO: 14)

VVIMVTESSDYSSY (VVGrBP5); (SEQ ID NO: 15)

SSIMVTESSDYSSY (SSGrBP5); (SEQ ID NO: 16)

LIATESSDYSSY (GrBP5 hydrophobic); (SEQ ID NO: 17)

AQTTESSDYSSY (GrBP 5 hydrophilic); (SEQ ID NO: 18)

IMVTASSAYSSY (GrBP 5 neutral); (SEQ ID NO: 19)

Bio-IMVTESSDYSSY (Bio-GrBP5); (SEQ ID NO: 20)

IMVTEPPDYSSY (Rigid GrBP5); (SEQ ID NO: 21)

CIMVTESSDYSSY (Cys-GrBP5); (SEQ ID NO: 22)

DOPA-IMVTESSDYSSY (DOPA-GrBP5); (SEQ ID NO: 23)

IMVTESSD(Nonnatural F)SSY (AminoF-GrBP5); (SEQ ID NO: 24)

IMVTESSD(F-Phenyl)SSY (F-Phenyl-GrBP5); (SEQ ID NO: 25)

IMVTESSDYSSY (D-GrBP5); (SEQ ID NO: 26)

EPIHRSTLTALL-SS-IMVTESSDYSSY (AntibodyBP-SS-GrBP5); (SEQ ID NO: 27)

IMVTNSSNWSSW (GrBP5 neutral WSSW); (SEQ ID NO: 28)

IMVTESSDFSSF; (SEQ ID NO: 29)

TQSTESSDYSSY; (SEQ ID NO: 30)
and

IMVTDSSAYSSY. (SEQ ID NO: 35)

14. The polypeptide of claim 1, wherein Z1 is present.

15. A structure, comprising:
(a) an inorganic solid surface; and
(b) a polypeptide array bound to the solid surface, wherein the polypeptide array comprises the polypeptide of claim 1.

16. The structure of claim 15, wherein the inorganic solid surface is selected from the group consisting of graphite, graphene, $MoS_2$, $MoSe_2$, $WSe_2$, $WS_2$, or BN, and combinations thereof.

17. The structure of claim 15, wherein the polypeptide array comprises a patterned array on the solid surface.

18. The structure of claim 17, wherein the patterned array is selected from the group consisting of an ordered polypeptide film, a porous confluent film, peptide clusters, nanowires, quantum dots, metallic and insulator nanoparticles (NPs, such as Au and silica, glass), nanoscale p-n junctions, and combinations thereof.

19. The structure of claim 15, wherein the inorganic solid surface is a single layer material.

20. The structure of claim 15, wherein the inorganic solid surface is part of a device selected from the group consisting of protein chips, peptide-molecular circuits, designer proteins, semiconductor structures, and sensors.

21. A structure, comprising:
(a) an inorganic solid surface; and
(b) a polypeptide array bound to the solid surface, wherein the polypeptide array comprises the polypeptide of claim 13.

22. The structure of claim 21, wherein the inorganic solid surface is selected from the group consisting of graphite, graphene, $MoS_2$, $MoSe_2$, $WSe_2$, $WS_2$, or BN, and combinations thereof.

23. The structure of claim 21, wherein the inorganic solid surface is a single layer material.

* * * * *

UNITED STATES PATENT AND TRADEMARK OFFICE
CERTIFICATE OF CORRECTION

| | | |
|---|---|---|
| PATENT NO. | : 9,493,513 B2 | Page 1 of 1 |
| APPLICATION NO. | : 14/349634 | |
| DATED | : November 15, 2016 | |
| INVENTOR(S) | : Mehmet Sarikaya et al. | |

It is certified that error appears in the above-identified patent and that said Letters Patent is hereby corrected as shown below:

On the Title Page

Item (72) Inventors: Please delete the first line and replace with the following:

"Mehmet Sarikaya, Seattle, WA (US)"

Signed and Sealed this
Twenty-fourth Day of January, 2017

Michelle K. Lee
*Director of the United States Patent and Trademark Office*